US008362323B2

(12) United States Patent
Douchkov et al.

(10) Patent No.: US 8,362,323 B2
(45) Date of Patent: Jan. 29, 2013

(54) USE OF ARMADILLO REPEAT (ARM1) POLYNUCLEOTIDES FOR OBTAINING PATHOGEN RESISTANCE IN PLANTS

(75) Inventors: Dimitar Douchkov, Gatersleben (DE); Patrick Schweizer, Ballenstedt (DE); Uwe Zierold, Meerane (DE)

(73) Assignee: BASF Plant Science GmbH (DE)

( * ) Notice: Subject to any disclaimer, the term of this patent is extended or adjusted under 35 U.S.C. 154(b) by 919 days.

(21) Appl. No.: 12/092,877

(22) PCT Filed: Oct. 27, 2006

(86) PCT No.: PCT/EP2006/067865
§ 371 (c)(1),
(2), (4) Date: May 7, 2008

(87) PCT Pub. No.: WO2007/054441
PCT Pub. Date: May 18, 2007

(65) Prior Publication Data
US 2009/0241215 A1    Sep. 24, 2009

(30) Foreign Application Priority Data

Nov. 8, 2005  (EP) .................................. 05110468

(51) Int. Cl.
*A01H 1/00* (2006.01)
*C12N 15/82* (2006.01)
*C07H 21/04* (2006.01)
(52) U.S. Cl. ....... 800/286; 800/285; 800/301; 536/23.6; 536/24.5
(58) Field of Classification Search .................. None
See application file for complete search history.

(56) References Cited

U.S. PATENT DOCUMENTS

| 5,565,350 | A | 10/1996 | Kmiec |
| 7,456,335 | B2 | 11/2008 | Kogel et al. |
| 2004/0038212 | A1* | 2/2004 | Kurochkin et al. ............... 435/6 |
| 2008/0047033 | A1 | 2/2008 | Kogel et al. |

FOREIGN PATENT DOCUMENTS

| CA | 2628505 A1 | 5/2007 |
| WO | WO-9804586 A2 | 2/1998 |
| WO | WO-99/47552 A2 | 9/1999 |
| WO | WO-00/01722 A1 | 1/2000 |
| WO | WO-00/15815 A1 | 3/2000 |
| WO | WO-03/020939 A1 | 3/2003 |
| WO | WO-2004/009820 A1 | 1/2004 |
| WO | WO-2007/054441 A2 | 5/2007 |

OTHER PUBLICATIONS

Stone et al. 1999, Science 286:1729-1731.*
Fourgoux-Nicol et al 1999, Plant Molecular Biology 40:857-872.*
Zeng, L-R., et al., "*Spotted leaf11*, a Negative Regulator of Plant Cell Death and Defense, Encodes 2 U-Box/Armadillo Repeat Protein Endowed with E3 Ubiquitin Ligase Activity", The Plant Cell, 2004, vol. 16, No. 10, pp. 2795-2808.

Coates, J. C., "Armadillo Repeat Proteins: Beyond the Animal Kingdom", Trends in Cell Biology, 2003, vol. 13, No. 9, pp. 463-471.
Zierold, U., et al., "Transcriptome Analysis of *mlo*-mediated Resistance in the Epidermis of Barley", Molecular Plant Pathology, 2005, vol. 6, No. 2, pp. 139-151.
Schweizer, P., et al., "Double-Stranded RNA Interferes with Gene Function at the Single-Cell Level in Cereals", The Plant Journal, 2000, vol. 24, No. 6, pp. 895-903.
Azevedo, C., et al., "The U-Box Protein Family in Plants", Trends in Plant Science, 2001, vol. 6, No. 8, pp. 354-358.
Amador, V., et al., "Gibberellins Signal Nuclear Import of PHOR1, a Photoperiod-Responsive Protein with Homology to *Drosophila armadillo*", Cell, 2001, vol. 106, pp. 343-354.
Gu, T., et al., "Binding of an Arm Repeat Protein to the Kinase Domain of the S-locus Receptor Kinase", Proc. Natl. Acad. Sci. USA, 1998, vol. 95, pp. 382-387.
Hatakeyama, S., et al., "U Box Proteins as a New Family of Ubiquitin-Protein Ligases", The Journal of Biological Chemistry, 2001, vol. 276, No. 35, pp. 33111-33120.
"Oryza sativa (japonica cultivar-group), mRNA", NCBI Database, Accession No. XM_479734.1, Nov. 9, 2004.
"Oryza sativa (japonica cultivar-group), predicted mRNA", NCBI Database, Accession No. XM_463544, Nov. 9, 2004.
"Oryza sativa (japonica cultivar-group), genomic DNA, chromosome 1, BAC clone:B1065E10.", EMBL Database, Accession No. AP003561, May 7, 2001.
"Predicted Oryza sativa (japonica cultivar-group), OJ1060_D03.106 mRNA", NCBI Database, Accession No. XM_506432, Nov. 9, 2004.
"Nicotiana tabacum arm repeat-containing protein mRNA, complete cds.", EMBL Database, Accession No. AY219234, Mar. 19, 2003.
"Arabidopsis thaliana armadillo/bete-catenin repeat family protein / U-box domain-containing protein (AT2G23140) mRNA, complete cds.", NCBI Database, Accession No. NM_127878, Apr. 20, 2007.
"Arabidopsis thaliana chromosome 2 cloneF21P24 map CIC06C07, complete sequence", EMBL Database, Accession No. AC004401, Mar. 16, 1998.
"Arabidopsis thaliana At5g67340 mRNA, complete cds.", EMBL Database, Accession No. BT020206, Nov. 14, 2004.
"Arabldopsls Mallana genomic DNA, chromosome 5, TAC clone,K8K14", EMBL Database, Accession No, AB007645, Oct. 31, 1997.
"Arabidopsis thaliana armadillo/beta-catenin repeat family protein / U-box domain-containing protein (AT3G54790) mRNA, complete cds." NCBI Database, Accession No. NM_115336, Apr. 30, 2008.
"Arabidopsis thaliana At3g54790 mRNA for unknown protein, complete cds, clone: RAFL19-87-C08,", EMBL Database, Accession No. AK118613, Dec. 13, 2002.

(Continued)

*Primary Examiner* — Li Zheng
(74) *Attorney, Agent, or Firm* — Connolly Bove Lodge & Hutz LLP

(57) ABSTRACT

The invention relates to a method of generating or increasing a pathogen resistance in plants by reducing the expression of at least one Armadillo repeat polypeptide or a functional equivalent thereof. The invention relates to novel nucleic acid sequences coding for a *Hordeum vulgare* Armadillo repeat (HvARM) polynucleotide and describes homologous sequences (ARM1) thereof, and to their use in methods for obtaining a pathogen resistance in plants e, and to nucleic acid constructs, expression cassettes and vectors which comprise these sequences and which are suitable for mediating a fungal resistance in plants. The invention furthermore relates to transgenic organisms, in particular plants, which are transformed with these expression cassettes or vectors, and to cultures, parts or transgenic propagation material derived therefrom.

18 Claims, 41 Drawing Sheets

OTHER PUBLICATIONS

Figure 4:
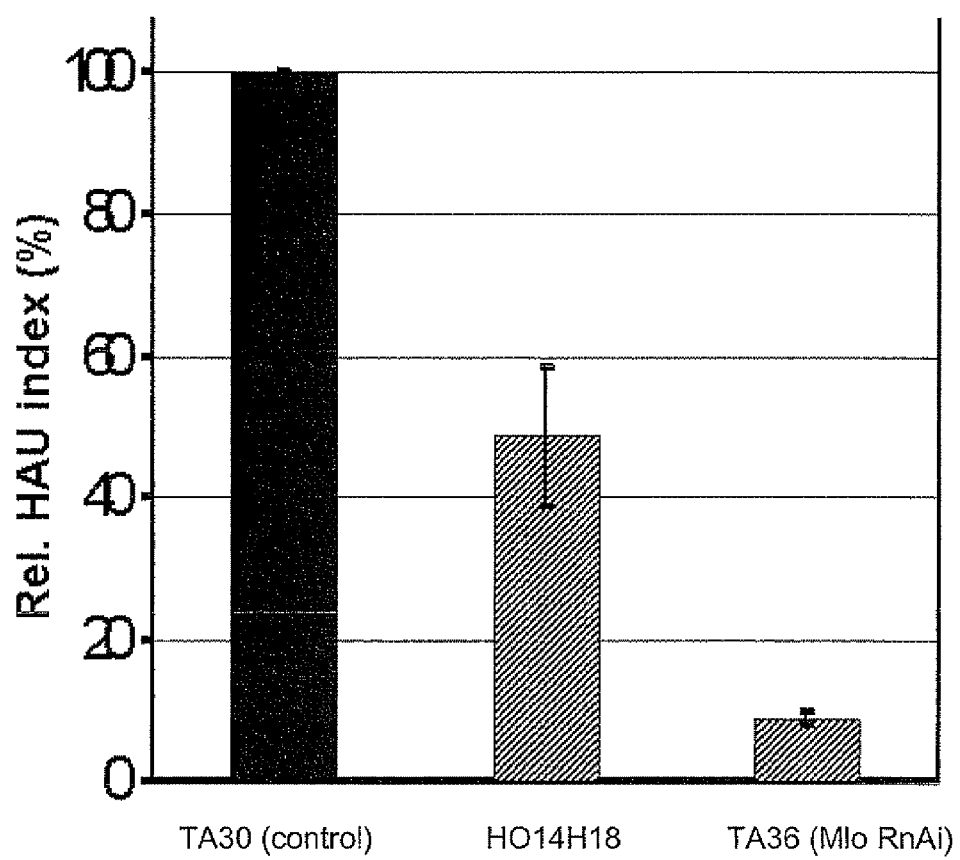

"Arabidopsis thaliana DNA chromosome 3, BAC clone T5N23", EMBL Database, Accession No. AL138650, Feb. 2, 2000.

"Arabidopsis thaliana DNA chromosome 3, BAC clone F12A12", EMBL Database, Accession No. AL133314. Dec. 2, 1999.

"Arabidopsis thaliana chromosome III BAC T13O15 genomic sequence, complete sequence", EMBL Database, Accession No. AC010870, Sep. 26, 1999.

"Arabidopsis thaliana AT3g01400/T13O15_4 mRNA, complete cds", EMBL Database, Acaoccion No. AY125543, Jul. 25, 2002.

"Arabidopsis thaliana clone 34582 mRNA, complete sequence", EMBL Database, Accession No. AY087360, Jun. 14, 2002.

"Arabidopsis thaliana genomic DNA, chromosome 5, P1 clone:MDH9", EMBL Database, Accession No. AB016888, Aug. 24, 1998.

"Arabidopsis thaliana mRNA for arm repeat containing protein, complete cds, clone: RAFL22-04-A03.", EMBL Database, Accession No. AK175585, Sep. 9, 2004.

"Arabidopsis thaliana DNA chromosome 3, BAC clone F28P10", EMBL Database, Accession No. AL049655, Apr. 20, 1999.

"Arabidopsis thaliana unknown protein (At3g54850) mRNA, complete cds.", EMBL Database, Accession No. AY096530, May 7, 2002.

"Arabidopsis thaliana At4g16490 mRNA for unknown protein, complete cds, clone RAFL21-08-B04,", EMBL Database, Accession No. AK118730, Dec. 13, 2002.

González-Lamothe, R., et al., "The U-Box Protein CMPG1 Is Required for Efficient Activation of Defense Mechanisms Triggered by Multiple Resistance Genes in Tobacco and Tomato", The Plant Cell, 2006, vol. 18, pp. 1067-1083.

Yang, C.-W., et al., "The E3 Ubiquitin Ligase Activity of Arabidopsis Plant U-Box17 and Its Functional Tobacco Homolog ACRE276 Are Required for Cell Death and Defense", The Plant Cell, 2006, vol. 18, pp. 1084-1098.

Fourgoux-Nicol, A., et al., "Isolation of Rapeseed Genes Expressed Early and Specifically During Development of the Male Gametophyte", Plant Molecular Biology, vol. 40, (1999), pp. 857-872.

Guo, H. H., et al., "Protein Tolerance to Random Amino Acid Change", PNAS, vol. 101, No. 25, (2004), pp. 9205-9210.

Keskin, O., et al., "A New, Structurally Nonredundant, Diverse Data Set of Protein-Protein Interfaces and its Implications", Protein Science, vol. 13, (2004), pp. 1043-1055.

\* cited by examiner

Figure 1A

HvARM: (SEQ ID NO. 1):

atgcaaatggctctgctagcaaggctttctcttgcaagttctgaaggaagagagtctagtttgg
aagaaagacatgctggttctgatgaacaaacttcagaacaatcaacgaaggaagcatttcaagc
atctcattttgacagtgattcacaggttcgtctaggcagatcttcagttaatgataatcttcct
aatacccgtcagcttgacgaggagtgtgacatcaacgatgggatgatacgagttccaggtgata
ggacaaattatagtagtgatgcgtctggagaggttgctgaccgtgggctttctatctcttctgc
ccctcaaagggaaaatgtaatcctgccaagattgggtcatgtctgcatggagggaccatttgtt
cagcggcaaacatctgacaagggattcccgagaataatttcgtcgttatccatggatgcccggg
atgatttctctgccatcgagaatcaggtacgcgagctaatcaatgatttgggaagtgattccat
agaaggtcagagatcagcaacatcagagattcgccttctagctaagcacaacatggagaacagg
attgccattgctaattgtggggctataaacttgctggttggccttcttcattcaccgatgcca
aaatccaagaaaatgcagtgacagcccttaatttgtcactcagtgatatcaataagattgc
catcgtgaatgcagatgctattgatcctctcatccatgtcctggaaacagggaaccctgaagct
aaagagaattcagcagctactttgttcagtctctcaattattgaagaaaacagagtgaggatag
ggcgatctggtgctgtaaagcctctcgtggacttgctgggaaatggggagcccacgaggaagaa
agatgcggttactgcattgtttaatttatccatacttcatgagaacaagggtcgaattgtgcaa
gctgatgcattgaagcacctagttgagcttatggaccctgctgctggaatggtcgataaagctg
tagctgtcttggcaaatcttgctacgataccagaaggaaggactgcgattgggcaggcgcgtgg
tattccggcccttgttgaagttgtcgaactgggtcagcgaaagcgaaggaaaatgctaccgcg
gcattgcttcagctatgcacaaacagcagcaggttttgcaacatagttcttcaagaggatgccg
tgcccctttagtcgcactgtcacagtcaggaacaccacgcgcaagagaaaaggcgcaggttct
cctcagctatttccgcagccaaagacatgggaactcgggaaggagatga

OS_1_XM_479734.1 (SEQ ID NO. 3):

atggaaaatttctccccgagaaccctgctcaatagtatcttgcgtatcactgtcttaacctccg
atggctctactgcaaggcccaagcccattcagaagtactgccaaaatgtgtgtgatatctcaag
cattgtgagccctctcatagaggatctatgtgagtctcctgaagagcaactcaatgaggtgtta
agggagcttggcactgctattaacagagcttcagggcttattgggaactggcaacagacaacca
gcaaaatatattttatatggcagattgaatcagtaatctcagatatccagggatgttctctaca
gctgtgccagcttgttaactctctattacctctctttgactggccgtgcatgcacatgtattgag
aaactccaagacataaattatgaaaacatgtttgatctggtaaaggagtcttcattggagctag
ttgagacggacacaacaagtcctgagaatctgtcgagactatctagttcattgagtttgtcaac
taacctggaattttacatggaagctgtttcccttgagaatctcagagcaagggcaatgcggagt
gagaaccgtgaagaaatggatctggctgacaagatgatcccccctggtcaactatatgcatgacc
accttctgagggaaacacaactgcttagcatcaatggggtgcccattcctgcagattttgctg
cccgctgtccctagagctgatgtcagatcctgttattgtagcatctggtcagacatatgagcgg
gtttatatcaagttatggcttgatgagggttttactatctgcccgaagacacgccaaagacttg
gtcactccaatttaattccaaattacaccgtgaaagctttgatagctaattggtgcgaatcaca
caacattaggcttcctgatcctatgaaatccttgaaattgaacttcccttggctgcgtctgct
ctccaggattcgagcaccacaggaagcagccctctacatcctactgtcgctgctaagggtaata
ttcctgggtccccggaagctgacctttatatgagaagcttgaatagagcatctcctccacacag
tgtagtccatcagaattctcatgcgcatgtgaaccgtgctggtcatgaagcctccattaagcaa
tcttcagaaaatgctaatggttctgcatcagatgtttcaaggttatctcttgcaggttctgaaa
caagagagtctagtctggaagaaagaaatgctggttctatcggtcaaacttcagaacagtcaat
tgaggaagcatttcaagcatctaatttggacagggattcacatgaccatgtgggtagttcttcg
gtgaatggtagccttccaaatagcggtcaacttgatgcagaatgtgacaatgggccaagcgaaa
ggacaaattacagtagtgatgcatctggagaagttacagatgggccttcagcatcttctgctcc
tcagagggagcatctaatcccttctagattggctgatgttcgtagtagaggccaatttgttcgg
cgaccatctgaaaggggtttccccagaataatatcttcctcatccatggatacacgagtgatc
tttccgccatcgagaatcaggtccgcaagttagttgatgatttaagaagtgattctgtagatgt
tcaaagatcagcgacatcagatatccgccttttagctaagcacaacatggagaacaggatcatc
attgcaaactgtggagctataaacttgctggttggtcttcttcattcgccagattccaaaaccc
aagagcatgccgtgacagcccttctgaatttgtcaatcaatgataataataagattgccattgc
aaatgctgatgctgttgaccccctcatccatgtccttgagactgggaaccctgaagccaaggag
aattcagcggctacattattcagtctctcgttattgaagaaaacaaagtgaggattggaagat
ccggtgccatcaaacctctcgtcgacctactaggaaatggggaccctcgaggaaagaaagatgc
agctactgcattgtttaatttatccatattacatgagaacaaggcgcgtattgtgcaggctgac
gctgtgaagtacctagttgaacttatggaccctgctgctggaatggttgacaaagctgtggctg
ttttggcaaaccttgctaccataccagaagggaggacagcaattggtcaagcgcgtggtattcc
agcccttgttgaagttgttgaactcggttcagcaaggggaaggaaaatgcggctgcagcattg
cttcagctatgtacaaacagcagcagattttgcagtatagttcttcaagagggtgctgtgcctc Figure 1B
ctctagttgcattgtcacagtcaggcacgccacgggcaagagagaaggcacaggctcttctcag
ctactttcgcagccaaaggcacgggaattcagcaaggagatga Os_2_XM_463544 (SEQ ID NO. 5):

atggcgtttgtttgtggtggtgggcaagtgatggattcagtgtcattgtcactactcgatagta
tttcaaatttccgggtgctgtcttcaagcaatgcctcgaaaacagagctagttaagaaatattg
ccaaacgatggatggcatccttgatcacttggaggtggccctaaacagagcttttcctcagatt
actccagatggtgaactaagtaaagttattcaggctgattcaattattgccaagatgcagatat
atgtattcgaattatgccaaattgtcaattctctcatgcagattgagtcaatgcatttggagga
tcttgaacacgatagctgtggaaaaatttcagatgtcattagggaggcttccagggctttagca
ggggaagttatgccaaattcagaggaatttggaaagattcaaactactttgagcttatccacaa
atcaggagttgctgatggaatatgttgcacttgttaaggttaaaacaaaaggtaatcatgaaga
taacaaagaaatggatgatattaacgatattgttgaattagtcaaccatatgcttgacaaacat
gtggaagaaaagcaaacacgtagcattaatggagtgaccattcctgctgattttgttgtcctc
tttcccttgaactaatgtcggatccagtgattgtggcatctggtcaaacgtatgagcatgtttt
tatcagaaaatggtttgatctgggatacaacatttgtccaaagacacgccaaatattgggacac
accaaattgattcctaacttcactgtcaaacagttgattgaaaattggtgtgaggtacatggta
taatgctaccagatcctgttaaactcttgagtttgtgcttccctgtttccctcaacatcacaga
tggaagtgcaagtgcagacaagtctggatcaccagaacactgccaattggtagctgcattgcat
ccaaaagcacagtgcgcatcggatgatagtcatcattataatttgatacatgaaaactctgatt
cagatgatagagtgtcatcatttggagacacagatgattctgaacctgattctttaagattatc
aacagaaactactgcagcaaacaatctctacttgatgaaaaaactgatcgttctgatggtctt
aagcaattgagagacaatggttttcaagtttctgatgaggaacagtatctcgaaaggaatggta
aaagtcatatcagcagccatcatcaacttgaagttgatggagagaatgtcagggtacaagcatc
aagtgacatcaatgcatctgaagttatgcaagatgatccggtcaccacatgttcaaaggtatca
gataaccctcctagattgggtggtgttcgttctcgaaatcagccaaactggtggagacagtcta
ataaaactattcctaggatcggattgtcatcttcgacagattcaaaaccagatttttctggcaa
tgatgctaaagtgcgtaatcttatcgaggaactgaaaagtgattctgctgaggtccaaaggtca
gcaacaggagagctccgcattctttctagacacagcttggagaatagaattgccatcgcaaact
gcggagcaatccccttcttggtgagtctacttcattctacagaccccagcacacaagaaaatgc
tgtgacaattctcctgaatttgtcattggatgacaataacaagattgccatagcaagtgctgag
gccattgagcctctcatcttcgttcttcaggtgggaaaccccgaagcgaaagccaactcagctg
caactttattcagcctctcagtcattgaagagaacaagatcaagattggacgttccggtgccat
cgaaccattagtagatttactgggagaaggtacccgcaagggaagaaggatgcagctactgca
ctcttcaatctgtcgatatttcatgaacacagacccgcattgttcaggctgggctgtcaacc
acctggtggagctgatggatccagctgctgggatggttgataaagctgttgctgtctggcaaa
ccttgcgactgtgcatgatggaaggaatgccattgctcaggcaggaggcatccgagtactggtt
gaggttgttgagctgggttctgcacgttcaaaggagaatgccgctgctgccctgctacaactct
gcacaaacagtaacaggttttgcaccctggttcttcaagaaggcgtcgtgccacctttggttgc
attgtcgcaatcaggcacagcccgtgcaagagagaaggctcaggttcttctaagctattttcgc
aaccagcgccacgtcagggttgggagagggcttagcttgctattagagttaaaacggaccacat
aa Os_3_AP003561 (SEQ ID NO. 7):

atggattcagtgtcattgtcactactcgatagtatttcaaatttccgggtgctgtcttcaagca
atgcctcgaaaacagagctagttaagaaatattgccaaacgatggatggcatccttgatcactt
ggaggtggccctaaacagagcttttcctcagattactccagatggtgaactaagtaaagtgctt
gaagaacttggcgctaccatcaatgaagcgactgagctagttggaggctggaatcaaatgatga
gcaagatttattttgttattcaggctgattcaattattgccaagatgcagatatatgtattcga
attatgccaaattgtcaattctctcatgcagattgagtcaatgcatttggaggatcttgaacac
gatagctgtggaaaaatttcagatgtcattagggaggcttccagggctttagcaggggaagtta
tgccaaattcagaggaatttggaaagattcaaactactttgagcttatccacaaatcaggagtt
gctgatggaatatgttgcacttgttaaggttaaaacaaaaggtaatcatgaagataacaaagaa
atggatgatattaacgatattgttgaattagtcaaccatatgcttgacaaacatgtggaagaaa
agcaaacacgtagcattaatggagtgaccattcctgctgattttgttgtcctctttcccttga
actaatgtcggatccagtgattgtggcatctggtcaaacgtatgagcatgttttatcagaaaa
tggtttgatctgggatacaacatttgtccaaagacacgccaaatattgggacacaccaaattga
ttcctaacttcactgtcaaacagttgattgaaaattggtgtgaggtacatggtataatgctacc
agatcctgttaaactcttgagtttgtgcttccctgtttccctcaacatcacagatggaagtgca
agtgcagacaagtctggatcaccagaacactgccaattggtagctgcattgcatccaaaagcac
agtgcgcatcggatgatagtcatcattataatttgatacatgaaaactctgattcagatgatag

Figure 1C agtgtcatcatttggagacacagatgattctgaacctgattctttaagattatcaacagaaact
actgcagcaaacaaatctctacttgatgaaaaaactgatcgttctgatggtcttaagcaattga
gagacaatggttttcaagtttctgatgaggaacagtatctcgaaaggaatggtaaaagtcatat
cagcagccatcatcaacttgaagttgatggagagaatgtcagggtacaagcatcaagtgacatc
aatgcatctgaagttatgcaagatgatccggtcaccacatgttcaaaggtatcagataaccctc
ctagattgggtggtgttcgttctcgaaatcagccaaactggtggagacagtctaataaaactat
tcctaggatcggattgtcatcttcgacagattcaaaaccagattttctggcaatgatgctaaa
gtgcgtaatcttatcgaggaactgaaaagtgattctgctgaggtccaaaggtcagcaacaggag
agctccgcattctttctagacacagcttggagaatagaattgccatcgcaaactgcggagcaat
cccttcttggtgagtctacttcattctacagaccccagcacacaagaaaatgctgtgacaatt
ctcctgaatttgtcattggatgacaataacaagattgccatagcaagtgctgaggccattgagc
ctctcatcttcgttcttcaggtgggaaacccgaagcgaaagccaactcagctgcaactttatt
cagcctctcagtcattgaagagaacaagatcaagattggacgttccggtgccatcgaaccatta
gtagatttactgggagaaggtaccccgcaagggaagaaggatgcagctactgcactcttcaatc
tgtcgatatttcatgaacacaagaccgcattgttcaggctggggctgtcaaccacctggtgga
gctgatggatccagctgctgggatggttgataaagctgttgctgttctggcaaaccttgcgact
gtgcatgatggaaggaatgccattgctcaggcaggaggcatccgagtactggttgaggttgttg
agctgggttctgcacgttcaaaggagaatgccgctgctgccctgctacaactctgcacaaacag
taacaggttttgcaccctggttcttcaagaaggcgtcgtgccacctttggttgcattgtcgcaa
tcaggcacagcccgtgcaagagagaaggctcaggttcttctaagctatttttcgcaaccagcgcc
acgtcagggttgggagagggtaa Os_4_XM_506432 (SEQ ID NO. 9):

atggtgtcgctagccggctcccagatcccgtcgccggggcagagtccgtgcgcggcggcgcggt
cgcagcgccgcggcgcggggtactccatgcggaccatccggtcggcgctgctgcagccggactc
ctgcccgggctcgccgcatgtggcggccgcgtacgacgcggcggggcggactcggacatggag
aacttgacggactccgtgattgatttccatctcagcgagctggcggccaccgcggggcccgcgc
accccgcggcggtggccaagtcgtcgtcggccaacgcggcggccacggagatgctcgagctctc
gcgggacttcagtgactactcgagcttcaactcggatatctccggcgagctcgagcggctcgcg
gcggcggcggcggcggtggtgacgcccagatccgacgcgccgcaggtgggcgccgtggatctga
atgagcttgagtcgatggatctgtccgtcgaggcggcgccgctggagcgcgtggagccgttcgt
gctggcgtgcgtgcgggcgctgggccgcgacgccgcagacgcgcggcgcaccgcggcggcg
aggataaggctgctggcgaagcacaggtcggacatccgcgagctgatcggcgtgtccggcgcca
tcccggcgctggtgccgctgctgcggagcaccgaccccggtggcgcaggagagcgcggtgacggc
gctgctcaacctctcgctcgaggagcggaaccggtcggccatcacggcggcggggggccatcaag
ccgctcgtgtacgcgctgcggacgggcaccgcgtcggccaagcagaacgccgcgtgcgcgctgc
tcagcctctcgggcatcgaggagaaccgcgccaccatcggcgcgtgcggcgccatccctcccct
cgtcgcgctgctctccgcgggctccacccgcggcaagaaggacgcgctcaccacgctctaccgg
ctctgctcggcgcgccggaacaaggagcgcgcggtcagcgccggcgccgtcgtgccgctcatcc
acctcgtcggcgagcgtggcagcgggacgtcggagaaggcaatggtggtcctcgccagcctcgc
gggcatcgtcgagggccgcgacgccgtggtggaggctggcgggataccggcgcttgtcgagacc
atcgaggacggcccggcgagggagagggagttcgccgtggtggcgctgctgcagctctgctccg
agtgccccgcaaccgcgcgcttcttgtccgtgagggcgccatcccaccgcttgtcgcgctctc
gcagtccggctctgcccgtgccaagcacaaggctgaaactttgcttgggtatctccgcgagcaa
cggcaaggaggtggtggctgcagggttgaacccgtggcagcttcgagcttggccaggtaa

NT_1_AY219234 (SEQ ID NO. 11):

atggagatatcattgttaaaagtgcttctcaacaatatctcctgttttcccatttatcatcaa
gtgatcacataagtggtgaactggttcgtagatattattgtaagattgaggatatactgaagct
tgtaaagccgattcttgacgccatcgttgatgttgaagctgcttctggtgagctgcttctgaaa
gcgtttgctgggctggctcaatgtgttgatgaactgagggagctattcgaaaccttggaaccgc
tgtgcagtaaagtttatttttgtcctgcaagctgaaccattgattgggaaaattcgatcatgtag
cctggaaatacttgagcttcttaaatcttctcataaaagccttccagctgatgtaactttgaca
actctcgagctctatatactgaaaattaagtatgtagattatgaaatgatatcagtgacaatca
caaaggttattaaagctcaagtggaaggcttgggaaccagctcagatagctttgccaaaattgc
tgattgcctaagcttgaactcaaaccaagagcttttgattgagcttgtggcccttgaaaaattg
aaagagaatgctgaacaagctgaaagagtgaagttgttgaatatattgagcaaatgataactc
ttgtttctcatatgcacgattgctttgttactacaaaacagtcccagagttgtaccgctgtgcc
aatacctcctgattttgctgtcctctttcacttgagttgatgactgaccctgtaattgtcgct
tctggtcaaacctatgagagggcttttattaggagatggattgatcttggcctcactgtttgcc
ccaaaacacggcaaactctgggacatacaaatctcattcctaattacactgttaaggcactgat

Figure 1D

```
cgcaaactggtgcgaaataaacaatgtaaagctgcctgatcccatgaagtctttgagcttgaac
cagccatctttgtcaccagactccacgcaatcttcaggttctccgagaaagagtttgatttcat
caactgtaagccaaagagaagaatcatctccatctcatcccgttcctcttcagaggaatcttt
acctggagttggtggtaatattcttgcttttgatgttgaaaggatgcgtattaagagtgaagac
cggatggcccactccggagagataagttcacatggtcatagtacattagtagctgatgaccagt
tccctctgggtcataatcgaacaacctcggcacctagcacgctttctaattcaaacttttcccc
ggtaattcctggtgatggaaacaagttgtcagaagattcttctgttgcttcaggggatgttggg
ttggattccaagcctgctgcttctgtccttccaaaggagccagaatttccatatacaccagaga
tgagacctcgtaatcaactgatctggcgcagaccaaccgagaggtttccaagaatagtttcttc
cgctacagttgaaagaagggctgatctttcagaagttgaggagcaagtaaaaaagttgattgag
gagttgaagagcacttcccttgatatgcagagaaatgctacagctgaactccggttacttgcca
agcataatatggataaccgtatggtaattgcaaattgtggcgctatcagctcgttggttaacct
acttcactcaaaagacatgaaagtacaggaagatgctgttactgcacttctcaacttgtcaatt
aatgacaacaacaagtgtgccattgcaaatgctgatgcaatcgaacctctgattcatgtcctcc
aaacagggagcgccgaggccaaagaaaattctgctgctactcttttagcctttccgtgatgga
ggaaaacaagatgaagattgggaggtctggagcaatcaaacctcttgttgatttactgggaaat
ggaactccaaggggcaagaaagatgcagcgacagctttatttaacttgtcaatacttcatgaga
acaagtctcgtataatacaggctggtgcggtaaagtatctcgtagagttgatggaccctgctac
tgggatggttgacaaggctgttgcagttttgtccaaccttgctaccattcccgagggacgagca
gaaatcggtcaggaaggagggattcctcttcttgttgaggttgttgagctgggctccgcaaggg
gtaaggagaatgcagcagctgctctcttgcaactatgcactaacagtagcaggttctgcaacat
ggttctccaggaaggagctgtacctccattagtggcattgtcacagtccggcacccaagagca
agagaaaaggctcaacaactacttagctacttccgaaatcaacgccatggtaatgcaggaagag
gttga
```

At_1_NM_127878 (SEQ ID NO. 13):

```
atggaagttcttctcagaagtatctcgtcgtttctaaatctgtcatcttctaaacatattgatt
tagacccgtttgagaagtactataagagagttgaagagttattgagagtgttgaagcctatagc
agatgttgttgttacctctgattttgttttgatgagaaacttggtaaagcatttgaagaattg
actcaggatgttgatcaatccattgatcttttcaggagttggcaagctttctctagtaaagtct
atttcgttcttcaaattgaatctttgctaccaaagatgcgggacaccattgtggatactttca
gtttctcatgtcttctaagaaccatctacctgatgagctaagcccagcttctcttgagcaatgt
ctagagaagattaagcatcttagttatgaagaaatatcttctgtcattgacggtgctttgaggg
atcagagagatggtgttggacctagccctgagatcttggtgaaaattggagagagaacactggtct
tagatcaaaccaggagattctgattgaagctgttgctctagagaggcagaaagagatggctgag
cagtctgagaataatgcagaagtcgagttccttgaccaactgattgttattgtaaaccgcatgc
atgaacgtcttcttctgatcaaacagactcagacttctagtgtcgccattcttgccgacttctt
ttgccctctgtcacttgaagtaatgactgatccagtgattgtgtcatcaggacaaacatatgaa
aaggcgtttatcaagagatggattgatttgggtttaaaagtgtgtcccaagactcgacagaccc
tgactcacactactctaatacccaattacaccgtgaaggccttaatcgctaactggtgtgagac
aaacgatgtcaagctgcctgatcccaataaatcaacaagtttaaatgagctttctcctcttta
tcatgtacagactccattcctagcacgggtgctgatgtttctgctcgtaaagttagcaacaagt
cacatgattgggatgcttcttcaagtgaaaccggtaagccctcgttctcaagccgagcaactga
aagagaaggtgcttctccttcacgtcctgcttctgccttgggtgcttcttcaccgggtatatct
ggaaatggttacggtttggacgccaggagggatcactaaatgattttgaagatagatcaaacg
attctcgagaactgaggacagatgcacctggtaggtcatctgtatcttcaactacacgaggctc
agtagaaaatggacaaacatctgagaaccaccatcataggtccccttctgctactagcactgtt
tccaatgaggagtttccaagggcagatgcgaatgagaattcagaagaatcagctcatgctacac
cttacagcagtgatgcttcaggagaaattagatcagggctcttgctgcaaccacttcagcagc
tactcgccgagatttgtctgatttttccccaaaattcatggatagacgtacccgtggtcaattt
tggcgacgtccatcagagagactcggttcaaggattgtttcagcgccttcgaatgagacaagac
gtgatctttctgaggtcgaaactcaagttaagaagttggtggaggagttgaaaagcagctcatt
ggatactcagagacaagcaaccgcagaactaaggttgctagccaagcacaacatggataatcgg
atagtcattgggaactctggagcaatcgtcttattggtggaactactttactcaactgactcag
ctacacaggaaaacgctgttaccgcacttctcaacttatctatcaatgacaacaacaaaaagc
aattgctgatgctggtgcaattgagccgctcattcacgtgcttgaaaatgggagctctgaagcc
aaggagaattcagctgctactctcttcagcctctctgtaataagaagaaacaagattaagattg
gtcagtcgggtgcaatcgggcctcttgtagatcttctcggtaacggtaccctcggggtaagaa
agacgctgctactgccttgtttaatctatcgatacatcaagaaaacaaggcgatgatcgtgcaa
tcaggtgctgtgagatatcttattgatctgatggacccagcagctgggatggtggataaagcag
ttgctgtttttggcaaatctagctacaattccggaaggaagaaacgcgattggtcaagaaggcgg
aatccctcttcttgttgaagtcgttgagttgggttcagctagagggaaagaaaacgcagcagca
```

Figure 1E

```
gctcttcttcaactttcaaccaacagtggtcggttctgcaacatggttcttcaagaaggcgccg
ttcctccactcgtcgctctctcacagtctggtactcctagagctagagaaaaggtacaaacttt
ataa
```

At_2_AC004401 (SEQ ID NO. 15):

```
atgattttgcggttttggcgggaaaacattattttgcggttttggcggaaaatccatgattttg
cggttttgaaactcattcagatgtatcatccagatgatccatccaaatacttgttaaattataa
aaaacaaacatcatttttcatctgcatttggatgaatcatttggatgaaaaacaaacaaggtct
gagtctgatttcacagtttccaaaagagatataagaagggtggaaatggaagttcttctcagaa
gtatctcgtcgtttctaaatctgtcatcttctaaacatattgatttagacccgtttgagaagta
ctataagagagttgaagagttattgagagtgttgaagcctatagcagatgttgttgttacctct
gattttgttttgatgagaaacttggtaaagcatttgaagaattgactcaggatgttgatcaat
ccattgatcttttcaggagttggcaagctttctctagtaaagtctatttcgttcttcaaattga
atctttgctaccaaagatgcgggacaccattgtggatacttttcagtttctcatgtcttctaag
aaccatctacctgatgagctaagcccagcttctcttgagcaatgtctagagaagattaagcatc
ttagttatgaagaaatatcttctgtcattgacggtgctttgagggatcagagagatggtgttgg
acctagccctgagatcttggtgaaaattggagagaacactggtcttagatcaaaccaggagatt
ctgattgaagctgttgctctagagaggcagaaagagatggctgagcagtctgagaataatgcag
aagtcgagttccttgaccaactgattgttattgtaaaccgcatgcatgaacgtcttcttctgat
caaacagactcagacttctagtgtcgccattcttgccgacttcttttgccctctgtcacttgaa
gtaatgactgatccagtgattgtgtcatcaggacaaacatatgaaaaggcgtttatcaagagat
ggattgatttgggtttaaaagtgtgtcccaagactcgacagaccctgactcacactactctaat
acccaattacaccgtgaaggccttaatcgctaactggtgtgagacaaacgatgtcaagctgcct
gatcccaataaatcaacaagtttaaatgagctttctcctctttttatcatgtacagactccattc
ctagcacgggtgctgatgtttctgctcgtaaagttagcaacaagtcacatgattgggatgcttc
ttcaagtgaaaccggtaagccctcgttctcaagccgagcaactgaaagagaaggtgcttctcct
tcacgtcctgcttctgccttgggtgcttcttcaccgggtatatctggaaatggttacggtttgg
acgccaggaggggatcactaaatgattttgaagatagatcaaacgattctcgagaactgaggac
agatgcacctggtaggtcatctgtatcttcaactacacgaggctcagtagaaaatggacaaaca
tctgagaaccaccatcataggtccccttctgctactagcactgtttccaatgaggagtttccaa
gggcagatgcgaatgagaattcagaagaatcagctcatgcacccttacagcagtgatgcttc
aggagaaattagatcagggcctcttgctgcaaccactcagcagctactcgccgagatttgtct
gattttccccaaaattcatggatagacgtacccgtggtcaattttggcgacgtccatcagaga
gactcggttcaaggattgtttcagcgccttcgaatgagacaagacgtgatctttctgaggtcga
aactcaagttaagaagttggtggaggagttgaaaagcagctcattggatactcagagacaagca
accgcagaactaaggttgctagccaagcacaacatggataatcggatagtcattgggaactctg
gagcaatcgtcttattggtggaactactttactcaactgactcagctacacaggaaaacgctgt
taccgcacttctcaacttatctatcaatgacaacaacaaaaagcaattgctgatgctggtgca
attgagccgctcattcacgtgcttgaaaatgggagctctgaagccaaggagaattcagctgcta
ctctcttcagcctctctgtaatagaagaaaacaagattaagattggtcagtcgggtgcaatcgg
gcctcttgtagatcttctcggtaacggtacccctcggggtaagaaagacgctgctactgccttg
tttaatctatcgatacatcaagaaaacaaggcgatgatcgtgcaatcaggtgctgtgagatatc
ttattgatctgatggaccccagcagctgggatggtggataaagcagttgctgttttggcaaatct
agctacaattccggaaggaagaaacgcgattggtcaagaaggcggaatccctcttcttgttgaa
gtcgttgagttgggttcagctagagggaaagaaaacgcagcagcagctcttcttcaactttcaa
ccaacagtggtcggttctgcaacatggttcttcaagaaggcgccgttcctccactcgtcgctct
ctcacagtctggtactcctagagctagagaaaagaaaccaacggcatggaaacgctgggcgtgg
ctgatgatggatgatgatgatgatgatgttgatgatgcacagattctggtctctcagtgcc
tatttttatgttttgtcttgtga
```

At_3_BT020206 (At5g67340) (SEQ ID NO. 17):

```
atgatggtacatatggaggtgtcttggttaagagttcttctagataacatctcctcctatctaa
gtttatcatctatggacgattatctcaaaccctgctcataagtactacaccagaggagaaga
tataggaaagcttatcaagcctgttcttgagaacctcattgactctgacgcggctcctagcgag
ttgcttaacaatggttttgaagaattagctcaatacgttgatgaactagagaacagtttcaga
gttggcaaccttcttcaactagaatcttttatgttcttcgaattgaatcattagcatcaaagtt
acgagaatccagtttggaagtcttttcagctcctcaaacactgcgaacaacatttgcctgctgac
ttgatctcaccttcttttgaggagtgcattgaattggtgaagttagtggcaagagacgaaatat
cgtatactattgatcaagctctaaaagatcaaagaaaggtgttggacctacttcagaggttct
ggtgaaaattgccgagagtactggtttaagatccaaccaggagattcttgttgaaggtgtggta
cttacaaacatgaaggaggatgctgagcttaccgataatgacaccgaagccgagtatctagacg
gattgatctctctaacaacacaaatgcatgagtaccttagcgacataaagcaggctcagttacg
```

Figure 1F

```
ttgtccagtacgcgtaccttctgatttccgctgctctctatctcttgagcttatgactgatcca
gtcattgtagcatctggtcaaacattcgaacgggttttatccagaaatggatcgatatgggac
tcatggtttgtccaaagacaaggcaggctttatctcataccactttgacacctaatttcattgt
cagagcttttcttgcaagttggtgtgaaactaacaatgtctatcctcctgatccattggagttg
attcactcaagtgagccattcccctcttcttgttgaatcagtgagagcttcatcatcagagaatg
gccattcagaatctttagatgcagaggaactgcgtcaggtctttagtaggtctgcttcggcgcc
aggcattgtctctgaagtggtttgcaaaaccaaaagaaacaacaatgctgctgcagatagatca
ctgacacggagtaatacccttggaaatttccagaagagaggcattggcgtcaccccgggatca
tcccagcgaccgtaagagaaacaggaagcagttcaagtatcgaaaccgaggtgaagaaactcat
tgatgatctcaagagttcttcattggatacacagagagaggccacagctagaatcaggatacta
gcaagaaacagtacagacaatcgcattgtcattgcgcggtgcgaagcaatcccttcgttagtca
gtcttctttactcaacggatgagagaatccaagcagacgcagtgacttgcttactaaacttatc
catcaacgacaacaacaagtccctcatcgcggaaagtggagccatcgtaccgcttattcacgtt
ctcaaaacaggatacttagaagaagctaaagcaaactcagcagcaactctattcagcttgtcgg
tgatcgaagagtacaagacagagataggagaagcaggagctatagagccacttgttgacctctt
aggaagtggaagtctcagtgggaagaaagatgcagccacggctttattcaacctctcaatacac
catgagaacaaaacgaaagtaatcgaagctggagcagtgagatacttagttgaactgatggatc
ctgctttgggatggtggagaaagctgtggtggtgctagcgaatcttgcaacggttagagaagg
aaagattgcgataggcgaagaaggaggaataccggtattggtggaagttgtggagttaggttca
gcaagaggcaaagagaatgcaactgcagcactattgcagctttgtacgcatagcccgaaattct
gcaacaatgtcataagagaaggagtgattccacctcttgtggcacttactaaatcaggaacagc
tagaggcaaagagaaggcacagaatcttctgaagtactttaaagcacacagacaaagcaatcag
aggagaggctga
```

At_4_AB007645 (SEQ ID NO. 19):

```
atggaggtgtcttggttaagagttcttctagataacatctcctcctatctaagtttatcatcta
tggacgatttatcttcaaaccctgctcataagtactacaccagaggagaagatataggaaagct
tatcaagcctgttcttgagaaccttcattgactctgacgcggctcctagcgagttgcttaacaat
ggttttgaagaattagctcaatacgttgatgaacttagagaacagtttcagagttggcaacctc
tttcaactagaatcttttatgtcttcgaattgaatcattagcatcaaagttacgagaatccag
tttggaagtctttcagctcctcaaacactgcgaacaacatttgcctgctgacttgatctcacct
tcttttgaggagtgcattgaattggtgaagttagtggcaagagacgaaatatcgtatactattg
atcaagctctaaaagatcaaagaaaggtgttggacctacttcagaggttctggtgaaaattgc
cgagagtactggtttaagatccaaccaggagattcttgttgaaggtgtggtacttacaaacatg
aaggaggatgctgagcttaccgataatgacaccgaagccgagtatctagacggattgatctctc
taacaacacaaatgcatgagtaccttagcgacataaagcaggctcagttacgttgtccagtacg
cgtaccttctgatttccgctgctctctatctcttgagcttatgactgatccagtcattgtagca
tctggtcaaacattcgaacgggttttatccagaaatggatcgatatgggactcatggtttgtc
caaagacaaggcaggctttatctcataccactttgacacctaatttcattgtcagagcttttct
tgcaagttggtgtgaaactaacaatgtctatcctcctgatccattggagttgattcactcaagt
gagccattcccctcttcttgttgaatcagtgagagcttcatcatcagagaatggccattcagaat
ctttagatgcagaggaactgcgtcaggtctttagtaggtctgcttcggcgccaggcattgtctc
tgaagtggtttgcaaaaccaaaagaaacaacaatgctgctgcagatagatcactgacacggagt
aatacccttggaaatttccagaagagaggcattggcgtcaccccgggatcatcccagcgaccg
taagagaaacaggaagcagttcaagtatcgaaaccgaggtgaagaaactcattgatgatctcaa
gagttcttcattggatacacagagagaggccacagctagaatcaggatactagcaagaaacagt
acagacaatcgcattgtcattgcgcggtgcgaagcaatcccttcgttagtcagtcttctttact
caacggatgagagaatccaagcagacgcagtgacttgcttactaaacttatccatcaacgacaa
caacaagtccctcatcgcggaaagtggagccatcgtaccgcttattcacgttctcaaaacagga
tacttagaagaagctaaagcaaactcagcagcaactctattcagcttgtcggtgatcgaagagt
acaagacagagataggagaagcaggagctatagagccacttgttgacctcttaggaagtggaag
tctcagtgggaagaaagatgcagccacggctttattcaacctctcaatacaccatgagaacaaa
acgaaagtaatcgaagctggagcagtgagatacttagttgaactgatggatcctgctttggga
tggtggagaaagctgtggtggtgctagcgaatcttgcaacggttagagaaggaaagattgcgat
aggcgaagaaggaggaataccggtattggtggaagttgtggagttaggttcagcaagaggcaaa
gagaatgcaactgcagcactattgcagctttgtacgcatagcccgaaattctgcaacaatgtca
taagagaaggagtgattccacctcttgtggcacttactaaatcaggaacagctagaggcaaaga
gaaggttctttttttgtttcctcttctttgtttggtaaatgtctcatga
```

At_5_NM_115336 (At3g54790) (SEQ ID NO. 21):

```
atggatcctgttcctgttcgatgtcttcttaacagtatatctcggtatcttcatctggttgcgt
gccagactataagatttaatcctattcaaacatgtattggaaatatggttctcttgttgaagct
```

Figure 1G cttgaaaccgttgctcgatgaagttgttgattgcaagataccttctgatgactgtttatataaa
ggatgtgaagaccttgattctgttgttaaccaggctcgggagttcttagaggactggtcaccaa
agttgagcaagttgtttggtgtgtttcaatgcgaggttttgttgggaaaggtccagacttgttc
gttggagattagtcgcatacttcttcagttatcacagtcaagtccggttacttcaagcgtacaa
agtgttgagcgctgcgtgcaggagactgagagttttaagcaagagggacattaatggaactca
tggagaatgctttacggaatcagaaagatgatattacctctttggataacaatcatctggaaag
cataattcaaatgcttggattgatatcaaaccaagatctcttaaaggaaagcattactgtggag
aaagagaggataagatcccaggccagtaagtcagaagaagatatggaacaaaccgaacagttga
tagaactcgtcttgtgcatccgtgaacacatgcttaaaactgagtttcttgaagtggctaaagg
tatctcgataccccgtatttccggtgtcctttgtcaacagaactcatgctggatccggtaata
gtagcttcaggacagacatttgacagaacatccattaagaaatggcttgataacgggttagctg
tttgtccaaggacgcggcaggtgctgactcatcaagaactcattcccaattacacggttaaggc
tatgatagcgagttggttggaggcaaacaggatcaaccttgctactaactcttgtcatcagtat
gatggtggtgatgcttcatccatggctaataatatgggttctcaagactttaaccgcaccgaga
gttttcgttttctttacggagcagcagtttaacctcaagatcatctcttgaaactggaaatgg
gtttgagaaactgaagattaacgtgtctgccagtttatgcggggaatctcaaagcaaggatctt
gaaatattcgagcttttgtctccggggcagtcttacactcacagcaggagtgaatcagtttgca
gtgttgtctcgtctgttgattatgtaccttcggtgacacatgagacagaaagtatactagggaa
tcaccaaagctccagtgagatgtctcccaagaaaaacttagaaagttcaaacaatgtaaatcat
gagcatagcgcagcaaagacttatgagtgttctgtacatgatttagatgattcaggaacaatga
cgacttcacataccataaaaattggtagaagatcttaaaagcgggtctaacaaagtgaagactgc
tgctgcagctgaaatacgtcatctcaccattaacagcattgaaaatcgtgttcacatcgggcgt
tgtggtgctattactccactgctgtcacttttatactcagaagaaaagctaactcaagaacacg
cagtcacggctcttttgaatctttccatcagtgaactaaacaaagccatgattgtggaagtcgg
ggcgatagaaccgcttgttcatgttttgaacacaggaaatgacagagccaaagagaattcagca
gcatcattgttcagtctgtctgttctgcaggtcaacagagaacgaataggccagtctaacgcag
cgatacaagctctggtgaatcttcttggtaaaggaacatttagaggaaagaaagacgccgcctc
tgctttgttcaatctatcgattactcatgataacaaggcccgtatcgtgcaagctaaggcggtt
aagtaccttgtggagctgttagacccagatttagagatggttgataaagcagttgctcttcttg
caaatctttctgcagttggagaagggcgtcaagccatcgtgagggaaggtgggattccattact
tgttgaaactgttgacttaggatctcagagagggaaagagaatgcagcttctgtgctgcttcag
ttgtgtctgaacagtcccaagttttgcactctggtcttgcaagaaggcgccatacctccgcttg
ttgccttgtctcagtctggtacacagagagcaaaagagaaggcacagcaacttcttagccactt
ccgaaaccagagagatgcaaggatgaagaaaggtagatcatga At_6_AK118613 (SEQ ID NO. 23):

atggatcctgttcctgttcgatgtcttcttaacagtatatctcggtatcttcatctggttgcgt
gccagactataagatttaatcctattcaaacatgtattggaaatatggttctcttgttgaagct
cttgaaaccgttgctcgatgaagttgttgattgcaagataccttctgatgactgtttatataaa
ggacgtgaagaccttgattctgttgttaaccaggctcgggagttcttagaggactggtcaccaa
agttgagcaagttgtttggtgtgtttcaatgcgaggttttgttgggaaaggtccagacttgttc
gttggagattagtcgcatacttcttcagttatcacagtcaagtccggttacttcaagcgtacaa
agtgttgagcgctgcgtgcaggagactgagagttttaagcaagagggacattaatggaactca
tggagaatgctttacggaatcagaaagatgatattacctctttggataacaatcatctggaaag
cataattcaaatgcttggattgatatcaaaccaagatctcttaaaggaaagcattactgtggag
aaagagaggataagatcccaggccagtaagtcagaagaagatatggaacaaaccgaacagttga
tagaactcgtcttgtgcatccgtgaacacatgcttaaaactgagtttcttgaagtggctaaagg
tatctcgataccccgtatttccggtgtcctttgtcaacagaactcatgctggatccggtaata
gtagcttcaggacagacatttgacagaacatccattaagaaatggcttgataacgggttagctg
tttgtccaaggacgcggcaggtgctgactcatcaagaactcattcccaattacacggttaaggc
tatgatagcgagttggttggaggcaaacaggatcaaccttgctactaactcttgtcatcagtat
gatggtggtgatgcttcatccatggctaataatatgggttctcaagactttaaccgcaccgaga
gttttcgttttctttacggagcagcagtttaacctcaagatcatctcttgaaactggaaatgg
gtttgagaaactgaagattaacgtgtctgccagtttatgcggggaatctcaaagcaaggatctt
gaaatattcgagcttttgtctccggggcagtcttacactcacagcaggagtgaatcagtttgca
gtgttgtctcgtctgttgattatgtaccttcggtgacacatgagacagaaagtatactagggaa
tcaccaaagctccagtgagatgtctcccaagaaaaacttagaaagttcaaacaatgtaaatcat
gagcatagcgcagcaaagacttatgagtgttctgtacatgatttagatgattcaggaacaatga
cgacttcacataccataaaaattggtagaagatcttaaaagcgggtctaacaaagtgaagactgc
tgctgcagctgaaatacgtcatctcaccattaacagcattgaaaatcgtgttcacatcgggcgt
tgtggtgctattactccactgctgtcacttttatactcagaagaaaagctaactcaagaacacg
cagtcacggctcttttgaatctttccatcagtgaactaaacaaagccatgattgtggaagtcgg
ggcggtagaaccgcttgttcatgttttgaacacaggaaatgacagagccaaagagaattcagca

Figure 1H

```
gcatcattgttcagtctgtctgttctgcaggtcaacagagaacgaataggccagtctaacgcag
cgatacaagctctggtgaatcttcttggtaaaggaacatttagaggaaagaaagacgccgcctc
tgctttgttcaatctatcgattactcatgataacaaggcccgtatcgtgcaagctaaggcggtt
aagtaccttgtggagctgttagacccagatttagagatggttgataaagcagttgctcttcttg
caaatctttctgcagttggagaagggcgtcaagccatcgtgagggaaggtgggattccattact
tgttgaaactgttgacttaggatctcagagagggaaagagaatgcagcttctgtgctgcttcag
ttgtgtctgaacagtcccaagttttgcactctggtcttgcaagaaggcgccatacctccgcttg
ttgccttgtctcagtctggtacacagagagcaaagagaaggcacagcaacttcttagccactt
ccgaaaccagagagatgcaaggatgaagaaaggtagatcatga
```

At_7_AL138650 (SEQ ID NO. 25):

```
atggttctcttgttgaagctcttgaaaccgttgctcgatgaagttgttgattgcaagatacctt
ctgatgactgtttatataaaggatgtgaagaccttgattctgttgttaaccaggctcgggagtt
cttagaggactggtcaccaaagttgagcaagttgtttggtgtgtttcaatgcgaggttttgttg
ggaaaggtccagacttgttcgttggagattagtcgcatacttcttcagttatcacagtcaagtc
cggttacttcaagcgtacaaagtgttgagcgctgcgtgcaggagactgagagttttaagcaaga
gggacattaatggaactcatggagaatgctttacggaatcagaagatgatattacctctttg
gataacaatcatctggaaagcataattcaaatgcttggattgatatcaaaccaagatctcttaa
aggaaagcattactgtggagaaagagaggataagatcccaggccagtaagtcagaagaagatat
ggaacaaaccgaacagttgatagaactcgtcttgtgcatccgtgaacacatgcttaaaactgag
tttcttgaagtggctaaaggtatctcgataccccccgtatttccggtgtcctttgtcaacagaac
tcatgctggatccggtaatagtagcttcaggacagacatttgacagaacatccattaagaaatg
gcttgataacgggttagctgtttgtccaaggacgcggcaggtgctgactcatcaagaactcatt
cccaattacacggttaaggctatgatagcgagttggttggaggcaaacaggatcaaccttgcta
ctaactcttgtcatcagtatgatggtggtgatgcttcatccatggctaataatatgggttctca
agactttaaccgcaccgagagttttcgttttctttacggagcagcagtttaacctcaagatca
tctcttgaaactggaaatgggtttgagaaactgaagattaacgtgtctgccagtttatgcgggg
aatctcaaagcaaggatcttgaaatattcgagcttttgtctccggggcagtcttacactcacag
caggagtgaatcagtttgcagtgttgtctcgtctgttgattatgtaccttcggtgacacatgag
acagaaagtatactagggaatcaccaaagctccagtgagatgtctcccaagaaaaacttagaaa
gttcaaacaatgtaaatcatgagcatagcgcagcaaagacttatgagtgttctgtacatgattt
agatgattcaggaacaatgacgacttcacatacataaaattggtagaagatcttaaaagcggg
tctaacaaagtgaagactgctgctgcagctgaaatacgtcatctcaccattaacagcattgaaa
atcgtgttcacatcgggcgttgtggtgctattactccactgctgtcacttttatactcagaaga
aaagctaactcaagaacacgcagtcacggctctttttgaatctttccatcagtgaactaaacaaa
gccatgattgtggaagtcggggcgatagaaccgcttgttcatgtttttgaacacaggaaatgaca
gagccaaagagaattcagcagcatcattgttcagtctgtctgttctgcaggtcaacagagaacg
aataggccagtctaacgcagcgatacaagctctggtgaatcttcttggtaaaggaacatttaga
ggaaagaaagacgccgcctctgctttgttcaatctatcgattactcatgataacaaggcccgta
tcgtgcaagctaaggcggttaagtaccttgtggagctgttagacccagatttagagatggttga
taaagcagttgctcttcttgcaaatctttctgcagttggagaagggcgtcaagccatcgtgagg
gaaggtgggattccattacttgttgaaactgttgacttaggatctcagagagggaaagagaatg
cagcttctgtgctgcttcagttgtgtctgaacagtcccaagttttgcactctggtcttgcaaga
aggcgccatacctccgcttgttgccttgtctcagtctggtacacagagagcaaagagaaggta
tactatattcttcttctgcggttacacgaaaacacaccaagttcagtttcttattgatcgag
atatctga
```

At_8_AL133314 (SEQ ID NO. 27):

```
atggaggaagagaaagcttctgctgcacagagcttaatcgatgtagttaacgagattgctgcga
tttctgattatcgtataacagtgaagaagctttgttataatctagcgaggagattaaagctgct
tgttcctatgtttgaggaaattagagaaagtaacgaaccgatcagcgaagatacgttgaagact
ttgatgaatttgaaggaagctatgtgttcagcgaaggattatctcaaattttgtagccaaggga
gcaagatttatctggtgatggagagggaacaagtgacaagtaaattgatggaggtgtctgttaa
gttagaacaatcttaagccagattccatatggaacactcgatatatcggatgaagttagagaa
caggttgagctggttcttagtcagtttcggcgagctaaaggaagagtagatgtatcagatgatg
agctatatgaagatcttcagtcgctttgcaacaaaagtagtgatgtagatgcttatcagcctgt
gctagagcgggttgcgaagaagttacatttgatggagattcctgacctagctcaagaatcagtg
gctctgcatgaaatggttgcttcaagcggtggagatgttggtgaaaatattgaggagatggcaa
tggtattaaagatgattaaggattttgtgcagacggaggatgataatggcgaggagcagaaagt
aggagttaactctagaagcaatggacagacttctacggcagcgagtcagaagatacctgtgatt
cctgatgattttcgctgtccgatttcgctggaaatgatgagagatccagttattgtttcatcag
ggcagacatacgaacgcacatgtattgagaaatggatagaaggtggacactcgacatgtccaaa
```

Figure 1I aacacagcaggcgctaacaagcacaaccctcacaccaaactatgttctccgtagtctcatagct
cagtggtgcgaggccaacgatattgagcctccaaagcctccgagcagtttaagacccagaaaag
tatcgtccttctcatctcccgcagaagcgaacaagattgaagatcttatgtggagacttgcgta
cggaaaccccgaggaccaacgatctgcagctggggaaatccgccttcttgcaaaacgaaatgca
gacaaccgcgtggccatagccgaagctggagccatacctcttctcgtaggtctcctctcaactc
ctgattctcgtattcaagaacattcggtaacagctcttctaaacctctccatatgtgagaacaa
caaaggagccattgtttcagctggagctattcctggtatagttcaagtgcttaagaaaggaagc
atggaggccagagagagaatgcggcggctacacttttcagtctatcagtgatcgatgaaaataaag
tgactatcggtgccttaggagcaattccgccactcgttgtattacttaatgaaggtacacaaag
aggcaagaaagatgctgctactgcactctttaacctctgtatataccaaggaaacaaaggaaaa
gctatacgtgcaggagtgattcccacgttgactagactcttgacagagcccggaagcggaatgg
tcgatgaggcactcgcgattttggcgattctctctagccaccccgaaggaaaagcaatcatagg
atcctctgatgcagtcccaagtttggttgagtttatcagaactggctcgcctagaaacagagaa
aacgcagctgctgttctagtccacctctgttctggagacccacaacatcttgtcgaagcgcaga
aactcggccttatgggtccattgatagatttagctggaaatgggacggatagagggaaacgaaa
agcagcgcagttgcttgaacgcatcagccgtctcgctgaacagcagaaggaaacggctgtgtca
caaccggaagaagaagctgaaccaacacatccagaatccaccacagaagctgcagatacttaa At_9_AC010870 (SEQ ID NO. 29):

atggagatggagaatcaccgccccggcagtttcacctacatgggccgcaaattcagcgatttaa
gtctcaacgatgactcctctgctttcagcgattgtaacagcgacagatccggcgaattccccac
tgcttcctccgagagccgtcgtctcctcctctcttgcgcctctgagaattccgatgatctcatc
aatcatctcgtgtcgcatcttgattcctcctattcgatcgatgagcagaagcaagctgctatgg
agatcaggctcttatccaagaacaaacctgagaatcggatcaaaatcgccaaggccggtgcgat
taagccgttgatttctctgatctcttcttcggatcttcagcttcaggagtatggtgtcactgca
atcttgaatctatctctctgcgacgagaacaaagagtcgattgcttcttccggtgcgattaagc
cgcttgtcagggctttgaaaatgggaacaccgactgctaaagagaacgctgcttgtgctctgct
ccgtctatcgcagatcgaggagaacaaagtcgccatcgggagatccggagcgattcctctgttg
gtgaaccttctagaaacaggcggattcagagcgaagaaggacgcgtcgacggctctgtactcgt
tgtgctcagctaaagagaacaaaatcagagccgtgcaatcgggaattatgaagccgcttgttga
attgatggcggatttcggatcaaacatggtggataaatcggcgtttgtgatgagtctgttaatg
tcggtgccggaatcgaaaccggcgattgtggaggaaggaggagttccggtgctggtggagatag
tagaggtgggaacacagagacagaaagagatggctgtgtcgatattgctacagctttgtgagga
gagtgttgtgtatagaacaatggtggctagagaaggagcgatacctccgctagtggctctgtcg
caggcaggaacaagtcgagctaagcaaaaggctgaggcgttgattgagcttctaaggcaaccaa
gatccattagtaatggtggtgctagatcatcgtcccaactctga At_10_AY125543 (At3g01400) (SEQ ID NO. 31):

atggagatggagaatcaccgccccggcagtttcacctacatgggccgcaaattcagcgatttaa
gtctcaacgatgactcctctgctttcagcgattgtaacagcgacagatccggcgaattccccac
tgcttcctccgagagccgtcgtctcctcctctcttgcgcctctgagaattccgatgatctcatc
aatcatctcgtgtcgcatcttgattcctcctattcgatcgatgagcagaagcaagctgctatgg
agatcaggctcttatccaagaacaaacctgagaatcggatcaaaatcgccaaggccggtgcgat
taagccgttgatttctctgatctcttcttcggatcttcagcttcaggagtatggtgtcactgca
atcttgaatctatctctctgcgacgagaacaaagagtcgattgcttcttccggtgcgattaagc
cgcttgtcagggctttgaaaatgggaacaccgactgctaaagagaacgctgcttgtgctctgct
ccgtctatcgcagatcgaggagaacaaagtcgccatcgggagatccggagcgattcctctgttg
gtgaaccttctagaaacaggcggattcagagcgaagaaggacgcgtcgacggctctgtactcgt
tgtgctcagctaaagagaacaaaatcagagccgtgcaatcgggaattatgaagccgcttgttga
attgatggcggatttcggatcaaacatggtggataaatcggcgtttgtgatgagtctgttaatg
tcggtgccggaatcgaaaccggcgattgtggaggaaggaggagttccggtgctggtggagatag
tagaggtgggaacacagagacagaaagagatggctgtgtcgatattgctacagctttgtgagga
gagtgttgtgtatagaacaatggtggctagagaaggagcgatacctccgctagtggctctgtcg
caggcaggaacaagtcgagctaagcaaaaggctgaggcgttgattgagcttctaaggcaactaa
gatccattagtaatggtggtgctagatcatcgtcccaactctga At_11_AY087360 (SEQ ID NO. 33):

atggagatggagaatcaccgccccggcagtttcacctacatgggccgcaaattcagcgatttaa
gtctcaacgatgactcctctgctttcagcgattgtaacagcgacagatccggcgaattccccac
tgcttcctccgagagccgtcgtctcctcctctcttgcgcctctgagaattccgatgatctcatc
aatcatctcgtgtcgcatcttgattcctcctattcgatcgatgagcagaagcaagctgctatgg

Figure 1J

```
agatcaggctcttatccaagaacaaacctgagaatcggatcaaaatcgccaaggccggtgcgat
taagccgttgatttctctgatctcttcttcggatcttcagcttcaggagtatggtgtcactgcw
atcttgaatctatctctctgcgacgagaacaaagagtcgattgcttcttccggtgcgattaagc
cgcttgtcagggctttgaaaatgggaacaccgactgctaaagataacgctgcttgtgctctgct
ccgtctatcgcagatcgaggagaacaaagtcgccatcgggagatccggagcgattcctctgttg
gtgaaccttctagaaacaggcggattcagagcgaagaaggacgcgtcgacggctctgtactcgt
tgtgctcagctaaagagaacaaaatcagagccgtgcaatcgggaattatgaagccgcttgttga
attgatggcggatttcggatcaaacatggtggataaatcggcgtttgtgatgagtctgttaatg
tcggtgccggaatcgaaccggcgattgtggaggaaggaggagttccggtgctggtggagatag
tagaggtgggaacacagagacagaaagagatggctgtgtcgatattgctacagctttgtgagga
gagtgttgtgtatagaacaatggtggctagagaaggagcgatacctccgctagtggctctgtcg
caggcaggaacaagtcgagctaagcaaaaggctgaggcgttgattgagcttctaaggcaaccaa
gatccattagtaatggtggtgctagatcatcgtcccaactctga
```

At_12_AB016888 (SEQ ID NO. 35):

```
atggatacagatgaagaagccacaggagatgcagagaaccgtgatgaagaagttaccgcagaag
aaccgattcacgatgaggttgtggatgcggtggagattcatgaggaagaagtgaaagaagatga
tgatgattgtgaaggattggtgagcgatatcgtatcgattgtcgagttttggatcagattaac
ggttatcgaagaacacaacaaaaagaatgttttaatctcgttagacgattgaagattcttattc
cattttttggatgagattcgaggttttgaatcaccaagttgcaagcatttttaaatcgtttgag
gaaagtgtttcttgctgccaagaaattattagaaacttgcagcaatggcagtaaaatctatatg
gcattggatggcgaaacaatgatgacgagatttcattcgatttacgaaaagttgaatcgtgttc
ttgttaaagctccttttgatgaattaatgatttctggtgatgcgaaagacgagattgattcatt
gtgtaaacaactgaaaaaagcaaaagaagaacagatacacaagacatagagctagcagtagac
atgatggtggtattctcaaaaaccgatcctcgaaacgcagatagcgcgataatagagaggctag
cgaaaaagcttgagctacaaacaattgatgatttaaagacagaaactatagccatacaaagctt
aatccaagacaaaggagggtttgaacatagagactaaacaacatatcattgagcttcttaacaag
ttcaagaagcttcaaggtcttgaagctaccgacattctctaccaacccgtcatcaataaagcaa
tcaccaagtcaacgtctctaatattacctcatgagttttgtgtcctataacactcgaaataat
gcttgacccggttatcatcgccactggacagacatatgagaaggagagtatacagaaatggttt
gacgcaggacataagacttgtcctaaaacaagacaggagttagatcatctctctcttgcaccta
acttcgctttaaagaacttgattatgcagtggtgtgagaagaacaatttcaagattccagagaa
agaagtaagtcctgactcacaaaatgagcagaaagatgaggtctctttgctggtggaagcgtta
tcgtcaagccaactggaagaacaacgaagatcagtgaagcagatgcgtttgctagccagagaaa
atcccgagaaccgcgttttaatagcgaatgcaggagcgattcctttgttagttcaactcctttc
ttaccctgattcaggaatccaagaaaacgcggtaacgacattgttgaatctatctatcgacgag
gtcaacaagaaactcatttcaaatgaaggagctattccaaacattattgaaatccttgaaaatg
gaaacagagaggcaagagagaactctgctgcagctttgtttagtttatcgatgctcgatgagaa
caaagtaactatcggattatcgaatgggataccgcctttagtcgatttactacaacatgggaca
ttaagagggaagaaagatgctctcactgcactctttaacttgtctcttaactcagctaataaag
gaagagctatcgatgctggtattgttcaacctttgcttaaccttcttaaagataaaaacttagg
gatgatcgatgaagcgctttcgattctgttgctgcttgcatcacaccctgaaggacgtcaagcc
attggacaactctccttcattgaaacacttgtggaattcatcagacaaggcaccccgaaaaaca
aagagtgtgcgacctcggtgctgcttgaactaggctctaacaactcgtcttttatcctcgcagc
gcttcaattcggagtttatgaatatctggtagaaataaccacctctggaacaaacagagctcag
agaaaagcaaatgctcttatacaactcataagcaaatctgaacaaatttag
```

At_13_AK175585 (SEQ ID NO. 37):

```
atggtcgatgtgatggatacagatgaagaagccacaggagatgcagagagccgtgatgaagaag
ttaccgcagaagaaccgattcacgatgaggttgtggatgcggtggagattcatgaggaagaagt
gaaagaagatgatgatgattgtgaaggattggtgagcgatatcgtatcgattgtcgagttttg
gatcagattaacggttatcgaagaacacaacaaaaagaatgttttaatctcgttagacgattga
agattcttattccattttttggatgagattcgaggttttgaatcaccaagttgcaagcatttttt
aaatcgtttgaggaaagtgtttcttgctgccaagaaattattagaaacttgcagcaatggcagt
aaaatctatatggcattggatggcgaaacaatgatgacgagatttcattcgatttacgaaaagt
tgaatcgtgttcttgttaaagctccttttgatgaattaatgatttctggtgatgcgaaagacga
gattgattcattgtgtaaacaactgaaaaaagcaaaagaagaacagatacacaagacatagag
ctagcagtagacatgatggtggtattctcaaaaaccgatcctcgaaacgcagatagcgcgataa
tagagaggctagcgaaaaagcttgagctacaaacaattgatgatttaaagacagaaactatagc
catacaaagcttaatccaagacaaaggagggtttgaacatagagactaaacaacatatcattgag
cttcttaacaagttcaagaagcttcaaggtcttgaagctaccgacattctctaccaacccgtca
tcaataaagcaatcaccaagtcaacgtctctaatattacctcatgagttttgtgtcctataac
```

Figure 1K actcggaataatgcttgacccggttatcatcgccactggacagacatatgagaaggagagtata
cagaaatggtttgacgcaggacataagacttgtcctaaaacaagacaggagttagatcatctct
ctcttgcacctaacttcgctttaaagaacttgattatgcagtggtgtgagaagaacaatttcaa
gattccagagaaagaagtaagtcctgactcacaaaatgagcagaaagatgaggtctcttgctg
gtggaagcgttatcgtcaagccaactggaagaacaacgaagatcagtgaagcagatgcgtttgc
tagccagagaaaatcccgagaaccgcgttttaatagcgaatgcaggagcgattcctttgttagt
tcaactccttctttaccctgattcaggaatccaagaaaacgcggtaacgacattgttgaatcta
tctatcgacgaggtcaacaagaaactcatttcaaatgaaggagctattccaaacattattgaaa
tccttgaaaatggaaacagagaggcaagagagaactctgctgcagctttgtttagtttatcgat
gctcgatgagaacaaagtaactatcggattatcgaatgggataccgcctttagtcgatttacta
caacatggacattaagagggaagaaagatgctctcactgcactcttaacttgtctcttaact
cagctaataaaggaagagctatcgatgctggtattgttcaacctttgcttaaccttcttaaaga
taaaaacttagggatgatcgatgaagcgctttcgattctgttgctgcttgcatcacaccctgaa
ggacgtcaagccattggacaactctccttcattgaaacacttgtggaattcatcagacaaggca
ccccgaaaaacaaagagtgtgcgacctcggtgctgcttgaactaggctctaacaactcgtcttt
tatcctcgcagcgcttcaattcggagtttatgaatatctggtagaaataaccacctctggaaca
aacagagctcagagaaaagcaaatgctcttatacaactcataagcaaatctgaacaaatttag At_14_AL049655 (SEQ ID NO. 39):

atgggattaacgaattgttgttcccacgaggagctaatgagtcgactcgttgactccgttaaag
aaatatcagggttttcatcttcaaggggttttattgggaagatccaaggcgatcttgttcgtag
gatcacgcttctcagcccttcttcgaggaattgattgacgtcaatgttgaattgaaaaaggat
cagattacagggtttgaggctatgagaatcgctcttgattcaagtcttgacttttcgatcgg
ttaatggaggaagcaagcttttcagcttttcgatagagattctcttgtggagaagttccgtga
catgacagtggagatagaagcagcgttaagtcagattccttatgagaagattgaggtatcagag
gaagtcagagaacaggttcagcttctgcattttcagttcaagagagcaaaagaagatgggagg
agtctgatctacagcttagccatgatctagctatggcagagaatgtgatggatcctgacccat
aatcctcaaaagactttcacaagagctccaacttactaccattgatgagctgaagaaagaatcg
catgcgatacatgagtattttctttcatatgatggagatcctgatgactgtttcgagaggatgt
cttcacttcttaaaaacctggtagactttgtaacaatggaaagttcagaccctgatccatccac
tggcagcagaatcgtttcgagacatcgttctcctgttataccagagtattttcggtgtccgata
tcacttgaactgatgaaggatcctgttatcgtctccactggacagctgaattttttcgacccttgc
agacatatgaaagatcatcaattcagaagtggcttgatgctggtcataaaacatgtccgaaatc
tcaggagacacttttacatgctggattaaccctaatttgtgttaaagagtctcattgctttg
tggtgtgaaagcaacggcattgagctaccgcaaaatcaagggagctgtagaaccacaaaaatag
gaggaagcagctcttcagattgtgatcgaacatttgtcctttccttgttagagaaattggccaa
cggtactacagaacagcaaagagctgcagctggagaattaaggttactagccaagaggaacgtg
gataacagagtttgtatcgctgaggctggagccataccactccttgtagagcttctatcctcac
cagatcctcggactcaggaacattctgtgacagctcttctgaatcttcccataaatgaagggaa
caaaggagccattgttgatgcaggagccataacggatatagtagaagtcctaaagaacggaagc
atggaagctagagagaacgctgctgcaacccttttcagtttatctgttatagatgaaaacaaag
tggcaataggtgctgctggagctatccaagcacttataagcttgcttgaggaagaacccgaag
aggcaaaaaagatgctgctacagcgattttcaacttatgcatataccaggggaacaaatcaagg
gcggttaaaggcggtattgttgaccctctgaccagattactgaaagatgcaggtggcggaatgg
tggatgaggctctggccattttagcaattctttcaactaaccaagaagggaaaacagcgatagc
tgaagcagaatctatcccggttttggttgagattataaggacagggtcaccaaggaaccgggaa
aatgctgcagcaatactttggtatctatgtattgggaatatagaaaggctaaatgtagcaagag
aggttggtgcagatgtggccttgaaggaacttactgagaatggcactgatagagcaaagaggaa
agctgcgagcttgttggagcttattcagcaaaccgaaggtgttgcagtaactactgttccatga At_15_AY096530 (At3g54850) (SEQ ID NO. 41):

atgggattaacgaattgttgttcccacgaggagctaatgagtcgactcgttgactccgttaaag
aaatatcagggttttcatcttcaaggggttttattgggaagatccaaggcgatcttgttcgtag
gatcacgcttctcagcccttcttcgaggaattgattgacgtcaatgttgaattgaaaaaggat
cagattacagggtttgaggctatgagaatcgctcttgattcaagtcttgacttttcgatcgg
ttaatggaggaagcaagcttttcagcttttcgatagagattctcttgtggagaagttccgtga
catgacagtggagatagaagcagcgttaagtcagattccttatgagaagattgaggtatcagag
gaagtcagagaacaggttcagcttctgcattttcagttcaagagagcaaaagaagatgggagg
agtctgatctacagcttagccatgatctagctatggcagagaatgtgatggatcctgacccat
aatcctcaaaagactttcacaagagctccaacttactaccattgatgagctgaagaaagaatcg
catgcgatacatgagtattttctttcatatgatggagatcctgatgactgtttcgagaggatgt
cttcacttcttaaaaacctggtagactttgtaacaatggaaagttcagaccctgatccatccac

Figure 1L

```
tggcagcagaatcgtttcgagacatcgttctcctgttataccagagtatttcggtgtccgata
tcacttgaactgatgaaggatcctgttatcgtctccactggacagacatatgaaagatcatcaa
ttcagaagtggcttgatgctggtcataaaacatgtccgaaatctcaggagacacttttacatgc
tggattaaccccctaattatgtgttaaagagtctcattgctttgtggtgtgaaagcaacggcatt
gagctaccgcaaaatcaagggagctgtagaaccacaaaaataggaggaagcagctcttcagatt
gtgatcgaacatttgtcctttccttgttagagaaattggccaacggtactacagaacagcaaag
agctgcagctggagaattaaggttactagccaagaggaacgtggataacagagtttgtatcgct
gaggctggagccataccactccttgtagagcttctatcctcaccagatcctcggactcaggaac
attctgtgacagctcttctgaatctttccataaatgaagggaacaaaggagccattgttgatgc
aggagccataacggatatagtagaagtcctaaagaacggaagcatggaagctagagagaacgct
gctgcaacccttttcagtttatctgttatagatgaaaacaaagtggcaataggtgctgctggag
ctatccaagcacttataagcttgcttgaggaaggaacccgaagaggcaaaaaagatgctgctac
agcgattttcaacttatgcataccaggggaacaaatcaagggcggttaaaggcggtattgtt
gaccctctgaccagattactgaaagatgcaggtggcggaatggtggatgaggctctggccattt
tagcaattctttcaactaaccaagaagggaaaacagcgatagctgaagcagaatctatccggt
tttggttgagattataaggacagggtcaccaaggaaccgggaaaatgctgcagcaatactttgg
tatctatgtattgggaatatagaaaggctaaatgtagcaagagaggttggtgcagatgtggcct
tgaaggaacttactgagaatggcactgatagagcaaagaggaaagctgcgagcttgttggagct
tattcagcaaaccgaaggtgttgcagtaactactgttccatga
```

At_16_AK118730 (At4g16490) (SEQ ID NO. 43):

```
atggtatcggtggaggaaccctttatctcattccaattccactcgctttccgttaacaaccgatt
tctacggttcatcatcgccgtcggcggcgaggttacaccgtcaagctggccggtcgatgagaac
agtgagatctaacttctatcaaagcggagatcaatcttgctcattcgtcggctcaatcggcgat
aaatcagagtatgcgtcggagtttctctcggattccgtcatcgacatgagactcggcgagcttg
ctttgaaaaacagtaattctctcaattcaaacgcttcctcaatgaaagaggaagcgtttctcga
catttctcaggcgtttagtgattttccgcttgtagtagtgatatctccggcgagttacagcgt
cttgcttgcttgccgtcgccggaggctgatagaaatgagagcggcggagataacgaagcggagc
atgatccagagttagagagagagccttgtctagggtttctacagagagaaaacttctctacaga
gattatcgagtgtatttcgccggaagatctgcagccaactgtgaaactatgcatcgacggactt
cgttcctcttcggtggcgataaagcgatctgctgcggcgaagctacggctattggcgaagaatc
gagcggataatcgtgtgttgattggggaatctggagctattcaagctttgattccacttcttcg
ttgtaacgatccatggacgcaagagcgcgcagttacagctctgttaaacctctcgttacacgac
cagaacaaagctgtaatcgccgcaggaggagcgattaaatcactagtgtgggtactcaaaacgg
ggacggagacttcaaagcagaacgctgcatgtgctttgcttagttggcgctattggaggagaa
caaaggctcaatcggagcttgcggtgctattccgccgctggtttctcttctgttgaacggatct
tgcaggggaaagaaggatgcgttgacggcgctctacaagctgtgtacgcttcagcaaaacaagg
agagagcggtcactgctggagcggtgaagccgttggtggaccttgtggctgaggaagggactgg
tatggcggagaaagctatggtggttctgagtagccttgcagcgatagatgatggcaaagaggct
attgtcgaggaaggagggatcgcagcgcttgttgaggccatcgaggatggatctgtgaaaggga
agaatttgcgatcttgacgctgttgcagctttgttctgatagcgttagaaaccgtgggttgct
tgtgagggaaggcgcgattcctccgcttgtgggcctctctcagagcggctccgtcagtgttaga
gctaagcgcaaggcagaaagacttctggggtatcttcgggagccaaggaaggaggcaagttcat
caagcccatga
```

Figure 2A

HvArm (SEQ ID NO. 2):

mqmallarlslassegressleerhagsdeqtseqstkeafqashfdsdsqvrlgrssvndnlpn
trqldeecdindgmirvpgdrtnyssdasgevadrglsissapqrenvilprlghvcmegpfvqr
qtsdkgfpriisslsmdarddfsaienqvrelindlgsdsiegqrsatseirllakhnmenriai
ancgainllvgllhspdakiqenavtallnlslsdinkiaivnadaidplihvletgnpeakens
aatlfslsiieenrvrigrsgavkplvdllgngsprgkkdavtalfnlsilhenkgrivqadalk
hlvelmdpaagmvdkavavlanlatipegrtaigqargipalvevvelgsakakenataallqlc
tnssrfcnivlqedavpplvalsqsgtprarekaqvllsyfrsqrhgnsgrr*

OS_1_XM_479734.1 (SEQ ID NO. 4):

menfsprtllnsilritvltsdgstarpkpiqkycqnvcdissivspliedlcespeeqlnevlr
elgtainrasglignwqqttskiyfiwqiesvisdiqgcslqlcqlvnsllpsltgractciekl
qdinyenmfdlvkesslelvetdttspenlsrlssslslstnlefymeavslenlraramrsenr
eemdladkmiplvnymhdhllretqllsingvpipadfccplslelmsdpvivasgqtyervyik
lwldegfticpktrqrlghsnlipnytvkalianwceshnirlpdpmkslklnfplaasalqdss
ttgssplhptvaakgnipgspeadlymrslnraspphsvvhqnshahvnragheasikqssenan
gsasdvsrlslagsetressleernagsigqtseqsieeafqasnldrdshdhvgsssvngslpn
sgqldaecdngpsertnyssdasgevtdgpsassapqrehlipsrladvrsrgqfvrrpsergfp
riissssmdtrsdlsaienqvrklvddlrsdsvdvqrsatsdirllakhnmenriiiancgainl
lvgllhspdsktqehavtallnlsindnnkiaianadavdplihvletgnpeakensaatlfsls
vieenkvrigrsgaikplvdllgngtprgkkdaatalfnlsilhenkarivqadavkylvelmdp
aagmvdkavavlanlatipegrtaigqargipalvevvelgsargkenaaaallqlctnssrfcs
ivlqegavpplvalsqsgtprarekaqallsyfrsqrhgnsarr (SEQ ID NO. 6):

mafvcgggqvmdsvslslldsisnfrvlsssnasktelvkkycqtmdgildhlevalnrafpqit
pdgelskviqadsiiakmqiyvfelcqivnslmqiesmhledlehdscgkisdvireasralage
vmpnseefgkiqttlslstnqellmeyvalvkvktkgnhednkemddindivelvnhmldkhvee
kqtrsingvtipadfccplslelmsdpvivasgqtyehvfirkwfdlgynicpktrqilghtkli
pnftvkqlienwcevhgimlpdpvkllslcfpvslnitdgsasadksgspehcqlvaalhpkaqc
asddshhynlihensdsddrvssfgdtddsepdslrlstettaanksllldektdrsdglkqlrdn
gfqvsdeeqylerngkshisshhqlevdgenvrvqassdinasevmqddpvttcskvsdnpprlg
gvrsrnqpnwrqsnktiprigisssstdskpdfsgndakvrnlieelksdsaevqrsatgelril
srhslenriaiancgaipflvsllhstdpstqenavtillnlslddnnkiaiasaeaieplifvl
qvgnpeakansaatlfslsvieenkikigrsgaieplvdllgegtpqgkkdaatalfnlsifheh
ktrivqagavnhlvelmdpaagmvdkavavlanlatvhdgrnaiaqaggirvlvevvelgsarsk
enaaaallqlctnsnrfctlvlqegvvpplvalsqsgtararekaqvllsyfrnqrhvrvgrgls
lllelkrtt (SEQ ID NO. 8):

mdsvslslldsisnfrvlsssnasktelvkkycqtmdgildhlevalnrafpqitpdgelskvle
elgtatineatelvggwnqmmskiyfviqadsiiakmqiyvfelcqivnslmqiesmhledlehds
cgkisdvireasralagevmpnseefgkiqttlslstnqellmeyvalvkvktkgnhednkemdd
indivelvnhmldkhveekqtrsingvtipadfccplslelmsdpvivasgqtyehvfirkwfdl
gynicpktrqilghtklipnftvkqlienwcevhgimlpdpvkllslcfpvslnitdgsasadks
gspehcqlvaalhpkaqcasddshhynlihensdsddrvssfgdtddsepdslrlstettaanks

Figure 2B lldektdrsdglkqlrdngfqvsdeeqylerngkshisshhqlevdgenvrvqassdinasevmq
ddpvttcskvsdnpprlggvrsrnqpnwwrqsnktipriglssstdskpdfsgndakvrnlieel
ksdsaevqrsatgelrilsrhslenriaiancgaipflvsllhstdpstqenavtillnlslddn
nkiaiasaeaieplifvlqvgnpeakansaatlfslsvieenkikigrsgaieplvdllgegtpq
gkkdaatalfnlsifhehktrivqagavnhlvelmdpaagmvdkavavlanlatvhdgrnaiaqa
ggirvlvevvelgsarskenaaaallqlctnsnrfctlvlqegvvpplvalsqsgtararekaqv
llsyfrnqrhvrvgrg (SEQ ID NO. 10):

mvslagsqipspgqspcaaarsqrrgagysmrtirsallqpdscpgsphvaaaydaagadsdmen
ltdsvidfhlselaatagpahpaavakssanaaatemlelsrdfsdyssfnsdisgelerlaaa
aaavvtprsdapqvgavdlnelesmdlsveaaplervepfvlacvralgpdaapdarrtaaarir
llakhrsdireligvsgaipalvpllrstdpvaqesavtallnlsleernrsaitaagaikplvy
alrtgtasakqnaacallslsgieenratigacgaipplvallsagstrgkkdalttlyrlcsar
rnkeravsagavvplihlvgergsgtsekamvvlaslagivegrdavveaggipalvetiedgpa
rerefavvallqlcsecprnrallvregaipplvalsqsgsarakhkaetllgylreqrqggggc
rvepvaasslar (SEQ ID NO. 12):

meisllkvllnniscfshlsssdhisgelvrryyckiedilklvkpildaivdveaasgelllka
faglaqcvdelrelfetleplcskvyfvlqaepligkirscsleilellksshkslpadvtlttl
elyilkikyvdyemisvtitkvikaqveglgtssdsfakiadclslnsnqellielvaleklken
aeqaeksevveyieqmitlvshmhdcfvttkqsqsctavpippdfccplslelmtdpvivasgqt
yerafirrwidlgltvcpktrqtlghtnlipnytvkalianwceinnvklpdpmkslslnqpsls
pdstqssgsprkslisstvsqreessphprssseeslpgvggnilafdvermriksedrmahsg
eisshghstlvaddqfplghnrttsapstlsnsnfspvipgdgnklsedssvasgdvgldskpaa
svlpkepefpytpemrprnqliwrrpterfprivssatverradlseveeqvkklieelkstsld
mqrnataelrllakhnmdnrmviancgaisslvnllhskdmkvqedavtallnlsindnnkcaia
nadaieplihvlqtgsaeakensaatlfslsvmeenkmkigrsgaikplvdllgngtprgkkdaa
talfnlsilhenksriiqagavkylvelmdpatgmvdkavavlsnlatipegraeigqeggipll
vevvelgsargkenaaaallqlctnssrfcnmvlqegavpplvalsqsgtprarekaqqllsyfr
nqrhgnagrg (SEQ ID NO. 14):

mevllrsissflnlssskhidldpfekyykrveellrvlkpiadvvvtsdfvfdeklgkafeelt
qdvdqsidlfrswqafsskvyfvlqiesllpkmrdtivdtfqflmssknhlpdelspasleqcle
kikhlsyeeissvidgalrdqrdgvgpspeilvkigentglrsnqeilieavalerqkemaeqse
nnaevefldqlivivnrmherlllikqtqtssvailadffcplslevmtdpvivssgqtyekafi
krwidlglkvcpktrqtlthttlipnytvkalianwcetndvklpdpnkstslnelspllsctds
ipstgadvsarkvsnkshdwdasssetgkpsfssrateregaspsrpasalgasspgisgngygl
darrgslndfedrsndsrelrtdapgrssvssttrgsvengqtsenhhhrspsatstvsneefpr
adanenseesahatpyssdasgeirsgplaattsaatrrdlsdfspkfmdrrtrgqfwrrpserl
gsrivsapsnetrrdlsevetqvkklveelksssldtqrqataelrllakhnmdnrivignsgai
vllvellystdsatqenavtallnlsindnnkkaiadagaieplihvlengsseakensaatlfs
lsvieenkikigqsgaigplvdllgngtprgkkdaatalfnlsihqenkamivqsgavrylidlm
dpaagmvdkavavlanlatipegrnaigqeggipllvevvelgsargkenaaaallqlstnsgrf
cnmvlqegavpplvalsqsgtprarekvqtl Figure 2C
(SEQ ID NO. 16):

milrfwreniilrfwrkihdfavlkliqmyhpddpskyllnykkqtsfficiwmnhldekqtrse
sdftvskrdirrvemevllrsissflnlssskhidldpfekyykrveellrvlkpiadvvvtsdf
vfdeklgkafeeltqdvdqsidlfrswqafsskvyfvlqiesllpkmrdtivdtfqflmssknhl
pdelspasleqclekikhlsyeeissvidgalrdqrdgvgpspeilvkigentglrsnqeiliea
valerqkemaeqsennaevefldqlivivnrmherllikqtqtssvailadffcplslevmtdp
vivssgqtyekafikrwidlglkvcpktrqtlthttlipnytvkalianwcetndvklpdpnkst
slnelspllsctdsipstgadvsarkvsnkshdwdasssetgkpsfssrateregaspsrpasal
gasspgisgngygldarrgslndfedrsndsrelrtdapgrssvssttrgsvengqtsenhhhrs
psatstvsneefpradanenseesahatpyssdasgeirsgplaattsaatrrdlsdfspkfmdr
rtrgqfwrrpserlgsrivsapsnetrrdlsevetqvkklveelksssldtqrqataelrllakh
nmdnrivignsgaivllvellystdsatqenavtallnlsindnnkkaiadagaieplihvleng
sseakensaatlfslsvieenkikigqsgaigplvdllgngtprgkkdaatalfnlsihqenkam
ivqsgavrylidlmdpaagmvdkavavlanlatipegrnaigqeggipllvevvelgsargkena
aaallqlstnsgrfcnmvlqegavpplvalsqsgtprarekkptawkrwawlmmddddddvdda
qilvsqclflcfvl (At5g67340) (SEQ ID NO. 18):

mmvhmevswlrvlldnissylslssmddlssnpahkyytrgedigklikpvlenlidsdaapsel
lnngfeelaqyvdelreqfqswqplstrifyvlrieslasklresslevfqllkhceqhlpadli
spsfeecielvklvardeisytidqalkdqkkgvgptsevlvkiaestglrsnqeilvegvvltn
mkedaeltdndteaeyldglisittqmheylsdikqaqlrcpvrvpsdfrcslslelmtdpviva
sgqtfervfiqkwidmglmvcpktrqalshttltpnfivraflaswcetnnvyppdplelihsse
pfpllvesvrasssenghsesldaeelrqvfsrsasapgivsevvcktkrnnnaaadrsltrsnt
pwkfpeerhwrhpgiipatvretgssssietevkkliddlksssldtqreatariirilarnstdn
riviarceaipslvsllystderiqadavtcllnlsindnnksliaesgaivplihvlktgylee
akansaatlfslsvieeykteigeagaieplvdllgsgslsgkkdaatalfnlsihhenktkvie
agavrylvelmdpafgmvekavvvlanlatvregkiaigeeggipvlvevvelgsargkenataa
llqlcthspkfcnnviregvipplvaltksgtargkekaqnllkyfkahrqsnqrrg (SEQ ID NO. 20):

mevswlrvlldnissylslssmddlssnpahkyytrgedigklikpvlenlidsdaapsellnng
feelaqyvdelreqfqswqplstrifyvlrieslasklresslevfqllkhceqhlpadlispsf
eecielvklvardeisytidqalkdqkkgvgptsevlvkiaestglrsnqeilvegvvltnmked
aeltdndteaeyldglisittqmheylsdikqaqlrcpvrvpsdfrcslslelmtdpvivasgqt
fervfiqkwidmglmvcpktrqalshttltpnfivraflaswcetnnvyppdplelihssepfpl
lvesvrasssenghsesldaeelrqvfsrsasapgivsevvcktkrnnnaaadrsltrsntpwkf
peerhwrhpgiipatvretgssssietevkkliddlksssldtqreatariirilarnstdnrivi
arceaipslvsllystderiqadavtcllnlsindnnksliaesgaivplihvlktgyleeakan
saatlfslsvieeykteigeagaieplvdllgsgslsgkkdaatalfnlsihhenktkvieagav
rylvelmdpafgmvekavvvlanlatvregkiaigeeggipvlvevvelgsargkenataallql
cthspkfcnnviregvipplvaltksgtargkekvlflfpllclvnvs (SEQ ID NO. 22):

mdpvpvrcllnsisrylhlvacqtirfnpiqtcignmvlllkllkplldevvdckipsddclykg
cedldsvvnqarefledwspklsklfgvfqcevllgkvqtcsleisrillqlsqsspvtssvqsv
ercvqetesfkqegtlmelmenalrnqkdditsldnnhlesiiqmlglisnqdllkesitveker
irsqaskseedmeqteqlielvlcirehmlkteflevakgisippyfrcplstelmldpvivasg Figure 2D
qtfdrtsikkwldnglavcprtrqvlthqelipnytvkamiaswleanrinlatnschqydggda
ssmannmgsqdfnrtesfrfslrsssltsrssletgngfeklkinvsaslcgesqskdleifell
spgqsythsrsesvcsvvssvdyvpsvthetesilgnhqsssemspkknlessnnvnhehsaakt
yecsvhdlddsgtmttshtiklvedlksgsnkvktaaaaeirhltinsienrvhigrcgaitpll
sllyseekltqehavtallnlsiselnkamivevgaieplvhvlntgndrakensaaslfslsvl
qvnrerigqsnaaiqalvnllgkgtfrgkkdaasalfnlsithdnkarivqakavkylvelldpd
lemvdkavallanlsavgegrqaivreggipllvetvdlgsqrgkenaasvllqlclnspkfctl
vlqegaipplvalsqsgtqrakekaqqllshfrnqrdarmkkgrs (SEQ ID NO. 24):

mdpvpvrcllnsisrylhlvacqtirfnpiqtcignmvlllkllkplldevvdckipsddclykg
redldsvvnqarefledwspklsklfgvfqcevllgkvqtcsleisrillqlsqsspvtssvqsv
ercvqetesfkqegtlmelmenalrnqkdditsldnnhlesiiqmlglisnqdllkesitveker
irsqaskseedmeqteqlielvlcirehmlkteflevakgisippyfrcplstelmldpvivasg
qtfdrtsikkwldnglavcprtrqvlthqelipnytvkamiaswleanrinlatnschqydggda
ssmannmgsqdfnrtesfrfslrsssltsrssletgngfeklkinvsaslcgesqskdleifell
spgqsythsrsesvcsvvssvdyvpsvthetesilgnhqsssemspkknlessnnvnhehsaakt
yecsvhdlddsgtmttshtiklvedlksgsnkvktaaaaeirhltinsienrvhigrcgaitpll
sllyseekltqehavtallnlsiselnkamivevgaveplvhvlntgndrakensaaslfslsvl
qvnrerigqsnaaiqalvnllgkgtfrgkkdaasalfnlsithdnkarivqakavkylvelldpd
lemvdkavallanlsavgegrqaivreggipllvetvdlgsqrgkenaasvllqlclnspkfctl
vlqegaipplvalsqsgtqrakekaqqllshfrnqrdarmkkgrs (SEQ ID NO. 26):

mvlllkllkplldevvdckipsddclykgcedldsvvnqarefledwspklsklfgvfqcevllg
kvqtcsleisrillqlsqsspvtssvqsvercvqetesfkqegtlmelmenalrnqkdditsldn
nhlesiiqmlglisnqdllkesitvekerirsqaskseedmeqteqlielvlcirehmlktefle
vakgisippyfrcplstelmldpvivasgqtfdrtsikkwldnglavcprtrqvlthqelipnyt
vkamiaswleanrinlatnschqydggdassmannmgsqdfnrtesfrfslrsssltsrssletg
ngfeklkinvsaslcgesqskdleifellspgqsythsrsesvcsvvssvdyvpsvthetesilg
nhqsssemspkknlessnnvnhehsaaktyecsvhdlddsgtmttshtiklvedlksgsnkvkta
aaaeirhltinsienrvhigrcgaitpllsllyseekltqehavtallnlsiselnkamivevga
ieplvhvlntgndrakensaaslfslsvlqvnrerigqsnaaiqalvnllgkgtfrgkkdaasal
fnlsithdnkarivqakavkylvelldpdlemvdkavallanlsavgegrqaivreggipllvet
vdlgsqrgkenaasvllqlclnspkfctlvlqegaipplvalsqsgtqrakekvytifffcgytk
thqvqflidrdi (SEQ ID NO. 28):

meeekasaaqslidvvneiaaisdyritvkklcynlarrlkllvpmfeeiresnepisedtlktl
mnlkeamcsakdylkfcsqgskiylvmereqvtsklmevsvkleqslsqipyeeldisdevreqv
elvlsqfrrakgrvdvsddelyedlqslcnkssdvdayqpvlervakklhlmeipdlaqesvalh
emvassggdvgenieemamvlkmikdfvqteddngeeqkvgvnsrsngqtstaasqkipvipddf
rcpislemmrdpvivssgqtyertciekwiegghstcpktqqaltsttltpnyvlrsliaqwcea
ndieppkppsslrprkvssfsspaeankiedlmwrlaygnpedqrsaageirllakrnadnrvai
aeagaipllvgllstpdsriqehsvtallnlsicennkgaivsagaipgivqvlkkgsmearena
aatlfslsvidenkvtigalgaipplvvllnegtqrgkkdaatalfnlciyqgnkgkairagvip
tltrlltepgsgmvdealailailsshpegkaiigssdavpslvefirtgsprnrenaaavlvhl
csgdpqhlveaqklglmgplidlagngtdrgkrkaaqllerisrlaeqqketavsqpeeeaepth
pestteaadt Figure 2E
(SEQ ID NO. 30):

memenhrpgsftymgrkfsdlslnddssafsdcnsdrsgefptassesrrlllscasensddlin
hlvshldssysideqkqaameirllsknkpenrikiakagaikplislisssdlqlqeygvtail
nlslcdenkesiassgaikplvralkmgtptakenaacallrlsqieenkvaigrsgaipllvnl
letggfrakkdastalyslcsakenkiravqsgimkplvelmadfgsnmvdksafvmsllmsvpe
skpaiveeggvpvlveivevgtqrqkemavsillqlceesvvyrtmvaregaipplvalsqagts
rakqkaealiellrqprsisnggarsssql (SEQ ID NO. 32):

memenhrpgsftymgrkfsdlslnddssafsdcnsdrsgefptassesrrlllscasensddlin
hlvshldssysideqkqaameirllsknkpenrikiakagaikplislisssdlqlqeygvtail
nlslcdenkesiassgaikplvralkmgtptakenaacallrlsqieenkvaigrsgaipllvnl
letggfrakkdastalyslcsakenkiravqsgimkplvelmadfgsnmvdksafvmsllmsvpe
skpaiveeggvpvlveivevgtqrqkemavsillqlceesvvyrtmvaregaipplvalsqagts
rakqkaealiellrqlrsisnggarsssql (SEQ ID NO. 34):

memenhrpgsftymgrkfsdlslnddssafsdcnsdrsgefptassesrrlllscasensddlin
hlvshldssysideqkqaameirllsknkpenrikiakagaikplislisssdlqlqeygvtail
nlslcdenkesiassgaikplvralkmgtptakdnaacallrlsqieenkvaigrsgaipllvnl
letggfrakkdastalyslcsakenkiravqsgimkplvelmadfgsnmvdksafvmsllmsvpe
skpaiveeggvpvlveivevgtqrqkemavsillqlceesvvyrtmvaregaipplvalsqagts
rakqkaealiellrqprsisnggarsssql (SEQ ID NO. 36):

mdtdeeatgdaenrdeevtaeepihdevvdaveiheeevkeddddceglvsdivsiveflddqing
yrrtqqkecfnlvrrlkilipfldeirgfespsckhflnrlrkvflaakkllletcsngskiymal
dgetmmtrfhsiyeklnrvlvkapfdelmisgdakdeidslckqlkkakrrtdtqdielavdmmv
vfsktdprnadsaiierlakklelqtiddlktetiaiqsliqdkgglnietkqhiiellnkfkkl
qgleatdilyqpvinkaitkststslilpheflcpitleimldpviiatgqtyekesiqkwfdaghk
tcpktrqeldhlslapnfalknlimqwceknnfkipekevspdsqneqkdevsllvealsssqle
eqrrsvkqmrllarenpenrvlianagaipllvqllsypdsgiqenavttllnlsidevnkklis
negaipniieilengnrearensaaalfslsmldenkvtiglsngipplvdllqhgtlrgkkdal
talfnlslnsankgraidagivqpllnllkdknlgmidealsillllashpegrqaigqlsfiet
lvefirqgtpknkecatsvllelgsnnssfilaalqfgvyeylveittsgtnraqrkanaliqli
skseqi (SEQ ID NO. 38):

mvdvmdtdeeatgdaesrdeevtaeepihdevvdaveiheeevkeddddceglvsdivsivefld
qingyrrtqqkecfnlvrrlkilipfldeirgfespsckhflnrlrkvflaakkllletcsngski
ymaldgetmmtrfhsiyeklnrvlvkapfdelmisgdakdeidslckqlkkakrrtdtqdielav
dmmvvfsktdprnadsaiierlakklelqtiddlktetiaiqsliqdkgglnietkqhiiellnk
fkklqgleatdilyqpvinkaitkststslilpheflcpitlgimldpviiatgqtyekesiqkwfd
aghktcpktrqeldhlslapnfalknlimqwceknnfkipekevspdsqneqkdevsllvealss
sqleeqrrsvkqmrllarenpenrvlianagaipllvqllsypdsgiqenavttllnlsidevnk
klisnegaipniieilengnrearensaaalfslsmldenkvtiglsngipplvdllqhgtlrgk
kdaltalfnlslnsankgraidagivqpllnllkdknlgmidealsillllashpegrqaigqls Figure 2F
fietlvefirqgtpknkecatsvllelgsnnssfilaalqfgvyeylveittsgtnraqrkanal
iqliskseqi (SEQ ID NO. 40):

mgltnccsheelmsrlvdsvkeisgfsssrgfigkiqgdlvrritllspffeelidvnvelkkdq
itgfeamrialdsslelfrsvnggsklfqlfdrdslvekfrdmtveieaalsqipyekievseev
reqvqllhfqfkrakerweesdlqlshdlamaenvmdpdpiilkrlsqelqlttidelkkeshai
heyflsydgdpddcfermssllknlvdfvtmessdpdpstgsrivsrhrspvipeyfrcpislel
mkdpvivstgqlnfstlqtyerssiqkwldaghktcpksqetllhagltpnyvlkslialwcesn
gielpqnqgscrttkiggssssdcdrtfvlslleklangtteqqraaagelrllakrnvdnrvci
aeagaipllvellsspdprtqehsvtallnlsinegnkgaivdagaitdivevlkngsmearena
aatlfslsvidenkvaigaagaiqalislleegtrrgkkdaataifnlciyqgnksravkggivd
pltrllkdagggmvdealailailstnqegktaiaeaesipvlveiirtgsprnrenaaailwyl
cignierlnvarevgadvalkeltengtdrakrkaaslleliqqtegvavttvp (SEQ ID NO. 42):

mgltnccsheelmsrlvdsvkeisgfsssrgfigkiqgdlvrritllspffeelidvnvelkkdq
itgfeamrialdsslelfrsvnggsklfqlfdrdslvekfrdmtveieaalsqipyekievseev
reqvqllhfqfkrakerweesdlqlshdlamaenvmdpdpiilkrlsqelqlttidelkkeshai
heyflsydgdpddcfermssllknlvdfvtmessdpdpstgsrivsrhrspvipeyfrcpislel
mkdpvivstgqtyerssiqkwldaghktcpksqetllhagltpnyvlkslialwcesngielpqn
qgscrttkiggssssdcdrtfvlslleklangtteqqraaagelrllakrnvdnrvciaeagaip
llvellsspdprtqehsvtallnlsinegnkgaivdagaitdivevlkngsmearenaaatlfsl
svidenkvaigaagaiqalislleegtrrgkkdaataifnlciyqgnksravkggivdpltrllk
dagggmvdealailailstnqegktaiaeaesipvlveiirtgsprnrenaaailwylcignier
lnvarevgadvalkeltengtdrakrkaaslleliqqtegvavttvp (SEQ ID NO. 44):

mvsveeplshsnstrfplttdfygssspsaarlhrqagrsmrtvrsnfyqsgdqscsfvgsigdk
seyaseflsdsvidmrlgelalknsnslnsnassmkeeafldisqafsdfsacssdisgelqrla
clpspeadrnesggdneaehdpelerepclgflqrenfsteiiecispedlqptvklcidglrss
svaikrsaaaklrllaknradnrvligesgaiqaliplircndpwtqeravtallnlslhdqnka
viaaggaikslvwvlktgtetskqnaacallslalleenkgsigacgaipplvslllngscrgkk
daltalyklctlqqnkeravtagavkplvdlvaeegtgmaekamvvlsslaaiddgkeaiveegg
iaalveaiedgsvkgkefailtllqlcsdsvrnrgllvregaipplvglsqsgsvsvrakrkaer
llgylreprkeassssp

Figure 3A

```
Translation of Armadillo ORF                                                           1                                                  50
                              AC010870  (1)  --------------------------------------------------
                              AB007645  (1)  --------------------------------------------------
                              AB016888  (1)  --------------------------------------------------
                              AC004401  (1)  ----------------------------------MDTDEEATGDAENRDE
                              AK118613  (1)  MILRFWRENIILRFWRKIHDFAVLKLIQMYHPDDPSKYLLNYKKQTSFFI
                              AK118730  (1)  --------------------------------------------------
                              AK175585  (1)  --------------------------------------------------
                              AL049655  (1)  -----------------------------MVDVMDTDEEATGDAESRDE
                              AL133314  (1)  --------------------------------------------------
                              AL138650  (1)  --------------------------------------------------
                              AP003561  (1)  --------------------------------------------------
                              AY087360  (1)  --------------------------------------------------
                              AY096530  (1)  --------------------------------------------------
                              AY125543  (1)  --------------------------------------------------
                              AY219234  (1)  --------------------------------------------------
                              BT020206  (1)  --------------------------------------------------
                              NM_115336 (1)  --------------------------------------------------
                              NM_127878 (1)  --------------------------------------------------
                              XM_463544 (1)  --------------------------------------------------
                           XM_479734.1  (1)  --------------------------------------------------
                              XM_506432 (1)  --------------------------------------------------
                              Consensus (1)  --------------------------------------------------
```

Figure 3B

```
Translation of Armadillo ORF
                        51                                                          100
AC010870         (1)   ---------------------------------------------------------------
AB007645         (1)   ------------------------------------------MEVSWLRVLLDNISSYLSLSSMDDLS
AB016888        (17)   EVTAEEPIHDEVVDAVEIHEEEVKEDDDDCEGLVSDIVSIVEFLDQINGY
AC004401        (51)   CIWMNHLDEKQTRSESDFTVSKRDIRRVEMEVLLRSISSFLNLSSKHID
AK118613         (1)   ------------------------------------------MDPVPVRCLINSISRYLHLVACQTIR
AK118730         (1)   ---------------------------------------------------------------
AK175585        (21)   EVTAEEPIHDEVVDAVEIHEEEVKEDDDDCEGLVSDIVSIVEFLDQINGY
AL049655         (1)   ------------------------------------------MGLTNCCSHEELMSRLVDSVKEISGFSSS
AL133314         (1)   ------------------------------------------MEEEKASAAQSLIDVVNEIAAISDY
AL138650         (1)   ---------------------------------------------------------------
AP003561         (1)   ------------------------------------------MDSVSLSLLDSISNFRVLSSSNASK
AY087360         (1)   ---------------------------------------------------------------
AY096530         (1)   ------------------------------------------MGLTNCCSHEELMSRLVDSVKEISGFSSS
AY125543         (1)   ------------------------------------------MEISLLKVLLNNISCFSHLSSSDHIS
AY219234         (1)   ------------------------------------------MMVHMEVSWLRVLLDNISSYLSLSSMDDLS
BT020206         (1)   ------------------------------------------MDPVPVRCLINSISRYLHLVACQTIR
NM_115336        (1)   ------------------------------------------MEVLLRSISSFLNLSSSKHID
NM_127878        (1)   ------------------------------------------MAFVCGGGQVMDSVSLSLLDSISNFRVLSSSNASK
XM_463544        (1)   ------------------------------------------MENFSPRTLLNSILRITVLTSDGST
XM_479734.I
XM_506432
Consensus       (51)                                                LL   I  L    S
```

Figure 3C

Translation of Armadillo ORF

```
                         101                                                      150
AC010870             (1)  ------------------------------------------------------
AB007645             (1)  ------------------------------------------------------
AB016888            (27)  SNPAHKYYTRGEDIGKIIKPVLENLIDSDAAPSELLNNGFEELAQYVDEL
AC004401            (67)  RRTQQKECFNEVRRLKILIPFLDERGFESPSCKHFLNRLRKVFLAAKKL
AK118613           (101)  LDPFEKYYKRVEELIRVLKPIADVVTSDFVFDEKLGKAFEELTQDVDQS
AK118730            (27)  FNPIQTCIGNMVLLLKLIKPLLIDEVVDCKIPSDDCLYKGREDLDSVNQA
AK175585             (1)  ------------------------------------------------------
AL049655            (71)  RRTQQKECFNEVRRLKILIPFLDERGFESPSCKHFLNRLRKVFLAAKKL
AL133314            (30)  RGFIGKIQGDLVRRITLISPFFEELIDVNVELKKDQITGFEAMRIALDSS
AL138650            (26)  RITVKKLCYNLARRLKLVPMFEERESNEPISEDTLKTLMNLKEAMCSA
AP003561             (1)  -----MVLLIKLIKPLIDEVVDCKIPSDDCLYKGCEDLDSVNQA
AY087360            (26)  TELVKKYCQTMDGILDHLEVALNRAFPQITPDGELSKVLEE-LGATINEA
AY096530             (1)  ------------------------------------------------------
AY125543            (30)  RGFIGKIQGDLVRRITLISPFFEELIDVNVELKKDQITGFEAMRIALDSS
AY219234            (27)  GELVRRYYCKIEDILKVKPILDAIVDVEAASGELLLKAFAGLAQCVDEL
BT020206            (31)  SNPAHKYYTRGEDIGKIIKPVLENLIDSDAAPSELLNNGFEELAQYVDEL
NM_115336           (27)  FNPIQTCIGNMVLLLKLIKPLLIDEVVDCKIPSDDCLYKGCEDLDSVNQA
NM_127878           (22)  LDPFEKYYKRVEELIRVLKPIADVVTSDFVFDEKLGKAFEELTQDVDQS
XM_463544           (36)  TELVKKYCQTMDGILDHLEVALNRAFPQITPDGELS---------
XM_479734.1         (26)  ARPKPIQKYCQNVCDISSIVSPLIEDLCESPEEQINEVLRE-LGTAINRA
XM_506432            (1)  ------------------------------------------------------
Consensus          (101)      K    L   LKLL   P  D V              E    E L    V
```

Figure 3D

Translation of Armadillo ORF

```
                          151                                                         200
AC010870              (1)  ------------------------------------------------------
AB007645              (1)  ------------------------------------------------------
AB016888             (77)  REQFQSWQPLSTRIFYVLRIESLASKLRESSLEVFQLLKHCEQHLPADLI
AC004401            (117)  LETCS--N--GSKIYMALDGETMTRFHSIYEKLNRVLVKAPFDELMISG
AK118613            (151)  IDLFRSWQAFSSKVYFVLQIESLLPKMRDTIVDTFQFLMSSKNHLPDELS
AK118730             (77)  REFLEDWSPKLSKLFGVFQCEVLLGKVQTCSLEISRILQLSQSSPVTSS
                      (1)  ------------------------------------------------------
AK175585            (121)  LETCS--N--GSKIYMALDGETMTRFHSIYEKLNRVLVKAPFDELMISG
AL049655             (80)  LRLFRSVNG-GSKLFQLFDRDSLVEKFRDMTVELEAALSQIPYEKIEVSE
AL133314             (76)  KDYLKFCSQ-GSKIYLVMEREQVTSKLMEVSVKLEQSLSQIPYEELDISD
AL386650             (41)  REFLEDWSPKLSKLFGVFQCEVLLGKVQTCSLEISRILQLSQSSPVTSS
AP003561             (75)  TELVGGWNQMMSKIYFVIQADSIIAKMQIYVFELCQIVNSLMQIES---
AY087360              (1)  ------------------------------------------------------
AY096530             (80)  LELFRSVNG-GSKLFQLFDRDSLVEKFRDMTVELEAALSQIPYEKIEVSE
AY125543              (1)  ------------------------------------------------------
AY219234             (77)  RELFETLEPLICSKVYFVLQAEPLIGKIRSCSLELKSSHKSLPADVT
BT020206             (81)  REQFQSWQPLSTRIFYVLRIESLASKLRESSLEVFQLLKHCEQHLPADLI
NM_115336            (77)  REFLEDWSPKLSKLFGVFQCEVLLGKVQTCSLEISRILQLSQSSPVTSS
NM_127878            (77)  IDLFRSWQAFSSKVYFVLQIESLLPKMRDTIVDTFQFLMSSKNHLPDELS
XM_463544            (72)  -K-----VIQADSIIAKMQIYVFELCQIVNSLMQIES---
XM_479734.1          (75)  SGLIGNWQQTTSKIYFIWQIESVISDLQGCSLQLCQIVNSLLPSLTGRA-
XM_506432             (1)  ------------------------------------------------------
Consensus           (151)  E        SKIY V   ESLL KM    LEI    IL
```

Figure 3E

Translation of Armadillo ORF

```
                                        201                                                                                              250
AC010870            (1)    ----------------------------------------------------
AB007645          (127)    SPSFEECIELVKLVARD-----EISYTIDQALKDQKK---GVGPTSEVLVK
AB016888          (163)    DAKDEIDSLCKQLKKAKRRTDTQDIELAVDMMVVFSKTDPRNADSAIIER
AC004401          (201)    PASLEQCLEKIKHLSYE----EISSVIDGALRDQRD---GVGPSPEILVK
AK118613          (127)    VQSVERCVQETESFKQEG----TLMELMENALRNQKDD---ITSLDNNHLES
AK118730            (1)    ----------------------------------------------------
AK175585          (167)    DAKDEIDSLCKQLKKAKRRTDTQDIELAVDMMVVFSKTDPRNADSAIIER
AL049655          (129)    EVREQVQLLHFQFKRAKERWEESDLQLSHDLAMAEN--VMDPDPIILKR
AL133314          (125)    EVREQVELVLSQFRRAKGRVDVSDDELYEDLQSLCNKSSDVDAYQPVLER
AL138650           (91)    VQSVERCVQETESFKQEG----TLMELMENALRNQKDD---ITSLDNNHLES
AP003561          (121)    ----MHLEDLEHDSCG------KISDVIREASRALAG---EVMPNSEEFGK
AY087360            (1)    ----------------------------------------------------
AY096530          (129)    EVREQVQLLHFQFKRAKERWEESDLQLSHDLAMAEN--VMDPDPIILKR
AY125543            (1)    ----------------------------------------------------
AY219234          (127)    LTTLELYILKIKYVDYE-----MISVTITKVIKAQVE--GLGTSSDSFAK
BT020206          (131)    SPSFEECIELVKLVARD-----EISYTIDQALKDQKK---GVGPTSEVLVK
NM_115336         (127)    VQSVERCVQETESFKQEG----TLMELMENALRNQKDD---ITSLDNNHLES
NM_127878         (122)    PASLEQCLEKIKHLSYE----EISSVIDGALRDQRD---GVGPSPEILVK
XM_463544         (103)    ----MHLEDLEHDSCG------KISDVIREASRALAG---EVMPNSEEFGK
XM_479734.1       (124)    ----CTCIEKLQDINYE-----NMFDLVKESSLELVE---TDTTSPENLSR
XM_506432           (1)    ----------------------------------------------------
Consensus         (201)             L                 I   I                L K
```

Figure 3F

Translation of Armadillo ORF

```
                         251                                                            300
Armadillo ORF     (1)    ------------------------------------------------
AC010870          (1)    ------------------------------------------------
AB007645        (170)    IAESTGLRSNQELVEGVVITNMKEDAELTDND-----TEAEYLDGLIS
AB016888        (213)    LAKKLELQTIDDLKTETIAIQSLIQDKGGLNIETKQHIIELLNKFKKLQG
AC004401        (244)    IGENTGLRSNQEILIEAVALERQKEMAEQSENN-----AEVEFLDQLIV
AK118613        (172)    IIQMLGLISNQDLLKESITVEKERIRSQASKSE-----EDMEQTEQLIE
AK118730          (1)    ------------------------------------------------
AK175585        (217)    LAKKLELQTIDDLKTETIAIQSLIQDKGGLNIETKQHIIELLNKFKKLQG
AL049655        (176)    LSQELQLTTIDELKKESHAIHEYFLSYDGDPDDCFERMSSLLKNLVDFVT
AL133314        (175)    VAKKLHLMEIPDLAQESVALHEMVASSGGDVGENIEEMAMVLKMIKDFVQ
AL138650        (136)    IIQMLGLISNQDLLKESITVEKERIRSQASKSE-----EDMEQTEQLIE
AP003561        (159)    IQTTLSLSTNQELLMEYVALVKVKTKGNHEDN-----KEMDDINDIVE
AY087360          (1)    ------------------------------------------------
AY096530        (176)    LSQELQLTTIDELKKESHAIHEYFLSYDGDPDDCFERMSSLLKNLVDFVT
AY125543          (1)    ------------------------------------------------
AY219234        (170)    IADCLSLNSNQELLIELVALEKLKENAEQAEKS-----EVVEYIEQMIT
BT020206        (174)    IAESTGLRSNQEILVEGVVITNMKEDAELTDND-----TEAEYLDGLIS
NM_115336       (172)    IIQMLGLISNQDLLKESITVEKERIRSQASKSE-----EDMEQTEQLIE
NM_127878       (165)    IGENTGLRSNQEILIEAVALERQKEMAEQSENN-----AEVEFLDQLIV
XM_463544       (141)    IQTTLSLSTNQELLMEYVALVKVKTKGNHEDN-----KEMDDINDIVE
XM_4797341.1    (163)    LSSSLSLSTNLEFYMEAVSLENIRARAMRSENR-----EEMDLADKMIP
XM_506432         (1)    ------------------------------------------------
Consensus       (251)    I  L L SN  EL   E  VAL  K              ME     LI
```

Figure 3G

Translation of Armadillo ORF

```
                            301                                                         350
AC010870              (1)   ------------------------------------------------------------
AB007645              (1)   ------------------------------------------------------------
AB016888            (214)   LTTQMHEYL---------------SDIKQAQLRCPVRVPSDFRCSLSLELMTDPVI
AC0044401           (263)   LEATDILYQP--------------VINKAITKSTSLILPHEFLCPITLELMLDPVI
AK118613            (288)   IVNRMHERL---------------LLIKQTQTSS-VAILADFFCPISLEVMTDPVI
AK118730            (216)   LVLCIREHM---------------LKTEFLEVAKGISIPPYFRCPLSTELMLDPVI
AK175585              (1)   ---------------------------------------------------MVSVEEPL
AL049655            (267)   LEATDILYQP--------------VINKAITKSTSLILPHEFLCPITLGIMLDPVI
AL133314            (226)   MESSDPDPS---------------TGSRIVSRHRSPVIPEYFRCPISLELMKDPVI
AL138650            (225)   TEDDNGEEQKVGVNSRSNGQTSTAASQKIPVIPDDFRCPISLEMRDPVI
AP003561            (180)   LVLCIREHM---------------LKTEFLEVAKGISIPPYFRCPISTELMLDPVI
AY087360            (202)   LVNHMLDKH---------------VEEKQTRSINGVTIPADFCCPLSLELMSDPVI
AY096530              (1)   ------------------------------------------------------------
AY125543            (226)   MESSDPDPS---------------TGSRIVSRHRSPVIPEYFRCPISLELMKDPVI
AY219234            (214)   LVSHMHDCF---------------VTTKQSQSCTAVPIPPDFCCPIPPDFCCPLSLELMTDPVI
BT020206            (218)   LTTQMHEYL---------------SDIKQAQLRCPVRVPSDFRCSLSLELMTDPVI
NM_115336           (216)   LVLCIREHM---------------LKTEFLEVAKGISIPPYFRCPLSTELMLDPVI
NM_127878           (209)   IVNRMHERL---------------LLIKQTQTSS-VAILADFFCPISLEVMTDPVI
XM_463544           (184)   LVNHMLDKH---------------VEEKQTRSINGVTIPADFCPISLEVMSDPVI
XM_479734.1         (207)   LVNYMHDHL---------------LRETQLLSINGVPIPADFCCPISLELMSDPVI
XM_506432             (1)   ---------------------------------------------------MVSLAGSQI
Consensus           (301)   L    M E      L   K              V IP DF CPLSLELM DPVI
```

Figure 3H

Translation of Armadillo ORF

```
                              351                                                                          400
AC010870          (1)  ------------------------------------------------
AB007645        (255)  VASGQT------------FERVFIQKWIDMGLMVCPKTRQALSHTTLTPNFIVRA
AB016888        (305)  IATGQT------------YEKESIQKWFDAGHKTCPKTRQELDHLSLAPNFALKN
AC004401        (328)  VSSGQT------------YEKAFIKRWIDLGLKVCPKTRQLTHTTLIPNYTVKA
AK118613        (257)  VASGQT------------FDRTSIKKWLDNGLAVCPRTRQVLTHQELIPNYTVKA
AK118730          (9)  SHSNST------------RFPLITDFYGSSSPSAARLHRQAGRSMRTVRSNFYQS
AK175585        (309)  IATGQT------------YEKESIQKWFDAGHKTCPKTRQELDHLSLAPNFALKN
AL049655        (267)  VSTGQLNFSTLQTYERSSIQKWLDAGHKTCPKSQETLLHAGITPNYVLKS
AL133314        (275)  VSSGQT------------YERTCIEKWIEGGHSTCPKTQQALISTTLTPNYVLRS
AL138650        (221)  VASGQT------------FDRTSIKKWLDNGLAVCPRTRQVLTHQELIPNYTVKA
AP003561        (243)  VASGQT------------YEHVFIRKWFDLGYNICPKTRQILGHTKLIPNFTVKQ
AY087360          (1)  ------------------------------------------------
AY096530        (267)  VSTGQT------------YERSSIQKWLDAGHKTCPKSQETLLHAGITPNYVLKS
AY125543          (1)  ------------------------------------------------
AY219234        (255)  VASGQT------------YERAFIRRWIDLGLTVCPKTRQTLGHTNLIPNYTVKA
BT020206        (259)  VASGQT------------FERVFIQKWIDMGLMVCPKTRQALSHTTLTPNFIVRA
NM_115336       (257)  VASGQT------------FDRTSIKKWLDNGLAVCPRTRQVLTHQELIPNYTVKA
NM_127878       (249)  VSSGQT------------YEKAFIKRWIDLGLKVCPKTRQTLTHTTLIPNYTVKA
XM_463544       (225)  VASGQT------------YEHVFIRKWFDLGYNICPKTRQILGHTKLIPNFTVKQ
XM_479734.1     (248)  VASGQT------------YERVYIKLWLDEGFTICPKTRQRIGHSNLIPNYTVKA
XM_506432        (10)  PSPGQS------------PCAAARSQRRGAGYSMRTIRSALLQPDSCPGSPHVAA
Consensus       (351)  VASGQT             YER   I KWID G  VCPKTRQ L H  L PNY  VKA
```

Figure 3I

```
                                    401                                                    450
Translation of Armadillo ORF   (1)   ------------------------------------------------
               AC010870        (1)   ------------------------------------------------
               AB007645      (298)   FLASWCETNNVYPPDPLELIHSSEPFPLLVESVRASSEN----------
               AB016888      (348)   LIMQWCEKNNFKIPE---------------------------------
               AC004401      (371)   LIANWCETNDVKLPDPNKSTSLNELSPLLSCTDSIPSTGADVSARKVSNK
               AK118613      (300)   MIASWLEANRINLATNSCHQYDGGDASSMANNMGSQDFNR---------
               AK118730       (52)   GDQSCSFVGSIGDKSEYASEFLSDSVIDMRLGELALKNSN--------
               AK175585     (352)   LIMQWCEKNNFKIPE---------------------------------
               AL049655     (317)   LIALWCESNGIELP-------------QNQG-----------------
               AL133314     (318)   LIAQWCEANDIEPPKP--------------------------------
               AL138650     (264)   MIASWLEANRINLATNSCHQYDGGDASSMANNMGSQDFNR---------
               AP003561     (286)   LIENWCEVHGIMLPDPVKLLSLCFPVSLNITDGSASADKS-------G
               AY087360       (1)   ------------------------------------------------
               AY096530     (310)   LIALWCESNGIELP-------------QNQG-----------------
               AY125543       (1)   ------------------------------------------------
               AY219234     (298)   LIANWCEINNVKLPDPMKSLSLNQPSLSPDSTQSSGSPRK---------
               BT020206     (302)   FLASWCETNNVYPPDPLELIHSSEPFPLLVESVRASSEN----------
               NM_115336    (300)   MIASWLEANRINLATNSCHQYDGGDASSMANNMGSQDFNR---------
               NM_127878    (292)   LIANWCETNDVKLPDPNKSTSLNELSPLLSCTDSIPSTGADVSARKVSNK
               XM_463544    (268)   LIENWCEVHGIMLPDPVKLLSLCFPVSLNITDGSASADKS-------G
               XM_479734.1  (291)   LIANWCESHNIRIPDPMKSLKLNFPLAASALQDSSTTGSSPLHPTVAAKG
               XM_506432     (53)   AYDAAGADSDMENLTDSVIDFHLSELAATAGPAHPAAVAK---------
               Consensus    (401)   LIA WCE N I  LP
```

Figure 3J

```
Translation of Armadillo ORF      451                                                              500
                            (1)   --------------------------------------------------
             AC010870       (1)   --------------------------------------------------
             AB007645     (338)   --------------------------------------------------
             AB016888     (363)   --------------------------------------------------
             AC004401     (421)   S-----HDWDASSSETGKPSFSSRATEREGASPSRPAASALGASSPGISGN
             AC118613     (340)   -------------TESFRFSLR---SSSLTSRSSLETGNG
             AK118730      (92)   --------------------------------------------------
             AK175585     (367)   --------------------------------------------------
             AL049655     (335)   --------------------------------------------------
             AL133314     (334)   --------------------------------------------------
             AL138650     (304)   -----------TESFRFSLRS---SSLTSRSSLETGNG
             AP003561     (327)   S-----PEHCQLVAALHPKAQCASDDSHHYNLIHENSDSDDRVSSFGDTD
             AY087360       (1)   --------------------------------------------------
             AY096530     (328)   --------------------------------------------------
             AY125543       (1)   --------------------------------------------------
             AY219234     (338)   -----------SLISSTVSQREESSPSHPRSSSEESLPGVGGN
             BT020206     (342)   --------------------------------------------------
             NM_115336    (340)   -----------TESFRFSLRS---SSLTSRSSLETGNG
             NM_127878    (342)   S-----HDWDASSSETGKPSFSSRATEREGASPSRPAASALGASSPGISGN
             XM_463544    (309)   S-----PEHCQLVAALHPKAQCASDDSHHYNLIHENSDSDDRVSSFGDTD
             XM_479734.1  (341)   NIPGSPEADLYMRSLNRASPPHSVVHQNSHAHVNRAGHEASIKQSSENAN
             XM_506432     (93)   --------------------------------------------------
             Consensus   (451)   --------------------------------------------------
```

Figure 3K

```
                              501                                                 550
Translation of Armadillo ORF  (1)   MQMALLARLSLASSEGRESSLEERHAGSD-------EQTSEQSTKEAFQ
                   AC010870   (1)   ----------------------------------------------ME
                   AB007645   (338) ---------------------------------------------GHS
                   AB016888   (363) ------------------------------------------------
                   AC004401   (466) GYGLDARRGSLNDFEDRSNDSRELRTDAPGRSSVSSTTRGSVENGQTSEN
                   AK118613   (364) FEKLKINVSASLCGESQSKDLEIFELLSPG---------------QSY
                   AK118730   (92)  -----SLNSNAS---------------------------------SMK
                   AK175585   (367) ------------------------------------------------
                   AL049655   (335) ------------------------------------------------
                   AL133314   (334) ------------------------------------------------
                   AL138650   (328) FEKLKINVSASLCGESQSKDLEIFELLSPG---------------QSY
                   AP003561   (372) DSEPDSLRLSTETTAANKSLLDEKTDRSDG----LKQLRDNGFQVSDE
                   AY087360   (1)   ----------------------------------------------ME
                   AY096530   (328) ------------------------------------------------
                   AY125543   (1)   ------------------------------------------------
                   AY219234   (370) ILAFDVERMRIKSEDRMAHSGEISSHGHS-----TLVADDQFPLGHN
                   BT020206   (342) ---------------------------------------------GHS
                   NM_115336  (364) FEKLKINVSASLCGESQSKDLEIFELLSPG---------------QSY
                   NM_127878  (387) GYGLDARRGSLNDFEDRSNDSRELRTDAPGRSSVSSTTRGSVENGQTSEN
                   XM_463544  (354) DSEPDSLRLSTETTAANKSLLDEKTDRSDG----LKQLRDNGFQVSDE
                   XM_479734.1 (391) GSASDVSRLSLAGSETRESSLEERNAGSI-------GQTSEQSIEEAFQ
                   XM_506432  (93)  ------------------------------------------------
                   Consensus  (501) ------SSS------------------------------------ANAA
```

Figure 3L

```
                                    551                                                          600
Translation of Armadillo ORF  (43)  ASHFDSDSQVRLGRSSVNDNLPNTRQLDEECDINDGMIRVPGDRTNYSSD
               AC010870        (3)  MENHRPGSFTYMGRKFSDLSLNDDSSAFSDCNSDR---------------
               AB007645      (341)  ESLDAEELRQVFSRSASAPGIVSEVVCKTKRNNN----------------
               AB016888      (363)  -------------KEVSPDSQNEQK-------------------------
               AC004401      (516)  HHHRSPSATSTVSNEEFPRADANENSEESAHATP-----------YSSD
               AK118613      (397)  THSRSESVCSVVSSVDYVPSVTHETESILGNHQS----------------
               AK118730      (102)  EEAFLDISQAFSDFSACSSDISGELQRLACLPSPE---------------
               AK175585      (367)  -------------KEVSPDSQNEQK-------------------------
               AL049655      (335)  ----------SCRTTKIGGSSS--S-------------------------
               AL133314      (334)  ----P-----SSLRPRKVSSFS----------------------------
               AL138650      (361)  THSRSESVCSVVSSVDYVPSVTHETESILGNHQS----------------
               AP003561      (416)  EQYLERNGKSHISSHHQLEVDGENVRVQASSDIN----------------
               AY087360        (3)  MENHRPGSFTYMGRKFSDLSLNDDSSAFSDCNSDR---------------
               AY096530      (328)  ----------SCRTTKIGGSSS----------------------------
               AY125543        (3)  MENHRPGSFTYMGRKFSDLSLNDDSSAFSDCNSDR---------------
               AY219234      (412)  RTTSAPSTLSNSNFSPVIPGDGNKLSEDSSVASG----------------
               BT020206      (345)  ESLDAEELRQVFSRSASAPGIVSEVVCKTKRNNN----------------
               NM_115336     (397)  THSRSESVCSVVSSVDYVPSVTHETESILGNHQS----------------
               NM_127878     (437)  HHHRSPSATSTVSNEEFPRADANENSEESAHATP-----------YSSD
               XM_463544     (398)  EQYLERNGKSHISSHHQLEVDGENVRVQASSDIN----------------
               XM_479734.1   (433)  ASNLDRDSHDHVGSSSVNGSIPNSGQLDAECDNG-------PSERTNYSSD
               XM_506432     (100)  ATEMLELSRDFSDYSSFNSDISGELERLAAAAAA----------------
               Consensus     (551)                    S V            I  E  S
```

Figure 3M

```
Translation of Armadillo ORF
                           601                                                650
AC010870            (93)   ASGEVADRGLSISSAPQRENVI---LPRLGHVCMEGPFVQRQTSDKGFPR
AB007645            (38)   -----SGE--FPTASSESRR------------------------------L
AB016888           (375)   ---AAADRSLTRSNTPWKFP----------------------EERHWRHPG
AC004401           (375)   --------------------------------------------------
AK118613           (554)   ASGEIRSGPLAATTSAATRRDLSDFSPKFMDRRTRGQFWRRP-SERLGSR
AK118730           (431)   ---SSEMSPKKNLESSNN--------------------------VNHEHSAAK
AK175585           (137)   ADRNESGGDNEAEHDPELER-----------------------EPCLGFLQR
AL049655           (379)   --------------------------------------------------
AL133314           (348)   --------------------------------------------------
AL138650           (347)   -----S--------------------------------------------
AP003561           (395)   ----SSEMSPKKNLESSNN-------------------------VNHEHSAAK
AY087360           (450)   AS-EVMQDDPVTTCSKVSDN-----------PPRLGGVRSRNQPNWWRQSNKTIPR
AY096530            (38)   -----SGE--FPTASSESRR------------------------------L
AY125543           (340)   -----S--------------------------------------------
AY219234            (38)   -----SGE--FPTASSESRR------------------------------L
BT020206           (446)   -D-VGLDSKPAASVLPKEPE-----------FPYTPEMRPRNQLIWRR-PTERFPR
NM_115336          (379)   ---AAADRSLTRSNTPWKFP----------------------EERHWRHPG
NM_127878          (431)   ---SSEMSPKKNLESSNN--------------------------VNHEHSAAK
XM_463544          (475)   ASGEIRSGPLAATTSAATRRDLSDFSPKFMDRRTRGQFWRRP-SERLGSR
XM_479734.1        (432)   -ASEVMQDDPVTTCSKVSDN-----------PPRLGGVRSRNQPNWWRQSNKTIPR
XM_506432          (477)   ASGEVTDG-PSASSAPQREHLI---PSRLADVRSRGQFVRRP-SERGFPR
                   (134)   ---VVTPRSDAPQVGAVDLN------------------------------EL
Consensus          (601)                       T                                  R
```

Figure 3N

Translation of Armadillo ORF

```
                    651                                                                    700
AC010870    (140)   IISSLSMDARDDFSAIENQVRELINDLGSDSIEGQRSATSEIRLLAKHNM
AB007645     (52)   LLSCASE----NSDDLINHLVSHLDSSYSIDEQKQAAMEIRLLSKNKP
AB016888    (401)   IIPATVRETGSS-SSIETEVKKLIDDLKSSSLDTQREATARIRLARNST
AC004401    (375)   ----------DEVSLIVEALSSSQLEEQRRSVKQMRLLARENP
AK118613    (603)   IVSAPSNETRRDLSEVETQVKKLVEELKSSSLDTQRQATAEIRLLAKHNM
AK118730    (455)   TYECSVHDLDDSGTMTTSHTIKLVEDLKSGSNKVKTAAAAIKRSAAAKIRLAKNRA
AK175585    (166)   ENFSTEIIECISPEDLQPTVKLCIDGLRSSSVAIKRSAAAKIRLAKNRA
AL049655    (379)   ----------DEVSLIVEALSSSQLEEQRRSVKQMRLLARENP
AL133314    (348)   ----------DCDRTFVLSLIEKLANGTTEQQRAAAGEIRLLAKRNV
AL138650    (348)   ----------PAEANKIEDLMWRLAYGNPEDQRSAAGEIRLLAKRNA
AP003561    (419)   TYECSVHDLDDSGTMTTSHTIKLVEDLKSGSNKVKTAAAAIRHLTINSI
AY003561    (494)   IGLSSSTDSKPDFSGNDAKVRNLIEELKSDSAEVQRSATGEIRTISRHSL
AY087360     (52)   LLSCASE----NSDDLINHLVSHLDSSYSIDEQKQAAMEIRLLSKNKP
AY096530    (341)   ----------DCDRTFVLSLIEKLANGTTEQQRAAAGEIRLLAKRNV
AY125543     (52)   LLSCASE----NSDDLINHLVSHLDSSYSIDEQKQAAMEIRLLSKNKP
AY219234    (488)   IVSSATVERRADLSEVEEQVKKIEELKSTSLDMQRNATAEIRLLAKHNM
BT020206    (405)   IIPATVRETGSS-SSIETEVKKLIDDIKSSSLDTQREATARIRLARNST
NM_115336   (455)   TYECSVHDLDDSGTMTTSHTIKLVEDIKSGSNKVKTAAAAIRHLTINSI
NM_127878   (524)   IVSAPSNETRRDLSEVETQVKKLVEELKSSSLDTQRQATAEIRLLAKHNM
XM_463544   (476)   IGLSSSTDSKPDFSGNDAKVRNLIEELKSDSAEVQRSATGEIRIISRHSL
XM_479734.1 (522)   IISSSSMDTRSDLSAIENQVRKLVDDLRSDSVDVQRSATSDIRLLAKHNM
XM_506432   (153)   ESMDLSVEAAPLERVEPFVLACVRALGPDAAPDARRTAAAIRLLAKHRS
Consensus   (651)           I      S  E  V  LVEDLKS  SLD  QRSAAAEIRLLAK   M
```

Figure 30

```
                              701                                                             750
Translation of Armadillo ORF (190) ENRIAIANCGAINLLIVGLLHSPDAKIQENAVTALLNLSLSDINKIAIVNA
                   AC010870   (96)  ENRIKIAKAGAIKPIISLISSSDLQLQEYGVTAILNLSLCDENKESIASS
                   AB007645  (450)  DNRIVIARCEAIPSIVSLLYSTDERIQADAVTCLLNLSINDNNKSLIAES
                   AB016888  (408)  ENRVLIANAGAIPLLVQLLSYPDSGIQENAVTTLLNLSIDEVNKKLISNE
                   AC004401  (653)  DNRIVIGNSGAIVLLVELLYSTDSATQENAVTALLNLSINDNNKKAIADA
                   AK118613  (505)  ENRVHIGRCGAITPLISLLYSEEKLTQEHAVTALLNLSISELNKAMIVEV
                   AK118730  (216)  ENRVLIGESGAIQALIPLLRCNDPWTQERAVTALLNLSLHDQNKAVIAAG
                   AK175585  (412)  ENRVLIANAGAIPLLVQLLSYPDSGIQENAVTTLLNLSIDEVNKKLISNE
                   AL049655  (385)  DNRVCIAEGAIPLIVELLSSPDPRTQEHSVTALLNLSINEGNKGAIVDA
                   AL133314  (385)  DNRVAIAEAGAIPLIVGLLSTPDSRIQEHSVTALLNLSICENNKGAIVSA
                   AL138650  (469)  ENRVHIGRCGAITPLISLLYSEEKLTQEHAVTALLNLSISELNKAMIVEV
                   AP003561  (544)  ENRIAIANCGAITPLISLLHSTDPSTQENAVTILNLSLCDENKESIASS
                   AY087360   (96)  DNRVCIAEAGAIPLIVELLSSPDPRTQEHSVTALLNLSINEGNKGAIVDA
                   AY096530  (378)  ENRIKIAKAGAIKPIISLISSSDLQLQEYGVTAILNLSLCDENKESIASS
                   AY125543   (96)  ENRIKIAKAGAIKPLISLIISSSDLQLQEYGVTAILNLSLCDENKESIASS
                   AY219234  (538)  DNRMVIANCGAISSIVNLLHSKDMKVQEDAVTALLNLSINDNNKCAIANA
                   BT020206  (454)  DNRIVIARCEAIPSIVSILYSTDERIQADAVTCLLNLSINDNNKSLIAES
                   NM_115336 (505)  ENRVHIGRCGAITPLISLLYSEEKLTQEHAVTALLNLSISELNKAMIVEV
                   NM_127878 (574)  DNRIVIGNSGAIVLLVELLYSTDSATQENAVTALLNLSINDNNKKAIADA
                   XM_463544 (526)  ENRIAIANCGAINLLIVGLPFIVSLLHSTDPSTQENAVTILNLSLDDNNKIAIASA
       XM_479734.1           (572)  ENRIIIANCGAINLLIVGLLHSPDSKTQEHAVTALLNLSINDNNKIAIANA
                   XM_506432 (203)  DIRELIGVSGAIPALVPLLRSTDPVAQESAVTALLNLSLFERNRSAITAA
                   Consensus (701)  ENRI  IA AGAI   LV LLYS D  TQE AVTALLNLSI D NK AIA A
```

Figure 3P

Translation of Armadillo ORF

```
                        751                                                         800
Armadillo ORF    (240)  DAIDPLIHVLETG-NPEAKENSAATLFSLSIIEENRVRIGRS-GAVKPLV
AC010870         (146)  GAIKPLVRALKMG-TPTAKENAACALLRLSQIEENKVAIGRS-GAIPLLV
AB007645         (500)  GAIVPLIHVLKTGYLEEAKANSAATLFSLSVIEEYKTEIGEA-GAIEPLV
AB016888         (458)  GAIPNIIEILENG-NREARENSAAALFSLSMLDENKVTIGLS-NGIPPLV
AC004401         (703)  GAIEPLIHVLENG-SSEAKENSAATLFSLSVIEENKIKIGQS-GAIGPLV
AK118613         (555)  GAVEPLVHVLNTG-NDRAKENSAASLFSLSVLQVNRERIGQSNAATQALV
AK118730         (266)  GAIKSLVWVLKTG-TETSKQNAACALLSLALLEENKGSIGAC-GAIPPLV
AK175585         (462)  GAIPNIIEILENG-NREARENSAAALFSLSMLDENKVTIGLS-NGIPPLV
AL049655         (435)  GAITDIVEVLKNG-SMEARENAAATLFSLSVIDENKVAIGAA-GAIQALI
AL133314         (435)  GAIPGIVQVLKKG-SMEARENAAATLFSLSVIDENKVTIGAL-GAIPPLV
AL138650         (519)  GAIEPLVHVLNTG-NDRAKENSAASLFSLSVLQVNRERIGQSNAAIQALV
AP003561         (594)  EAIEPLIFVLQVG-NPEAKANSAATLFSLSVIEENKIKIGRS-GAIEPLV
AY087360         (146)  GAIKPLVRALKMG-TPTAKDNAACALLRISFLSVIEENKVAIGRS-GAIPLLV
AY096530         (428)  GAITDIVEVLKNG-SMEARENAAATLFSLSVIDENKVAIGAA-GAIQALI
AY125543         (146)  GAIKPLVRALKMG-TPTAKENAACALLRLSQIEENKVAIGRS-GAIPLLV
AY219234         (588)  DAIEPLIHVLQTG-SAEAKENSAATLFSLSVMEENKMKIGRS-GAIKPLV
BT020206         (504)  GAIVPLIHVLKTGYLEEAKANSAATLFSLSVIEEYKTEIGEA-GAIEPLV
NM_115336        (555)  GAIEPLVHVLENG-SSEAKENSAATLFSLSVIEENKIKIGQS-GAIGPLV
NM_127878        (624)  GAIEPLIFVLQVG-NPEAKANSAATLFSLSVIEENKIKIGRS-GAIEPLV
XM_463544        (576)  EAIEPLIFVLQVG-NPEAKANSAATLFSLSVIEENKIKIGRS-GAIEPLV
XM_479734.1      (622)  DAVDPLIHVLETG-NPEAKENSAATLFSLSVIEENKVRIGRS-GAIKPLV
XM_506432        (253)  GAIKPLVYALRTG-TASAKQNAACALLSLSGIEENRATIGAC-GAIPPLV
Consensus        (751)  GAI PLIHVL   G  S EAKENSAATLFSLSVIEENKV IG S  GAI PLV
```

Figure 3Q

```
                              801                                                      850
Translation of Armadillo ORF  (288) DLLGNGSPRGKKDAVTALFNLSILHENKGRIVQADALKHLVELM-DPAAG
                    AC010870  (194) NLLETGGFRAKKDASTALYSLCSAKENKIRAVQSGIMKPLVELMADFGSN
                    AB007645  (549) DLLGSGSLSGKKDAATALFNLSIHHENKTKVIEAGAVRYLVELM-DPAFG
                    AB016888  (506) DLLQHGTLRGKKDALTALFNLSLNSANKGRAIDAGIVQPILNLLKDKNLG
                    AC004401  (751) DLLGNGTPRGKKDAATALFNLSIHQENKAMTVQSGAVRYLIDLM-DPAAG
                    AK118613  (604) NLLGKGTFRGKKDAASALFNLTALYKLCTLQQNKERAVTAGAVKPLVDLVAEEGTG
                    AK118730  (314) SLLLNGSCRGKKDALTALYKLCTLQQNKERAVTAGAVKPIVDLVAEEGTG
                    AK175585  (510) DLLQHGTLRGKKDALTALFNLSLNSANKGRAIDAGIVQPILNLLKDKNLG
                    AL049655  (483) SLLEEGTRRGKKDAATALFNLCIYQGNKSRAVKGGIVDPLTRLLKDAGGG
                    AL133314  (483) VLLNEGTQRGKKDAATALFNLCIYQGNKGKAIRAGVIPTLTRLLTEPGSG
                    AL138650  (568) NLLGKGTPQGKKDAATALFNLSITHDNKARIVQAKVKYLVELL-DPDLE
                    AP003561  (642) DLLGEGTPQGKKDAATAIFNLSIFHEHKTRIVQAGAVNHLVELM-DPAAG
                    AY087360  (194) NLLETGGFRAKKDASTALYSLCSAKENKIRAVQSGIMKPLVELMADFGSN
                    AY096530  (476) SLLEEGTRRGKKDASTALYSLCSAKENKIRAVQSGIMKPLVELMADFGSN
                    AY125543  (194) NLLETGGFRAKKDASTALYSLCSAKENKIRAVQSGIMKPIVELMADFGSN
                    AY219234  (636) DLLGNGTPRGKKDAATALFNLSIHENKSRIIQAEGAVRYIVELM-DPATG
                    BT020206  (553) DLLGSGSLSGKKDAATALFNLSIHHENKTKVIEAGAVRYLVELM-DPAFG
                    NM_115336  (604) NLLGKGTFRGKKDAASALFNLSITHDNKARIVQAKVKYLVELL-DPDLE
                    NM_127878  (672) DLLGNGTPRGKKDAATALFNLSIHQENKAMTVQSGAVRYLIDLM-DPAAG
                    XM_463544  (624) DLLGNGTPQGKKDAATALFNLSIFHEHKTRIVQAGAVNHLVELM-DPAAG
                 XM_479734.1  (670) DLLGNGTPRGKKDAATALFNLSIHENKARIVQADAVKYLVELM-DPAAG
                    XM_506432  (301) ALLSAGSTRGKKDALTTLYRLCSARRNKERAVSAGAVVPLIHIVGERGSG
                    Consensus  (801) DLLG GT RGKKDAATALFNLSI  ENK RIVQAGAVKYLVELM DPAAG
```

Figure 3R

Figure 3S

Translation of Armadillo ORF

```
                            901                                                              950
AC010870            (387)   LQLCTNSSRFCNTVLQEDAVPPLVALSQSG--TPRAREKAQVLLSYFRSQ
AB007645            (294)   LQLCEESVVYRTMVAREGAIPPLVALSQAG--TSRAKQKAEALIELLRQP
AB016888            (648)   LQLCTHSPKFCNNVIREGVLPPLVALTKSG--TARGKEKVLFLFPLLCLV
AC004401            (606)   LELGSNNSSFILAALQFGVYEYLVEITTSG--INRAQRKANALIQLISKS
AK118613            (850)   LQLCTNSPKFCNMVLQEGAVPPLVALSQSG--TPRAREKKPTAWKRWAWL
AK118730            (703)   LQLCSDSVRNRGLLVREGAIPPLVGLSQSGSVSVRAKRKAERLLGYLREP
AK175585            (414)   LELGSNNSSFILAALQFGVYEYLVEITTSG--INRAQRKANALIQLISKS
AL049655            (610)   WYLCIGNIERLNVAREVGADVALKELTENG--TDRAKRKAASLLELIQQT
AL133314            (583)   VHLCSGDPQHLVEAQKLGLMGPLIDIAGNG--TDRGKRKAAQLLERISRL
AL138650            (583)   LQLCTNSNRFCTLVLQEGVVPPLVALSQSG--TQRAKEKVYTIFFFCGYT
AP003561            (667)   LQLCTNSPKFCTLVLQEGAIPPLVALSQAG--TARAREKAQVLLSYFRNQ
AY087360            (741)   LQLCEESVVYRTMVAREGAIPPLVALSQAG--TSRAKQKAEALIELLRQP
AY096530            (294)   WYLCIGNIERLNVAREVGADVALKELTENG--TDRAKRKAASLLELIQQT
AY125543            (576)   LQLCEESVVYRTMVAREGAIPPLVALSQAG--TSRAKQKAEALIELLRQL
AY219234            (294)   LQLCTNSSRFCNMVLQEGAVPPLVALSQSG--TPRAREKAQQLLSYFRNQ
BT020206            (735)   LQLCTHSPKFCNNVIREGVIPPLVALTKSG--TARGKEKAQNLLKYFKAH
NM_115336           (652)   LQLCLNSPKFCTLVLQEGAIPPLVALSQSG--TQRAKEKAQQLLSHFRNQ
NM_127878           (703)   LQLSTNSGRFCNMVLQEGAVPPLVPPLVALSQSG--TPRAREKVQTL----
XM_463544           (771)   LQLCTNSNRFCTIVLQEGVPPLVALSQSG--TARAREKAQVLLSYFRNQ
XM_479734.1         (723)   LQLCTNSSRFCSIVLQEGAVPPLVALSQSG--TPRAREKAQALLSYFRSQ
XM_506432           (769)   LQLCSECPRNRALLVREGAIPPLVALSQSG--SARAKHKAETLLGYLREQ
Consensus           (901)   LQLCTNS RFC LVLQEGAIPPLVALSQSG  T RAKEKAQ LL   LR
```

Figure 3T

```
                                  951                                          980
Translation of Armadillo ORF (435) RHGNSGRR-----------------------------
                  AC010870   (342) RSISNGGARSSSQL----------------------
                  AB007645   (696) NVS---------------------------------
                  AB016888   (654) EQI---------------------------------
                  AC004401   (898) MMDDDDDDVDDAQILVSQCLFLCFVL----------
                  AK118613   (751) RDARMKKGRS--------------------------
                  AK118730   (464) RKEASSSSP---------------------------
                  AK175585   (658) EQI---------------------------------
                  AL049655   (631) EGVAVTTVP---------------------------
                  AL133314   (631) AEQQKETAVSQPEEEAEPTHPESTTEAADT
                  AL138650   (715) KTHQVQFLIDRDI-----------------------
                  AP003561   (789) RHVRVGRG----------------------------
                  AY087360   (342) RSISNGGARSSSQL----------------------
                  AY096530   (624) EGVAVTTVP---------------------------
                  AY125543   (342) RSISNGGARSSSQL----------------------
                  AY219234   (783) RHGNAGRG----------------------------
                  BT020206   (700) RQSNQRRG----------------------------
                  NM_115336  (751) RDARMKKGRS--------------------------
                  NM_127878  (812) RHVRVGRGLSLLLELKRTT-----------------
                  XM_463544  (771) RHGNSARR----------------------------
               XM_479734.1   (817) RQGGGGCRVEPVAASSLAR-----------------
                  XM_506432  (449) R
                  Consensus  (951)
```

Figure 5A

Consensus sequence 1 (Seq ID NO.: 60):
(yellow matches)

RXLAXXXXXRXXIXXXXAIXXLXXXXXXXXQXXXVTXXLNLSXXXXXXNXXIXXXXAIXXXXXLXXGXXX
XXXXNXAXXLXXLXXXXXXIGXXXXXXLXXLLXXGXXXXKKDAXXXXXLXXXXXKXXXXXXXXX
XLXXLXXXXXXXXXXXXXLVEXXXXGXXXXEAXXXLXXLXXXXXX
XXXXXXXXXXXLXXXXGXXXXRXXXXKXX

Consensus sequence 2 (Seq ID NO.: 61):
(yellow and blue matches)

RLLAKXXXENRIXIAXXGAIXXLVXLLXSXDXXTQEXAVTALLNLSIXDXNKXAIAXAGAIXPLXXVLXXGXXXEAK
ENSAATLFSLSVIEENKXXIGXSXGAIXPLVDLLGXGTXRGKKDAATALFNLSIXXENKXRXVQAGAVXXLVELMXD
PXXGMVDKAVAVLANLATXPEGRXAIXXEGGIPXLVEXVELGSXRXKENAAAXLLQLCXNSXXFCXXVLQEGAXPP
LVALSQSGXXTXRAKEKAX

Figure 5B

Consensus sequence_3 (Seq ID NO.: 61):
(yellow, blue, green matches and alternative AA)

RLLAKXXMENRIXIAXAGAIXXLVXLLYSXDXXTQEXAVTALLNLSIXDXNKXAIAXAGAI
 I SR     LD   V GS    L  IHT E       G  I    LE R S S  V
    I     M                S                          G
          V

XPLIHVLXXGXSXEAKENSAATLFSLSVIEENKVXIGXSXGAIXPLVDLLGXGTXRGKKDA
            T   SRD A  S     AMLD  RI   A AGV   I       S  A
                              LM   M
                               I

ATALFNLSIXXENKXXRIVQAGAVKYLVELMXDPAAGMVDKAVAVLANLATVPEGRXAIGX
SS   IY    L D    KVI S MRH ID  V L    IE  SMSLMS  SS I D K  VA
                   G               L                L

EGGIPVLVEVYELGSXRGKENAAAVLLQLCTNSXRFCXLV QEGAIPPLVALSQSGXXTXR
 AV  L    IDV T KAR           SI  V   S     KY I LV   IGIT A  S
                                                  M I       A
                                                    V

AKEKAQ
GR   N

SEQUENCE LISTING

<160> NUMBER OF SEQ ID NOS: 62

<210> SEQ ID NO 1
<211> LENGTH: 1329
<212> TYPE: DNA
<213> ORGANISM: Hordeum vulgare
<220> FEATURE:
<221> NAME/KEY: CDS
<222> LOCATION: (1)..(1329)

<400> SEQUENCE: 1

```
atg caa atg gct ctg cta gca agg ctt tct ctt gca agt tct gaa gga      48
Met Gln Met Ala Leu Leu Ala Arg Leu Ser Leu Ala Ser Ser Glu Gly
1               5                   10                  15 aga gag tct agt ttg gaa gaa aga cat gct ggt tct gat gaa caa act      96
Arg Glu Ser Ser Leu Glu Glu Arg His Ala Gly Ser Asp Glu Gln Thr
            20                  25                  30 tca gaa caa tca acg aag gaa gca ttt caa gca tct cat ttt gac agt     144
Ser Glu Gln Ser Thr Lys Glu Ala Phe Gln Ala Ser His Phe Asp Ser
        35                  40                  45
```

```
gat tca cag gtt cgt cta ggc aga tct tca gtt aat gat aat ctt cct      192
Asp Ser Gln Val Arg Leu Gly Arg Ser Ser Val Asn Asp Asn Leu Pro
 50              55                  60 aat acc cgt cag ctt gac gag gag tgt gac atc aac gat ggg atg ata      240
Asn Thr Arg Gln Leu Asp Glu Glu Cys Asp Ile Asn Asp Gly Met Ile
 65              70                  75                  80 cga gtt cca ggt gat agg aca aat tat agt agt gat gcg tct gga gag      288
Arg Val Pro Gly Asp Arg Thr Asn Tyr Ser Ser Asp Ala Ser Gly Glu
                 85                  90                  95 gtt gct gac cgt ggg ctt tct atc tct tct gcc cct caa agg gaa aat      336
Val Ala Asp Arg Gly Leu Ser Ile Ser Ser Ala Pro Gln Arg Glu Asn
            100                 105                 110 gta atc ctg cca aga ttg ggt cat gtc tgc atg gag gga cca ttt gtt      384
Val Ile Leu Pro Arg Leu Gly His Val Cys Met Glu Gly Pro Phe Val
            115                 120                 125 cag cgg caa aca tct gac aag gga ttc ccg aga ata att tcg tcg tta      432
Gln Arg Gln Thr Ser Asp Lys Gly Phe Pro Arg Ile Ile Ser Ser Leu
130                 135                 140 tcc atg gat gcc cgg gat gat ttc tct gcc atc gag aat cag gta cgc      480
Ser Met Asp Ala Arg Asp Asp Phe Ser Ala Ile Glu Asn Gln Val Arg
145                 150                 155                 160 gag cta atc aat gat ttg gga agt gat tcc ata gaa ggt cag aga tca      528
Glu Leu Ile Asn Asp Leu Gly Ser Asp Ser Ile Glu Gly Gln Arg Ser
                165                 170                 175 gca aca tca gag att cgc ctt cta gct aag cac aac atg gag aac agg      576
Ala Thr Ser Glu Ile Arg Leu Leu Ala Lys His Asn Met Glu Asn Arg
            180                 185                 190 att gcc att gct aat tgt ggg gct ata aac ttg ctg gtt ggc ctt ctt      624
Ile Ala Ile Ala Asn Cys Gly Ala Ile Asn Leu Leu Val Gly Leu Leu
            195                 200                 205 cat tca ccc gat gcc aaa atc caa gaa aat gca gtg aca gcc ctc ctt      672
His Ser Pro Asp Ala Lys Ile Gln Glu Asn Ala Val Thr Ala Leu Leu
            210                 215                 220 aat ttg tca ctc agt gat atc aat aag att gcc atc gtg aat gca gat      720
Asn Leu Ser Leu Ser Asp Ile Asn Lys Ile Ala Ile Val Asn Ala Asp
225                 230                 235                 240 gct att gat cct ctc atc cat gtc ctg gaa aca ggg aac cct gaa gct      768
Ala Ile Asp Pro Leu Ile His Val Leu Glu Thr Gly Asn Pro Glu Ala
                245                 250                 255 aaa gag aat tca gca gct act ttg ttc agt ctc tca att att gaa gaa      816
Lys Glu Asn Ser Ala Ala Thr Leu Phe Ser Leu Ser Ile Ile Glu Glu
            260                 265                 270 aac aga gtg agg ata ggg cga tct ggt gct gta aag cct ctc gtg gac      864
Asn Arg Val Arg Ile Gly Arg Ser Gly Ala Val Lys Pro Leu Val Asp
            275                 280                 285 ttg ctg gga aat ggg agc cca cga gga aag aaa gat gcg gtt act gca      912
Leu Leu Gly Asn Gly Ser Pro Arg Gly Lys Lys Asp Ala Val Thr Ala
            290                 295                 300 ttg ttt aat tta tcc ata ctt cat gag aac aag ggt cga att gtg caa      960
Leu Phe Asn Leu Ser Ile Leu His Glu Asn Lys Gly Arg Ile Val Gln
305                 310                 315                 320 gct gat gca ttg aag cac cta gtt gag ctt atg gac cct gct gct gga     1008
Ala Asp Ala Leu Lys His Leu Val Glu Leu Met Asp Pro Ala Ala Gly
                325                 330                 335 atg gtc gat aaa gct gta gct gtc ttg gca aat ctt gct acg ata cca     1056
Met Val Asp Lys Ala Val Ala Val Leu Ala Asn Leu Ala Thr Ile Pro
            340                 345                 350 gaa gga agg act gcg att ggg cag gcg cgt ggt att ccg gcc ctt gtt     1104
Glu Gly Arg Thr Ala Ile Gly Gln Ala Arg Gly Ile Pro Ala Leu Val
            355                 360                 365
```

```
gaa gtt gtc gaa ctg ggt tca gcg aaa gcg aag gaa aat gct acc gcg      1152
Glu Val Val Glu Leu Gly Ser Ala Lys Ala Lys Glu Asn Ala Thr Ala
370                 375                 380 gca ttg ctt cag cta tgc aca aac agc agc agg ttt tgc aac ata gtt      1200
Ala Leu Leu Gln Leu Cys Thr Asn Ser Ser Arg Phe Cys Asn Ile Val
385                 390                 395                 400 ctt caa gag gat gcc gtg ccc cct tta gtc gca ctg tca cag tca gga      1248
Leu Gln Glu Asp Ala Val Pro Pro Leu Val Ala Leu Ser Gln Ser Gly
                405                 410                 415 aca cca cgc gca aga gaa aag gcg cag gtt ctc ctc agc tat ttc cgc      1296
Thr Pro Arg Ala Arg Glu Lys Ala Gln Val Leu Leu Ser Tyr Phe Arg
            420                 425                 430 agc caa aga cat ggg aac tcg gga agg aga tga                          1329
Ser Gln Arg His Gly Asn Ser Gly Arg Arg
        435                 440

<210> SEQ ID NO 2
<211> LENGTH: 442
<212> TYPE: PRT
<213> ORGANISM: Hordeum vulgare

<400> SEQUENCE: 2

Met Gln Met Ala Leu Leu Ala Arg Leu Ser Leu Ala Ser Ser Glu Gly
1               5                   10                  15

Arg Glu Ser Ser Leu Glu Glu Arg His Ala Gly Ser Asp Glu Gln Thr
                20                  25                  30

Ser Glu Gln Ser Thr Lys Glu Ala Phe Gln Ala Ser His Phe Asp Ser
            35                  40                  45

Asp Ser Gln Val Arg Leu Gly Arg Ser Ser Val Asn Asp Asn Leu Pro
        50                  55                  60

Asn Thr Arg Gln Leu Asp Glu Glu Cys Asp Ile Asn Asp Gly Met Ile
65                  70                  75                  80

Arg Val Pro Gly Asp Arg Thr Asn Tyr Ser Ser Asp Ala Ser Gly Glu
                85                  90                  95

Val Ala Asp Arg Gly Leu Ser Ile Ser Ser Ala Pro Gln Arg Glu Asn
            100                 105                 110

Val Ile Leu Pro Arg Leu Gly His Val Cys Met Glu Gly Pro Phe Val
        115                 120                 125

Gln Arg Gln Thr Ser Asp Lys Gly Phe Pro Arg Ile Ile Ser Ser Leu
130                 135                 140

Ser Met Asp Ala Arg Asp Phe Ser Ala Ile Glu Asn Gln Val Arg
145                 150                 155                 160

Glu Leu Ile Asn Asp Leu Gly Ser Asp Ser Ile Glu Gly Gln Arg Ser
                165                 170                 175

Ala Thr Ser Glu Ile Arg Leu Leu Ala Lys His Asn Met Glu Asn Arg
            180                 185                 190

Ile Ala Ile Ala Asn Cys Gly Ala Ile Asn Leu Leu Val Gly Leu Leu
        195                 200                 205

His Ser Pro Asp Ala Lys Ile Gln Glu Asn Ala Val Thr Ala Leu Leu
210                 215                 220

Asn Leu Ser Leu Ser Asp Ile Asn Lys Ile Ala Ile Val Asn Ala Asp
225                 230                 235                 240

Ala Ile Asp Pro Leu Ile His Val Leu Glu Thr Gly Asn Pro Glu Ala
                245                 250                 255

Lys Glu Asn Ser Ala Ala Thr Leu Phe Ser Leu Ser Ile Ile Glu Glu
            260                 265                 270
```

```
Asn Arg Val Arg Ile Gly Arg Ser Gly Ala Val Lys Pro Leu Val Asp
        275                 280                 285

Leu Leu Gly Asn Gly Ser Pro Arg Gly Lys Lys Asp Ala Val Thr Ala
        290                 295                 300

Leu Phe Asn Leu Ser Ile Leu His Glu Asn Lys Gly Arg Ile Val Gln
305                 310                 315                 320

Ala Asp Ala Leu Lys His Leu Val Glu Leu Met Asp Pro Ala Ala Gly
                325                 330                 335

Met Val Asp Lys Ala Val Ala Val Leu Ala Asn Leu Ala Thr Ile Pro
                340                 345                 350

Glu Gly Arg Thr Ala Ile Gly Gln Ala Arg Gly Ile Pro Ala Leu Val
                355                 360                 365

Glu Val Val Glu Leu Gly Ser Ala Lys Ala Lys Glu Asn Ala Thr Ala
        370                 375                 380

Ala Leu Leu Gln Leu Cys Thr Asn Ser Ser Arg Phe Cys Asn Ile Val
385                 390                 395                 400

Leu Gln Glu Asp Ala Val Pro Pro Leu Val Ala Leu Ser Gln Ser Gly
                405                 410                 415

Thr Pro Arg Ala Arg Glu Lys Ala Gln Val Leu Leu Ser Tyr Phe Arg
                420                 425                 430

Ser Gln Arg His Gly Asn Ser Gly Arg Arg
        435                 440

<210> SEQ ID NO 3
<211> LENGTH: 2475
<212> TYPE: DNA
<213> ORGANISM: Oryza sativa
<220> FEATURE:
<221> NAME/KEY: CDS
<222> LOCATION: (1)..(2475)

<400> SEQUENCE: 3 atg gaa aat ttc tcc ccg aga acc ctg ctc aat agt atc ttg cgt atc      48
Met Glu Asn Phe Ser Pro Arg Thr Leu Leu Asn Ser Ile Leu Arg Ile
1               5                   10                  15 act gtc tta acc tcc gat ggc tct act gca agg ccc aag ccc att cag      96
Thr Val Leu Thr Ser Asp Gly Ser Thr Ala Arg Pro Lys Pro Ile Gln
            20                  25                  30 aag tac tgc caa aat gtg tgt gat atc tca agc att gtg agc cct ctc     144
Lys Tyr Cys Gln Asn Val Cys Asp Ile Ser Ser Ile Val Ser Pro Leu
        35                  40                  45 ata gag gat cta tgt gag tct cct gaa gag caa ctc aat gag gtg tta     192
Ile Glu Asp Leu Cys Glu Ser Pro Glu Glu Gln Leu Asn Glu Val Leu
    50                  55                  60 agg gag ctt ggc act gct att aac aga gct tca ggg ctt att ggg aac     240
Arg Glu Leu Gly Thr Ala Ile Asn Arg Ala Ser Gly Leu Ile Gly Asn
65                  70                  75                  80 tgg caa cag aca acc agc aaa ata tat ttt ata tgg cag att gaa tca     288
Trp Gln Gln Thr Thr Ser Lys Ile Tyr Phe Ile Trp Gln Ile Glu Ser
                85                  90                  95 gta atc tca gat atc cag gga tgt tct cta cag ctg tgc cag ctt gtt     336
Val Ile Ser Asp Ile Gln Gly Cys Ser Leu Gln Leu Cys Gln Leu Val
            100                 105                 110 aac tct cta tta cct tct ttg act ggc cgt gca tgc aca tgt att gag     384
Asn Ser Leu Leu Pro Ser Leu Thr Gly Arg Ala Cys Thr Cys Ile Glu
        115                 120                 125 aaa ctc caa gac ata aat tat gaa aac atg ttt gat ctg gta aag gag     432
Lys Leu Gln Asp Ile Asn Tyr Glu Asn Met Phe Asp Leu Val Lys Glu
    130                 135                 140
```

```
tct tca ttg gag cta gtt gag acg gac aca aca agt cct gag aat ctg      480
Ser Ser Leu Glu Leu Val Glu Thr Asp Thr Thr Ser Pro Glu Asn Leu
145                 150                 155                 160 tcg aga cta tct agt tca ttg agt ttg tca act aac ctg gaa ttt tac      528
Ser Arg Leu Ser Ser Ser Leu Ser Leu Ser Thr Asn Leu Glu Phe Tyr
                165                 170                 175 atg gaa gct gtt tcc ctt gag aat ctc aga gca agg gca atg cgg agt      576
Met Glu Ala Val Ser Leu Glu Asn Leu Arg Ala Arg Ala Met Arg Ser
            180                 185                 190 gag aac cgt gaa gaa atg gat ctg gct gac aag atg atc ccc ctg gtc      624
Glu Asn Arg Glu Glu Met Asp Leu Ala Asp Lys Met Ile Pro Leu Val
        195                 200                 205 aac tat atg cat gac cac ctt ctg agg gaa aca caa ctg ctt agc atc      672
Asn Tyr Met His Asp His Leu Leu Arg Glu Thr Gln Leu Leu Ser Ile
    210                 215                 220 aat ggg gtg ccc att cct gca gat ttt tgc tgc ccg ctg tcc cta gag      720
Asn Gly Val Pro Ile Pro Ala Asp Phe Cys Cys Pro Leu Ser Leu Glu
225                 230                 235                 240 ctg atg tca gat cct gtt att gta gca tct ggt cag aca tat gag cgg      768
Leu Met Ser Asp Pro Val Ile Val Ala Ser Gly Gln Thr Tyr Glu Arg
                245                 250                 255 gtt tat atc aag tta tgg ctt gat gag ggt ttt act atc tgc ccg aag      816
Val Tyr Ile Lys Leu Trp Leu Asp Glu Gly Phe Thr Ile Cys Pro Lys
            260                 265                 270 aca cgc caa aga ctt ggt cac tcc aat tta att cca aat tac acc gtg      864
Thr Arg Gln Arg Leu Gly His Ser Asn Leu Ile Pro Asn Tyr Thr Val
        275                 280                 285 aaa gct ttg ata gct aat tgg tgc gaa tca cac aac att agg ctt cct      912
Lys Ala Leu Ile Ala Asn Trp Cys Glu Ser His Asn Ile Arg Leu Pro
    290                 295                 300 gat cct atg aaa tcc ttg aaa ttg aac ttc cct ttg gct gcg tct gct      960
Asp Pro Met Lys Ser Leu Lys Leu Asn Phe Pro Leu Ala Ala Ser Ala
305                 310                 315                 320 ctc cag gat tcg agc acc aca gga agc agc cct cta cat cct act gtc     1008
Leu Gln Asp Ser Ser Thr Thr Gly Ser Ser Pro Leu His Pro Thr Val
                325                 330                 335 gct gct aag ggt aat att cct ggg tcc ccg gaa gct gac ctt tat atg     1056
Ala Ala Lys Gly Asn Ile Pro Gly Ser Pro Glu Ala Asp Leu Tyr Met
            340                 345                 350 aga agc ttg aat aga gca tct cct cca cac agt gta gtc cat cag aat     1104
Arg Ser Leu Asn Arg Ala Ser Pro Pro His Ser Val Val His Gln Asn
        355                 360                 365 tct cat gcg cat gtg aac cgt gct ggt cat gaa gcc tcc att aag caa     1152
Ser His Ala His Val Asn Arg Ala Gly His Glu Ala Ser Ile Lys Gln
    370                 375                 380 tct tca gaa aat gct aat ggt tct gca tca gat gtt tca agg tta tct     1200
Ser Ser Glu Asn Ala Asn Gly Ser Ala Ser Asp Val Ser Arg Leu Ser
385                 390                 395                 400 ctt gca ggt tct gaa aca aga gag tct agt ctg gaa gaa aga aat gct     1248
Leu Ala Gly Ser Glu Thr Arg Glu Ser Ser Leu Glu Glu Arg Asn Ala
                405                 410                 415 ggt tct atc ggt caa act tca gaa cag tca att gag gaa gca ttt caa     1296
Gly Ser Ile Gly Gln Thr Ser Glu Gln Ser Ile Glu Glu Ala Phe Gln
            420                 425                 430 gca tct aat ttg gac agg gat tca cat gac cat gtg ggt agt tct tcg     1344
Ala Ser Asn Leu Asp Arg Asp Ser His Asp His Val Gly Ser Ser Ser
        435                 440                 445 gtg aat ggt agc ctt cca aat agc ggt caa ctt gat gca gaa tgt gac     1392
Val Asn Gly Ser Leu Pro Asn Ser Gly Gln Leu Asp Ala Glu Cys Asp
    450                 455                 460
```

```
aat ggg cca agc gaa agg aca aat tac agt agt gat gca tct gga gaa    1440
Asn Gly Pro Ser Glu Arg Thr Asn Tyr Ser Ser Asp Ala Ser Gly Glu
465             470                 475                 480 gtt aca gat ggg cct tca gca tct tct gct cct cag agg gag cat cta    1488
Val Thr Asp Gly Pro Ser Ala Ser Ser Ala Pro Gln Arg Glu His Leu
                485                 490                 495 atc cct tct aga ttg gct gat gtt cgt agt aga ggc caa ttt gtt cgg    1536
Ile Pro Ser Arg Leu Ala Asp Val Arg Ser Arg Gly Gln Phe Val Arg
        500                 505                 510 cga cca tct gaa agg ggt ttc ccc aga ata ata tct tcc tca tcc atg    1584
Arg Pro Ser Glu Arg Gly Phe Pro Arg Ile Ile Ser Ser Ser Ser Met
    515                 520                 525 gat aca cgg agt gat ctt tcc gcc atc gag aat cag gtc cgc aag tta    1632
Asp Thr Arg Ser Asp Leu Ser Ala Ile Glu Asn Gln Val Arg Lys Leu
530                 535                 540 gtt gat gat tta aga agt gat tct gta gat gtt caa aga tca gcg aca    1680
Val Asp Asp Leu Arg Ser Asp Ser Val Asp Val Gln Arg Ser Ala Thr
545             550                 555                 560 tca gat atc cgc ctt tta gct aag cac aac atg gag aac agg atc atc    1728
Ser Asp Ile Arg Leu Leu Ala Lys His Asn Met Glu Asn Arg Ile Ile
                565                 570                 575 att gca aac tgt gga gct ata aac ttg ctg gtt ggt ctt ctt cat tcg    1776
Ile Ala Asn Cys Gly Ala Ile Asn Leu Leu Val Gly Leu Leu His Ser
            580                 585                 590 cca gat tcc aaa acc caa gag cat gcc gtg aca gcc ctt ctg aat ttg    1824
Pro Asp Ser Lys Thr Gln Glu His Ala Val Thr Ala Leu Leu Asn Leu
        595                 600                 605 tca atc aat gat aat aat aag att gcc att gca aat gct gat gct gtt    1872
Ser Ile Asn Asp Asn Asn Lys Ile Ala Ile Ala Asn Ala Asp Ala Val
    610                 615                 620 gac ccc ctc atc cat gtc ctt gag act ggg aac cct gaa gcc aag gag    1920
Asp Pro Leu Ile His Val Leu Glu Thr Gly Asn Pro Glu Ala Lys Glu
625                 630                 635                 640 aat tca gcg gct aca tta ttc agt ctc tcg gtt att gaa gaa aac aaa    1968
Asn Ser Ala Ala Thr Leu Phe Ser Leu Ser Val Ile Glu Glu Asn Lys
                645                 650                 655 gtg agg att gga aga tcc ggt gcc atc aaa cct ctc gtc gac cta cta    2016
Val Arg Ile Gly Arg Ser Gly Ala Ile Lys Pro Leu Val Asp Leu Leu
            660                 665                 670 gga aat ggg acc cct cga gga aag aaa gat gca gct act gca ttg ttt    2064
Gly Asn Gly Thr Pro Arg Gly Lys Lys Asp Ala Ala Thr Ala Leu Phe
        675                 680                 685 aat tta tcc ata tta cat gag aac aag gcg cgt att gtg cag gct gac    2112
Asn Leu Ser Ile Leu His Glu Asn Lys Ala Arg Ile Val Gln Ala Asp
    690                 695                 700 gct gtg aag tac cta gtt gaa ctt atg gac cct gct gct gga atg gtt    2160
Ala Val Lys Tyr Leu Val Glu Leu Met Asp Pro Ala Ala Gly Met Val
705                 710                 715                 720 gac aaa gct gtg gct gtt ttg gca aac ctt gct acc ata cca gaa ggg    2208
Asp Lys Ala Val Ala Val Leu Ala Asn Leu Ala Thr Ile Pro Glu Gly
                725                 730                 735 agg aca gca att ggt caa gcg cgt ggt att cca gcc ctt gtt gaa gtt    2256
Arg Thr Ala Ile Gly Gln Ala Arg Gly Ile Pro Ala Leu Val Glu Val
            740                 745                 750 gtt gaa ctc ggt tca gca agg ggg aag gaa aat gcg gct gca gca ttg    2304
Val Glu Leu Gly Ser Ala Arg Gly Lys Glu Asn Ala Ala Ala Ala Leu
        755                 760                 765 ctt cag cta tgt aca aac agc agc aga ttt tgc agt ata gtt ctt caa    2352
Leu Gln Leu Cys Thr Asn Ser Ser Arg Phe Cys Ser Ile Val Leu Gln
    770                 775                 780
```

-continued

```
gag ggt gct gtg cct cct cta gtt gca ttg tca cag tca ggc acg cca      2400
Glu Gly Ala Val Pro Pro Leu Val Ala Leu Ser Gln Ser Gly Thr Pro
785                 790                 795                 800 cgg gca aga gag aag gca cag gct ctt ctc agc tac ttt cgc agc caa      2448
Arg Ala Arg Glu Lys Ala Gln Ala Leu Leu Ser Tyr Phe Arg Ser Gln
                805                 810                 815 agg cac ggg aat tca gca agg aga tga                                  2475
Arg His Gly Asn Ser Ala Arg Arg
                820
```

<210> SEQ ID NO 4
<211> LENGTH: 824
<212> TYPE: PRT
<213> ORGANISM: Oryza sativa

<400> SEQUENCE: 4

```
Met Glu Asn Phe Ser Pro Arg Thr Leu Leu Asn Ser Ile Leu Arg Ile
1               5                   10                  15

Thr Val Leu Thr Ser Asp Gly Ser Thr Ala Arg Pro Lys Pro Ile Gln
            20                  25                  30

Lys Tyr Cys Gln Asn Val Cys Asp Ile Ser Ser Ile Val Ser Pro Leu
        35                  40                  45

Ile Glu Asp Leu Cys Glu Ser Pro Glu Glu Gln Leu Asn Glu Val Leu
    50                  55                  60

Arg Glu Leu Gly Thr Ala Ile Asn Arg Ala Ser Gly Leu Ile Gly Asn
65                  70                  75                  80

Trp Gln Gln Thr Thr Ser Lys Ile Tyr Phe Ile Trp Gln Ile Glu Ser
                85                  90                  95

Val Ile Ser Asp Ile Gln Gly Cys Ser Leu Gln Leu Cys Gln Leu Val
            100                 105                 110

Asn Ser Leu Leu Pro Ser Leu Thr Gly Arg Ala Cys Thr Cys Ile Glu
        115                 120                 125

Lys Leu Gln Asp Ile Asn Tyr Glu Asn Met Phe Asp Leu Val Lys Glu
    130                 135                 140

Ser Ser Leu Glu Leu Val Glu Thr Asp Thr Thr Ser Pro Glu Asn Leu
145                 150                 155                 160

Ser Arg Leu Ser Ser Ser Leu Ser Leu Ser Thr Asn Leu Glu Phe Tyr
                165                 170                 175

Met Glu Ala Val Ser Leu Glu Asn Leu Arg Ala Arg Ala Met Arg Ser
            180                 185                 190

Glu Asn Arg Glu Glu Met Asp Leu Ala Asp Lys Met Ile Pro Leu Val
        195                 200                 205

Asn Tyr Met His Asp His Leu Leu Arg Glu Thr Gln Leu Leu Ser Ile
    210                 215                 220

Asn Gly Val Pro Ile Pro Ala Asp Phe Cys Cys Pro Leu Ser Leu Glu
225                 230                 235                 240

Leu Met Ser Asp Pro Val Ile Val Ala Ser Gly Gln Thr Tyr Glu Arg
                245                 250                 255

Val Tyr Ile Lys Leu Trp Leu Asp Glu Gly Phe Thr Ile Cys Pro Lys
            260                 265                 270

Thr Arg Gln Arg Leu Gly His Ser Asn Leu Ile Pro Asn Tyr Thr Val
        275                 280                 285

Lys Ala Leu Ile Ala Asn Trp Cys Glu Ser His Asn Ile Arg Leu Pro
    290                 295                 300

Asp Pro Met Lys Ser Leu Lys Leu Asn Phe Pro Leu Ala Ala Ser Ala
305                 310                 315                 320
```

```
Leu Gln Asp Ser Ser Thr Thr Gly Ser Ser Pro Leu His Pro Thr Val
            325                 330                 335

Ala Ala Lys Gly Asn Ile Pro Gly Ser Pro Glu Ala Asp Leu Tyr Met
            340                 345                 350

Arg Ser Leu Asn Arg Ala Ser Pro Pro His Ser Val Val His Gln Asn
            355                 360                 365

Ser His Ala His Val Asn Arg Ala Gly His Glu Ala Ser Ile Lys Gln
            370                 375                 380

Ser Ser Glu Asn Ala Asn Gly Ser Ala Ser Asp Val Ser Arg Leu Ser
385                 390                 395                 400

Leu Ala Gly Ser Glu Thr Arg Glu Ser Leu Glu Glu Arg Asn Ala
            405                 410                 415

Gly Ser Ile Gly Gln Thr Ser Glu Gln Ser Ile Glu Glu Ala Phe Gln
            420                 425                 430

Ala Ser Asn Leu Asp Arg Asp Ser His Asp His Val Gly Ser Ser Ser
            435                 440                 445

Val Asn Gly Ser Leu Pro Asn Ser Gly Gln Leu Asp Ala Glu Cys Asp
            450                 455                 460

Asn Gly Pro Ser Glu Arg Thr Asn Tyr Ser Ser Asp Ala Ser Gly Glu
465                 470                 475                 480

Val Thr Asp Gly Pro Ser Ala Ser Ser Ala Pro Gln Arg Glu His Leu
            485                 490                 495

Ile Pro Ser Arg Leu Ala Asp Val Arg Ser Arg Gly Gln Phe Val Arg
            500                 505                 510

Arg Pro Ser Glu Arg Gly Phe Pro Arg Ile Ile Ser Ser Ser Ser Met
            515                 520                 525

Asp Thr Arg Ser Asp Leu Ser Ala Ile Glu Asn Gln Val Arg Lys Leu
            530                 535                 540

Val Asp Asp Leu Arg Ser Asp Ser Val Asp Val Gln Arg Ser Ala Thr
545                 550                 555                 560

Ser Asp Ile Arg Leu Leu Ala Lys His Asn Met Glu Asn Arg Ile Ile
            565                 570                 575

Ile Ala Asn Cys Gly Ala Ile Asn Leu Leu Val Gly Leu Leu His Ser
            580                 585                 590

Pro Asp Ser Lys Thr Gln Glu His Ala Val Thr Ala Leu Leu Asn Leu
            595                 600                 605

Ser Ile Asn Asp Asn Asn Lys Ile Ala Ile Ala Asn Ala Asp Ala Val
            610                 615                 620

Asp Pro Leu Ile His Val Leu Glu Thr Gly Asn Pro Glu Ala Lys Glu
625                 630                 635                 640

Asn Ser Ala Ala Thr Leu Phe Ser Leu Ser Val Ile Glu Glu Asn Lys
            645                 650                 655

Val Arg Ile Gly Arg Ser Gly Ala Ile Lys Pro Leu Val Asp Leu Leu
            660                 665                 670

Gly Asn Gly Thr Pro Arg Gly Lys Lys Asp Ala Ala Thr Ala Leu Phe
            675                 680                 685

Asn Leu Ser Ile Leu His Glu Asn Lys Ala Arg Ile Val Gln Ala Asp
            690                 695                 700

Ala Val Lys Tyr Leu Val Glu Leu Met Asp Pro Ala Ala Gly Met Val
705                 710                 715                 720

Asp Lys Ala Val Ala Val Leu Ala Asn Leu Ala Thr Ile Pro Glu Gly
            725                 730                 735

Arg Thr Ala Ile Gly Gln Ala Arg Gly Ile Pro Ala Leu Val Glu Val
            740                 745                 750
```

```
Val Glu Leu Gly Ser Ala Arg Gly Lys Glu Asn Ala Ala Ala Leu
        755                 760                 765

Leu Gln Leu Cys Thr Asn Ser Ser Arg Phe Cys Ser Ile Val Leu Gln
770                 775                 780

Glu Gly Ala Val Pro Leu Val Ala Leu Ser Gln Ser Gly Thr Pro
785                 790                 795                 800

Arg Ala Arg Glu Lys Ala Gln Ala Leu Leu Ser Tyr Phe Arg Ser Gln
                805                 810                 815

Arg His Gly Asn Ser Ala Arg Arg
            820

<210> SEQ ID NO 5
<211> LENGTH: 2370
<212> TYPE: DNA
<213> ORGANISM: Oryza sativa
<220> FEATURE:
<221> NAME/KEY: CDS
<222> LOCATION: (1)..(2370)

<400> SEQUENCE: 5
```

| | | | | | | | | | | | | | | | | |
|---|---|---|---|---|---|---|---|---|---|---|---|---|---|---|---|---|
| atg | gcg | ttt | gtt | tgt | ggt | ggt | ggg | caa | gtg | atg | gat | tca | gtg | tca | ttg | 48 |
| Met | Ala | Phe | Val | Cys | Gly | Gly | Gly | Gln | Val | Met | Asp | Ser | Val | Ser | Leu | |
| 1 | | | | 5 | | | | | 10 | | | | | 15 | | |
| tca | cta | ctc | gat | agt | att | tca | aat | ttc | cgg | gtg | ctg | tct | tca | agc | aat | 96 |
| Ser | Leu | Leu | Asp | Ser | Ile | Ser | Asn | Phe | Arg | Val | Leu | Ser | Ser | Ser | Asn | |
| | | | 20 | | | | | 25 | | | | | 30 | | | |
| gcc | tcg | aaa | aca | gag | cta | gtt | aag | aaa | tat | tgc | caa | acg | atg | gat | ggc | 144 |
| Ala | Ser | Lys | Thr | Glu | Leu | Val | Lys | Lys | Tyr | Cys | Gln | Thr | Met | Asp | Gly | |
| | 35 | | | | | 40 | | | | | 45 | | | | | |
| atc | ctt | gat | cac | ttg | gag | gtg | gcc | cta | aac | aga | gct | ttt | cct | cag | att | 192 |
| Ile | Leu | Asp | His | Leu | Glu | Val | Ala | Leu | Asn | Arg | Ala | Phe | Pro | Gln | Ile | |
| 50 | | | | | 55 | | | | | 60 | | | | | | |
| act | cca | gat | ggt | gaa | cta | agt | aaa | gtt | att | cag | gct | gat | tca | att | att | 240 |
| Thr | Pro | Asp | Gly | Glu | Leu | Ser | Lys | Val | Ile | Gln | Ala | Asp | Ser | Ile | Ile | |
| 65 | | | | 70 | | | | | 75 | | | | | 80 | | |
| gcc | aag | atg | cag | ata | tat | gta | ttc | gaa | tta | tgc | caa | att | gtc | aat | tct | 288 |
| Ala | Lys | Met | Gln | Ile | Tyr | Val | Phe | Glu | Leu | Cys | Gln | Ile | Val | Asn | Ser | |
| | | | | 85 | | | | | 90 | | | | | 95 | | |
| ctc | atg | cag | att | gag | tca | atg | cat | ttg | gag | gat | ctt | gaa | cac | gat | agc | 336 |
| Leu | Met | Gln | Ile | Glu | Ser | Met | His | Leu | Glu | Asp | Leu | Glu | His | Asp | Ser | |
| | | | | 100 | | | | | 105 | | | | | 110 | | |
| tgt | gga | aaa | att | tca | gat | gtc | att | agg | gag | gct | tcc | agg | gct | tta | gca | 384 |
| Cys | Gly | Lys | Ile | Ser | Asp | Val | Ile | Arg | Glu | Ala | Ser | Arg | Ala | Leu | Ala | |
| | | 115 | | | | | 120 | | | | | 125 | | | | |
| ggg | gaa | gtt | atg | cca | aat | tca | gag | gaa | ttt | gga | aag | att | caa | act | act | 432 |
| Gly | Glu | Val | Met | Pro | Asn | Ser | Glu | Glu | Phe | Gly | Lys | Ile | Gln | Thr | Thr | |
| 130 | | | | | 135 | | | | | 140 | | | | | | |
| ttg | agc | tta | tcc | aca | aat | cag | gag | ttg | ctg | atg | gaa | tat | gtt | gca | ctt | 480 |
| Leu | Ser | Leu | Ser | Thr | Asn | Gln | Glu | Leu | Leu | Met | Glu | Tyr | Val | Ala | Leu | |
| 145 | | | | | 150 | | | | | 155 | | | | | 160 | |
| gtt | aag | gtt | aaa | aca | aaa | ggt | aat | cat | gaa | gat | aac | aaa | gaa | atg | gat | 528 |
| Val | Lys | Val | Lys | Thr | Lys | Gly | Asn | His | Glu | Asp | Asn | Lys | Glu | Met | Asp | |
| | | | | 165 | | | | | 170 | | | | | 175 | | |
| gat | att | aac | gat | att | gtt | gaa | tta | gtc | aac | cat | atg | ctt | gac | aaa | cat | 576 |
| Asp | Ile | Asn | Asp | Ile | Val | Glu | Leu | Val | Asn | His | Met | Leu | Asp | Lys | His | |
| | | | 180 | | | | | 185 | | | | | 190 | | | |
| gtg | gaa | gaa | aag | caa | aca | cgt | agc | att | aat | gga | gtg | acc | att | cct | gct | 624 |
| Val | Glu | Glu | Lys | Gln | Thr | Arg | Ser | Ile | Asn | Gly | Val | Thr | Ile | Pro | Ala | |
| | 195 | | | | | 200 | | | | | 205 | | | | | |
| gat | ttt | tgt | tgt | cct | ctt | tcc | ctt | gaa | cta | atg | tcg | gat | cca | gtg | att | 672 |

```
              Asp Phe Cys Cys Pro Leu Ser Leu Glu Leu Met Ser Asp Pro Val Ile
                  210                 215                 220 gtg gca tct ggt caa acg tat gag cat gtt ttt atc aga aaa tgg ttt          720
Val Ala Ser Gly Gln Thr Tyr Glu His Val Phe Ile Arg Lys Trp Phe
225                 230                 235                 240 gat ctg gga tac aac att tgt cca aag aca cgc caa ata ttg gga cac          768
Asp Leu Gly Tyr Asn Ile Cys Pro Lys Thr Arg Gln Ile Leu Gly His
                245                 250                 255 acc aaa ttg att cct aac ttc act gtc aaa cag ttg att gaa aat tgg          816
Thr Lys Leu Ile Pro Asn Phe Thr Val Lys Gln Leu Ile Glu Asn Trp
            260                 265                 270 tgt gag gta cat ggt ata atg cta cca gat cct gtt aaa ctc ttg agt          864
Cys Glu Val His Gly Ile Met Leu Pro Asp Pro Val Lys Leu Leu Ser
        275                 280                 285 ttg tgc ttc cct gtt tcc ctc aac atc aca gat gga agt gca agt gca          912
Leu Cys Phe Pro Val Ser Leu Asn Ile Thr Asp Gly Ser Ala Ser Ala
    290                 295                 300 gac aag tct gga tca cca gaa cac tgc caa ttg gta gct gca ttg cat          960
Asp Lys Ser Gly Ser Pro Glu His Cys Gln Leu Val Ala Ala Leu His
305                 310                 315                 320 cca aaa gca cag tgc gca tcg gat gat agt cat cat tat aat ttg ata        1008
Pro Lys Ala Gln Cys Ala Ser Asp Asp Ser His His Tyr Asn Leu Ile
                325                 330                 335 cat gaa aac tct gat tca gat gat aga gtg tca tca ttt gga gac aca        1056
His Glu Asn Ser Asp Ser Asp Asp Arg Val Ser Ser Phe Gly Asp Thr
            340                 345                 350 gat gat tct gaa cct gat tct tta aga tta tca aca gaa act act gca        1104
Asp Asp Ser Glu Pro Asp Ser Leu Arg Leu Ser Thr Glu Thr Thr Ala
        355                 360                 365 gca aac aaa tct cta ctt gat gaa aaa act gat cgt tct gat ggt ctt        1152
Ala Asn Lys Ser Leu Leu Asp Glu Lys Thr Asp Arg Ser Asp Gly Leu
    370                 375                 380 aag caa ttg aga gac aat ggt ttt caa gtt tct gat gag gaa cag tat        1200
Lys Gln Leu Arg Asp Asn Gly Phe Gln Val Ser Asp Glu Glu Gln Tyr
385                 390                 395                 400 ctc gaa agg aat ggt aaa agt cat atc agc agc cat cat caa ctt gaa        1248
Leu Glu Arg Asn Gly Lys Ser His Ile Ser Ser His His Gln Leu Glu
                405                 410                 415 gtt gat gga gag aat gtc agg gta caa gca tca agt gac atc aat gca        1296
Val Asp Gly Glu Asn Val Arg Val Gln Ala Ser Ser Asp Ile Asn Ala
            420                 425                 430 tct gaa gtt atg caa gat gat ccg gtc acc aca tgt tca aag gta tca        1344
Ser Glu Val Met Gln Asp Asp Pro Val Thr Thr Cys Ser Lys Val Ser
        435                 440                 445 gat aac cct cct aga ttg ggt ggt gtt cgt tct cga aat cag cca aac        1392
Asp Asn Pro Pro Arg Leu Gly Gly Val Arg Ser Arg Asn Gln Pro Asn
    450                 455                 460 tgg tgg aga cag tct aat aaa act att cct agg atc gga ttg tca tct        1440
Trp Trp Arg Gln Ser Asn Lys Thr Ile Pro Arg Ile Gly Leu Ser Ser
465                 470                 475                 480 tcg aca gat tca aaa cca gat ttt tct ggc aat gat gct aaa gtg cgt        1488
Ser Thr Asp Ser Lys Pro Asp Phe Ser Gly Asn Asp Ala Lys Val Arg
                485                 490                 495 aat ctt atc gag gaa ctg aaa agt gat tct gct gag gtc caa agg tca        1536
Asn Leu Ile Glu Glu Leu Lys Ser Asp Ser Ala Glu Val Gln Arg Ser
            500                 505                 510 gca aca gga gag ctc cgc att ctt tct aga cac agc ttg gag aat aga        1584
Ala Thr Gly Glu Leu Arg Ile Leu Ser Arg His Ser Leu Glu Asn Arg
        515                 520                 525 att gcc atc gca aac tgc gga gca atc ccc ttc ttg gtg agt cta ctt        1632
```

| | | | | | | | | | | | | |
|---|---|---|---|---|---|---|---|---|---|---|---|---|
|Ile|Ala|Ile|Ala|Asn|Cys|Gly|Ala|Ile|Pro|Phe|Leu|Val|Ser|Leu|Leu|
| |530| | | |535| | | |540| | | |

```
cat tct aca gac ccc agc aca caa gaa aat gct gtg aca att ctc ctg     1680
His Ser Thr Asp Pro Ser Thr Gln Glu Asn Ala Val Thr Ile Leu Leu
545                 550                 555                 560 aat ttg tca ttg gat gac aat aac aag att gcc ata gca agt gct gag     1728
Asn Leu Ser Leu Asp Asp Asn Asn Lys Ile Ala Ile Ala Ser Ala Glu
                565                 570                 575 gcc att gag cct ctc atc ttc gtt ctt cag gtg gga aac ccc gaa gcg     1776
Ala Ile Glu Pro Leu Ile Phe Val Leu Gln Val Gly Asn Pro Glu Ala
            580                 585                 590 aaa gcc aac tca gct gca act tta ttc agc ctc tca gtc att gaa gag     1824
Lys Ala Asn Ser Ala Ala Thr Leu Phe Ser Leu Ser Val Ile Glu Glu
        595                 600                 605 aac aag atc aag att gga cgt tcc ggt gcc atc gaa cca tta gta gat     1872
Asn Lys Ile Lys Ile Gly Arg Ser Gly Ala Ile Glu Pro Leu Val Asp
    610                 615                 620 tta ctg gga gaa ggt acc ccg caa ggg aag aag gat gca gct act gca     1920
Leu Leu Gly Glu Gly Thr Pro Gln Gly Lys Lys Asp Ala Ala Thr Ala
625                 630                 635                 640 ctc ttc aat ctg tcg ata ttt cat gaa cac aag acc cgc att gtt cag     1968
Leu Phe Asn Leu Ser Ile Phe His Glu His Lys Thr Arg Ile Val Gln
                645                 650                 655 gct ggg gct gtc aac cac ctg gtg gag ctg atg gat cca gct gct ggg     2016
Ala Gly Ala Val Asn His Leu Val Glu Leu Met Asp Pro Ala Ala Gly
            660                 665                 670 atg gtt gat aaa gct gtt gct gtt ctg gca aac ctt gcg act gtg cat     2064
Met Val Asp Lys Ala Val Ala Val Leu Ala Asn Leu Ala Thr Val His
        675                 680                 685 gat gga agg aat gcc att gct cag gca gga ggc atc cga gta ctg gtt     2112
Asp Gly Arg Asn Ala Ile Ala Gln Ala Gly Gly Ile Arg Val Leu Val
    690                 695                 700 gag gtt gtt gag ctg ggt tct gca cgt tca aag gag aat gcc gct gct     2160
Glu Val Val Glu Leu Gly Ser Ala Arg Ser Lys Glu Asn Ala Ala Ala
705                 710                 715                 720 gcc ctg cta caa ctc tgc aca aac agt aac agg ttt tgc acc ctg gtt     2208
Ala Leu Leu Gln Leu Cys Thr Asn Ser Asn Arg Phe Cys Thr Leu Val
                725                 730                 735 ctt caa gaa ggc gtc gtg cca cct ttg gtt gca ttg tcg caa tca ggc     2256
Leu Gln Glu Gly Val Val Pro Pro Leu Val Ala Leu Ser Gln Ser Gly
            740                 745                 750 aca gcc cgt gca aga gag aag gct cag gtt ctt cta agc tat ttt cgc     2304
Thr Ala Arg Ala Arg Glu Lys Ala Gln Val Leu Leu Ser Tyr Phe Arg
        755                 760                 765 aac cag cgc cac gtc agg gtt ggg aga ggg ctt agc ttg cta tta gag     2352
Asn Gln Arg His Val Arg Val Gly Arg Gly Leu Ser Leu Leu Leu Glu
    770                 775                 780 tta aaa cgg acc aca taa                                             2370
Leu Lys Arg Thr Thr
785

<210> SEQ ID NO 6
<211> LENGTH: 789
<212> TYPE: PRT
<213> ORGANISM: Oryza sativa

<400> SEQUENCE: 6

Met Ala Phe Val Cys Gly Gly Gly Gln Val Met Asp Ser Val Ser Leu
1               5                   10                  15

Ser Leu Leu Asp Ser Ile Ser Asn Phe Arg Val Leu Ser Ser Ser Asn
            20                  25                  30
```

Ala Ser Lys Thr Glu Leu Val Lys Lys Tyr Cys Gln Thr Met Asp Gly
         35                  40                  45

Ile Leu Asp His Leu Glu Val Ala Leu Asn Arg Ala Phe Pro Gln Ile
     50                  55                  60

Thr Pro Asp Gly Glu Leu Ser Lys Val Ile Gln Ala Asp Ser Ile Ile
 65                  70                  75                  80

Ala Lys Met Gln Ile Tyr Val Phe Glu Leu Cys Gln Ile Val Asn Ser
                 85                  90                  95

Leu Met Gln Ile Glu Ser Met His Leu Glu Asp Leu Glu His Asp Ser
                100                 105                 110

Cys Gly Lys Ile Ser Asp Val Ile Arg Glu Ala Ser Arg Ala Leu Ala
             115                 120                 125

Gly Glu Val Met Pro Asn Ser Glu Glu Phe Gly Lys Ile Gln Thr Thr
         130                 135                 140

Leu Ser Leu Ser Thr Asn Gln Glu Leu Leu Met Glu Tyr Val Ala Leu
145                 150                 155                 160

Val Lys Val Lys Thr Lys Gly Asn His Glu Asp Asn Lys Glu Met Asp
                 165                 170                 175

Asp Ile Asn Asp Ile Val Glu Leu Val Asn His Met Leu Asp Lys His
             180                 185                 190

Val Glu Glu Lys Gln Thr Arg Ser Ile Asn Gly Val Thr Ile Pro Ala
         195                 200                 205

Asp Phe Cys Cys Pro Leu Ser Leu Glu Leu Met Ser Asp Pro Val Ile
     210                 215                 220

Val Ala Ser Gly Gln Thr Tyr Glu His Val Phe Ile Arg Lys Trp Phe
225                 230                 235                 240

Asp Leu Gly Tyr Asn Ile Cys Pro Lys Thr Arg Gln Ile Leu Gly His
                 245                 250                 255

Thr Lys Leu Ile Pro Asn Phe Thr Val Lys Gln Leu Ile Glu Asn Trp
             260                 265                 270

Cys Glu Val His Gly Ile Met Leu Pro Asp Pro Val Lys Leu Leu Ser
         275                 280                 285

Leu Cys Phe Pro Val Ser Leu Asn Ile Thr Asp Gly Ser Ala Ser Ala
     290                 295                 300

Asp Lys Ser Gly Ser Pro Glu His Cys Gln Leu Val Ala Ala Leu His
305                 310                 315                 320

Pro Lys Ala Gln Cys Ala Ser Asp Asp Ser His His Tyr Asn Leu Ile
                 325                 330                 335

His Glu Asn Ser Asp Ser Asp Asp Arg Val Ser Ser Phe Gly Asp Thr
             340                 345                 350

Asp Asp Ser Glu Pro Asp Ser Leu Arg Leu Ser Thr Glu Thr Thr Ala
         355                 360                 365

Ala Asn Lys Ser Leu Leu Asp Glu Lys Thr Asp Arg Ser Asp Gly Leu
     370                 375                 380

Lys Gln Leu Arg Asp Asn Gly Phe Gln Val Ser Asp Glu Glu Gln Tyr
385                 390                 395                 400

Leu Glu Arg Asn Gly Lys Ser His Ile Ser Ser His His Gln Leu Glu
                 405                 410                 415

Val Asp Gly Glu Asn Val Arg Val Gln Ala Ser Ser Asp Ile Asn Ala
             420                 425                 430

Ser Glu Val Met Gln Asp Asp Pro Val Thr Thr Cys Ser Lys Val Ser
         435                 440                 445

Asp Asn Pro Pro Arg Leu Gly Gly Val Arg Ser Arg Asn Gln Pro Asn

```
                    450                 455                 460
Trp Trp Arg Gln Ser Asn Lys Thr Ile Pro Arg Ile Gly Leu Ser Ser
465                 470                 475                 480

Ser Thr Asp Ser Lys Pro Asp Phe Ser Gly Asn Asp Ala Lys Val Arg
                    485                 490                 495

Asn Leu Ile Glu Glu Leu Lys Ser Asp Ser Ala Glu Val Gln Arg Ser
                    500                 505                 510

Ala Thr Gly Glu Leu Arg Ile Leu Ser Arg His Ser Leu Glu Asn Arg
                    515                 520                 525

Ile Ala Ile Ala Asn Cys Gly Ala Ile Pro Phe Leu Val Ser Leu Leu
                    530                 535                 540

His Ser Thr Asp Pro Ser Thr Gln Glu Asn Ala Val Thr Ile Leu Leu
545                 550                 555                 560

Asn Leu Ser Leu Asp Asp Asn Lys Ile Ala Ile Ser Ala Glu
                    565                 570                 575

Ala Ile Glu Pro Leu Ile Phe Val Leu Gln Val Gly Asn Pro Glu Ala
                    580                 585                 590

Lys Ala Asn Ser Ala Ala Thr Leu Phe Ser Leu Ser Val Ile Glu Glu
                    595                 600                 605

Asn Lys Ile Lys Ile Gly Arg Ser Gly Ala Ile Glu Pro Leu Val Asp
610                 615                 620

Leu Leu Gly Glu Gly Thr Pro Gln Gly Lys Lys Asp Ala Ala Thr Ala
625                 630                 635                 640

Leu Phe Asn Leu Ser Ile Phe His Glu His Lys Thr Arg Ile Val Gln
                    645                 650                 655

Ala Gly Ala Val Asn His Leu Val Glu Leu Met Asp Pro Ala Ala Gly
                    660                 665                 670

Met Val Asp Lys Ala Val Ala Val Leu Ala Asn Leu Ala Thr Val His
675                 680                 685

Asp Gly Arg Asn Ala Ile Ala Gln Ala Gly Ile Arg Val Leu Val
                    690                 695                 700

Glu Val Val Glu Leu Gly Ser Ala Arg Ser Lys Glu Asn Ala Ala Ala
705                 710                 715                 720

Ala Leu Leu Gln Leu Cys Thr Asn Ser Asn Arg Phe Cys Thr Leu Val
                    725                 730                 735

Leu Gln Glu Gly Val Val Pro Pro Leu Val Ala Leu Ser Gln Ser Gly
                    740                 745                 750

Thr Ala Arg Ala Arg Glu Lys Ala Gln Val Leu Leu Ser Tyr Phe Arg
                    755                 760                 765

Asn Gln Arg His Val Arg Val Gly Arg Gly Leu Ser Leu Leu Leu Glu
                    770                 775                 780

Leu Lys Arg Thr Thr
785

<210> SEQ ID NO 7
<211> LENGTH: 2391
<212> TYPE: DNA
<213> ORGANISM: Oryza sativa
<220> FEATURE:
<221> NAME/KEY: CDS
<222> LOCATION: (1)..(2391)

<400> SEQUENCE: 7 atg gat tca gtg tca ttg tca cta ctc gat agt att tca aat ttc cgg       48
Met Asp Ser Val Ser Leu Ser Leu Leu Asp Ser Ile Ser Asn Phe Arg
1               5                   10                  15
```

| | | |
|---|---|---|
| gtg ctg tct tca agc aat gcc tcg aaa aca gag cta gtt aag aaa tat<br>Val Leu Ser Ser Ser Asn Ala Ser Lys Thr Glu Leu Val Lys Lys Tyr<br>20 25 30 | | 96 |
| tgc caa acg atg gat ggc atc ctt gat cac ttg gag gtg gcc cta aac<br>Cys Gln Thr Met Asp Gly Ile Leu Asp His Leu Glu Val Ala Leu Asn<br>35 40 45 | | 144 |
| aga gct ttt cct cag att act cca gat ggt gaa cta agt aaa gtg ctt<br>Arg Ala Phe Pro Gln Ile Thr Pro Asp Gly Glu Leu Ser Lys Val Leu<br>50 55 60 | | 192 |
| gaa gaa ctt ggc gct acc atc aat gaa gcg act gag cta gtt gga ggc<br>Glu Glu Leu Gly Ala Thr Ile Asn Glu Ala Thr Glu Leu Val Gly Gly<br>65 70 75 80 | | 240 |
| tgg aat caa atg atg agc aag att tat ttt gtt att cag gct gat tca<br>Trp Asn Gln Met Met Ser Lys Ile Tyr Phe Val Ile Gln Ala Asp Ser<br>85 90 95 | | 288 |
| att att gcc aag atg cag ata tat gta ttc gaa tta tgc caa att gtc<br>Ile Ile Ala Lys Met Gln Ile Tyr Val Phe Glu Leu Cys Gln Ile Val<br>100 105 110 | | 336 |
| aat tct ctc atg cag att gag tca atg cat ttg gag gat ctt gaa cac<br>Asn Ser Leu Met Gln Ile Glu Ser Met His Leu Glu Asp Leu Glu His<br>115 120 125 | | 384 |
| gat agc tgt gga aaa att tca gat gtc att agg gag gct tcc agg gct<br>Asp Ser Cys Gly Lys Ile Ser Asp Val Ile Arg Glu Ala Ser Arg Ala<br>130 135 140 | | 432 |
| tta gca ggg gaa gtt atg cca aat tca gag gaa ttt gga aag att caa<br>Leu Ala Gly Glu Val Met Pro Asn Ser Glu Glu Phe Gly Lys Ile Gln<br>145 150 155 160 | | 480 |
| act act ttg agc tta tcc aca aat cag gag ttg ctg atg gaa tat gtt<br>Thr Thr Leu Ser Leu Ser Thr Asn Gln Glu Leu Leu Met Glu Tyr Val<br>165 170 175 | | 528 |
| gca ctt gtt aag gtt aaa aca aaa ggt aat cat gaa gat aac aaa gaa<br>Ala Leu Val Lys Val Lys Thr Lys Gly Asn His Glu Asp Asn Lys Glu<br>180 185 190 | | 576 |
| atg gat gat att aac gat att gtt gaa tta gtc aac cat atg ctt gac<br>Met Asp Asp Ile Asn Asp Ile Val Glu Leu Val Asn His Met Leu Asp<br>195 200 205 | | 624 |
| aaa cat gtg gaa gaa aag caa aca cgt agc att aat gga gtg acc att<br>Lys His Val Glu Glu Lys Gln Thr Arg Ser Ile Asn Gly Val Thr Ile<br>210 215 220 | | 672 |
| cct gct gat ttt tgt tgt cct ctt tcc ctt gaa cta atg tcg gat cca<br>Pro Ala Asp Phe Cys Cys Pro Leu Ser Leu Glu Leu Met Ser Asp Pro<br>225 230 235 240 | | 720 |
| gtg att gtg gca tct ggt caa acg tat gag cat gtt ttt atc aga aaa<br>Val Ile Val Ala Ser Gly Gln Thr Tyr Glu His Val Phe Ile Arg Lys<br>245 250 255 | | 768 |
| tgg ttt gat ctg gga tac aac att tgt cca aag aca cgc caa ata ttg<br>Trp Phe Asp Leu Gly Tyr Asn Ile Cys Pro Lys Thr Arg Gln Ile Leu<br>260 265 270 | | 816 |
| gga cac acc aaa ttg att cct aac ttc act gtc aaa cag ttg att gaa<br>Gly His Thr Lys Leu Ile Pro Asn Phe Thr Val Lys Gln Leu Ile Glu<br>275 280 285 | | 864 |
| aat tgg tgt gag gta cat ggt ata atg cta cca gat cct gtt aaa ctc<br>Asn Trp Cys Glu Val His Gly Ile Met Leu Pro Asp Pro Val Lys Leu<br>290 295 300 | | 912 |
| ttg agt ttg tgc ttc cct gtt tcc ctc aac atc aca gat gga agt gca<br>Leu Ser Leu Cys Phe Pro Val Ser Leu Asn Ile Thr Asp Gly Ser Ala<br>305 310 315 320 | | 960 |
| agt gca gac aag tct gga tca cca gaa cac tgc caa ttg gta gct gca<br>Ser Ala Asp Lys Ser Gly Ser Pro Glu His Cys Gln Leu Val Ala Ala<br>325 330 335 | | 1008 |

```
ttg cat cca aaa gca cag tgc gca tcg gat gat agt cat cat tat aat    1056
Leu His Pro Lys Ala Gln Cys Ala Ser Asp Asp Ser His His Tyr Asn
        340             345             350 ttg ata cat gaa aac tct gat tca gat gat aga gtg tca tca ttt gga    1104
Leu Ile His Glu Asn Ser Asp Ser Asp Asp Arg Val Ser Ser Phe Gly
        355             360             365 gac aca gat gat tct gaa cct gat tct tta aga tta tca aca gaa act    1152
Asp Thr Asp Asp Ser Glu Pro Asp Ser Leu Arg Leu Ser Thr Glu Thr
    370             375             380 act gca gca aac aaa tct cta ctt gat gaa aaa act gat cgt tct gat    1200
Thr Ala Ala Asn Lys Ser Leu Leu Asp Glu Lys Thr Asp Arg Ser Asp
385             390             395             400 ggt ctt aag caa ttg aga gac aat ggt ttt caa gtt tct gat gag gaa    1248
Gly Leu Lys Gln Leu Arg Asp Asn Gly Phe Gln Val Ser Asp Glu Glu
            405             410             415 cag tat ctc gaa agg aat ggt aaa agt cat atc agc agc cat cat caa    1296
Gln Tyr Leu Glu Arg Asn Gly Lys Ser His Ile Ser Ser His His Gln
        420             425             430 ctt gaa gtt gat gga gag aat gtc agg gta caa gca tca agt gac atc    1344
Leu Glu Val Asp Gly Glu Asn Val Arg Val Gln Ala Ser Ser Asp Ile
        435             440             445 aat gca tct gaa gtt atg caa gat gat ccg gtc acc aca tgt tca aag    1392
Asn Ala Ser Glu Val Met Gln Asp Asp Pro Val Thr Thr Cys Ser Lys
450             455             460 gta tca gat aac cct cct aga ttg ggt ggt gtt cgt tct cga aat cag    1440
Val Ser Asp Asn Pro Pro Arg Leu Gly Gly Val Arg Ser Arg Asn Gln
465             470             475             480 cca aac tgg tgg aga cag tct aat aaa act att cct agg atc gga ttg    1488
Pro Asn Trp Trp Arg Gln Ser Asn Lys Thr Ile Pro Arg Ile Gly Leu
            485             490             495 tca tct tcg aca gat tca aaa cca gat ttt tct ggc aat gat gct aaa    1536
Ser Ser Ser Thr Asp Ser Lys Pro Asp Phe Ser Gly Asn Asp Ala Lys
        500             505             510 gtg cgt aat ctt atc gag gaa ctg aaa agt gat tct gct gag gtc caa    1584
Val Arg Asn Leu Ile Glu Glu Leu Lys Ser Asp Ser Ala Glu Val Gln
        515             520             525 agg tca gca aca gga gag ctc cgc att ctt tct aga cac agc ttg gag    1632
Arg Ser Ala Thr Gly Glu Leu Arg Ile Leu Ser Arg His Ser Leu Glu
530             535             540 aat aga att gcc atc gca aac tgc gga gca atc ccc ttc ttg gtg agt    1680
Asn Arg Ile Ala Ile Ala Asn Cys Gly Ala Ile Pro Phe Leu Val Ser
545             550             555             560 cta ctt cat tct aca gac ccc agc aca caa gaa aat gct gtg aca att    1728
Leu Leu His Ser Thr Asp Pro Ser Thr Gln Glu Asn Ala Val Thr Ile
            565             570             575 ctc ctg aat ttg tca ttg gat gac aat aac aag att gcc ata gca agt    1776
Leu Leu Asn Leu Ser Leu Asp Asp Asn Asn Lys Ile Ala Ile Ala Ser
        580             585             590 gct gag gcc att gag cct ctc atc ttc gtt ctt cag gtg gga aac ccc    1824
Ala Glu Ala Ile Glu Pro Leu Ile Phe Val Leu Gln Val Gly Asn Pro
        595             600             605 gaa gcg aaa gcc aac tca gct gca act tta ttc agc ctc tca gtc att    1872
Glu Ala Lys Ala Asn Ser Ala Ala Thr Leu Phe Ser Leu Ser Val Ile
    610             615             620 gaa gag aac aag atc aag att gga cgt tcc ggt gcc atc gaa cca tta    1920
Glu Glu Asn Lys Ile Lys Ile Gly Arg Ser Gly Ala Ile Glu Pro Leu
625             630             635             640 gta gat tta ctg gga gaa ggt acc ccg caa ggg aag aag gat gca gct    1968
Val Asp Leu Leu Gly Glu Gly Thr Pro Gln Gly Lys Lys Asp Ala Ala
            645             650             655
```

```
act gca ctc ttc aat ctg tcg ata ttt cat gaa cac aag acc cgc att    2016
Thr Ala Leu Phe Asn Leu Ser Ile Phe His Glu His Lys Thr Arg Ile
        660                 665                 670 gtt cag gct ggg gct gtc aac cac ctg gtg gag ctg atg gat cca gct    2064
Val Gln Ala Gly Ala Val Asn His Leu Val Glu Leu Met Asp Pro Ala
            675                 680                 685 gct ggg atg gtt gat aaa gct gtt gct gtt ctg gca aac ctt gcg act    2112
Ala Gly Met Val Asp Lys Ala Val Ala Val Leu Ala Asn Leu Ala Thr
690                 695                 700 gtg cat gat gga agg aat gcc att gct cag gca gga ggc atc cga gta    2160
Val His Asp Gly Arg Asn Ala Ile Ala Gln Ala Gly Gly Ile Arg Val
705                 710                 715                 720 ctg gtt gag gtt gtt gag ctg ggt tct gca cgt tca aag gag aat gcc    2208
Leu Val Glu Val Val Glu Leu Gly Ser Ala Arg Ser Lys Glu Asn Ala
                725                 730                 735 gct gcc gcc ctg cta caa ctc tgc aca aac agt aac agg ttt tgc acc    2256
Ala Ala Ala Leu Leu Gln Leu Cys Thr Asn Ser Asn Arg Phe Cys Thr
            740                 745                 750 ctg gtt ctt caa gaa ggc gtc gtg cca cct ttg gtt gca ttg tcg caa    2304
Leu Val Leu Gln Glu Gly Val Val Pro Pro Leu Val Ala Leu Ser Gln
        755                 760                 765 tca ggc aca gcc cgt gca aga gag aag gct cag gtt ctt cta agc tat    2352
Ser Gly Thr Ala Arg Ala Arg Glu Lys Ala Gln Val Leu Leu Ser Tyr
770                 775                 780 ttt cgc aac cag cgc cac gtc agg gtt ggg aga ggg taa                2391
Phe Arg Asn Gln Arg His Val Arg Val Gly Arg Gly
785                 790                 795
```

<210> SEQ ID NO 8
<211> LENGTH: 796
<212> TYPE: PRT
<213> ORGANISM: Oryza sativa

<400> SEQUENCE: 8

```
Met Asp Ser Val Ser Leu Ser Leu Asp Ser Ile Ser Asn Phe Arg
1               5                   10                  15

Val Leu Ser Ser Ser Asn Ala Ser Lys Thr Glu Leu Val Lys Lys Tyr
            20                  25                  30

Cys Gln Thr Met Asp Gly Ile Leu Asp His Leu Glu Val Ala Leu Asn
        35                  40                  45

Arg Ala Phe Pro Gln Ile Thr Pro Asp Gly Glu Leu Ser Lys Val Leu
    50                  55                  60

Glu Glu Leu Gly Ala Thr Ile Asn Glu Ala Thr Glu Leu Val Gly Gly
65                  70                  75                  80

Trp Asn Gln Met Met Ser Lys Ile Tyr Phe Val Ile Gln Ala Asp Ser
                85                  90                  95

Ile Ile Ala Lys Met Gln Ile Tyr Val Phe Glu Leu Cys Gln Ile Val
            100                 105                 110

Asn Ser Leu Met Gln Ile Glu Ser Met His Leu Glu Asp Leu Glu His
        115                 120                 125

Asp Ser Cys Gly Lys Ile Ser Asp Val Ile Arg Glu Ala Ser Arg Ala
    130                 135                 140

Leu Ala Gly Glu Val Met Pro Asn Ser Glu Glu Phe Gly Lys Ile Gln
145                 150                 155                 160

Thr Thr Leu Ser Leu Ser Thr Asn Gln Glu Leu Leu Met Glu Tyr Val
                165                 170                 175

Ala Leu Val Lys Val Lys Thr Lys Gly Asn His Glu Asp Asn Lys Glu
            180                 185                 190
```

-continued

```
Met Asp Asp Ile Asn Asp Ile Val Glu Leu Val Asn His Met Leu Asp
            195                 200                 205

Lys His Val Glu Glu Lys Gln Thr Arg Ser Ile Asn Gly Val Thr Ile
    210                 215                 220

Pro Ala Asp Phe Cys Cys Pro Leu Ser Leu Glu Leu Met Ser Asp Pro
225                 230                 235                 240

Val Ile Val Ala Ser Gly Gln Thr Tyr Glu His Val Phe Ile Arg Lys
                245                 250                 255

Trp Phe Asp Leu Gly Tyr Asn Ile Cys Pro Lys Thr Arg Gln Ile Leu
            260                 265                 270

Gly His Thr Lys Leu Ile Pro Asn Phe Thr Val Lys Gln Leu Ile Glu
        275                 280                 285

Asn Trp Cys Glu Val His Gly Ile Met Leu Pro Asp Pro Val Lys Leu
    290                 295                 300

Leu Ser Leu Cys Phe Pro Val Ser Leu Asn Ile Thr Asp Gly Ser Ala
305                 310                 315                 320

Ser Ala Asp Lys Ser Gly Ser Pro Glu His Cys Gln Leu Val Ala Ala
                325                 330                 335

Leu His Pro Lys Ala Gln Cys Ala Ser Asp Asp Ser His His Tyr Asn
            340                 345                 350

Leu Ile His Glu Asn Ser Asp Ser Asp Asp Arg Val Ser Ser Phe Gly
        355                 360                 365

Asp Thr Asp Asp Ser Glu Pro Asp Ser Leu Arg Leu Ser Thr Glu Thr
    370                 375                 380

Thr Ala Ala Asn Lys Ser Leu Leu Asp Glu Lys Thr Asp Arg Ser Asp
385                 390                 395                 400

Gly Leu Lys Gln Leu Arg Asp Asn Gly Phe Gln Val Ser Asp Glu Glu
                405                 410                 415

Gln Tyr Leu Glu Arg Asn Gly Lys Ser His Ile Ser Ser His His Gln
            420                 425                 430

Leu Glu Val Asp Gly Glu Asn Val Arg Val Gln Ala Ser Ser Asp Ile
        435                 440                 445

Asn Ala Ser Glu Val Met Gln Asp Asp Pro Val Thr Thr Cys Ser Lys
    450                 455                 460

Val Ser Asp Asn Pro Pro Arg Leu Gly Gly Val Arg Ser Arg Asn Gln
465                 470                 475                 480

Pro Asn Trp Trp Arg Gln Ser Asn Lys Thr Ile Pro Arg Ile Gly Leu
                485                 490                 495

Ser Ser Ser Thr Asp Ser Lys Pro Asp Phe Ser Gly Asn Asp Ala Lys
            500                 505                 510

Val Arg Asn Leu Ile Glu Glu Leu Lys Ser Asp Ser Ala Glu Val Gln
        515                 520                 525

Arg Ser Ala Thr Gly Glu Leu Arg Ile Leu Ser Arg His Ser Leu Glu
    530                 535                 540

Asn Arg Ile Ala Ile Ala Asn Cys Gly Ala Ile Pro Phe Leu Val Ser
545                 550                 555                 560

Leu Leu His Ser Thr Asp Pro Ser Thr Gln Glu Asn Ala Val Thr Ile
                565                 570                 575

Leu Leu Asn Leu Ser Leu Asp Asp Asn Asn Lys Ile Ala Ile Ala Ser
            580                 585                 590

Ala Glu Ala Ile Glu Pro Leu Ile Phe Val Leu Gln Val Gly Asn Pro
        595                 600                 605

Glu Ala Lys Ala Asn Ser Ala Ala Thr Leu Phe Ser Leu Ser Val Ile
    610                 615                 620
```

```
Glu Glu Asn Lys Ile Lys Ile Gly Arg Ser Gly Ala Ile Glu Pro Leu
625                 630                 635                 640

Val Asp Leu Leu Gly Glu Gly Thr Pro Gln Gly Lys Lys Asp Ala Ala
            645                 650                 655

Thr Ala Leu Phe Asn Leu Ser Ile Phe His Glu His Lys Thr Arg Ile
            660                 665                 670

Val Gln Ala Gly Ala Val Asn His Leu Val Glu Leu Met Asp Pro Ala
        675                 680                 685

Ala Gly Met Val Asp Lys Ala Val Ala Val Leu Ala Asn Leu Ala Thr
    690                 695                 700

Val His Asp Gly Arg Asn Ala Ile Ala Gln Ala Gly Gly Ile Arg Val
705                 710                 715                 720

Leu Val Glu Val Val Glu Leu Gly Ser Ala Arg Ser Lys Glu Asn Ala
                725                 730                 735

Ala Ala Ala Leu Leu Gln Leu Cys Thr Asn Ser Asn Arg Phe Cys Thr
            740                 745                 750

Leu Val Leu Gln Glu Gly Val Val Pro Pro Leu Val Ala Leu Ser Gln
        755                 760                 765

Ser Gly Thr Ala Arg Ala Arg Glu Lys Ala Gln Val Leu Leu Ser Tyr
    770                 775                 780

Phe Arg Asn Gln Arg His Val Arg Val Gly Arg Gly
785                 790                 795

<210> SEQ ID NO 9
<211> LENGTH: 1404
<212> TYPE: DNA
<213> ORGANISM: Oryza sativa
<220> FEATURE:
<221> NAME/KEY: CDS
<222> LOCATION: (1)..(1404)

<400> SEQUENCE: 9 atg gtg tcg cta gcc ggc tcc cag atc ccg tcg ccg ggg cag agt ccg      48
Met Val Ser Leu Ala Gly Ser Gln Ile Pro Ser Pro Gly Gln Ser Pro
1               5                   10                  15 tgc gcg gcg gcg cgg tcg cag cgc cgc ggc gcg ggg tac tcc atg cgg      96
Cys Ala Ala Ala Arg Ser Gln Arg Arg Gly Ala Gly Tyr Ser Met Arg
            20                  25                  30 acc atc cgg tcg gcg ctg ctg cag ccg gac tcc tgc ccg ggc tcg ccg     144
Thr Ile Arg Ser Ala Leu Leu Gln Pro Asp Ser Cys Pro Gly Ser Pro
        35                  40                  45 cat gtg gcg gcc gcg tac gac gcg gcg ggg gcg gac tcg gac atg gag     192
His Val Ala Ala Ala Tyr Asp Ala Ala Gly Ala Asp Ser Asp Met Glu
    50                  55                  60 aac ttg acg gac tcc gtg att gat ttc cat ctc agc gag ctg gcg gcc     240
Asn Leu Thr Asp Ser Val Ile Asp Phe His Leu Ser Glu Leu Ala Ala
65                  70                  75                  80 acc gcg ggg ccc gcg cac ccc gcg gcg gtg gcc aag tcg tcg tcg gcc     288
Thr Ala Gly Pro Ala His Pro Ala Ala Val Ala Lys Ser Ser Ser Ala
                85                  90                  95 aac gcg gcg gcc acg gag atg ctc gag ctc tcg cgg gac ttc agt gac     336
Asn Ala Ala Ala Thr Glu Met Leu Glu Leu Ser Arg Asp Phe Ser Asp
            100                 105                 110 tac tcg agc ttc aac tcg gat atc tcc ggc gag ctc gag cgg ctc gcg     384
Tyr Ser Ser Phe Asn Ser Asp Ile Ser Gly Glu Leu Glu Arg Leu Ala
        115                 120                 125 gcg gcg gcg gcg gtg gtg acg ccc aga tcc gac gcg ccg cag gtg          432
Ala Ala Ala Ala Val Val Thr Pro Arg Ser Asp Ala Pro Gln Val
    130                 135                 140
```

| | | |
|---|---|---|
| ggc gcc gtg gat ctg aat gag ctt gag tcg atg gat ctg tcc gtc gag<br>Gly Ala Val Asp Leu Asn Glu Leu Glu Ser Met Asp Leu Ser Val Glu<br>145                       150                   155                    160 | 480 |
| gcg gcg ccg ctg gag cgc gtg gag ccg ttc gtg ctg gcg tgc gtg cgg<br>Ala Ala Pro Leu Glu Arg Val Glu Pro Phe Val Leu Ala Cys Val Arg<br>                 165                   170                    175 | 528 |
| gcg ctg ggg ccc gac gcc gcg cca gac gcg cgg cgc acc gcg gcg gcg<br>Ala Leu Gly Pro Asp Ala Ala Pro Asp Ala Arg Arg Thr Ala Ala Ala<br>         180                   185                   190 | 576 |
| agg ata agg ctg ctg gcg aag cac agg tcg gac atc cgc gag ctg atc<br>Arg Ile Arg Leu Leu Ala Lys His Arg Ser Asp Ile Arg Glu Leu Ile<br>                 195                   200                   205 | 624 |
| ggc gtg tcc ggc gcc atc ccg gcg ctg gtg ccg ctg ctg cgg agc acc<br>Gly Val Ser Gly Ala Ile Pro Ala Leu Val Pro Leu Leu Arg Ser Thr<br>210                       215                   220 | 672 |
| gac ccg gtg gcg cag gag agc gcg gtg acg gcg ctg ctc aac ctc tcg<br>Asp Pro Val Ala Gln Glu Ser Ala Val Thr Ala Leu Leu Asn Leu Ser<br>225                       230                   235                   240 | 720 |
| ctc gag gag cgg aac cgg tcg gcc atc acg gcg gcg ggg gcc atc aag<br>Leu Glu Glu Arg Asn Arg Ser Ala Ile Thr Ala Ala Gly Ala Ile Lys<br>                 245                   250                   255 | 768 |
| ccg ctc gtg tac gcg ctg cgg acg ggc acc gcg tcg gcc aag cag aac<br>Pro Leu Val Tyr Ala Leu Arg Thr Gly Thr Ala Ser Ala Lys Gln Asn<br>         260                   265                   270 | 816 |
| gcc gcg tgc gcg ctg ctc agc ctc tcg ggc atc gag gag aac cgc gcc<br>Ala Ala Cys Ala Leu Leu Ser Leu Ser Gly Ile Glu Glu Asn Arg Ala<br>275                       280                   285 | 864 |
| acc atc ggc gcg tgc ggc gcc atc cct ccc ctc gtc gcg ctg ctc tcc<br>Thr Ile Gly Ala Cys Gly Ala Ile Pro Pro Leu Val Ala Leu Leu Ser<br>         290                   295                   300 | 912 |
| gcg ggc tcc acc cgc ggc aag aag gac gcg ctc acc acg ctc tac cgg<br>Ala Gly Ser Thr Arg Gly Lys Lys Asp Ala Leu Thr Thr Leu Tyr Arg<br>305                       310                   315                   320 | 960 |
| ctc tgc tcg gcg cgc cgg aac aag gag cgc gcg gtc agc gcc ggc gcc<br>Leu Cys Ser Ala Arg Arg Asn Lys Glu Arg Ala Val Ser Ala Gly Ala<br>                 325                   330                   335 | 1008 |
| gtc gtg ccg ctc atc cac ctc gtc ggc gag cgt ggc agc ggg acg tcg<br>Val Val Pro Leu Ile His Leu Val Gly Glu Arg Gly Ser Gly Thr Ser<br>         340                   345                   350 | 1056 |
| gag aag gca atg gtg gtc ctc gcc agc ctc gcg ggc atc gtc gag ggc<br>Glu Lys Ala Met Val Val Leu Ala Ser Leu Ala Gly Ile Val Glu Gly<br>355                       360                   365 | 1104 |
| cgc gac gcc gtg gtg gag gct ggc ggg ata ccg gcg ctt gtc gag acc<br>Arg Asp Ala Val Val Glu Ala Gly Gly Ile Pro Ala Leu Val Glu Thr<br>         370                   375                   380 | 1152 |
| atc gag gac ggc ccg gcg agg gag agg gag ttc gcc gtg gtg gcg ctg<br>Ile Glu Asp Gly Pro Ala Arg Glu Arg Glu Phe Ala Val Val Ala Leu<br>385                       390                   395                   400 | 1200 |
| ctg cag ctc tgc tcc gag tgc ccc cgc aac cgc gcg ctt ctt gtc cgt<br>Leu Gln Leu Cys Ser Glu Cys Pro Arg Asn Arg Ala Leu Leu Val Arg<br>                 405                   410                   415 | 1248 |
| gag ggc gcc atc cca ccg ctt gtc gcg ctc tcg cag tcc ggc tct gcc<br>Glu Gly Ala Ile Pro Pro Leu Val Ala Leu Ser Gln Ser Gly Ser Ala<br>         420                   425                   430 | 1296 |
| cgt gcc aag cac aag gct gaa act ttg ctt ggg tat ctc cgc gag caa<br>Arg Ala Lys His Lys Ala Glu Thr Leu Leu Gly Tyr Leu Arg Glu Gln<br>435                       440                   445 | 1344 |
| cgg caa gga ggt ggt ggc tgc agg gtt gaa ccc gtg gca gct tcg agc<br>Arg Gln Gly Gly Gly Gly Cys Arg Val Glu Pro Val Ala Ala Ser Ser<br>450                       455                   460 | 1392 |

-continued

```
ttg gcc agg taa                                              1404
Leu Ala Arg
465

<210> SEQ ID NO 10
<211> LENGTH: 467
<212> TYPE: PRT
<213> ORGANISM: Oryza sativa

<400> SEQUENCE: 10

Met Val Ser Leu Ala Gly Ser Gln Ile Pro Ser Pro Gly Gln Ser Pro
1               5                   10                  15

Cys Ala Ala Ala Arg Ser Gln Arg Arg Gly Ala Gly Tyr Ser Met Arg
            20                  25                  30

Thr Ile Arg Ser Ala Leu Leu Gln Pro Asp Ser Cys Pro Gly Ser Pro
        35                  40                  45

His Val Ala Ala Ala Tyr Asp Ala Gly Ala Asp Ser Asp Met Glu
    50                  55                  60

Asn Leu Thr Asp Ser Val Ile Asp Phe His Leu Ser Glu Leu Ala Ala
65                  70                  75                  80

Thr Ala Gly Pro Ala His Pro Ala Ala Val Ala Lys Ser Ser Ser Ala
                85                  90                  95

Asn Ala Ala Ala Thr Glu Met Leu Glu Leu Ser Arg Asp Phe Ser Asp
            100                 105                 110

Tyr Ser Ser Phe Asn Ser Asp Ile Ser Gly Glu Leu Glu Arg Leu Ala
        115                 120                 125

Ala Ala Ala Ala Val Val Thr Pro Arg Ser Asp Ala Pro Gln Val
    130                 135                 140

Gly Ala Val Asp Leu Asn Glu Leu Glu Ser Met Asp Leu Ser Val Glu
145                 150                 155                 160

Ala Ala Pro Leu Glu Arg Val Glu Pro Phe Val Leu Ala Cys Val Arg
                165                 170                 175

Ala Leu Gly Pro Asp Ala Ala Pro Asp Ala Arg Arg Thr Ala Ala Ala
            180                 185                 190

Arg Ile Arg Leu Leu Ala Lys His Arg Ser Asp Ile Arg Glu Leu Ile
        195                 200                 205

Gly Val Ser Gly Ala Ile Pro Ala Leu Val Pro Leu Leu Arg Ser Thr
    210                 215                 220

Asp Pro Val Ala Gln Glu Ser Ala Val Thr Ala Leu Leu Asn Leu Ser
225                 230                 235                 240

Leu Glu Glu Arg Asn Arg Ser Ala Ile Thr Ala Ala Gly Ala Ile Lys
                245                 250                 255

Pro Leu Val Tyr Ala Leu Arg Thr Gly Thr Ala Ser Ala Lys Gln Asn
            260                 265                 270

Ala Ala Cys Ala Leu Leu Ser Leu Ser Gly Ile Glu Glu Asn Arg Ala
        275                 280                 285

Thr Ile Gly Ala Cys Gly Ala Ile Pro Pro Leu Val Ala Leu Leu Ser
    290                 295                 300

Ala Gly Ser Thr Arg Gly Lys Lys Asp Ala Leu Thr Thr Leu Tyr Arg
305                 310                 315                 320

Leu Cys Ser Ala Arg Arg Asn Lys Glu Arg Ala Val Ser Ala Gly Ala
                325                 330                 335

Val Val Pro Leu Ile His Leu Val Gly Glu Arg Gly Ser Gly Thr Ser
            340                 345                 350

Glu Lys Ala Met Val Val Leu Ala Ser Leu Ala Gly Ile Val Glu Gly
```

```
                355                 360                 365
Arg Asp Ala Val Val Glu Ala Gly Gly Ile Pro Ala Leu Val Glu Thr
        370                 375                 380

Ile Glu Asp Gly Pro Ala Arg Glu Arg Glu Phe Ala Val Val Ala Leu
385                 390                 395                 400

Leu Gln Leu Cys Ser Glu Cys Pro Arg Asn Arg Ala Leu Leu Val Arg
                405                 410                 415

Glu Gly Ala Ile Pro Pro Leu Val Ala Leu Ser Gln Ser Gly Ser Ala
        420                 425                 430

Arg Ala Lys His Lys Ala Glu Thr Leu Leu Gly Tyr Leu Arg Glu Gln
                435                 440                 445

Arg Gln Gly Gly Gly Cys Arg Val Glu Pro Val Ala Ala Ser Ser
        450                 455                 460

Leu Ala Arg
465

<210> SEQ ID NO 11
<211> LENGTH: 2373
<212> TYPE: DNA
<213> ORGANISM: Nicotiana tabacum
<220> FEATURE:
<221> NAME/KEY: CDS
<222> LOCATION: (1)..(2373)

<400> SEQUENCE: 11 atg gag ata tca ttg tta aaa gtg ctt ctc aac aat atc tcc tgt ttt    48
Met Glu Ile Ser Leu Leu Lys Val Leu Leu Asn Asn Ile Ser Cys Phe
1               5                   10                  15 tcc cat tta tca tca agt gat cac ata agt ggt gaa ctg gtt cgt aga    96
Ser His Leu Ser Ser Ser Asp His Ile Ser Gly Glu Leu Val Arg Arg
            20                  25                  30 tat tat tgt aag att gag gat ata ctg aag ctt gta aag ccg att ctt   144
Tyr Tyr Cys Lys Ile Glu Asp Ile Leu Lys Leu Val Lys Pro Ile Leu
        35                  40                  45 gac gcc atc gtt gat gtt gaa gct gct tct ggt gag ctg ctt ctg aaa   192
Asp Ala Ile Val Asp Val Glu Ala Ala Ser Gly Glu Leu Leu Leu Lys
    50                  55                  60 gcg ttt gct ggg ctg gct caa tgt gtt gat gaa ctg agg gag cta ttc   240
Ala Phe Ala Gly Leu Ala Gln Cys Val Asp Glu Leu Arg Glu Leu Phe
65                  70                  75                  80 gaa acc ttg gaa ccg ctg tgc agt aaa gtt tat ttt gtc ctg caa gct   288
Glu Thr Leu Glu Pro Leu Cys Ser Lys Val Tyr Phe Val Leu Gln Ala
                85                  90                  95 gaa cca ttg att ggg aaa att cga tca tgt agc ctg gaa ata ctt gag   336
Glu Pro Leu Ile Gly Lys Ile Arg Ser Cys Ser Leu Glu Ile Leu Glu
            100                 105                 110 ctt ctt aaa tct tct cat aaa agc ctt cca gct gat gta act ttg aca   384
Leu Leu Lys Ser Ser His Lys Ser Leu Pro Ala Asp Val Thr Leu Thr
        115                 120                 125 act ctc gag ctc tat ata ctg aaa att aag tat gta gat tat gaa atg   432
Thr Leu Glu Leu Tyr Ile Leu Lys Ile Lys Tyr Val Asp Tyr Glu Met
    130                 135                 140 ata tca gtg aca atc aca aag gtt att aaa gct caa gtg gaa ggc ttg   480
Ile Ser Val Thr Ile Thr Lys Val Ile Lys Ala Gln Val Glu Gly Leu
145                 150                 155                 160 gga acc agc tca gat agc ttt gcc aaa att gct gat tgc cta agc ttg   528
Gly Thr Ser Ser Asp Ser Phe Ala Lys Ile Ala Asp Cys Leu Ser Leu
                165                 170                 175 aac tca aac caa gag ctt ttg att gag ctt gtg gcc ctt gaa aaa ttg   576
Asn Ser Asn Gln Glu Leu Leu Ile Glu Leu Val Ala Leu Glu Lys Leu
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 180 |     |     |     |     | 185 |     |     |     |     | 190 |     |     |      |
| aaa | gag | aat | gct | gaa | caa | gct | gaa | aag | agt | gaa | gtt | gtt | gaa | tat | att | 624  |
| Lys | Glu | Asn | Ala | Glu | Gln | Ala | Glu | Lys | Ser | Glu | Val | Val | Glu | Tyr | Ile |      |
|     |     |     | 195 |     |     |     |     | 200 |     |     |     |     | 205 |     |     |      |
| gag | caa | atg | ata | act | ctt | gtt | tct | cat | atg | cac | gat | tgc | ttt | gtt | act | 672  |
| Glu | Gln | Met | Ile | Thr | Leu | Val | Ser | His | Met | His | Asp | Cys | Phe | Val | Thr |      |
|     |     | 210 |     |     |     |     | 215 |     |     |     |     | 220 |     |     |     |      |
| aca | aaa | cag | tcc | cag | agt | tgt | acc | gct | gtg | cca | ata | cct | cct | gat | ttt | 720  |
| Thr | Lys | Gln | Ser | Gln | Ser | Cys | Thr | Ala | Val | Pro | Ile | Pro | Pro | Asp | Phe |      |
| 225 |     |     |     |     | 230 |     |     |     |     | 235 |     |     |     |     | 240 |      |
| tgc | tgt | cct | ctt | tca | ctt | gag | ttg | atg | act | gac | cct | gta | att | gtc | gct | 768  |
| Cys | Cys | Pro | Leu | Ser | Leu | Glu | Leu | Met | Thr | Asp | Pro | Val | Ile | Val | Ala |      |
|     |     |     |     | 245 |     |     |     |     | 250 |     |     |     |     | 255 |     |      |
| tct | ggt | caa | acc | tat | gag | agg | gct | ttt | att | agg | aga | tgg | att | gat | ctt | 816  |
| Ser | Gly | Gln | Thr | Tyr | Glu | Arg | Ala | Phe | Ile | Arg | Arg | Trp | Ile | Asp | Leu |      |
|     |     |     | 260 |     |     |     |     | 265 |     |     |     |     | 270 |     |     |      |
| ggc | ctc | act | gtt | tgc | ccc | aaa | aca | cgg | caa | act | ctg | gga | cat | aca | aat | 864  |
| Gly | Leu | Thr | Val | Cys | Pro | Lys | Thr | Arg | Gln | Thr | Leu | Gly | His | Thr | Asn |      |
|     |     | 275 |     |     |     |     | 280 |     |     |     |     | 285 |     |     |     |      |
| ctc | att | cct | aat | tac | act | gtt | aag | gca | ctg | atc | gca | aac | tgg | tgc | gaa | 912  |
| Leu | Ile | Pro | Asn | Tyr | Thr | Val | Lys | Ala | Leu | Ile | Ala | Asn | Trp | Cys | Glu |      |
| 290 |     |     |     |     | 295 |     |     |     |     | 300 |     |     |     |     |     |      |
| ata | aac | aat | gta | aag | ctg | cct | gat | ccc | atg | aag | tct | ttg | agc | ttg | aac | 960  |
| Ile | Asn | Asn | Val | Lys | Leu | Pro | Asp | Pro | Met | Lys | Ser | Leu | Ser | Leu | Asn |      |
| 305 |     |     |     |     | 310 |     |     |     |     | 315 |     |     |     |     | 320 |      |
| cag | cca | tct | ttg | tca | cca | gac | tcc | acg | caa | tct | tca | ggt | tct | ccg | aga | 1008 |
| Gln | Pro | Ser | Leu | Ser | Pro | Asp | Ser | Thr | Gln | Ser | Ser | Gly | Ser | Pro | Arg |      |
|     |     |     |     | 325 |     |     |     |     | 330 |     |     |     |     | 335 |     |      |
| aag | agt | ttg | att | tca | tca | act | gta | agc | caa | aga | gaa | gaa | tca | tct | cca | 1056 |
| Lys | Ser | Leu | Ile | Ser | Ser | Thr | Val | Ser | Gln | Arg | Glu | Glu | Ser | Ser | Pro |      |
|     |     |     | 340 |     |     |     |     | 345 |     |     |     |     | 350 |     |     |      |
| tct | cat | ccc | cgt | tcc | tct | tca | gag | gaa | tct | tta | cct | gga | gtt | ggt | ggt | 1104 |
| Ser | His | Pro | Arg | Ser | Ser | Ser | Glu | Glu | Ser | Leu | Pro | Gly | Val | Gly | Gly |      |
|     |     | 355 |     |     |     |     | 360 |     |     |     |     | 365 |     |     |     |      |
| aat | att | ctt | gct | ttt | gat | gtt | gaa | agg | atg | cgt | att | aag | agt | gaa | gac | 1152 |
| Asn | Ile | Leu | Ala | Phe | Asp | Val | Glu | Arg | Met | Arg | Ile | Lys | Ser | Glu | Asp |      |
|     | 370 |     |     |     |     | 375 |     |     |     |     | 380 |     |     |     |     |      |
| cgg | atg | gcc | cac | tcc | gga | gag | ata | agt | tca | cat | ggt | cat | agt | aca | tta | 1200 |
| Arg | Met | Ala | His | Ser | Gly | Glu | Ile | Ser | Ser | His | Gly | His | Ser | Thr | Leu |      |
| 385 |     |     |     |     | 390 |     |     |     |     | 395 |     |     |     |     | 400 |      |
| gta | gct | gat | gac | cag | ttc | cct | ctg | ggt | cat | aat | cga | aca | acc | tcg | gca | 1248 |
| Val | Ala | Asp | Asp | Gln | Phe | Pro | Leu | Gly | His | Asn | Arg | Thr | Thr | Ser | Ala |      |
|     |     |     |     | 405 |     |     |     |     | 410 |     |     |     |     | 415 |     |      |
| cct | agc | acg | ctt | tct | aat | tca | aac | ttt | tcc | ccg | gta | att | cct | ggt | gat | 1296 |
| Pro | Ser | Thr | Leu | Ser | Asn | Ser | Asn | Phe | Ser | Pro | Val | Ile | Pro | Gly | Asp |      |
|     |     |     | 420 |     |     |     |     | 425 |     |     |     |     | 430 |     |     |      |
| gga | aac | aag | ttg | tca | gaa | gat | tct | tct | gtt | gct | tca | ggg | gat | gtt | ggg | 1344 |
| Gly | Asn | Lys | Leu | Ser | Glu | Asp | Ser | Ser | Val | Ala | Ser | Gly | Asp | Val | Gly |      |
|     |     | 435 |     |     |     |     | 440 |     |     |     |     | 445 |     |     |     |      |
| ttg | gat | tcc | aag | cct | gct | gct | tct | gtc | ctt | cca | aag | gag | cca | gaa | ttt | 1392 |
| Leu | Asp | Ser | Lys | Pro | Ala | Ala | Ser | Val | Leu | Pro | Lys | Glu | Pro | Glu | Phe |      |
| 450 |     |     |     |     | 455 |     |     |     |     | 460 |     |     |     |     |     |      |
| cca | tat | aca | cca | gag | atg | aga | cct | cgt | aat | caa | ctg | atc | tgg | cgc | aga | 1440 |
| Pro | Tyr | Thr | Pro | Glu | Met | Arg | Pro | Arg | Asn | Gln | Leu | Ile | Trp | Arg | Arg |      |
| 465 |     |     |     |     | 470 |     |     |     |     | 475 |     |     |     |     | 480 |      |
| cca | acc | gag | agg | ttt | cca | aga | ata | gtt | tct | tcc | gct | aca | gtt | gaa | aga | 1488 |
| Pro | Thr | Glu | Arg | Phe | Pro | Arg | Ile | Val | Ser | Ser | Ala | Thr | Val | Glu | Arg |      |
|     |     |     |     | 485 |     |     |     |     | 490 |     |     |     |     | 495 |     |      |
| agg | gct | gat | ctt | tca | gaa | gtt | gag | gag | caa | gta | aaa | aag | ttg | att | gag | 1536 |
| Arg | Ala | Asp | Leu | Ser | Glu | Val | Glu | Glu | Gln | Val | Lys | Lys | Leu | Ile | Glu |      |

```
                    500              505              510
gag ttg aag agc act tcc ctt gat atg cag aga aat gct aca gct gaa      1584
Glu Leu Lys Ser Thr Ser Leu Asp Met Gln Arg Asn Ala Thr Ala Glu
            515                  520                  525 ctc cgg tta ctt gcc aag cat aat atg gat aac cgt atg gta att gca      1632
Leu Arg Leu Leu Ala Lys His Asn Met Asp Asn Arg Met Val Ile Ala
530                  535                  540 aat tgt ggc gct atc agc tcg ttg gtt aac cta ctt cac tca aaa gac      1680
Asn Cys Gly Ala Ile Ser Ser Leu Val Asn Leu Leu His Ser Lys Asp
545                  550                  555                  560 atg aaa gta cag gaa gat gct gtt act gca ctt ctc aac ttg tca att      1728
Met Lys Val Gln Glu Asp Ala Val Thr Ala Leu Leu Asn Leu Ser Ile
                565                  570                  575 aat gac aac aac aag tgt gcc att gca aat gct gat gca atc gaa cct      1776
Asn Asp Asn Asn Lys Cys Ala Ile Ala Asn Ala Asp Ala Ile Glu Pro
            580                  585                  590 ctg att cat gtc ctc caa aca ggg agc gcc gag gcc aaa gaa aat tct      1824
Leu Ile His Val Leu Gln Thr Gly Ser Ala Glu Ala Lys Glu Asn Ser
        595                  600                  605 gct gct act ctt ttt agc ctt tcc gtg atg gag gaa aac aag atg aag      1872
Ala Ala Thr Leu Phe Ser Leu Ser Val Met Glu Glu Asn Lys Met Lys
610                  615                  620 att ggg agg tct gga gca atc aaa cct ctt gtt gat tta ctg gga aat      1920
Ile Gly Arg Ser Gly Ala Ile Lys Pro Leu Val Asp Leu Leu Gly Asn
625                  630                  635                  640 gga act cca agg ggc aag aaa gat gcg acg gct tta ttt aac ttg           1968
Gly Thr Pro Arg Gly Lys Lys Asp Ala Thr Ala Leu Phe Asn Leu
                645                  650                  655 tca ata ctt cat gag aac aag tct cgt ata ata cag gct ggt gcg gta      2016
Ser Ile Leu His Glu Asn Lys Ser Arg Ile Ile Gln Ala Gly Ala Val
            660                  665                  670 aag tat ctc gta gag ttg atg gac cct gct act ggg atg gtt gac aag      2064
Lys Tyr Leu Val Glu Leu Met Asp Pro Ala Thr Gly Met Val Asp Lys
        675                  680                  685 gct gtt gca gtt ttg tcc aac ctt gct acc att ccc gag gga cga gca      2112
Ala Val Ala Val Leu Ser Asn Leu Ala Thr Ile Pro Glu Gly Arg Ala
690                  695                  700 gaa atc ggt cag gaa gga ggg att cct ctt ctt gtt gag gtt gtt gag      2160
Glu Ile Gly Gln Glu Gly Gly Ile Pro Leu Leu Val Glu Val Val Glu
705                  710                  715                  720 ctg ggc tcc gca agg ggt aag gag aat gca gca gct gct ctc ttg caa      2208
Leu Gly Ser Ala Arg Gly Lys Glu Asn Ala Ala Ala Ala Leu Leu Gln
                725                  730                  735 cta tgc act aac agt agc agg ttc tgc aac atg gtt ctc cag gaa gga      2256
Leu Cys Thr Asn Ser Ser Arg Phe Cys Asn Met Val Leu Gln Glu Gly
            740                  745                  750 gct gta cct cca tta gtg gca ttg tca cag tcc ggc acc cca aga gca      2304
Ala Val Pro Pro Leu Val Ala Leu Ser Gln Ser Gly Thr Pro Arg Ala
        755                  760                  765 aga gaa aag gct caa caa cta ctt agc tac ttc cga aat caa cgc cat      2352
Arg Glu Lys Ala Gln Gln Leu Leu Ser Tyr Phe Arg Asn Gln Arg His
770                  775                  780 ggt aat gca gga aga ggt tga                                           2373
Gly Asn Ala Gly Arg Gly
785                  790

<210> SEQ ID NO 12
<211> LENGTH: 790
<212> TYPE: PRT
<213> ORGANISM: Nicotiana tabacum
```

<400> SEQUENCE: 12

```
Met Glu Ile Ser Leu Leu Lys Val Leu Leu Asn Asn Ile Ser Cys Phe
1               5                   10                  15

Ser His Leu Ser Ser Ser Asp His Ile Ser Gly Glu Leu Val Arg Arg
            20                  25                  30

Tyr Tyr Cys Lys Ile Glu Asp Ile Leu Lys Leu Val Lys Pro Ile Leu
            35                  40                  45

Asp Ala Ile Val Asp Val Glu Ala Ala Ser Gly Glu Leu Leu Leu Lys
        50                  55                  60

Ala Phe Ala Gly Leu Ala Gln Cys Val Asp Glu Leu Arg Glu Leu Phe
65                  70                  75                  80

Glu Thr Leu Glu Pro Leu Cys Ser Lys Val Tyr Phe Val Leu Gln Ala
                85                  90                  95

Glu Pro Leu Ile Gly Lys Ile Arg Ser Cys Ser Leu Glu Ile Leu Glu
            100                 105                 110

Leu Leu Lys Ser Ser His Lys Ser Leu Pro Ala Asp Val Thr Leu Thr
        115                 120                 125

Thr Leu Glu Leu Tyr Ile Leu Lys Ile Lys Tyr Val Asp Tyr Glu Met
130                 135                 140

Ile Ser Val Thr Ile Thr Lys Val Ile Lys Ala Gln Val Glu Gly Leu
145                 150                 155                 160

Gly Thr Ser Ser Asp Ser Phe Ala Lys Ile Ala Asp Cys Leu Ser Leu
                165                 170                 175

Asn Ser Asn Gln Glu Leu Leu Ile Glu Leu Val Ala Leu Glu Lys Leu
            180                 185                 190

Lys Glu Asn Ala Glu Gln Ala Glu Lys Ser Glu Val Val Glu Tyr Ile
        195                 200                 205

Glu Gln Met Ile Thr Leu Val Ser His Met His Asp Cys Phe Val Thr
210                 215                 220

Thr Lys Gln Ser Gln Ser Cys Thr Ala Val Pro Ile Pro Pro Asp Phe
225                 230                 235                 240

Cys Cys Pro Leu Ser Leu Glu Leu Met Thr Asp Pro Val Ile Val Ala
                245                 250                 255

Ser Gly Gln Thr Tyr Glu Arg Ala Phe Ile Arg Arg Trp Ile Asp Leu
            260                 265                 270

Gly Leu Thr Val Cys Pro Lys Thr Arg Gln Thr Leu Gly His Thr Asn
        275                 280                 285

Leu Ile Pro Asn Tyr Thr Val Lys Ala Leu Ile Ala Asn Trp Cys Glu
290                 295                 300

Ile Asn Asn Val Lys Leu Pro Asp Pro Met Lys Ser Leu Ser Leu Asn
305                 310                 315                 320

Gln Pro Ser Leu Ser Pro Asp Ser Thr Gln Ser Ser Gly Ser Pro Arg
                325                 330                 335

Lys Ser Leu Ile Ser Ser Thr Val Ser Gln Arg Glu Gly Ser Ser Pro
            340                 345                 350

Ser His Pro Arg Ser Ser Glu Glu Ser Leu Pro Gly Val Gly Gly
        355                 360                 365

Asn Ile Leu Ala Phe Asp Val Glu Arg Met Arg Ile Lys Ser Glu Asp
370                 375                 380

Arg Met Ala His Ser Gly Glu Ile Ser Ser His Gly His Ser Thr Leu
385                 390                 395                 400

Val Ala Asp Asp Gln Phe Pro Leu Gly His Asn Arg Thr Thr Ser Ala
                405                 410                 415
```

```
Pro Ser Thr Leu Ser Asn Ser Asn Phe Ser Pro Val Ile Pro Gly Asp
            420                 425                 430

Gly Asn Lys Leu Ser Glu Asp Ser Val Ala Ser Gly Asp Val Gly
            435                 440                 445

Leu Asp Ser Lys Pro Ala Ala Ser Val Leu Pro Lys Glu Pro Glu Phe
450                 455                 460

Pro Tyr Thr Pro Glu Met Arg Pro Arg Asn Gln Leu Ile Trp Arg Arg
465                 470                 475                 480

Pro Thr Glu Arg Phe Pro Arg Ile Val Ser Ala Thr Val Glu Arg
            485                 490                 495

Arg Ala Asp Leu Ser Glu Val Glu Glu Gln Val Lys Lys Leu Ile Glu
            500                 505                 510

Glu Leu Lys Ser Thr Ser Leu Asp Met Gln Arg Asn Ala Thr Ala Glu
            515                 520                 525

Leu Arg Leu Leu Ala Lys His Asn Met Asp Asn Arg Met Val Ile Ala
            530                 535                 540

Asn Cys Gly Ala Ile Ser Ser Leu Val Asn Leu Leu His Ser Lys Asp
545                 550                 555                 560

Met Lys Val Gln Glu Asp Ala Val Thr Ala Leu Leu Asn Leu Ser Ile
            565                 570                 575

Asn Asp Asn Asn Lys Cys Ala Ile Ala Asn Ala Asp Ala Ile Glu Pro
            580                 585                 590

Leu Ile His Val Leu Gln Thr Gly Ser Ala Glu Ala Lys Glu Asn Ser
            595                 600                 605

Ala Ala Thr Leu Phe Ser Leu Ser Val Met Glu Glu Asn Lys Met Lys
610                 615                 620

Ile Gly Arg Ser Gly Ala Ile Lys Pro Leu Val Asp Leu Leu Gly Asn
625                 630                 635                 640

Gly Thr Pro Arg Gly Lys Lys Asp Ala Ala Thr Ala Leu Phe Asn Leu
            645                 650                 655

Ser Ile Leu His Glu Asn Lys Ser Arg Ile Ile Gln Ala Gly Ala Val
            660                 665                 670

Lys Tyr Leu Val Glu Leu Met Asp Pro Ala Thr Gly Met Val Asp Lys
            675                 680                 685

Ala Val Ala Val Leu Ser Asn Leu Ala Thr Ile Pro Glu Gly Arg Ala
690                 695                 700

Glu Ile Gly Gln Glu Gly Gly Ile Pro Leu Leu Val Glu Val Val Glu
705                 710                 715                 720

Leu Gly Ser Ala Arg Gly Lys Glu Asn Ala Ala Ala Leu Leu Gln
            725                 730                 735

Leu Cys Thr Asn Ser Ser Arg Phe Cys Asn Met Val Leu Gln Glu Gly
            740                 745                 750

Ala Val Pro Pro Leu Val Ala Leu Ser Gln Ser Gly Thr Pro Arg Ala
            755                 760                 765

Arg Glu Lys Ala Gln Gln Leu Leu Ser Tyr Phe Arg Asn Gln Arg His
            770                 775                 780

Gly Asn Ala Gly Arg Gly
785                 790

<210> SEQ ID NO 13
<211> LENGTH: 2436
<212> TYPE: DNA
<213> ORGANISM: Arabidopsis thaliana
<220> FEATURE:
<221> NAME/KEY: CDS
<222> LOCATION: (1)..(2436)
```

<400> SEQUENCE: 13

| | | | | | | | | | | | | | | | |
|---|---|---|---|---|---|---|---|---|---|---|---|---|---|---|---|
| atg | gaa | gtt | ctt | ctc | aga | agt | atc | tcg | tcg | ttt | cta | aat | ctg | tca | tct | 48 |
| Met | Glu | Val | Leu | Leu | Arg | Ser | Ile | Ser | Ser | Phe | Leu | Asn | Leu | Ser | Ser |
| 1 | | | | 5 | | | | | 10 | | | | | 15 | |

| tct | aaa | cat | att | gat | tta | gac | ccg | ttt | gag | aag | tac | tat | aag | aga | gtt | 96 |
| Ser | Lys | His | Ile | Asp | Leu | Asp | Pro | Phe | Glu | Lys | Tyr | Tyr | Lys | Arg | Val |
| | | | 20 | | | | | 25 | | | | | 30 | | |

| gaa | gag | tta | ttg | aga | gtg | ttg | aag | cct | ata | gca | gat | gtt | gtt | gtt | acc | 144 |
| Glu | Glu | Leu | Leu | Arg | Val | Leu | Lys | Pro | Ile | Ala | Asp | Val | Val | Val | Thr |
| | | 35 | | | | | 40 | | | | | 45 | | | |

| tct | gat | ttt | gtt | ttt | gat | gag | aaa | ctt | ggt | aaa | gca | ttt | gaa | gaa | ttg | 192 |
| Ser | Asp | Phe | Val | Phe | Asp | Glu | Lys | Leu | Gly | Lys | Ala | Phe | Glu | Glu | Leu |
| 50 | | | | | 55 | | | | | 60 | | | | | |

| act | cag | gat | gtt | gat | caa | tcc | att | gat | ctt | ttc | agg | agt | tgg | caa | gct | 240 |
| Thr | Gln | Asp | Val | Asp | Gln | Ser | Ile | Asp | Leu | Phe | Arg | Ser | Trp | Gln | Ala |
| 65 | | | | | 70 | | | | | 75 | | | | | 80 |

| ttc | tct | agt | aaa | gtc | tat | ttc | gtt | ctt | caa | att | gaa | tct | ttg | cta | cca | 288 |
| Phe | Ser | Ser | Lys | Val | Tyr | Phe | Val | Leu | Gln | Ile | Glu | Ser | Leu | Leu | Pro |
| | | | | 85 | | | | | 90 | | | | | 95 | |

| aag | atg | cgg | gac | acc | att | gtg | gat | act | ttt | cag | ttt | ctc | atg | tct | tct | 336 |
| Lys | Met | Arg | Asp | Thr | Ile | Val | Asp | Thr | Phe | Gln | Phe | Leu | Met | Ser | Ser |
| | | | 100 | | | | | 105 | | | | | 110 | | |

| aag | aac | cat | cta | cct | gat | gag | cta | agc | cca | gct | tct | ctt | gag | caa | tgt | 384 |
| Lys | Asn | His | Leu | Pro | Asp | Glu | Leu | Ser | Pro | Ala | Ser | Leu | Glu | Gln | Cys |
| | | | 115 | | | | | 120 | | | | | 125 | | |

| cta | gag | aag | att | aag | cat | ctt | agt | tat | gaa | gaa | ata | tct | tct | gtc | att | 432 |
| Leu | Glu | Lys | Ile | Lys | His | Leu | Ser | Tyr | Glu | Glu | Ile | Ser | Ser | Val | Ile |
| | 130 | | | | | 135 | | | | | 140 | | | | |

| gac | ggt | gct | ttg | agg | gat | cag | aga | gat | ggt | gtt | gga | cct | agc | cct | gag | 480 |
| Asp | Gly | Ala | Leu | Arg | Asp | Gln | Arg | Asp | Gly | Val | Gly | Pro | Ser | Pro | Glu |
| 145 | | | | | 150 | | | | | 155 | | | | | 160 |

| atc | ttg | gtg | aaa | att | gga | gag | aac | act | ggt | ctt | aga | tca | aac | cag | gag | 528 |
| Ile | Leu | Val | Lys | Ile | Gly | Glu | Asn | Thr | Gly | Leu | Arg | Ser | Asn | Gln | Glu |
| | | | | 165 | | | | | 170 | | | | | 175 | |

| att | ctg | att | gaa | gct | gtt | gct | cta | gag | agg | cag | aaa | gag | atg | gct | gag | 576 |
| Ile | Leu | Ile | Glu | Ala | Val | Ala | Leu | Glu | Arg | Gln | Lys | Glu | Met | Ala | Glu |
| | | | 180 | | | | | 185 | | | | | 190 | | |

| cag | tct | gag | aat | aat | gca | gaa | gtc | gag | ttc | ctt | gac | caa | ctg | att | gtt | 624 |
| Gln | Ser | Glu | Asn | Asn | Ala | Glu | Val | Glu | Phe | Leu | Asp | Gln | Leu | Ile | Val |
| | | 195 | | | | | 200 | | | | | 205 | | | |

| att | gta | aac | cgc | atg | cat | gaa | cgt | ctt | ctt | ctg | atc | aaa | cag | act | cag | 672 |
| Ile | Val | Asn | Arg | Met | His | Glu | Arg | Leu | Leu | Leu | Ile | Lys | Gln | Thr | Gln |
| | 210 | | | | | 215 | | | | | 220 | | | | |

| act | tct | agt | gtc | gcc | att | ctt | gcc | gac | ttc | ttt | tgc | cct | ctg | tca | ctt | 720 |
| Thr | Ser | Ser | Val | Ala | Ile | Leu | Ala | Asp | Phe | Phe | Cys | Pro | Leu | Ser | Leu |
| 225 | | | | | 230 | | | | | 235 | | | | | 240 |

| gaa | gta | atg | act | gat | cca | gtg | att | gtg | tca | tca | gga | caa | aca | tat | gaa | 768 |
| Glu | Val | Met | Thr | Asp | Pro | Val | Ile | Val | Ser | Ser | Gly | Gln | Thr | Tyr | Glu |
| | | | | 245 | | | | | 250 | | | | | 255 | |

| aag | gcg | ttt | atc | aag | aga | tgg | att | gat | ttg | ggt | tta | aaa | gtg | tgt | ccc | 816 |
| Lys | Ala | Phe | Ile | Lys | Arg | Trp | Ile | Asp | Leu | Gly | Leu | Lys | Val | Cys | Pro |
| | | | 260 | | | | | 265 | | | | | 270 | | |

| aag | act | cga | cag | acc | ctg | act | cac | act | act | cta | ata | ccc | aat | tac | acc | 864 |
| Lys | Thr | Arg | Gln | Thr | Leu | Thr | His | Thr | Thr | Leu | Ile | Pro | Asn | Tyr | Thr |
| | | 275 | | | | | 280 | | | | | 285 | | | |

| gtg | aag | gcc | tta | atc | gct | aac | tgg | tgt | gag | aca | aac | gat | gtc | aag | ctg | 912 |
| Val | Lys | Ala | Leu | Ile | Ala | Asn | Trp | Cys | Glu | Thr | Asn | Asp | Val | Lys | Leu |
| | 290 | | | | | 295 | | | | | 300 | | | | |

| cct | gat | ccc | aat | aaa | tca | aca | agt | tta | aat | gag | ctt | tct | cct | ctt | tta | 960 |

```
                        -continued

Pro Asp Pro Asn Lys Ser Thr Ser Leu Asn Glu Leu Ser Pro Leu Leu
305             310                 315                 320 tca tgt aca gac tcc att cct agc acg ggt gct gat gtt tct gct cgt      1008
Ser Cys Thr Asp Ser Ile Pro Ser Thr Gly Ala Asp Val Ser Ala Arg
                325                 330                 335 aaa gtt agc aac aag tca cat gat tgg gat gct tct tca agt gaa acc      1056
Lys Val Ser Asn Lys Ser His Asp Trp Asp Ala Ser Ser Ser Glu Thr
                340                 345                 350 ggt aag ccc tcg ttc tca agc cga gca act gaa aga gaa ggt gct tct      1104
Gly Lys Pro Ser Phe Ser Ser Arg Ala Thr Glu Arg Glu Gly Ala Ser
                355                 360                 365 cct tca cgt cct gct tct gcc ttg ggt gct tct tca ccg ggt ata tct      1152
Pro Ser Arg Pro Ala Ser Ala Leu Gly Ala Ser Ser Pro Gly Ile Ser
        370                 375                 380 gga aat ggt tac ggt ttg gac gcc agg agg gga tca cta aat gat ttt      1200
Gly Asn Gly Tyr Gly Leu Asp Ala Arg Arg Gly Ser Leu Asn Asp Phe
385             390                 395                 400 gaa gat aga tca aac gat tct cga gaa ctg agg aca gat gca cct ggt      1248
Glu Asp Arg Ser Asn Asp Ser Arg Glu Leu Arg Thr Asp Ala Pro Gly
                405                 410                 415 agg tca tct gta tct tca act aca cga ggc tca gta gaa aat gga caa      1296
Arg Ser Ser Val Ser Ser Thr Thr Arg Gly Ser Val Glu Asn Gly Gln
                420                 425                 430 aca tct gag aac cac cat cat agg tcc cct tct gct act agc act gtt      1344
Thr Ser Glu Asn His His His Arg Ser Pro Ser Ala Thr Ser Thr Val
                435                 440                 445 tcc aat gag gag ttt cca agg gca gat gcg aat gag aat tca gaa gaa      1392
Ser Asn Glu Glu Phe Pro Arg Ala Asp Ala Asn Glu Asn Ser Glu Glu
                450                 455                 460 tca gct cat gct aca cct tac agc agt gat gct tca gga gaa att aga      1440
Ser Ala His Ala Thr Pro Tyr Ser Ser Asp Ala Ser Gly Glu Ile Arg
465             470                 475                 480 tca ggg cct ctt gct gca acc act tca gca gct act cgc cga gat ttg      1488
Ser Gly Pro Leu Ala Ala Thr Thr Ser Ala Ala Thr Arg Arg Asp Leu
                485                 490                 495 tct gat ttt tcc cca aaa ttc atg gat aga cgt acc cgt ggt caa ttt      1536
Ser Asp Phe Ser Pro Lys Phe Met Asp Arg Arg Thr Arg Gly Gln Phe
                500                 505                 510 tgg cga cgt cca tca gag aga ctc ggt tca agg att gtt tca gcg cct      1584
Trp Arg Arg Pro Ser Glu Arg Leu Gly Ser Arg Ile Val Ser Ala Pro
                515                 520                 525 tcg aat gag aca aga cgt gat ctt tct gag gtc gaa act caa gtt aag      1632
Ser Asn Glu Thr Arg Arg Asp Leu Ser Glu Val Glu Thr Gln Val Lys
                530                 535                 540 aag ttg gtg gag gag ttg aaa agc agc tca ttg gat act cag aga caa      1680
Lys Leu Val Glu Glu Leu Lys Ser Ser Ser Leu Asp Thr Gln Arg Gln
545             550                 555                 560 gca acc gca gaa cta agg ttg cta gcc aag cac aac atg gat aat cgg      1728
Ala Thr Ala Glu Leu Arg Leu Leu Ala Lys His Asn Met Asp Asn Arg
                565                 570                 575 ata gtc att ggg aac tct gga gca atc gtc tta ttg gtg gaa cta ctt      1776
Ile Val Ile Gly Asn Ser Gly Ala Ile Val Leu Leu Val Glu Leu Leu
                580                 585                 590 tac tca act gac tca gct aca cag gaa aac gct gtt acc gca ctt ctc      1824
Tyr Ser Thr Asp Ser Ala Thr Gln Glu Asn Ala Val Thr Ala Leu Leu
                595                 600                 605 aac tta tct atc aat gac aac aac aaa aaa gca att gct gat gct ggt      1872
Asn Leu Ser Ile Asn Asp Asn Asn Lys Lys Ala Ile Ala Asp Ala Gly
        610                 615                 620 gca att gag ccg ctc att cac gtg ctt gaa aat ggg agc tct gaa gcc      1920
```

```
Ala Ile Glu Pro Leu Ile His Val Leu Glu Asn Gly Ser Ser Glu Ala
625                 630                 635                 640 aag gag aat tca gct gct act ctc ttc agc ctc tct gta ata gaa gaa    1968
Lys Glu Asn Ser Ala Ala Thr Leu Phe Ser Leu Ser Val Ile Glu Glu
                645                 650                 655 aac aag att aag att ggt cag tcg ggt gca atc ggg cct ctt gta gat    2016
Asn Lys Ile Lys Ile Gly Gln Ser Gly Ala Ile Gly Pro Leu Val Asp
            660                 665                 670 ctt ctc ggt aac ggt acc cct cgg ggt aag aaa gac gct gct act gcc    2064
Leu Leu Gly Asn Gly Thr Pro Arg Gly Lys Lys Asp Ala Ala Thr Ala
        675                 680                 685 ttg ttt aat cta tcg ata cat caa gaa aac aag gcg atg atc gtg caa    2112
Leu Phe Asn Leu Ser Ile His Gln Glu Asn Lys Ala Met Ile Val Gln
    690                 695                 700 tca ggt gct gtg aga tat ctt att gat ctg atg gac cca gca gct ggg    2160
Ser Gly Ala Val Arg Tyr Leu Ile Asp Leu Met Asp Pro Ala Ala Gly
705                 710                 715                 720 atg gtg gat aaa gca gtt gct gtt ttg gca aat cta gct aca att ccg    2208
Met Val Asp Lys Ala Val Ala Val Leu Ala Asn Leu Ala Thr Ile Pro
                725                 730                 735 gaa gga aga aac gcg att ggt caa gaa ggc gga atc cct ctt ctt gtt    2256
Glu Gly Arg Asn Ala Ile Gly Gln Glu Gly Gly Ile Pro Leu Leu Val
            740                 745                 750 gaa gtc gtt gag ttg ggt tca gct aga ggg aaa gaa aac gca gca gca    2304
Glu Val Val Glu Leu Gly Ser Ala Arg Gly Lys Glu Asn Ala Ala Ala
        755                 760                 765 gct ctt ctt caa ctt tca acc aac agt ggt cgg ttc tgc aac atg gtt    2352
Ala Leu Leu Gln Leu Ser Thr Asn Ser Gly Arg Phe Cys Asn Met Val
    770                 775                 780 ctt caa gaa ggc gcc gtt cct cca ctc gtc gct ctc tca cag tct ggt    2400
Leu Gln Glu Gly Ala Val Pro Pro Leu Val Ala Leu Ser Gln Ser Gly
785                 790                 795                 800 act cct aga gct aga gaa aag gta caa act tta taa                    2436
Thr Pro Arg Ala Arg Glu Lys Val Gln Thr Leu
                805                 810

<210> SEQ ID NO 14
<211> LENGTH: 811
<212> TYPE: PRT
<213> ORGANISM: Arabidopsis thaliana

<400> SEQUENCE: 14

Met Glu Val Leu Leu Arg Ser Ile Ser Ser Phe Leu Asn Leu Ser Ser
1               5                   10                  15

Ser Lys His Ile Asp Leu Asp Pro Phe Glu Lys Tyr Tyr Lys Arg Val
            20                  25                  30

Glu Glu Leu Leu Arg Val Leu Lys Pro Ile Ala Asp Val Val Thr
        35                  40                  45

Ser Asp Phe Val Phe Asp Glu Lys Leu Gly Lys Ala Phe Glu Glu Leu
    50                  55                  60

Thr Gln Asp Val Asp Gln Ser Ile Asp Leu Phe Arg Ser Trp Gln Ala
65                  70                  75                  80

Phe Ser Ser Lys Val Tyr Phe Val Leu Gln Ile Glu Ser Leu Leu Pro
                85                  90                  95

Lys Met Arg Asp Thr Ile Val Asp Thr Phe Gln Phe Leu Met Ser Ser
            100                 105                 110

Lys Asn His Leu Pro Asp Glu Leu Ser Pro Ala Ser Leu Glu Gln Cys
        115                 120                 125

Leu Glu Lys Ile Lys His Leu Ser Tyr Glu Glu Ile Ser Ser Val Ile
```

```
              130                 135                 140
Asp Gly Ala Leu Arg Asp Gln Arg Asp Val Gly Pro Ser Pro Glu
145                 150                 155                 160

Ile Leu Val Lys Ile Gly Glu Asn Thr Gly Leu Arg Ser Asn Gln Glu
                165                 170                 175

Ile Leu Ile Glu Ala Val Ala Leu Glu Arg Gln Lys Glu Met Ala Glu
                180                 185                 190

Gln Ser Glu Asn Asn Ala Glu Val Glu Phe Leu Asp Gln Leu Ile Val
                195                 200                 205

Ile Val Asn Arg Met His Glu Arg Leu Leu Leu Ile Lys Gln Thr Gln
210                 215                 220

Thr Ser Ser Val Ala Ile Leu Ala Asp Phe Phe Cys Pro Leu Ser Leu
225                 230                 235                 240

Glu Val Met Thr Asp Pro Val Ile Val Ser Gly Gln Thr Tyr Glu
                245                 250                 255

Lys Ala Phe Ile Lys Arg Trp Ile Asp Leu Gly Leu Lys Val Cys Pro
                260                 265                 270

Lys Thr Arg Gln Thr Leu Thr His Thr Thr Leu Ile Pro Asn Tyr Thr
                275                 280                 285

Val Lys Ala Leu Ile Ala Asn Trp Cys Glu Thr Asn Asp Val Lys Leu
                290                 295                 300

Pro Asp Pro Asn Lys Ser Thr Ser Leu Asn Glu Leu Ser Pro Leu Leu
305                 310                 315                 320

Ser Cys Thr Asp Ser Ile Pro Ser Thr Gly Ala Asp Val Ser Ala Arg
                325                 330                 335

Lys Val Ser Asn Lys Ser His Asp Trp Asp Ala Ser Ser Ser Glu Thr
                340                 345                 350

Gly Lys Pro Ser Phe Ser Ser Arg Ala Thr Glu Arg Glu Gly Ala Ser
                355                 360                 365

Pro Ser Arg Pro Ala Ser Ala Leu Gly Ala Ser Ser Pro Gly Ile Ser
370                 375                 380

Gly Asn Gly Tyr Gly Leu Asp Ala Arg Arg Gly Ser Leu Asn Asp Phe
385                 390                 395                 400

Glu Asp Arg Ser Asn Asp Ser Arg Glu Leu Arg Thr Asp Ala Pro Gly
                405                 410                 415

Arg Ser Ser Val Ser Ser Thr Thr Arg Gly Ser Val Glu Asn Gly Gln
                420                 425                 430

Thr Ser Glu Asn His His His Arg Ser Pro Ser Ala Thr Ser Thr Val
                435                 440                 445

Ser Asn Glu Glu Phe Pro Arg Ala Asp Ala Asn Glu Asn Ser Glu Glu
450                 455                 460

Ser Ala His Ala Thr Pro Tyr Ser Ser Asp Ala Ser Gly Glu Ile Arg
465                 470                 475                 480

Ser Gly Pro Leu Ala Ala Thr Ser Ala Ala Thr Arg Arg Asp Leu
                485                 490                 495

Ser Asp Phe Ser Pro Lys Phe Met Asp Arg Arg Thr Gly Gln Phe
                500                 505                 510

Trp Arg Arg Pro Ser Glu Arg Leu Gly Ser Arg Ile Val Ser Ala Pro
                515                 520                 525

Ser Asn Glu Thr Arg Arg Asp Leu Ser Glu Val Glu Thr Gln Val Lys
                530                 535                 540

Lys Leu Val Glu Glu Leu Lys Ser Ser Ser Leu Asp Thr Gln Arg Gln
545                 550                 555                 560
```

```
Ala Thr Ala Glu Leu Arg Leu Leu Ala Lys His Asn Met Asp Asn Arg
                565                 570                 575
Ile Val Ile Gly Asn Ser Gly Ala Ile Val Leu Leu Val Glu Leu Leu
            580                 585                 590
Tyr Ser Thr Asp Ser Ala Thr Gln Glu Asn Ala Val Thr Ala Leu Leu
        595                 600                 605
Asn Leu Ser Ile Asn Asp Asn Lys Lys Ala Ile Ala Asp Ala Gly
    610                 615                 620
Ala Ile Glu Pro Leu Ile His Val Leu Glu Asn Gly Ser Ser Glu Ala
625                 630                 635                 640
Lys Glu Asn Ser Ala Ala Thr Leu Phe Ser Leu Ser Val Ile Glu Glu
                645                 650                 655
Asn Lys Ile Lys Ile Gly Gln Ser Gly Ala Ile Gly Pro Leu Val Asp
            660                 665                 670
Leu Leu Gly Asn Gly Thr Pro Arg Gly Lys Lys Asp Ala Ala Thr Ala
        675                 680                 685
Leu Phe Asn Leu Ser Ile His Gln Glu Asn Lys Ala Met Ile Val Gln
    690                 695                 700
Ser Gly Ala Val Arg Tyr Leu Ile Asp Leu Met Asp Pro Ala Ala Gly
705                 710                 715                 720
Met Val Asp Lys Ala Val Ala Val Leu Ala Asn Leu Ala Thr Ile Pro
                725                 730                 735
Glu Gly Arg Asn Ala Ile Gly Gln Glu Gly Gly Ile Pro Leu Leu Val
            740                 745                 750
Glu Val Val Glu Leu Gly Ser Ala Arg Gly Lys Glu Asn Ala Ala Ala
        755                 760                 765
Ala Leu Leu Gln Leu Ser Thr Asn Ser Gly Arg Phe Cys Asn Met Val
    770                 775                 780
Leu Gln Glu Gly Ala Val Pro Pro Leu Val Ala Leu Ser Gln Ser Gly
785                 790                 795                 800
Thr Pro Arg Ala Arg Glu Lys Val Gln Thr Leu
                805                 810

<210> SEQ ID NO 15
<211> LENGTH: 2775
<212> TYPE: DNA
<213> ORGANISM: Arabidopsis thaliana
<220> FEATURE:
<221> NAME/KEY: CDS
<222> LOCATION: (1)..(2775)

<400> SEQUENCE: 15 atg att ttg cgg ttt tgg cgg gaa aac att att ttg cgg ttt tgg cgg      48
Met Ile Leu Arg Phe Trp Arg Glu Asn Ile Ile Leu Arg Phe Trp Arg
1               5                   10                  15 aaa atc cat gat ttt gcg gtt ttg aaa ctc att cag atg tat cat cca      96
Lys Ile His Asp Phe Ala Val Leu Lys Leu Ile Gln Met Tyr His Pro
            20                  25                  30 gat gat cca tcc aaa tac ttg tta aat tat aaa aaa caa aca tca ttt     144
Asp Asp Pro Ser Lys Tyr Leu Leu Asn Tyr Lys Lys Gln Thr Ser Phe
        35                  40                  45 ttc atc tgc att tgg atg aat cat ttg gat gaa aaa caa aca agg tct     192
Phe Ile Cys Ile Trp Met Asn His Leu Asp Glu Lys Gln Thr Arg Ser
    50                  55                  60 gag tct gat ttc aca gtt tcc aaa aga gat ata aga agg gtg gaa atg     240
Glu Ser Asp Phe Thr Val Ser Lys Arg Asp Ile Arg Arg Val Glu Met
65                  70                  75                  80 gaa gtt ctt ctc aga agt atc tcg tcg ttt cta aat ctg tca tct tct     288
```

-continued

| | | |
|---|---|---|
| Glu Val Leu Leu Arg Ser Ile Ser Ser Phe Leu Asn Leu Ser Ser Ser<br>                        85                        90                        95 | |
| aaa cat att gat tta gac ccg ttt gag aag tac tat aag aga gtt gaa<br>Lys His Ile Asp Leu Asp Pro Phe Glu Lys Tyr Tyr Lys Arg Val Glu<br>                  100                      105                      110 | 336 |
| gag tta ttg aga gtg ttg aag cct ata gca gat gtt gtt acc tct<br>Glu Leu Leu Arg Val Leu Lys Pro Ile Ala Asp Val Val Thr Ser<br>           115                      120                      125 | 384 |
| gat ttt gtt ttt gat gag aaa ctt ggt aaa gca ttt gaa gaa ttg act<br>Asp Phe Val Phe Asp Glu Lys Leu Gly Lys Ala Phe Glu Glu Leu Thr<br>        130                      135                      140 | 432 |
| cag gat gtt gat caa tcc att gat ctt ttc agg agt tgg caa gct ttc<br>Gln Asp Val Asp Gln Ser Ile Asp Leu Phe Arg Ser Trp Gln Ala Phe<br>145                      150                      155                  160 | 480 |
| tct agt aaa gtc tat ttc gtt ctt caa att gaa tct ttg cta cca aag<br>Ser Ser Lys Val Tyr Phe Val Leu Gln Ile Glu Ser Leu Leu Pro Lys<br>                      165                      170                  175 | 528 |
| atg cgg gac acc att gtg gat act ttt cag ttt ctc atg tct tct aag<br>Met Arg Asp Thr Ile Val Asp Thr Phe Gln Phe Leu Met Ser Ser Lys<br>                180                      185                      190 | 576 |
| aac cat cta cct gat gag cta agc cca gct tct ctt gag caa tgt cta<br>Asn His Leu Pro Asp Glu Leu Ser Pro Ala Ser Leu Glu Gln Cys Leu<br>           195                      200                      205 | 624 |
| gag aag att aag cat ctt agt tat gaa gaa ata tct tct gtc att gac<br>Glu Lys Ile Lys His Leu Ser Tyr Glu Glu Ile Ser Ser Val Ile Asp<br>210                      215                      220 | 672 |
| ggt gct ttg agg gat cag aga gat ggt gtt gga cct agc cct gag atc<br>Gly Ala Leu Arg Asp Gln Arg Asp Gly Val Gly Pro Ser Pro Glu Ile<br>225                      230                      235                  240 | 720 |
| ttg gtg aaa att gga gag aac act ggt ctt aga tca aac cag gag att<br>Leu Val Lys Ile Gly Glu Asn Thr Gly Leu Arg Ser Asn Gln Glu Ile<br>                245                      250                  255 | 768 |
| ctg att gaa gct gtt gct cta gag agg cag aaa gag atg gct gag cag<br>Leu Ile Glu Ala Val Ala Leu Glu Arg Gln Lys Glu Met Ala Glu Gln<br>           260                      265                      270 | 816 |
| tct gag aat aat gca gaa gtc gag ttc ctt gac caa ctg att gtt att<br>Ser Glu Asn Asn Ala Glu Val Glu Phe Leu Asp Gln Leu Ile Val Ile<br>        275                      280                      285 | 864 |
| gta aac cgc atg cat gaa cgt ctt ctt ctg atc aaa cag act cag act<br>Val Asn Arg Met His Glu Arg Leu Leu Leu Ile Lys Gln Thr Gln Thr<br>290                      295                      300 | 912 |
| tct agt gtc gcc att ctt gcc gac ttc ttt tgc cct ctg tca ctt gaa<br>Ser Ser Val Ala Ile Leu Ala Asp Phe Phe Cys Pro Leu Ser Leu Glu<br>305                      310                      315                  320 | 960 |
| gta atg act gat cca gtg att gtg tca tca gga caa aca tat gaa aag<br>Val Met Thr Asp Pro Val Ile Val Ser Ser Gly Gln Thr Tyr Glu Lys<br>                  325                      330                  335 | 1008 |
| gcg ttt atc aag aga tgg att gat ttg ggt tta aaa gtg tgt ccc aag<br>Ala Phe Ile Lys Arg Trp Ile Asp Leu Gly Leu Lys Val Cys Pro Lys<br>                340                      345                  350 | 1056 |
| act cga cag acc ctg act cac act act cta ata ccc aat tac acc gtg<br>Thr Arg Gln Thr Leu Thr His Thr Thr Leu Ile Pro Asn Tyr Thr Val<br>           355                      360                      365 | 1104 |
| aag gcc tta atc gct aac tgg tgt gag aca aac gat gtc aag ctg cct<br>Lys Ala Leu Ile Ala Asn Trp Cys Glu Thr Asn Asp Val Lys Leu Pro<br>370                      375                      380 | 1152 |
| gat ccc aat aaa tca aca agt tta aat gag ctt tct cct ctt tta tca<br>Asp Pro Asn Lys Ser Thr Ser Leu Asn Glu Leu Ser Pro Leu Leu Ser<br>385                      390                      395                  400 | 1200 |
| tgt aca gac tcc att cct agc acg ggt gct gat gtt tct gct cgt aaa | 1248 |

|     |     |     |     |     |     |     |     |     |     |     |     |     |      |
|-----|-----|-----|-----|-----|-----|-----|-----|-----|-----|-----|-----|-----|------|
| Cys | Thr | Asp | Ser | Ile | Pro | Ser | Thr | Gly | Ala | Asp | Val | Ser | Ala Arg Lys |
|     |     |     |     | 405 |     |     |     | 410 |     |     |     | 415 |      |

```
gtt agc aac aag tca cat gat tgg gat gct tct tca agt gaa acc ggt      1296
Val Ser Asn Lys Ser His Asp Trp Asp Ala Ser Ser Ser Glu Thr Gly
            420                 425                 430 aag ccc tcg ttc tca agc cga gca act gaa aga gaa ggt gct tct cct      1344
Lys Pro Ser Phe Ser Ser Arg Ala Thr Glu Arg Glu Gly Ala Ser Pro
            435                 440                 445 tca cgt cct gct tct gcc ttg ggt gct tct tca ccg ggt ata tct gga      1392
Ser Arg Pro Ala Ser Ala Leu Gly Ala Ser Ser Pro Gly Ile Ser Gly
    450                 455                 460 aat ggt tac ggt ttg gac gcc agg agg gga tca cta aat gat ttt gaa      1440
Asn Gly Tyr Gly Leu Asp Ala Arg Arg Gly Ser Leu Asn Asp Phe Glu
465                 470                 475                 480 gat aga tca aac gat tct cga gaa ctg agg aca gat gca cct ggt agg      1488
Asp Arg Ser Asn Asp Ser Arg Glu Leu Arg Thr Asp Ala Pro Gly Arg
            485                 490                 495 tca tct gta tct tca act aca cga ggc tca gta gaa aat gga caa aca      1536
Ser Ser Val Ser Ser Thr Thr Arg Gly Ser Val Glu Asn Gly Gln Thr
    500                 505                 510 tct gag aac cac cat cat agg tcc cct tct gct act agc act gtt tcc      1584
Ser Glu Asn His His His Arg Ser Pro Ser Ala Thr Ser Thr Val Ser
515                 520                 525 aat gag gag ttt cca agg gca gat gcg aat gag aat tca gaa gaa tca      1632
Asn Glu Glu Phe Pro Arg Ala Asp Ala Asn Glu Asn Ser Glu Glu Ser
            530                 535                 540 gct cat gct aca cct tac agc agt gat gct tca gga gaa att aga tca      1680
Ala His Ala Thr Pro Tyr Ser Ser Asp Ala Ser Gly Glu Ile Arg Ser
545                 550                 555                 560 ggg cct ctt gct gca acc act tca gca gct act cgc cga gat ttg tct      1728
Gly Pro Leu Ala Ala Thr Thr Ser Ala Ala Thr Arg Arg Asp Leu Ser
            565                 570                 575 gat ttt tcc cca aaa ttc atg gat aga cgt acc cgt ggt caa ttt tgg      1776
Asp Phe Ser Pro Lys Phe Met Asp Arg Arg Thr Arg Gly Gln Phe Trp
            580                 585                 590 cga cgt cca tca gag aga ctc ggt tca agg att gtt tca gcg cct tcg      1824
Arg Arg Pro Ser Glu Arg Leu Gly Ser Arg Ile Val Ser Ala Pro Ser
    595                 600                 605 aat gag aca aga cgt gat ctt tct gag gtc gaa act caa gtt aag aag      1872
Asn Glu Thr Arg Arg Asp Leu Ser Glu Val Glu Thr Gln Val Lys Lys
610                 615                 620 ttg gtg gag gag ttg aaa agc agc tca ttg gat act cag aga caa gca      1920
Leu Val Glu Glu Leu Lys Ser Ser Ser Leu Asp Thr Gln Arg Gln Ala
625                 630                 635                 640 acc gca gaa cta agg ttg cta gcc aag cac aac atg gat aat cgg ata      1968
Thr Ala Glu Leu Arg Leu Leu Ala Lys His Asn Met Asp Asn Arg Ile
            645                 650                 655 gtc att ggg aac tct gga gca atc gtc tta ttg gtg gaa cta ctt tac      2016
Val Ile Gly Asn Ser Gly Ala Ile Val Leu Leu Val Glu Leu Leu Tyr
            660                 665                 670 tca act gac tca gct aca cag gaa aac gct gtt acc gca ctt ctc aac      2064
Ser Thr Asp Ser Ala Thr Gln Glu Asn Ala Val Thr Ala Leu Leu Asn
            675                 680                 685 tta tct atc aat gac aac aac aaa aaa gca att gct gat gct ggt gca      2112
Leu Ser Ile Asn Asp Asn Asn Lys Lys Ala Ile Ala Asp Ala Gly Ala
            690                 695                 700 att gag ccg ctc att cac gtg ctt gaa aat ggg agc tct gaa gcc aag      2160
Ile Glu Pro Leu Ile His Val Leu Glu Asn Gly Ser Ser Glu Ala Lys
705                 710                 715                 720 gag aat tca gct gct act ctc ttc agc ctc tct gta ata gaa gaa aac      2208
```

```
Glu Asn Ser Ala Ala Thr Leu Phe Ser Leu Ser Val Ile Glu Glu Asn
                725                 730                 735 aag att aag att ggt cag tcg ggt gca atc ggg cct ctt gta gat ctt    2256
Lys Ile Lys Ile Gly Gln Ser Gly Ala Ile Gly Pro Leu Val Asp Leu
                740                 745                 750 ctc ggt aac ggt acc cct cgg ggt aag aaa gac gct gct act gcc ttg    2304
Leu Gly Asn Gly Thr Pro Arg Gly Lys Lys Asp Ala Ala Thr Ala Leu
                755                 760                 765 ttt aat cta tcg ata cat caa gaa aac aag gcg atg atc gtg caa tca    2352
Phe Asn Leu Ser Ile His Gln Glu Asn Lys Ala Met Ile Val Gln Ser
                770                 775                 780 ggt gct gtg aga tat ctt att gat ctg atg gac cca gca gct ggg atg    2400
Gly Ala Val Arg Tyr Leu Ile Asp Leu Met Asp Pro Ala Ala Gly Met
785                 790                 795                 800 gtg gat aaa gca gtt gct gtt ttg gca aat cta gct aca att ccg gaa    2448
Val Asp Lys Ala Val Ala Val Leu Ala Asn Leu Ala Thr Ile Pro Glu
                805                 810                 815 gga aga aac gcg att ggt caa gaa ggc gga atc cct ctt ctt gtt gaa    2496
Gly Arg Asn Ala Ile Gly Gln Glu Gly Gly Ile Pro Leu Leu Val Glu
                820                 825                 830 gtc gtt gag ttg ggt tca gct aga ggg aaa gaa aac gca gca gca gct    2544
Val Val Glu Leu Gly Ser Ala Arg Gly Lys Glu Asn Ala Ala Ala Ala
                835                 840                 845 ctt ctt caa ctt tca acc aac agt ggt cgg ttc tgc aac atg gtt ctt    2592
Leu Leu Gln Leu Ser Thr Asn Ser Gly Arg Phe Cys Asn Met Val Leu
850                 855                 860 caa gaa ggc gcc gtt cct cca ctc gtc gct ctc tca cag tct ggt act    2640
Gln Glu Gly Ala Val Pro Pro Leu Val Ala Leu Ser Gln Ser Gly Thr
865                 870                 875                 880 cct aga gct aga gaa aag aaa cca acg gca tgg aaa cgc tgg gcg tgg    2688
Pro Arg Ala Arg Glu Lys Lys Pro Thr Ala Trp Lys Arg Trp Ala Trp
                885                 890                 895 ctg atg atg gat gat gat gat gat gat gtt gat gat gca cag att       2736
Leu Met Met Asp Asp Asp Asp Asp Asp Val Asp Asp Ala Gln Ile
                900                 905                 910 ctg gtc tct cag tgc cta ttt tta tgt ttt gtc ttg tga               2775
Leu Val Ser Gln Cys Leu Phe Leu Cys Phe Val Leu
                915                 920

<210> SEQ ID NO 16
<211> LENGTH: 924
<212> TYPE: PRT
<213> ORGANISM: Arabidopsis thaliana

<400> SEQUENCE: 16

Met Ile Leu Arg Phe Trp Arg Glu Asn Ile Ile Leu Arg Phe Trp Arg
1               5                   10                  15

Lys Ile His Asp Phe Ala Val Leu Lys Leu Ile Gln Met Tyr His Pro
                20                  25                  30

Asp Asp Pro Ser Lys Tyr Leu Leu Asn Tyr Lys Lys Gln Thr Ser Phe
                35                  40                  45

Phe Ile Cys Ile Trp Met Asn His Leu Asp Glu Lys Gln Thr Arg Ser
            50                  55                  60

Glu Ser Asp Phe Thr Val Ser Lys Arg Asp Ile Arg Arg Val Glu Met
65                  70                  75                  80

Glu Val Leu Leu Arg Ser Ile Ser Ser Phe Leu Asn Leu Ser Ser Ser
                    85                  90                  95

Lys His Ile Asp Leu Asp Pro Phe Glu Lys Tyr Tyr Lys Arg Val Glu
                100                 105                 110
```

```
Glu Leu Leu Arg Val Leu Lys Pro Ile Ala Asp Val Val Thr Ser
    115                 120                 125
Asp Phe Val Phe Asp Glu Lys Leu Gly Lys Ala Phe Glu Glu Leu Thr
    130                 135                 140
Gln Asp Val Asp Gln Ser Ile Asp Leu Phe Arg Ser Trp Gln Ala Phe
145                 150                 155                 160
Ser Ser Lys Val Tyr Phe Val Leu Gln Ile Glu Ser Leu Leu Pro Lys
                165                 170                 175
Met Arg Asp Thr Ile Val Asp Thr Phe Gln Phe Leu Met Ser Ser Lys
                180                 185                 190
Asn His Leu Pro Asp Glu Leu Ser Pro Ala Ser Leu Glu Gln Cys Leu
                195                 200                 205
Glu Lys Ile Lys His Leu Ser Tyr Glu Glu Ile Ser Ser Val Ile Asp
    210                 215                 220
Gly Ala Leu Arg Asp Gln Arg Asp Gly Val Gly Pro Ser Pro Glu Ile
225                 230                 235                 240
Leu Val Lys Ile Gly Glu Asn Thr Gly Leu Arg Ser Asn Gln Glu Ile
                245                 250                 255
Leu Ile Glu Ala Val Ala Leu Glu Arg Gln Lys Glu Met Ala Glu Gln
        260                 265                 270
Ser Glu Asn Asn Ala Glu Val Glu Phe Leu Asp Gln Leu Ile Val Ile
        275                 280                 285
Val Asn Arg Met His Glu Arg Leu Leu Leu Ile Lys Gln Thr Gln Thr
    290                 295                 300
Ser Ser Val Ala Ile Leu Ala Asp Phe Phe Cys Pro Leu Ser Leu Glu
305                 310                 315                 320
Val Met Thr Asp Pro Val Ile Val Ser Ser Gly Gln Thr Tyr Glu Lys
                325                 330                 335
Ala Phe Ile Lys Arg Trp Ile Asp Leu Gly Leu Lys Val Cys Pro Lys
                340                 345                 350
Thr Arg Gln Thr Leu Thr His Thr Thr Leu Ile Pro Asn Tyr Thr Val
                355                 360                 365
Lys Ala Leu Ile Ala Asn Trp Cys Glu Thr Asn Asp Val Lys Leu Pro
    370                 375                 380
Asp Pro Asn Lys Ser Thr Ser Leu Asn Glu Leu Ser Pro Leu Leu Ser
385                 390                 395                 400
Cys Thr Asp Ser Ile Pro Ser Thr Gly Ala Asp Val Ser Ala Arg Lys
                405                 410                 415
Val Ser Asn Lys Ser His Asp Trp Asp Ala Ser Ser Glu Thr Gly
                420                 425                 430
Lys Pro Ser Phe Ser Ser Arg Ala Thr Glu Arg Glu Gly Ala Ser Pro
                435                 440                 445
Ser Arg Pro Ala Ser Ala Leu Gly Ala Ser Pro Gly Ile Ser Gly
    450                 455                 460
Asn Gly Tyr Gly Leu Asp Ala Arg Arg Gly Ser Leu Asn Asp Phe Glu
465                 470                 475                 480
Asp Arg Ser Asn Asp Ser Arg Glu Leu Arg Thr Asp Ala Pro Gly Arg
                485                 490                 495
Ser Ser Val Ser Ser Thr Thr Arg Gly Ser Val Glu Asn Gly Gln Thr
                500                 505                 510
Ser Glu Asn His His His Arg Ser Pro Ser Ala Thr Ser Thr Val Ser
    515                 520                 525
Asn Glu Glu Phe Pro Arg Ala Asp Ala Asn Glu Asn Ser Glu Glu Ser
    530                 535                 540
```

```
Ala His Ala Thr Pro Tyr Ser Ser Asp Ala Ser Gly Glu Ile Arg Ser
545                 550                 555                 560

Gly Pro Leu Ala Ala Thr Thr Ser Ala Ala Thr Arg Arg Asp Leu Ser
            565                 570                 575

Asp Phe Ser Pro Lys Phe Met Asp Arg Arg Thr Arg Gly Gln Phe Trp
        580                 585                 590

Arg Arg Pro Ser Glu Arg Leu Gly Ser Arg Ile Val Ser Ala Pro Ser
        595                 600                 605

Asn Glu Thr Arg Arg Asp Leu Ser Glu Val Glu Thr Gln Val Lys Lys
    610                 615                 620

Leu Val Glu Glu Leu Lys Ser Ser Ser Leu Asp Thr Gln Arg Gln Ala
625                 630                 635                 640

Thr Ala Glu Leu Arg Leu Leu Ala Lys His Asn Met Asp Asn Arg Ile
                645                 650                 655

Val Ile Gly Asn Ser Gly Ala Ile Val Leu Val Glu Leu Leu Tyr
            660                 665                 670

Ser Thr Asp Ser Ala Thr Gln Glu Asn Ala Val Thr Ala Leu Leu Asn
        675                 680                 685

Leu Ser Ile Asn Asp Asn Lys Lys Ala Ile Ala Asp Ala Gly Ala
690                 695                 700

Ile Glu Pro Leu Ile His Val Leu Glu Asn Gly Ser Ser Glu Ala Lys
705                 710                 715                 720

Glu Asn Ser Ala Ala Thr Leu Phe Ser Leu Ser Val Ile Glu Asn
                725                 730                 735

Lys Ile Lys Ile Gly Gln Ser Gly Ala Ile Gly Pro Leu Val Asp Leu
                740                 745                 750

Leu Gly Asn Gly Thr Pro Arg Gly Lys Lys Asp Ala Ala Thr Ala Leu
            755                 760                 765

Phe Asn Leu Ser Ile His Gln Glu Asn Lys Ala Met Ile Val Gln Ser
        770                 775                 780

Gly Ala Val Arg Tyr Leu Ile Asp Leu Met Asp Pro Ala Ala Gly Met
785                 790                 795                 800

Val Asp Lys Ala Val Ala Val Leu Ala Asn Leu Ala Thr Ile Pro Glu
            805                 810                 815

Gly Arg Asn Ala Ile Gly Gln Glu Gly Gly Ile Pro Leu Leu Val Glu
        820                 825                 830

Val Val Glu Leu Gly Ser Ala Arg Gly Lys Glu Asn Ala Ala Ala Ala
    835                 840                 845

Leu Leu Gln Leu Ser Thr Asn Ser Gly Arg Phe Cys Asn Met Val Leu
850                 855                 860

Gln Glu Gly Ala Val Pro Pro Leu Val Ala Leu Ser Gln Ser Gly Thr
865                 870                 875                 880

Pro Arg Ala Arg Glu Lys Lys Pro Thr Ala Trp Lys Arg Trp Ala Trp
                885                 890                 895

Leu Met Met Asp Asp Asp Asp Asp Val Asp Asp Ala Gln Ile
            900                 905                 910

Leu Val Ser Gln Cys Leu Phe Leu Cys Phe Val Leu
            915                 920
```

<210> SEQ ID NO 17
<211> LENGTH: 2124
<212> TYPE: DNA
<213> ORGANISM: Arabidopsis thaliana
<220> FEATURE:
<221> NAME/KEY: CDS

<222> LOCATION: (1)..(2124)

<400> SEQUENCE: 17

| | | | | | | | | | | | | | | | | |
|---|---|---|---|---|---|---|---|---|---|---|---|---|---|---|---|---|
| atg | atg | gta | cat | atg | gag | gtg | tct | tgg | tta | aga | gtt | ctt | cta | gat | aac | 48 |
| Met | Met | Val | His | Met | Glu | Val | Ser | Trp | Leu | Arg | Val | Leu | Leu | Asp | Asn | |
| 1 | | | | 5 | | | | | 10 | | | | | 15 | | |

| atc | tcc | tcc | tat | cta | agt | tta | tca | tct | atg | gac | gat | tta | tct | tca | aac | 96 |
|---|---|---|---|---|---|---|---|---|---|---|---|---|---|---|---|---|
| Ile | Ser | Ser | Tyr | Leu | Ser | Leu | Ser | Ser | Met | Asp | Asp | Leu | Ser | Ser | Asn | |
| | | | 20 | | | | | 25 | | | | | 30 | | | |

| cct | gct | cat | aag | tac | tac | acc | aga | gga | gaa | gat | ata | gga | aag | ctt | atc | 144 |
|---|---|---|---|---|---|---|---|---|---|---|---|---|---|---|---|---|
| Pro | Ala | His | Lys | Tyr | Tyr | Thr | Arg | Gly | Glu | Asp | Ile | Gly | Lys | Leu | Ile | |
| | | 35 | | | | | 40 | | | | | 45 | | | | |

| aag | cct | gtt | ctt | gag | aac | ctc | att | gac | tct | gac | gcg | gct | cct | agc | gag | 192 |
|---|---|---|---|---|---|---|---|---|---|---|---|---|---|---|---|---|
| Lys | Pro | Val | Leu | Glu | Asn | Leu | Ile | Asp | Ser | Asp | Ala | Ala | Pro | Ser | Glu | |
| 50 | | | | | 55 | | | | | 60 | | | | | | |

| ttg | ctt | aac | aat | ggt | ttt | gaa | gaa | tta | gct | caa | tac | gtt | gat | gaa | ctt | 240 |
|---|---|---|---|---|---|---|---|---|---|---|---|---|---|---|---|---|
| Leu | Leu | Asn | Asn | Gly | Phe | Glu | Glu | Leu | Ala | Gln | Tyr | Val | Asp | Glu | Leu | |
| 65 | | | | | 70 | | | | | 75 | | | | | 80 | |

| aga | gaa | cag | ttt | cag | agt | tgg | caa | cct | ctt | tca | act | aga | atc | ttt | tat | 288 |
|---|---|---|---|---|---|---|---|---|---|---|---|---|---|---|---|---|
| Arg | Glu | Gln | Phe | Gln | Ser | Trp | Gln | Pro | Leu | Ser | Thr | Arg | Ile | Phe | Tyr | |
| | | | | 85 | | | | | 90 | | | | | 95 | | |

| gtt | ctt | cga | att | gaa | tca | tta | gca | tca | aag | tta | cga | gaa | tcc | agt | ttg | 336 |
|---|---|---|---|---|---|---|---|---|---|---|---|---|---|---|---|---|
| Val | Leu | Arg | Ile | Glu | Ser | Leu | Ala | Ser | Lys | Leu | Arg | Glu | Ser | Ser | Leu | |
| | | | 100 | | | | | 105 | | | | | 110 | | | |

| gaa | gtc | ttt | cag | ctc | ctc | aaa | cac | tgc | gaa | caa | cat | ttg | cct | gct | gac | 384 |
|---|---|---|---|---|---|---|---|---|---|---|---|---|---|---|---|---|
| Glu | Val | Phe | Gln | Leu | Leu | Lys | His | Cys | Glu | Gln | His | Leu | Pro | Ala | Asp | |
| | | 115 | | | | | 120 | | | | | 125 | | | | |

| ttg | atc | tca | cct | tct | ttt | gag | gag | tgc | att | gaa | ttg | gtg | aag | tta | gtg | 432 |
|---|---|---|---|---|---|---|---|---|---|---|---|---|---|---|---|---|
| Leu | Ile | Ser | Pro | Ser | Phe | Glu | Glu | Cys | Ile | Glu | Leu | Val | Lys | Leu | Val | |
| 130 | | | | | 135 | | | | | 140 | | | | | | |

| gca | aga | gac | gaa | ata | tcg | tat | act | att | gat | caa | gct | cta | aaa | gat | caa | 480 |
|---|---|---|---|---|---|---|---|---|---|---|---|---|---|---|---|---|
| Ala | Arg | Asp | Glu | Ile | Ser | Tyr | Thr | Ile | Asp | Gln | Ala | Leu | Lys | Asp | Gln | |
| 145 | | | | | 150 | | | | | 155 | | | | | 160 | |

| aag | aaa | ggt | gtt | gga | cct | act | tca | gag | gtt | ctg | gtg | aaa | att | gcc | gag | 528 |
|---|---|---|---|---|---|---|---|---|---|---|---|---|---|---|---|---|
| Lys | Lys | Gly | Val | Gly | Pro | Thr | Ser | Glu | Val | Leu | Val | Lys | Ile | Ala | Glu | |
| | | | | 165 | | | | | 170 | | | | | 175 | | |

| agt | act | ggt | tta | aga | tcc | aac | cag | gag | att | ctt | gtt | gaa | ggt | gtg | gta | 576 |
|---|---|---|---|---|---|---|---|---|---|---|---|---|---|---|---|---|
| Ser | Thr | Gly | Leu | Arg | Ser | Asn | Gln | Glu | Ile | Leu | Val | Glu | Gly | Val | Val | |
| | | | 180 | | | | | 185 | | | | | 190 | | | |

| ctt | aca | aac | atg | aag | gag | gat | gct | gag | ctt | acc | gat | aat | gac | acc | gaa | 624 |
|---|---|---|---|---|---|---|---|---|---|---|---|---|---|---|---|---|
| Leu | Thr | Asn | Met | Lys | Glu | Asp | Ala | Glu | Leu | Thr | Asp | Asn | Asp | Thr | Glu | |
| | | 195 | | | | | 200 | | | | | 205 | | | | |

| gcc | gag | tat | cta | gac | gga | ttg | atc | tct | cta | aca | aca | caa | atg | cat | gag | 672 |
|---|---|---|---|---|---|---|---|---|---|---|---|---|---|---|---|---|
| Ala | Glu | Tyr | Leu | Asp | Gly | Leu | Ile | Ser | Leu | Thr | Thr | Gln | Met | His | Glu | |
| 210 | | | | | 215 | | | | | 220 | | | | | | |

| tac | ctt | agc | gac | ata | aag | cag | gct | cag | tta | cgt | tgt | cca | gta | cgc | gta | 720 |
|---|---|---|---|---|---|---|---|---|---|---|---|---|---|---|---|---|
| Tyr | Leu | Ser | Asp | Ile | Lys | Gln | Ala | Gln | Leu | Arg | Cys | Pro | Val | Arg | Val | |
| 225 | | | | | 230 | | | | | 235 | | | | | 240 | |

| cct | tct | gat | ttc | cgc | tgc | tct | cta | tct | ctt | gag | ctt | atg | act | gat | cca | 768 |
|---|---|---|---|---|---|---|---|---|---|---|---|---|---|---|---|---|
| Pro | Ser | Asp | Phe | Arg | Cys | Ser | Leu | Ser | Leu | Glu | Leu | Met | Thr | Asp | Pro | |
| | | | | 245 | | | | | 250 | | | | | 255 | | |

| gtc | att | gta | gca | tct | ggt | caa | aca | ttc | gaa | cgg | gtt | ttt | atc | cag | aaa | 816 |
|---|---|---|---|---|---|---|---|---|---|---|---|---|---|---|---|---|
| Val | Ile | Val | Ala | Ser | Gly | Gln | Thr | Phe | Glu | Arg | Val | Phe | Ile | Gln | Lys | |
| | | | 260 | | | | | 265 | | | | | 270 | | | |

| tgg | atc | gat | atg | gga | ctc | atg | gtt | tgt | cca | aag | aca | agg | cag | gct | tta | 864 |
|---|---|---|---|---|---|---|---|---|---|---|---|---|---|---|---|---|
| Trp | Ile | Asp | Met | Gly | Leu | Met | Val | Cys | Pro | Lys | Thr | Arg | Gln | Ala | Leu | |
| | | | 275 | | | | | 280 | | | | | 285 | | | |

| tct | cat | acc | act | ttg | aca | cct | aat | ttc | att | gtc | aga | gct | ttt | ctt | gca | 912 |
|---|---|---|---|---|---|---|---|---|---|---|---|---|---|---|---|---|
| Ser | His | Thr | Thr | Leu | Thr | Pro | Asn | Phe | Ile | Val | Arg | Ala | Phe | Leu | Ala | |
| | | 290 | | | | | 295 | | | | | 300 | | | | |

```
agt tgg tgt gaa act aac aat gtc tat cct cct gat cca ttg gag ttg      960
Ser Trp Cys Glu Thr Asn Asn Val Tyr Pro Pro Asp Pro Leu Glu Leu
305             310                 315                 320 att cac tca agt gag cca ttc cct ctt ctt gtt gaa tca gtg aga gct     1008
Ile His Ser Ser Glu Pro Phe Pro Leu Leu Val Glu Ser Val Arg Ala
            325                 330                 335 tca tca tca gag aat ggc cat tca gaa tct tta gat gca gag gaa ctg     1056
Ser Ser Ser Glu Asn Gly His Ser Glu Ser Leu Asp Ala Glu Glu Leu
        340                 345                 350 cgt cag gtc ttt agt agg tct gct tcg gcg cca ggc att gtc tct gaa     1104
Arg Gln Val Phe Ser Arg Ser Ala Ser Ala Pro Gly Ile Val Ser Glu
    355                 360                 365 gtg gtt tgc aaa acc aaa aga aac aac aat gct gct gca gat aga tca     1152
Val Val Cys Lys Thr Lys Arg Asn Asn Asn Ala Ala Ala Asp Arg Ser
370                 375                 380 ctg aca cgg agt aat acc cct tgg aaa ttt cca gaa gag agg cat tgg     1200
Leu Thr Arg Ser Asn Thr Pro Trp Lys Phe Pro Glu Glu Arg His Trp
385             390                 395                 400 cgt cac ccc ggg atc atc cca gcg acc gta aga gaa aca gga agc agt     1248
Arg His Pro Gly Ile Ile Pro Ala Thr Val Arg Glu Thr Gly Ser Ser
            405                 410                 415 tca agt atc gaa acc gag gtg aag aaa ctc att gat gat ctc aag agt     1296
Ser Ser Ile Glu Thr Glu Val Lys Lys Leu Ile Asp Asp Leu Lys Ser
        420                 425                 430 tct tca ttg gat aca cag aga gag gcc aca gct aga atc agg ata cta     1344
Ser Ser Leu Asp Thr Gln Arg Glu Ala Thr Ala Arg Ile Arg Ile Leu
    435                 440                 445 gca aga aac agt aca gac aat cgc att gtc att gcg cgg tgc gaa gca     1392
Ala Arg Asn Ser Thr Asp Asn Arg Ile Val Ile Ala Arg Cys Glu Ala
450                 455                 460 atc cct tcg tta gtc agt ctt ctt tac tca acg gat gag aga atc caa     1440
Ile Pro Ser Leu Val Ser Leu Leu Tyr Ser Thr Asp Glu Arg Ile Gln
465             470                 475                 480 gca gac gca gtg act tgc tta cta aac tta tcc atc aac gac aac aac     1488
Ala Asp Ala Val Thr Cys Leu Leu Asn Leu Ser Ile Asn Asp Asn Asn
            485                 490                 495 aag tcc ctc atc gcg gaa agt gga gcc atc gta ccg ctt att cac gtt     1536
Lys Ser Leu Ile Ala Glu Ser Gly Ala Ile Val Pro Leu Ile His Val
        500                 505                 510 ctc aaa aca gga tac tta gaa gaa gct aaa gca aac tca gca gca act     1584
Leu Lys Thr Gly Tyr Leu Glu Glu Ala Lys Ala Asn Ser Ala Ala Thr
    515                 520                 525 cta ttc agc ttg tcg gtg atc gaa gag tac aag aca gag ata gga gaa     1632
Leu Phe Ser Leu Ser Val Ile Glu Glu Tyr Lys Thr Glu Ile Gly Glu
530                 535                 540 gca gga gct ata gag cca ctt gtt gac ctc tta gga agt gga agt ctc     1680
Ala Gly Ala Ile Glu Pro Leu Val Asp Leu Leu Gly Ser Gly Ser Leu
545             550                 555                 560 agt ggg aag aaa gat gca gcc acg gct tta ttc aac ctc tca ata cac     1728
Ser Gly Lys Lys Asp Ala Ala Thr Ala Leu Phe Asn Leu Ser Ile His
            565                 570                 575 cat gag aac aaa acg aaa gta atc gaa gct gga gca gtg aga tac tta     1776
His Glu Asn Lys Thr Lys Val Ile Glu Ala Gly Ala Val Arg Tyr Leu
        580                 585                 590 gtt gaa ctg atg gat cct gct ttt ggg atg gtg gag aaa gct gtg gtg     1824
Val Glu Leu Met Asp Pro Ala Phe Gly Met Val Glu Lys Ala Val Val
    595                 600                 605 gtg cta gcg aat ctt gca acg gtt aga gaa gga aag att gcg ata ggc     1872
Val Leu Ala Asn Leu Ala Thr Val Arg Glu Gly Lys Ile Ala Ile Gly
610                 615                 620
```

```
gaa gaa gga gga ata ccg gta ttg gtg gaa gtt gtg gag tta ggt tca    1920
Glu Glu Gly Gly Ile Pro Val Leu Val Glu Val Val Glu Leu Gly Ser
625                 630                 635                 640 gca aga ggc aaa gag aat gca act gca gca cta ttg cag ctt tgt acg    1968
Ala Arg Gly Lys Glu Asn Ala Thr Ala Ala Leu Leu Gln Leu Cys Thr
            645                 650                 655 cat agc ccg aaa ttc tgc aac aat gtc ata aga gaa gga gtg att cca    2016
His Ser Pro Lys Phe Cys Asn Asn Val Ile Arg Glu Gly Val Ile Pro
        660                 665                 670 cct ctt gtg gca ctt act aaa tca gga aca gct aga ggc aaa gag aag    2064
Pro Leu Val Ala Leu Thr Lys Ser Gly Thr Ala Arg Gly Lys Glu Lys
    675                 680                 685 gca cag aat ctt ctg aag tac ttt aaa gca cac aga caa agc aat cag    2112
Ala Gln Asn Leu Leu Lys Tyr Phe Lys Ala His Arg Gln Ser Asn Gln
690                 695                 700 agg aga ggc tga                                                    2124
Arg Arg Gly
705
```

<210> SEQ ID NO 18
<211> LENGTH: 707
<212> TYPE: PRT
<213> ORGANISM: Arabidopsis thaliana

<400> SEQUENCE: 18

```
Met Met Val His Met Glu Val Ser Trp Leu Arg Val Leu Leu Asp Asn
1               5                   10                  15

Ile Ser Ser Tyr Leu Ser Leu Ser Ser Met Asp Asp Leu Ser Ser Asn
            20                  25                  30

Pro Ala His Lys Tyr Tyr Thr Arg Gly Glu Asp Ile Gly Lys Leu Ile
        35                  40                  45

Lys Pro Val Leu Glu Asn Leu Ile Asp Ser Asp Ala Ala Pro Ser Glu
    50                  55                  60

Leu Leu Asn Asn Gly Phe Glu Glu Leu Ala Gln Tyr Val Asp Glu Leu
65                  70                  75                  80

Arg Glu Gln Phe Gln Ser Trp Gln Pro Leu Ser Thr Arg Ile Phe Tyr
                85                  90                  95

Val Leu Arg Ile Glu Ser Leu Ala Ser Lys Leu Arg Glu Ser Ser Leu
            100                 105                 110

Glu Val Phe Gln Leu Lys His Cys Glu Gln His Leu Pro Ala Asp
        115                 120                 125

Leu Ile Ser Pro Ser Phe Glu Glu Cys Ile Glu Leu Val Lys Leu Val
    130                 135                 140

Ala Arg Asp Glu Ile Ser Tyr Thr Ile Asp Gln Ala Leu Lys Asp Gln
145                 150                 155                 160

Lys Lys Gly Val Gly Pro Thr Ser Glu Val Leu Val Lys Ile Ala Glu
                165                 170                 175

Ser Thr Gly Leu Arg Ser Asn Gln Glu Ile Leu Val Glu Gly Val Val
            180                 185                 190

Leu Thr Asn Met Lys Glu Asp Ala Glu Leu Thr Asp Asn Asp Thr Glu
        195                 200                 205

Ala Glu Tyr Leu Asp Gly Leu Ile Ser Leu Thr Gln Met His Glu
    210                 215                 220

Tyr Leu Ser Asp Ile Lys Gln Ala Gln Leu Arg Cys Pro Val Arg Val
225                 230                 235                 240

Pro Ser Asp Phe Arg Cys Ser Leu Ser Leu Glu Leu Met Thr Asp Pro
                245                 250                 255
```

-continued

```
Val Ile Val Ala Ser Gly Gln Thr Phe Glu Arg Val Phe Ile Gln Lys
            260                 265                 270

Trp Ile Asp Met Gly Leu Met Val Cys Pro Lys Thr Arg Gln Ala Leu
            275                 280                 285

Ser His Thr Thr Leu Thr Pro Asn Phe Ile Val Arg Ala Phe Leu Ala
            290                 295                 300

Ser Trp Cys Glu Thr Asn Asn Val Tyr Pro Pro Asp Pro Leu Glu Leu
305                 310                 315                 320

Ile His Ser Ser Glu Pro Phe Pro Leu Leu Val Ser Val Arg Ala
                    325                 330                 335

Ser Ser Ser Glu Asn Gly His Ser Glu Ser Leu Asp Ala Glu Glu Leu
            340                 345                 350

Arg Gln Val Phe Ser Arg Ser Ala Ser Ala Pro Gly Ile Val Ser Glu
            355                 360                 365

Val Val Cys Lys Thr Lys Arg Asn Asn Asn Ala Ala Ala Asp Arg Ser
            370                 375                 380

Leu Thr Arg Ser Asn Thr Pro Trp Lys Phe Pro Glu Glu Arg His Trp
385                 390                 395                 400

Arg His Pro Gly Ile Ile Pro Ala Thr Val Arg Glu Thr Gly Ser Ser
                    405                 410                 415

Ser Ser Ile Glu Thr Glu Val Lys Lys Leu Ile Asp Asp Leu Lys Ser
            420                 425                 430

Ser Ser Leu Asp Thr Gln Arg Glu Ala Thr Ala Arg Ile Arg Ile Leu
            435                 440                 445

Ala Arg Asn Ser Thr Asp Asn Arg Ile Val Ile Ala Arg Cys Glu Ala
            450                 455                 460

Ile Pro Ser Leu Val Ser Leu Leu Tyr Ser Thr Asp Glu Arg Ile Gln
465                 470                 475                 480

Ala Asp Ala Val Thr Cys Leu Leu Asn Leu Ser Ile Asn Asp Asn Asn
                    485                 490                 495

Lys Ser Leu Ile Ala Glu Ser Gly Ala Ile Val Pro Leu Ile His Val
            500                 505                 510

Leu Lys Thr Gly Tyr Leu Glu Glu Ala Lys Ala Asn Ser Ala Ala Thr
            515                 520                 525

Leu Phe Ser Leu Ser Val Ile Glu Glu Tyr Lys Thr Glu Ile Gly Glu
            530                 535                 540

Ala Gly Ala Ile Glu Pro Leu Val Asp Leu Leu Gly Ser Gly Ser Leu
545                 550                 555                 560

Ser Gly Lys Lys Asp Ala Ala Thr Ala Leu Phe Asn Leu Ser Ile His
                    565                 570                 575

His Glu Asn Lys Thr Lys Val Ile Glu Ala Gly Ala Val Arg Tyr Leu
            580                 585                 590

Val Glu Leu Met Asp Pro Ala Phe Gly Met Val Glu Lys Ala Val Val
            595                 600                 605

Val Leu Ala Asn Leu Ala Thr Val Arg Glu Gly Lys Ile Ala Ile Gly
            610                 615                 620

Glu Glu Gly Gly Ile Pro Val Leu Val Glu Val Val Glu Leu Gly Ser
625                 630                 635                 640

Ala Arg Gly Lys Glu Asn Ala Thr Ala Ala Leu Leu Gln Leu Cys Thr
                    645                 650                 655

His Ser Pro Lys Phe Cys Asn Asn Val Ile Arg Glu Gly Val Ile Pro
            660                 665                 670

Pro Leu Val Ala Leu Thr Lys Ser Gly Thr Ala Arg Gly Lys Glu Lys
            675                 680                 685
```

```
Ala Gln Asn Leu Leu Lys Tyr Phe Lys Ala His Arg Gln Ser Asn Gln
    690             695                 700

Arg Arg Gly
705

<210> SEQ ID NO 19
<211> LENGTH: 2097
<212> TYPE: DNA
<213> ORGANISM: Arabidopsis thaliana
<220> FEATURE:
<221> NAME/KEY: CDS
<222> LOCATION: (1)..(2097)

<400> SEQUENCE: 19 atg gag gtg tct tgg tta aga gtt ctt cta gat aac atc tcc tcc tat        48
Met Glu Val Ser Trp Leu Arg Val Leu Leu Asp Asn Ile Ser Ser Tyr
1               5                   10                  15 cta agt tta tca tct atg gac gat tta tct tca aac cct gct cat aag        96
Leu Ser Leu Ser Ser Met Asp Asp Leu Ser Ser Asn Pro Ala His Lys
                20                  25                  30 tac tac acc aga gga gaa gat ata gga aag ctt atc aag cct gtt ctt       144
Tyr Tyr Thr Arg Gly Glu Asp Ile Gly Lys Leu Ile Lys Pro Val Leu
            35                  40                  45 gag aac ctc att gac tct gac gcg gct cct agc gag ttg ctt aac aat       192
Glu Asn Leu Ile Asp Ser Asp Ala Ala Pro Ser Glu Leu Leu Asn Asn
        50                  55                  60 ggt ttt gaa gaa tta gct caa tac gtt gat gaa ctt aga gaa cag ttt       240
Gly Phe Glu Glu Leu Ala Gln Tyr Val Asp Glu Leu Arg Glu Gln Phe
65                  70                  75                  80 cag agt tgg caa cct ctt tca act aga atc ttt tat gtt ctt cga att       288
Gln Ser Trp Gln Pro Leu Ser Thr Arg Ile Phe Tyr Val Leu Arg Ile
                85                  90                  95 gaa tca tta gca tca aag tta cga gaa tcc agt ttg gaa gtc ttt cag       336
Glu Ser Leu Ala Ser Lys Leu Arg Glu Ser Ser Leu Glu Val Phe Gln
            100                 105                 110 ctc ctc aaa cac tgc gaa caa cat ttg cct gct gac ttg atc tca cct       384
Leu Leu Lys His Cys Glu Gln His Leu Pro Ala Asp Leu Ile Ser Pro
        115                 120                 125 tct ttt gag gag tgc att gaa ttg gtg aag tta gtg gca aga gac gaa       432
Ser Phe Glu Glu Cys Ile Glu Leu Val Lys Leu Val Ala Arg Asp Glu
    130                 135                 140 ata tcg tat act att gat caa gct cta aaa gat caa aag aaa ggt gtt       480
Ile Ser Tyr Thr Ile Asp Gln Ala Leu Lys Asp Gln Lys Lys Gly Val
145                 150                 155                 160 gga cct act tca gag gtt ctg gtg aaa att gcc gag agt act ggt tta       528
Gly Pro Thr Ser Glu Val Leu Val Lys Ile Ala Glu Ser Thr Gly Leu
                165                 170                 175 aga tcc aac cag gag att ctt gtt gaa ggt gtg gta ctt aca aac atg       576
Arg Ser Asn Gln Glu Ile Leu Val Glu Gly Val Val Leu Thr Asn Met
            180                 185                 190 aag gag gat gct gag ctt acc gat aat gac acc gaa gcc gag tat cta       624
Lys Glu Asp Ala Glu Leu Thr Asp Asn Asp Thr Glu Ala Glu Tyr Leu
        195                 200                 205 gac gga ttg atc tct cta aca aca caa atg cat gag tac ctt agc gac       672
Asp Gly Leu Ile Ser Leu Thr Thr Gln Met His Glu Tyr Leu Ser Asp
    210                 215                 220 ata aag cag gct cag tta cgt tgt cca gta cgc gta cct tct gat ttc       720
Ile Lys Gln Ala Gln Leu Arg Cys Pro Val Arg Val Pro Ser Asp Phe
225                 230                 235                 240 cgc tgc tct cta tct ctt gag ctt atg act gat cca gtc att gta gca       768
Arg Cys Ser Leu Ser Leu Glu Leu Met Thr Asp Pro Val Ile Val Ala
```

```
                    245                 250                 255
tct ggt caa aca ttc gaa cgg gtt ttt atc cag aaa tgg atc gat atg    816
Ser Gly Gln Thr Phe Glu Arg Val Phe Ile Gln Lys Trp Ile Asp Met
            260                 265                 270 gga ctc atg gtt tgt cca aag aca agg cag gct tta tct cat acc act    864
Gly Leu Met Val Cys Pro Lys Thr Arg Gln Ala Leu Ser His Thr Thr
        275                 280                 285 ttg aca cct aat ttc att gtc aga gct ttt ctt gca agt tgg tgt gaa    912
Leu Thr Pro Asn Phe Ile Val Arg Ala Phe Leu Ala Ser Trp Cys Glu
    290                 295                 300 act aac aat gtc tat cct cct gat cca ttg gag ttg att cac tca agt    960
Thr Asn Asn Val Tyr Pro Pro Asp Pro Leu Glu Leu Ile His Ser Ser
305                 310                 315                 320 gag cca ttc cct ctt ctt gtt gaa tca gtg aga gct tca tca tca gag   1008
Glu Pro Phe Pro Leu Leu Val Glu Ser Val Arg Ala Ser Ser Ser Glu
                325                 330                 335 aat ggc cat tca gaa tct tta gat gca gag gaa ctg cgt cag gtc ttt   1056
Asn Gly His Ser Glu Ser Leu Asp Ala Glu Glu Leu Arg Gln Val Phe
            340                 345                 350 agt agg tct gct tcg gcg cca ggc att gtc tct gaa gtg gtt tgc aaa   1104
Ser Arg Ser Ala Ser Ala Pro Gly Ile Val Ser Glu Val Val Cys Lys
        355                 360                 365 acc aaa aga aac aac aat gct gct gca gat aga tca ctg aca cgg agt   1152
Thr Lys Arg Asn Asn Asn Ala Ala Ala Asp Arg Ser Leu Thr Arg Ser
    370                 375                 380 aat acc cct tgg aaa ttt cca gaa gag agg cat tgg cgt cac ccc ggg   1200
Asn Thr Pro Trp Lys Phe Pro Glu Glu Arg His Trp Arg His Pro Gly
385                 390                 395                 400 atc atc cca gcg acc gta aga gaa aca gga agc agt tca agt atc gaa   1248
Ile Ile Pro Ala Thr Val Arg Glu Thr Gly Ser Ser Ser Ile Glu
                405                 410                 415 acc gag gtg aag aaa ctc att gat gat ctc aag agt tct tca ttg gat   1296
Thr Glu Val Lys Lys Leu Ile Asp Asp Leu Lys Ser Ser Ser Leu Asp
            420                 425                 430 aca cag aga gag gcc aca gct aga atc agg ata cta gca aga aac agt   1344
Thr Gln Arg Glu Ala Thr Ala Arg Ile Arg Ile Leu Ala Arg Asn Ser
        435                 440                 445 aca gac aat cgc att gtc att gcg cgg tgc gaa gca atc cct tcg tta   1392
Thr Asp Asn Arg Ile Val Ile Ala Arg Cys Glu Ala Ile Pro Ser Leu
    450                 455                 460 gtc agt ctt ctt tac tca acg gat gag aga atc caa gca gac gca gtg   1440
Val Ser Leu Leu Tyr Ser Thr Asp Glu Arg Ile Gln Ala Asp Ala Val
465                 470                 475                 480 act tgc tta cta aac tta tcc atc aac gac aac aag tcc ctc atc       1488
Thr Cys Leu Leu Asn Leu Ser Ile Asn Asp Asn Asn Lys Ser Leu Ile
                485                 490                 495 gcg gaa agt gga gcc atc gta ccg ctt att cac gtt ctc aaa aca gga   1536
Ala Glu Ser Gly Ala Ile Val Pro Leu Ile His Val Leu Lys Thr Gly
            500                 505                 510 tac tta gaa gaa gct aaa gca aac tca gca gca act cta ttc agc ttg   1584
Tyr Leu Glu Glu Ala Lys Ala Asn Ser Ala Ala Thr Leu Phe Ser Leu
        515                 520                 525 tcg gtg atc gaa gag tac aag aca gag ata gga gaa gca gga gct ata   1632
Ser Val Ile Glu Glu Tyr Lys Thr Glu Ile Gly Glu Ala Gly Ala Ile
    530                 535                 540 gag cca ctt gtt gac ctc tta gga agt gga agt ctc agt ggg aag aaa   1680
Glu Pro Leu Val Asp Leu Leu Gly Ser Gly Ser Leu Ser Gly Lys Lys
545                 550                 555                 560 gat gca gcc acg gct tta ttc aac ctc tca ata cac cat gag aac aaa   1728
Asp Ala Ala Thr Ala Leu Phe Asn Leu Ser Ile His His Glu Asn Lys
```

```
                  565                 570                 575
acg aaa gta atc gaa gct gga gca gtg aga tac tta gtt gaa ctg atg       1776
Thr Lys Val Ile Glu Ala Gly Ala Val Arg Tyr Leu Val Glu Leu Met
            580                 585                 590 gat cct gct ttt ggg atg gtg gag aaa gct gtg gtg gtg cta gcg aat       1824
Asp Pro Ala Phe Gly Met Val Glu Lys Ala Val Val Val Leu Ala Asn
        595                 600                 605 ctt gca acg gtt aga gaa gga aag att gcg ata ggc gaa gaa gga gga       1872
Leu Ala Thr Val Arg Glu Gly Lys Ile Ala Ile Gly Glu Glu Gly Gly
    610                 615                 620 ata ccg gta ttg gtg gaa gtt gtg gag tta ggt tca gca aga ggc aaa       1920
Ile Pro Val Leu Val Glu Val Val Glu Leu Gly Ser Ala Arg Gly Lys
625                 630                 635                 640 gag aat gca act gca gca cta ttg cag ctt tgt acg cat agc ccg aaa       1968
Glu Asn Ala Thr Ala Ala Leu Leu Gln Leu Cys Thr His Ser Pro Lys
                645                 650                 655 ttc tgc aac aat gtc ata aga gaa gga gtg att cca cct ctt gtg gca       2016
Phe Cys Asn Asn Val Ile Arg Glu Gly Val Ile Pro Pro Leu Val Ala
            660                 665                 670 ctt act aaa tca gga aca gct aga ggc aaa gag aag gtt ctt ttt ttg       2064
Leu Thr Lys Ser Gly Thr Ala Arg Gly Lys Glu Lys Val Leu Phe Leu
        675                 680                 685 ttt cct ctt ctt tgt ttg gta aat gtc tca tga                           2097
Phe Pro Leu Leu Cys Leu Val Asn Val Ser
    690                 695

<210> SEQ ID NO 20
<211> LENGTH: 698
<212> TYPE: PRT
<213> ORGANISM: Arabidopsis thaliana

<400> SEQUENCE: 20

Met Glu Val Ser Trp Leu Arg Val Leu Leu Asp Asn Ile Ser Ser Tyr
1               5                   10                  15

Leu Ser Leu Ser Ser Met Asp Asp Leu Ser Ser Asn Pro Ala His Lys
            20                  25                  30

Tyr Tyr Thr Arg Gly Glu Asp Ile Gly Lys Leu Ile Lys Pro Val Leu
        35                  40                  45

Glu Asn Leu Ile Asp Ser Asp Ala Ala Pro Ser Glu Leu Leu Asn Asn
    50                  55                  60

Gly Phe Glu Glu Leu Ala Gln Tyr Val Asp Glu Leu Arg Glu Gln Phe
65                  70                  75                  80

Gln Ser Trp Gln Pro Leu Ser Thr Arg Ile Phe Tyr Val Leu Arg Ile
                85                  90                  95

Glu Ser Leu Ala Ser Lys Leu Arg Glu Ser Ser Leu Glu Val Phe Gln
            100                 105                 110

Leu Leu Lys His Cys Glu Gln His Leu Pro Ala Asp Leu Ile Ser Pro
        115                 120                 125

Ser Phe Glu Glu Cys Ile Glu Leu Val Lys Leu Val Ala Arg Asp Glu
    130                 135                 140

Ile Ser Tyr Thr Ile Asp Gln Ala Leu Lys Asp Gln Lys Lys Gly Val
145                 150                 155                 160

Gly Pro Thr Ser Glu Val Leu Val Lys Ile Ala Glu Ser Thr Gly Leu
                165                 170                 175

Arg Ser Asn Gln Glu Ile Leu Val Glu Gly Val Val Leu Thr Asn Met
            180                 185                 190

Lys Glu Asp Ala Glu Leu Thr Asp Asn Asp Thr Glu Ala Glu Tyr Leu
        195                 200                 205
```

```
Asp Gly Leu Ile Ser Leu Thr Thr Gln Met His Glu Tyr Leu Ser Asp
    210                 215                 220
Ile Lys Gln Ala Gln Leu Arg Cys Pro Val Arg Val Pro Ser Asp Phe
225                 230                 235                 240
Arg Cys Ser Leu Ser Leu Glu Leu Met Thr Asp Pro Val Ile Val Ala
                245                 250                 255
Ser Gly Gln Thr Phe Glu Arg Val Phe Ile Gln Lys Trp Ile Asp Met
                260                 265                 270
Gly Leu Met Val Cys Pro Lys Thr Arg Gln Ala Leu Ser His Thr Thr
            275                 280                 285
Leu Thr Pro Asn Phe Ile Val Arg Ala Phe Leu Ala Ser Trp Cys Glu
    290                 295                 300
Thr Asn Asn Val Tyr Pro Pro Asp Pro Leu Glu Leu Ile His Ser Ser
305                 310                 315                 320
Glu Pro Phe Pro Leu Leu Val Glu Ser Val Arg Ala Ser Ser Ser Glu
                325                 330                 335
Asn Gly His Ser Glu Ser Leu Asp Ala Glu Glu Leu Arg Gln Val Phe
                340                 345                 350
Ser Arg Ser Ala Ser Ala Pro Gly Ile Val Ser Glu Val Cys Lys
            355                 360                 365
Thr Lys Arg Asn Asn Asn Ala Ala Ala Asp Arg Ser Leu Thr Arg Ser
    370                 375                 380
Asn Thr Pro Trp Lys Phe Pro Glu Glu Arg His Trp Arg His Pro Gly
385                 390                 395                 400
Ile Ile Pro Ala Thr Val Arg Glu Thr Gly Ser Ser Ser Ile Glu
                405                 410                 415
Thr Glu Val Lys Lys Leu Ile Asp Asp Leu Lys Ser Ser Ser Leu Asp
            420                 425                 430
Thr Gln Arg Glu Ala Thr Ala Arg Ile Arg Ile Leu Ala Arg Asn Ser
    435                 440                 445
Thr Asp Asn Arg Ile Val Ile Ala Arg Cys Glu Ala Ile Pro Ser Leu
450                 455                 460
Val Ser Leu Leu Tyr Ser Thr Asp Glu Arg Ile Gln Ala Asp Ala Val
465                 470                 475                 480
Thr Cys Leu Leu Asn Leu Ser Ile Asn Asp Asn Asn Lys Ser Leu Ile
                485                 490                 495
Ala Glu Ser Gly Ala Ile Val Pro Leu Ile His Val Leu Lys Thr Gly
            500                 505                 510
Tyr Leu Glu Glu Ala Lys Ala Asn Ser Ala Ala Thr Leu Phe Ser Leu
    515                 520                 525
Ser Val Ile Glu Glu Tyr Lys Thr Glu Ile Gly Glu Ala Gly Ala Ile
    530                 535                 540
Glu Pro Leu Val Asp Leu Leu Gly Ser Gly Ser Leu Ser Gly Lys Lys
545                 550                 555                 560
Asp Ala Ala Thr Ala Leu Phe Asn Leu Ser Ile His His Glu Asn Lys
                565                 570                 575
Thr Lys Val Ile Glu Ala Gly Ala Val Arg Tyr Leu Val Glu Leu Met
            580                 585                 590
Asp Pro Ala Phe Gly Met Val Glu Lys Ala Val Val Leu Ala Asn
    595                 600                 605
Leu Ala Thr Val Arg Glu Gly Lys Ile Ala Ile Gly Glu Glu Gly Gly
    610                 615                 620
Ile Pro Val Leu Val Glu Val Val Glu Leu Gly Ser Ala Arg Gly Lys
```

```
                625                 630                 635                 640

Glu Asn Ala Thr Ala Ala Leu Leu Gln Leu Cys Thr His Ser Pro Lys
                    645                 650                 655

Phe Cys Asn Asn Val Ile Arg Glu Gly Val Ile Pro Pro Leu Val Ala
                    660                 665                 670

Leu Thr Lys Ser Gly Thr Ala Arg Gly Lys Glu Lys Val Leu Phe Leu
                    675                 680                 685

Phe Pro Leu Leu Cys Leu Val Asn Val Ser
                    690                 695

<210> SEQ ID NO 21
<211> LENGTH: 2283
<212> TYPE: DNA
<213> ORGANISM: Arabidopsis thaliana
<220> FEATURE:
<221> NAME/KEY: CDS
<222> LOCATION: (1)..(2283)

<400> SEQUENCE: 21 atg gat cct gtt cct gtt cga tgt ctt ctt aac agt ata tct cgg tat       48
Met Asp Pro Val Pro Val Arg Cys Leu Leu Asn Ser Ile Ser Arg Tyr
1               5                   10                  15 ctt cat ctg gtt gcg tgc cag act ata aga ttt aat cct att caa aca       96
Leu His Leu Val Ala Cys Gln Thr Ile Arg Phe Asn Pro Ile Gln Thr
                20                  25                  30 tgt att gga aat atg gtt ctc ttg ttg aag ctc ttg aaa ccg ttg ctc      144
Cys Ile Gly Asn Met Val Leu Leu Leu Lys Leu Leu Lys Pro Leu Leu
            35                  40                  45 gat gaa gtt gtt gat tgc aag ata cct tct gat gac tgt tta tat aaa      192
Asp Glu Val Val Asp Cys Lys Ile Pro Ser Asp Asp Cys Leu Tyr Lys
        50                  55                  60 gga tgt gaa gac ctt gat tct gtt gtt aac cag gct cgg gag ttc tta      240
Gly Cys Glu Asp Leu Asp Ser Val Val Asn Gln Ala Arg Glu Phe Leu
65                  70                  75                  80 gag gac tgg tca cca aag ttg agc aag ttg ttt ggt gtg ttt caa tgc      288
Glu Asp Trp Ser Pro Lys Leu Ser Lys Leu Phe Gly Val Phe Gln Cys
                85                  90                  95 gag gtt ttg ttg gga aag gtc cag act tgt tcg ttg gag att agt cgc      336
Glu Val Leu Leu Gly Lys Val Gln Thr Cys Ser Leu Glu Ile Ser Arg
            100                 105                 110 ata ctt ctt cag tta tca cag tca agt ccg gtt act tca agc gta caa      384
Ile Leu Leu Gln Leu Ser Gln Ser Ser Pro Val Thr Ser Ser Val Gln
        115                 120                 125 agt gtt gag cgc tgc gtg cag gag act gag agt ttt aag caa gag ggg      432
Ser Val Glu Arg Cys Val Gln Glu Thr Glu Ser Phe Lys Gln Glu Gly
    130                 135                 140 aca tta atg gaa ctc atg gag aat gct tta cgg aat cag aaa gat gat      480
Thr Leu Met Glu Leu Met Glu Asn Ala Leu Arg Asn Gln Lys Asp Asp
145                 150                 155                 160 att acc tct ttg gat aac aat cat ctg gaa agc ata att caa atg ctt      528
Ile Thr Ser Leu Asp Asn Asn His Leu Glu Ser Ile Ile Gln Met Leu
                165                 170                 175 gga ttg ata tca aac caa gat ctc tta aag gaa agc att act gtg gag      576
Gly Leu Ile Ser Asn Gln Asp Leu Leu Lys Glu Ser Ile Thr Val Glu
            180                 185                 190 aaa gag agg ata aga tcc cag gcc agt aag tca gaa gaa gat atg gaa      624
Lys Glu Arg Ile Arg Ser Gln Ala Ser Lys Ser Glu Glu Asp Met Glu
        195                 200                 205 caa acc gaa cag ttg ata gaa ctc gtc ttg tgc atc cgt gaa cac atg      672
Gln Thr Glu Gln Leu Ile Glu Leu Val Leu Cys Ile Arg Glu His Met
    210                 215                 220
```

| | | |
|---|---|---|
| ctt aaa act gag ttt ctt gaa gtg gct aaa ggt atc tcg ata ccc ccg<br>Leu Lys Thr Glu Phe Leu Glu Val Ala Lys Gly Ile Ser Ile Pro Pro<br>225                          230                      235                 240 | 720 |
| tat ttc cgg tgt cct ttg tca aca gaa ctc atg ctg gat ccg gta ata<br>Tyr Phe Arg Cys Pro Leu Ser Thr Glu Leu Met Leu Asp Pro Val Ile<br>                     245                     250                     255 | 768 |
| gta gct tca gga cag aca ttt gac aga aca tcc att aag aaa tgg ctt<br>Val Ala Ser Gly Gln Thr Phe Asp Arg Thr Ser Ile Lys Lys Trp Leu<br>             260                     265                     270 | 816 |
| gat aac ggg tta gct gtt tgt cca agg acg cgg cag gtg ctg act cat<br>Asp Asn Gly Leu Ala Val Cys Pro Arg Thr Arg Gln Val Leu Thr His<br>                 275                     280                     285 | 864 |
| caa gaa ctc att ccc aat tac acg gtt aag gct atg ata gcg agt tgg<br>Gln Glu Leu Ile Pro Asn Tyr Thr Val Lys Ala Met Ile Ala Ser Trp<br>290                          295                      300 | 912 |
| ttg gag gca aac agg atc aac ctt gct act aac tct tgt cat cag tat<br>Leu Glu Ala Asn Arg Ile Asn Leu Ala Thr Asn Ser Cys His Gln Tyr<br>305                          310                     315                 320 | 960 |
| gat ggt ggt gat gct tca tcc atg gct aat aat atg ggt tct caa gac<br>Asp Gly Gly Asp Ala Ser Ser Met Ala Asn Asn Met Gly Ser Gln Asp<br>                       325                     330                     335 | 1008 |
| ttt aac cgc acc gag agt ttt cgt ttt tct tta cgg agc agc agt tta<br>Phe Asn Arg Thr Glu Ser Phe Arg Phe Ser Leu Arg Ser Ser Ser Leu<br>                     340                     345                     350 | 1056 |
| acc tca aga tca tct ctt gaa act gga aat ggg ttt gag aaa ctg aag<br>Thr Ser Arg Ser Ser Leu Glu Thr Gly Asn Gly Phe Glu Lys Leu Lys<br>           355                     360                     365 | 1104 |
| att aac gtg tct gcc agt tta tgc ggg gaa tct caa agc aag gat ctt<br>Ile Asn Val Ser Ala Ser Leu Cys Gly Glu Ser Gln Ser Lys Asp Leu<br>370                        375                     380 | 1152 |
| gaa ata ttc gag ctt ttg tct ccg ggg cag tct tac act cac agc agg<br>Glu Ile Phe Glu Leu Leu Ser Pro Gly Gln Ser Tyr Thr His Ser Arg<br>385                          390                     395                 400 | 1200 |
| agt gaa tca gtt tgc agt gtt gtc tcg tct gtt gat tat gta cct tcg<br>Ser Glu Ser Val Cys Ser Val Val Ser Ser Val Asp Tyr Val Pro Ser<br>                     405                     410                     415 | 1248 |
| gtg aca cat gag aca gaa agt ata cta ggg aat cac caa agc tcc agt<br>Val Thr His Glu Thr Glu Ser Ile Leu Gly Asn His Gln Ser Ser Ser<br>             420                     425                     430 | 1296 |
| gag atg tct ccc aag aaa aac tta gaa agt tca aac aat gta aat cat<br>Glu Met Ser Pro Lys Lys Asn Leu Glu Ser Ser Asn Asn Val Asn His<br>           435                     440                     445 | 1344 |
| gag cat agc gca gca aag act tat gag tgt tct gta cat gat tta gat<br>Glu His Ser Ala Ala Lys Thr Tyr Glu Cys Ser Val His Asp Leu Asp<br>450                        455                     460 | 1392 |
| gat tca gga aca atg acg act tca cat acc ata aaa ttg gta gaa gat<br>Asp Ser Gly Thr Met Thr Thr Ser His Thr Ile Lys Leu Val Glu Asp<br>465                          470                     475                 480 | 1440 |
| ctt aaa agc ggg tct aac aaa gtg aag act gct gct gca gct gaa ata<br>Leu Lys Ser Gly Ser Asn Lys Val Lys Thr Ala Ala Ala Ala Glu Ile<br>                     485                     490                     495 | 1488 |
| cgt cat ctc acc att aac agc att gaa aat cgt gtt cac atc ggg cgt<br>Arg His Leu Thr Ile Asn Ser Ile Glu Asn Arg Val His Ile Gly Arg<br>             500                     505                     510 | 1536 |
| tgt ggt gct att act cca ctg ctg tca ctt tta tac tca gaa gaa aag<br>Cys Gly Ala Ile Thr Pro Leu Leu Ser Leu Leu Tyr Ser Glu Glu Lys<br>           515                     520                     525 | 1584 |
| cta act caa gaa cac gca gtc acg gct ctt ttg aat ctt tcc atc agt<br>Leu Thr Gln Glu His Ala Val Thr Ala Leu Leu Asn Leu Ser Ile Ser<br>530                          535                     540 | 1632 |

| | | | | | | | | | | | | | | | |
|---|---|---|---|---|---|---|---|---|---|---|---|---|---|---|---|
| gaa | cta | aac | aaa | gcc | atg | att | gtg | gaa | gtc | ggg | gcg | ata | gaa | ccg | ctt | 1680 |
| Glu | Leu | Asn | Lys | Ala | Met | Ile | Val | Glu | Val | Gly | Ala | Ile | Glu | Pro | Leu | |
| 545 | | | | 550 | | | | 555 | | | | 560 | | | | | gtt cat gtt ttg aac aca gga aat gac aga gcc aaa gag aat tca gca   1728
Val His Val Leu Asn Thr Gly Asn Asp Arg Ala Lys Glu Asn Ser Ala
            565                 570                 575 gca tca ttg ttc agt ctg tct gtt ctg cag gtc aac aga gaa cga ata   1776
Ala Ser Leu Phe Ser Leu Ser Val Leu Gln Val Asn Arg Glu Arg Ile
        580                 585                 590 ggc cag tct aac gca gcg ata caa gct ctg gtg aat ctt ctt ggt aaa   1824
Gly Gln Ser Asn Ala Ala Ile Gln Ala Leu Val Asn Leu Leu Gly Lys
    595                 600                 605 gga aca ttt aga gga aag aaa gac gcc gcc tct gct ttg ttc aat cta   1872
Gly Thr Phe Arg Gly Lys Lys Asp Ala Ala Ser Ala Leu Phe Asn Leu
610                 615                 620 tcg att act cat gat aac aag gcc cgt atc gtg caa gct aag gcg gtt   1920
Ser Ile Thr His Asp Asn Lys Ala Arg Ile Val Gln Ala Lys Ala Val
625                 630                 635                 640 aag tac ctt gtg gag ctg tta gac cca gat tta gag atg gtt gat aaa   1968
Lys Tyr Leu Val Glu Leu Leu Asp Pro Asp Leu Glu Met Val Asp Lys
            645                 650                 655 gca gtt gct ctt ctt gca aat ctt tct gca gtt gga gaa ggg cgt caa   2016
Ala Val Ala Leu Leu Ala Asn Leu Ser Ala Val Gly Glu Gly Arg Gln
        660                 665                 670 gcc atc gtg agg gaa ggt ggg att cca tta ctt gtt gaa act gtt gac   2064
Ala Ile Val Arg Glu Gly Gly Ile Pro Leu Leu Val Glu Thr Val Asp
    675                 680                 685 tta gga tct cag aga ggg aaa gag aat gca gct tct gtg ctg ctt cag   2112
Leu Gly Ser Gln Arg Gly Lys Glu Asn Ala Ala Ser Val Leu Leu Gln
690                 695                 700 ttg tgt ctg aac agt ccc aag ttt tgc act ctg gtc ttg caa gaa ggc   2160
Leu Cys Leu Asn Ser Pro Lys Phe Cys Thr Leu Val Leu Gln Glu Gly
705                 710                 715                 720 gcc ata cct ccg ctt gtt gcc ttg tct cag tct ggt aca cag aga gca   2208
Ala Ile Pro Pro Leu Val Ala Leu Ser Gln Ser Gly Thr Gln Arg Ala
            725                 730                 735 aaa gag aag gca cag caa ctt ctt agc cac ttc cga aac cag aga gat   2256
Lys Glu Lys Ala Gln Gln Leu Leu Ser His Phe Arg Asn Gln Arg Asp
        740                 745                 750 gca agg atg aag aaa ggt aga tca tga                               2283
Ala Arg Met Lys Lys Gly Arg Ser
    755                 760

<210> SEQ ID NO 22
<211> LENGTH: 760
<212> TYPE: PRT
<213> ORGANISM: Arabidopsis thaliana

<400> SEQUENCE: 22

Met Asp Pro Val Pro Val Arg Cys Leu Leu Asn Ser Ile Ser Arg Tyr
1               5                   10                  15

Leu His Leu Val Ala Cys Gln Thr Ile Arg Phe Asn Pro Ile Gln Thr
            20                  25                  30

Cys Ile Gly Asn Met Val Leu Leu Lys Leu Leu Lys Pro Leu Leu
        35                  40                  45

Asp Glu Val Val Asp Cys Lys Ile Pro Ser Asp Asp Cys Leu Tyr Lys
    50                  55                  60

Gly Cys Glu Asp Leu Asp Ser Val Val Asn Gln Ala Arg Glu Phe Leu
65                  70                  75                  80

```
Glu Asp Trp Ser Pro Lys Leu Ser Lys Leu Phe Gly Val Phe Gln Cys
                85                  90                  95

Glu Val Leu Leu Gly Lys Val Gln Thr Cys Ser Leu Glu Ile Ser Arg
            100                 105                 110

Ile Leu Leu Gln Leu Ser Gln Ser Ser Pro Val Thr Ser Ser Val Gln
        115                 120                 125

Ser Val Glu Arg Cys Val Gln Glu Thr Glu Ser Phe Lys Gln Glu Gly
130                 135                 140

Thr Leu Met Glu Leu Met Glu Asn Ala Leu Arg Asn Gln Lys Asp Asp
145                 150                 155                 160

Ile Thr Ser Leu Asp Asn Asn His Leu Glu Ser Ile Ile Gln Met Leu
                165                 170                 175

Gly Leu Ile Ser Asn Gln Asp Leu Leu Lys Glu Ser Ile Thr Val Glu
            180                 185                 190

Lys Glu Arg Ile Arg Ser Gln Ala Ser Lys Ser Glu Glu Asp Met Glu
        195                 200                 205

Gln Thr Glu Gln Leu Ile Glu Leu Val Leu Cys Ile Arg Glu His Met
210                 215                 220

Leu Lys Thr Glu Phe Leu Glu Val Ala Lys Gly Ile Ser Ile Pro Pro
225                 230                 235                 240

Tyr Phe Arg Cys Pro Leu Ser Thr Glu Leu Met Leu Asp Pro Val Ile
                245                 250                 255

Val Ala Ser Gly Gln Thr Phe Asp Arg Thr Ser Ile Lys Lys Trp Leu
            260                 265                 270

Asp Asn Gly Leu Ala Val Cys Pro Arg Thr Arg Gln Val Leu Thr His
        275                 280                 285

Gln Glu Leu Ile Pro Asn Tyr Thr Val Lys Ala Met Ile Ala Ser Trp
290                 295                 300

Leu Glu Ala Asn Arg Ile Asn Leu Ala Thr Asn Ser Cys His Gln Tyr
305                 310                 315                 320

Asp Gly Gly Asp Ala Ser Ser Met Ala Asn Asn Met Gly Ser Gln Asp
                325                 330                 335

Phe Asn Arg Thr Glu Ser Phe Arg Phe Ser Leu Arg Ser Ser Ser Leu
            340                 345                 350

Thr Ser Arg Ser Ser Leu Glu Thr Gly Asn Gly Phe Glu Lys Leu Lys
        355                 360                 365

Ile Asn Val Ser Ala Ser Leu Cys Gly Glu Ser Gln Ser Lys Asp Leu
370                 375                 380

Glu Ile Phe Glu Leu Leu Ser Pro Gly Gln Ser Tyr Thr His Ser Arg
385                 390                 395                 400

Ser Glu Ser Val Cys Ser Val Val Ser Ser Val Asp Tyr Val Pro Ser
                405                 410                 415

Val Thr His Glu Thr Glu Ser Ile Leu Gly Asn His Gln Ser Ser Ser
            420                 425                 430

Glu Met Ser Pro Lys Lys Asn Leu Glu Ser Ser Asn Asn Val Asn His
        435                 440                 445

Glu His Ser Ala Ala Lys Thr Tyr Glu Cys Ser Val His Asp Leu Asp
450                 455                 460

Asp Ser Gly Thr Met Thr Thr Ser His Thr Ile Lys Leu Val Glu Asp
465                 470                 475                 480

Leu Lys Ser Gly Ser Asn Lys Val Lys Thr Ala Ala Ala Glu Ile
                485                 490                 495

Arg His Leu Thr Ile Asn Ser Ile Glu Asn Arg Val His Ile Gly Arg
            500                 505                 510
```

```
Cys Gly Ala Ile Thr Pro Leu Leu Ser Leu Leu Tyr Ser Glu Glu Lys
            515                 520                 525

Leu Thr Gln Glu His Ala Val Thr Ala Leu Leu Asn Leu Ser Ile Ser
        530                 535                 540

Glu Leu Asn Lys Ala Met Ile Val Glu Val Gly Ala Ile Glu Pro Leu
545                 550                 555                 560

Val His Val Leu Asn Thr Gly Asn Asp Arg Ala Lys Glu Asn Ser Ala
                565                 570                 575

Ala Ser Leu Phe Ser Leu Ser Val Leu Gln Val Asn Arg Glu Arg Ile
            580                 585                 590

Gly Gln Ser Asn Ala Ala Ile Gln Ala Leu Val Asn Leu Leu Gly Lys
        595                 600                 605

Gly Thr Phe Arg Gly Lys Lys Asp Ala Ala Ser Ala Leu Phe Asn Leu
    610                 615                 620

Ser Ile Thr His Asp Asn Lys Ala Arg Ile Val Gln Ala Lys Ala Val
625                 630                 635                 640

Lys Tyr Leu Val Glu Leu Leu Asp Pro Asp Leu Glu Met Val Asp Lys
                645                 650                 655

Ala Val Ala Leu Leu Ala Asn Leu Ser Ala Val Gly Glu Gly Arg Gln
            660                 665                 670

Ala Ile Val Arg Glu Gly Gly Ile Pro Leu Leu Val Glu Thr Val Asp
        675                 680                 685

Leu Gly Ser Gln Arg Gly Lys Glu Asn Ala Ala Ser Val Leu Leu Gln
    690                 695                 700

Leu Cys Leu Asn Ser Pro Lys Phe Cys Thr Leu Val Leu Gln Glu Gly
705                 710                 715                 720

Ala Ile Pro Pro Leu Val Ala Leu Ser Gln Ser Gly Thr Gln Arg Ala
                725                 730                 735

Lys Glu Lys Ala Gln Gln Leu Leu Ser His Phe Arg Asn Gln Arg Asp
            740                 745                 750

Ala Arg Met Lys Lys Gly Arg Ser
        755                 760

<210> SEQ ID NO 23
<211> LENGTH: 2283
<212> TYPE: DNA
<213> ORGANISM: Arabidopsis thaliana
<220> FEATURE:
<221> NAME/KEY: CDS
<222> LOCATION: (1)..(2283)

<400> SEQUENCE: 23 atg gat cct gtt cct gtt cga tgt ctt ctt aac agt ata tct cgg tat    48
Met Asp Pro Val Pro Val Arg Cys Leu Leu Asn Ser Ile Ser Arg Tyr
1               5                   10                  15 ctt cat ctg gtt gcg tgc cag act ata aga ttt aat cct att caa aca    96
Leu His Leu Val Ala Cys Gln Thr Ile Arg Phe Asn Pro Ile Gln Thr
            20                  25                  30 tgt att gga aat atg gtt ctc ttg ttg aag ctc ttg aaa ccg ttg ctc   144
Cys Ile Gly Asn Met Val Leu Leu Leu Lys Leu Leu Lys Pro Leu Leu
        35                  40                  45 gat gaa gtt gtt gat tgc aag ata cct tct gat gac tgt tta tat aaa   192
Asp Glu Val Val Asp Cys Lys Ile Pro Ser Asp Asp Cys Leu Tyr Lys
    50                  55                  60 gga cgt gaa gac ctt gat tct gtt gtt aac cag gct cgg gag ttc tta   240
Gly Arg Glu Asp Leu Asp Ser Val Val Asn Gln Ala Arg Glu Phe Leu
65                  70                  75                  80
```

```
gag gac tgg tca cca aag ttg agc aag ttg ttt ggt gtg ttt caa tgc        288
Glu Asp Trp Ser Pro Lys Leu Ser Lys Leu Phe Gly Val Phe Gln Cys
            85                  90                  95 gag gtt ttg ttg gga aag gtc cag act tgt tcg ttg gag att agt cgc        336
Glu Val Leu Leu Gly Lys Val Gln Thr Cys Ser Leu Glu Ile Ser Arg
        100                 105                 110 ata ctt ctt cag tta tca cag tca agt ccg gtt act tca agc gta caa        384
Ile Leu Leu Gln Leu Ser Gln Ser Ser Pro Val Thr Ser Ser Val Gln
    115                 120                 125 agt gtt gag cgc tgc gtg cag gag act gag agt ttt aag caa gag ggg        432
Ser Val Glu Arg Cys Val Gln Glu Thr Glu Ser Phe Lys Gln Glu Gly
130                 135                 140 aca tta atg gaa ctc atg gag aat gct tta cgg aat cag aaa gat gat        480
Thr Leu Met Glu Leu Met Glu Asn Ala Leu Arg Asn Gln Lys Asp Asp
145                 150                 155                 160 att acc tct ttg gat aac aat cat ctg gaa agc ata att caa atg ctt        528
Ile Thr Ser Leu Asp Asn Asn His Leu Glu Ser Ile Ile Gln Met Leu
                165                 170                 175 gga ttg ata tca aac caa gat ctc tta aag gaa agc att act gtg gag        576
Gly Leu Ile Ser Asn Gln Asp Leu Leu Lys Glu Ser Ile Thr Val Glu
            180                 185                 190 aaa gag agg ata aga tcc cag gcc agt aag tca gaa gaa gat atg gaa        624
Lys Glu Arg Ile Arg Ser Gln Ala Ser Lys Ser Glu Glu Asp Met Glu
        195                 200                 205 caa acc gaa cag ttg ata gaa ctc gtc ttg tgc atc cgt gaa cac atg        672
Gln Thr Glu Gln Leu Ile Glu Leu Val Leu Cys Ile Arg Glu His Met
    210                 215                 220 ctt aaa act gag ttt ctt gaa gtg gct aaa ggt atc tcg ata ccc ccg        720
Leu Lys Thr Glu Phe Leu Glu Val Ala Lys Gly Ile Ser Ile Pro Pro
225                 230                 235                 240 tat ttc cgg tgt cct ttg tca aca gaa ctc atg ctg gat ccg gta ata        768
Tyr Phe Arg Cys Pro Leu Ser Thr Glu Leu Met Leu Asp Pro Val Ile
                245                 250                 255 gta gct tca gga cag aca ttt gac aga aca tcc att aag aaa tgg ctt        816
Val Ala Ser Gly Gln Thr Phe Asp Arg Thr Ser Ile Lys Lys Trp Leu
            260                 265                 270 gat aac ggg tta gct gtt tgt cca agg acg cgg cag gtg ctg act cat        864
Asp Asn Gly Leu Ala Val Cys Pro Arg Thr Arg Gln Val Leu Thr His
        275                 280                 285 caa gaa ctc att ccc aat tac acg gtt aag gct atg ata gcg agt tgg        912
Gln Glu Leu Ile Pro Asn Tyr Thr Val Lys Ala Met Ile Ala Ser Trp
    290                 295                 300 ttg gag gca aac agg atc aac ctt gct act aac tct tgt cat cag tat        960
Leu Glu Ala Asn Arg Ile Asn Leu Ala Thr Asn Ser Cys His Gln Tyr
305                 310                 315                 320 gat ggt ggt gat gct tca tcc atg gct aat aat atg ggt tct caa gac       1008
Asp Gly Gly Asp Ala Ser Ser Met Ala Asn Asn Met Gly Ser Gln Asp
                325                 330                 335 ttt aac cgc acc gag agt ttt cgt ttt tct tta cgg agc agc agt tta       1056
Phe Asn Arg Thr Glu Ser Phe Arg Phe Ser Leu Arg Ser Ser Ser Leu
            340                 345                 350 acc tca aga tca tct ctt gaa act gga aat ggg ttt gag aaa ctg aag       1104
Thr Ser Arg Ser Ser Leu Glu Thr Gly Asn Gly Phe Glu Lys Leu Lys
        355                 360                 365 att aac gtg tct gcc agt tta tgc ggg gaa tct caa agc aag gat ctt       1152
Ile Asn Val Ser Ala Ser Leu Cys Gly Glu Ser Gln Ser Lys Asp Leu
    370                 375                 380 gaa ata ttc gag ctt ttg tct ccg ggg cag tct tac act cac agc agg       1200
Glu Ile Phe Glu Leu Leu Ser Pro Gly Gln Ser Tyr Thr His Ser Arg
385                 390                 395                 400
```

```
agt gaa tca gtt tgc agt gtt gtc tcg tct gtt gat tat gta cct tcg    1248
Ser Glu Ser Val Cys Ser Val Val Ser Ser Val Asp Tyr Val Pro Ser
            405                 410                 415 gtg aca cat gag aca gaa agt ata cta ggg aat cac caa agc tcc agt    1296
Val Thr His Glu Thr Glu Ser Ile Leu Gly Asn His Gln Ser Ser Ser
        420                 425                 430 gag atg tct ccc aag aaa aac tta gaa agt tca aac aat gta aat cat    1344
Glu Met Ser Pro Lys Lys Asn Leu Glu Ser Ser Asn Asn Val Asn His
    435                 440                 445 gag cat agc gca gca aag act tat gag tgt tct gta cat gat tta gat    1392
Glu His Ser Ala Ala Lys Thr Tyr Glu Cys Ser Val His Asp Leu Asp
450                 455                 460 gat tca gga aca atg acg act tca cat acc ata aaa ttg gta gaa gat    1440
Asp Ser Gly Thr Met Thr Thr Ser His Thr Ile Lys Leu Val Glu Asp
465                 470                 475                 480 ctt aaa agc ggg tct aac aaa gtg aag act gct gct gca gct gaa ata    1488
Leu Lys Ser Gly Ser Asn Lys Val Lys Thr Ala Ala Ala Ala Glu Ile
                485                 490                 495 cgt cat ctc acc att aac agc att gaa aat cgt gtt cac atc ggg cgt    1536
Arg His Leu Thr Ile Asn Ser Ile Glu Asn Arg Val His Ile Gly Arg
            500                 505                 510 tgt ggt gct att act cca ctg ctg tca ctt tta tac tca gaa gaa aag    1584
Cys Gly Ala Ile Thr Pro Leu Leu Ser Leu Leu Tyr Ser Glu Glu Lys
        515                 520                 525 cta act caa gaa cac gca gtc acg gct ctt ttg aat ctt tcc atc agt    1632
Leu Thr Gln Glu His Ala Val Thr Ala Leu Leu Asn Leu Ser Ile Ser
    530                 535                 540 gaa cta aac aaa gcc atg att gtg gaa gtc ggg gcg gta gaa ccg ctt    1680
Glu Leu Asn Lys Ala Met Ile Val Glu Val Gly Ala Val Glu Pro Leu
545                 550                 555                 560 gtt cat gtt ttg aac aca gga aat gac aga gcc aaa gag aat tca gca    1728
Val His Val Leu Asn Thr Gly Asn Asp Arg Ala Lys Glu Asn Ser Ala
                565                 570                 575 gca tca ttg ttc agt ctg tct gtt ctg cag gtc aac aga gaa cga ata    1776
Ala Ser Leu Phe Ser Leu Ser Val Leu Gln Val Asn Arg Glu Arg Ile
            580                 585                 590 ggc cag tct aac gca gcg ata caa gct ctg gtg aat ctt ctt ggt aaa    1824
Gly Gln Ser Asn Ala Ala Ile Gln Ala Leu Val Asn Leu Leu Gly Lys
        595                 600                 605 gga aca ttt aga gga aag aaa gac gcc gcc tct gct ttg ttc aat cta    1872
Gly Thr Phe Arg Gly Lys Lys Asp Ala Ala Ser Ala Leu Phe Asn Leu
    610                 615                 620 tcg att act cat gat aac aag gcc cgt atc gtg caa gct aag gcg gtt    1920
Ser Ile Thr His Asp Asn Lys Ala Arg Ile Val Gln Ala Lys Ala Val
625                 630                 635                 640 aag tac ctt gtg gag ctg tta gac cca gat tta gag atg gtt gat aaa    1968
Lys Tyr Leu Val Glu Leu Leu Asp Pro Asp Leu Glu Met Val Asp Lys
                645                 650                 655 gca gtt gct ctt ctt gca aat ctt tct gca gtt gga gaa ggg cgt caa    2016
Ala Val Ala Leu Leu Ala Asn Leu Ser Ala Val Gly Glu Gly Arg Gln
            660                 665                 670 gcc atc gtg agg gaa ggt ggg att cca tta ctt gtt gaa act gtt gac    2064
Ala Ile Val Arg Glu Gly Gly Ile Pro Leu Leu Val Glu Thr Val Asp
        675                 680                 685 tta gga tct cag aga ggg aaa gag aat gca gct tct gtg ctg ctt cag    2112
Leu Gly Ser Gln Arg Gly Lys Glu Asn Ala Ala Ser Val Leu Leu Gln
    690                 695                 700 ttg tgt ctg aac agt ccc aag ttt tgc act ctg gtc ttg caa gaa ggc    2160
Leu Cys Leu Asn Ser Pro Lys Phe Cys Thr Leu Val Leu Gln Glu Gly
705                 710                 715                 720
```

-continued

```
gcc ata cct ccg ctt gtt gcc ttg tct cag tct ggt aca cag aga gca      2208
Ala Ile Pro Pro Leu Val Ala Leu Ser Gln Ser Gly Thr Gln Arg Ala
        725                 730                 735 aaa gag aag gca cag caa ctt ctt agc cac ttc cga aac cag aga gat      2256
Lys Glu Lys Ala Gln Gln Leu Leu Ser His Phe Arg Asn Gln Arg Asp
    740                 745                 750 gca agg atg aag aaa ggt aga tca tga                                  2283
Ala Arg Met Lys Lys Gly Arg Ser
        755                 760

<210> SEQ ID NO 24
<211> LENGTH: 760
<212> TYPE: PRT
<213> ORGANISM: Arabidopsis thaliana

<400> SEQUENCE: 24

Met Asp Pro Val Pro Val Arg Cys Leu Leu Asn Ser Ile Ser Arg Tyr
1               5                   10                  15

Leu His Leu Val Ala Cys Gln Thr Ile Arg Phe Asn Pro Ile Gln Thr
            20                  25                  30

Cys Ile Gly Asn Met Val Leu Leu Lys Leu Leu Lys Pro Leu Leu
        35                  40                  45

Asp Glu Val Val Asp Cys Lys Ile Pro Ser Asp Cys Leu Tyr Lys
    50                  55                  60

Gly Arg Glu Asp Leu Asp Ser Val Val Asn Gln Ala Arg Glu Phe Leu
65                  70                  75                  80

Glu Asp Trp Ser Pro Lys Leu Ser Lys Leu Phe Gly Val Phe Gln Cys
                85                  90                  95

Glu Val Leu Leu Gly Lys Val Gln Thr Cys Ser Leu Glu Ile Ser Arg
            100                 105                 110

Ile Leu Leu Gln Leu Ser Gln Ser Ser Pro Val Thr Ser Ser Val Gln
        115                 120                 125

Ser Val Glu Arg Cys Val Gln Glu Thr Glu Ser Phe Lys Gln Glu Gly
    130                 135                 140

Thr Leu Met Glu Leu Met Glu Asn Ala Leu Arg Asn Gln Lys Asp Asp
145                 150                 155                 160

Ile Thr Ser Leu Asp Asn Asn His Leu Glu Ser Ile Ile Gln Met Leu
                165                 170                 175

Gly Leu Ile Ser Asn Gln Asp Leu Leu Lys Glu Ser Ile Thr Val Glu
            180                 185                 190

Lys Glu Arg Ile Arg Ser Gln Ala Ser Lys Ser Glu Glu Asp Met Glu
        195                 200                 205

Gln Thr Glu Gln Leu Ile Glu Leu Val Leu Cys Ile Arg Glu His Met
    210                 215                 220

Leu Lys Thr Glu Phe Leu Glu Val Ala Lys Gly Ile Ser Ile Pro Pro
225                 230                 235                 240

Tyr Phe Arg Cys Pro Leu Ser Thr Glu Leu Met Leu Asp Pro Val Ile
                245                 250                 255

Val Ala Ser Gly Gln Thr Phe Asp Arg Thr Ser Ile Lys Lys Trp Leu
            260                 265                 270

Asp Asn Gly Leu Ala Val Cys Pro Arg Thr Arg Gln Val Leu Thr His
        275                 280                 285

Gln Glu Leu Ile Pro Asn Tyr Thr Val Lys Ala Met Ile Ala Ser Trp
    290                 295                 300

Leu Glu Ala Asn Arg Ile Asn Leu Ala Thr Asn Ser Cys His Gln Tyr
305                 310                 315                 320
```

-continued

Asp Gly Gly Asp Ala Ser Ser Met Ala Asn Asn Met Gly Ser Gln Asp
            325                 330                 335

Phe Asn Arg Thr Glu Ser Phe Arg Phe Ser Leu Arg Ser Ser Ser Leu
            340                 345                 350

Thr Ser Arg Ser Ser Leu Glu Thr Gly Asn Gly Phe Glu Lys Leu Lys
            355                 360                 365

Ile Asn Val Ser Ala Ser Leu Cys Gly Glu Ser Gln Ser Lys Asp Leu
            370                 375                 380

Glu Ile Phe Glu Leu Leu Ser Pro Gly Gln Ser Tyr Thr His Ser Arg
385                 390                 395                 400

Ser Glu Ser Val Cys Ser Val Val Ser Val Asp Tyr Val Pro Ser
            405                 410                 415

Val Thr His Glu Thr Glu Ser Ile Leu Gly Asn His Gln Ser Ser Ser
            420                 425                 430

Glu Met Ser Pro Lys Lys Asn Leu Glu Ser Ser Asn Val Asn His
            435                 440                 445

Glu His Ser Ala Ala Lys Thr Tyr Glu Cys Ser Val His Asp Leu Asp
        450                 455                 460

Asp Ser Gly Thr Met Thr Thr Ser His Thr Ile Lys Leu Val Glu Asp
465                 470                 475                 480

Leu Lys Ser Gly Ser Asn Lys Val Lys Thr Ala Ala Ala Glu Ile
            485                 490                 495

Arg His Leu Thr Ile Asn Ser Ile Glu Asn Arg Val His Ile Gly Arg
            500                 505                 510

Cys Gly Ala Ile Thr Pro Leu Leu Ser Leu Leu Tyr Ser Glu Glu Lys
            515                 520                 525

Leu Thr Gln Glu His Ala Val Thr Ala Leu Leu Asn Leu Ser Ile Ser
        530                 535                 540

Glu Leu Asn Lys Ala Met Ile Val Glu Val Gly Ala Val Glu Pro Leu
545                 550                 555                 560

Val His Val Leu Asn Thr Gly Asn Asp Arg Ala Lys Glu Asn Ser Ala
            565                 570                 575

Ala Ser Leu Phe Ser Leu Ser Val Leu Gln Val Asn Arg Glu Arg Ile
            580                 585                 590

Gly Gln Ser Asn Ala Ala Ile Gln Ala Leu Val Asn Leu Leu Gly Lys
            595                 600                 605

Gly Thr Phe Arg Gly Lys Lys Asp Ala Ala Ser Ala Leu Phe Asn Leu
            610                 615                 620

Ser Ile Thr His Asp Asn Lys Ala Arg Ile Val Gln Ala Lys Ala Val
625                 630                 635                 640

Lys Tyr Leu Val Glu Leu Leu Asp Pro Asp Leu Glu Met Val Asp Lys
            645                 650                 655

Ala Val Ala Leu Leu Ala Asn Leu Ser Ala Val Gly Glu Gly Arg Gln
            660                 665                 670

Ala Ile Val Arg Glu Gly Gly Ile Pro Leu Leu Val Glu Thr Val Asp
            675                 680                 685

Leu Gly Ser Gln Arg Gly Lys Glu Asn Ala Ala Ser Val Leu Leu Gln
            690                 695                 700

Leu Cys Leu Asn Ser Pro Lys Phe Cys Thr Leu Val Leu Gln Glu Gly
705                 710                 715                 720

Ala Ile Pro Pro Leu Val Ala Leu Ser Gln Ser Gly Thr Gln Arg Ala
            725                 730                 735

Lys Glu Lys Ala Gln Gln Leu Leu Ser His Phe Arg Asn Gln Arg Asp
            740                 745                 750

```
Ala Arg Met Lys Lys Gly Arg Ser
        755             760

<210> SEQ ID NO 25
<211> LENGTH: 2184
<212> TYPE: DNA
<213> ORGANISM: Arabidopsis thaliana
<220> FEATURE:
<221> NAME/KEY: CDS
<222> LOCATION: (1)..(2184)

<400> SEQUENCE: 25 atg gtt ctc ttg ttg aag ctc ttg aaa ccg ttg ctc gat gaa gtt gtt        48
Met Val Leu Leu Leu Lys Leu Leu Lys Pro Leu Leu Asp Glu Val Val
1               5                   10                  15 gat tgc aag ata cct tct gat gac tgt tta tat aaa gga tgt gaa gac        96
Asp Cys Lys Ile Pro Ser Asp Asp Cys Leu Tyr Lys Gly Cys Glu Asp
            20                  25                  30 ctt gat tct gtt gtt aac cag gct cgg gag ttc tta gag gac tgg tca       144
Leu Asp Ser Val Val Asn Gln Ala Arg Glu Phe Leu Glu Asp Trp Ser
        35                  40                  45 cca aag ttg agc aag ttg ttt ggt gtg ttt caa tgc gag gtt ttg ttg       192
Pro Lys Leu Ser Lys Leu Phe Gly Val Phe Gln Cys Glu Val Leu Leu
    50                  55                  60 gga aag gtc cag act tgt tcg ttg gag att agt cgc ata ctt ctt cag       240
Gly Lys Val Gln Thr Cys Ser Leu Glu Ile Ser Arg Ile Leu Leu Gln
65                  70                  75                  80 tta tca cag tca agt ccg gtt act tca agc gta caa agt gtt gag cgc       288
Leu Ser Gln Ser Ser Pro Val Thr Ser Ser Val Gln Ser Val Glu Arg
                85                  90                  95 tgc gtg cag gag act gag agt ttt aag caa gag ggg aca tta atg gaa       336
Cys Val Gln Glu Thr Glu Ser Phe Lys Gln Glu Gly Thr Leu Met Glu
            100                 105                 110 ctc atg gag aat gct tta cgg aat cag aaa gat gat att acc tct ttg       384
Leu Met Glu Asn Ala Leu Arg Asn Gln Lys Asp Asp Ile Thr Ser Leu
        115                 120                 125 gat aac aat cat ctg gaa agc ata att caa atg ctt gga ttg ata tca       432
Asp Asn Asn His Leu Glu Ser Ile Ile Gln Met Leu Gly Leu Ile Ser
    130                 135                 140 aac caa gat ctc tta aag gaa agc att act gtg gag aaa gag agg ata       480
Asn Gln Asp Leu Leu Lys Glu Ser Ile Thr Val Glu Lys Glu Arg Ile
145                 150                 155                 160 aga tcc cag gcc agt aag tca gaa gaa gat atg gaa caa acc gaa cag       528
Arg Ser Gln Ala Ser Lys Ser Glu Glu Asp Met Glu Gln Thr Glu Gln
                165                 170                 175 ttg ata gaa ctc gtc ttg tgc atc cgt gaa cac atg ctt aaa act gag       576
Leu Ile Glu Leu Val Leu Cys Ile Arg Glu His Met Leu Lys Thr Glu
            180                 185                 190 ttt ctt gaa gtg gct aaa ggt atc tcg ata ccc ccg tat ttc cgg tgt       624
Phe Leu Glu Val Ala Lys Gly Ile Ser Ile Pro Pro Tyr Phe Arg Cys
        195                 200                 205 cct ttg tca aca gaa ctc atg ctg gat ccg gta ata gta gct tca gga       672
Pro Leu Ser Thr Glu Leu Met Leu Asp Pro Val Ile Val Ala Ser Gly
    210                 215                 220 cag aca ttt gac aga aca tcc att aag aaa tgg ctt gat aac ggg tta       720
Gln Thr Phe Asp Arg Thr Ser Ile Lys Lys Trp Leu Asp Asn Gly Leu
225                 230                 235                 240 gct gtt tgt cca agg acg cgg cag gtg ctg act cat caa gaa ctc att       768
Ala Val Cys Pro Arg Thr Arg Gln Val Leu Thr His Gln Glu Leu Ile
                245                 250                 255 ccc aat tac acg gtt aag gct atg ata gcg agt tgg ttg gag gca aac       816
```

```
                Pro Asn Tyr Thr Val Lys Ala Met Ile Ala Ser Trp Leu Glu Ala Asn
                                260                 265                 270 agg atc aac ctt gct act aac tct tgt cat cag tat gat ggt ggt gat        864
Arg Ile Asn Leu Ala Thr Asn Ser Cys His Gln Tyr Asp Gly Gly Asp
            275                 280                 285 gct tca tcc atg gct aat aat atg ggt tct caa gac ttt aac cgc acc        912
Ala Ser Ser Met Ala Asn Asn Met Gly Ser Gln Asp Phe Asn Arg Thr
290                 295                 300 gag agt ttt cgt ttt tct tta cgg agc agc agt tta acc tca aga tca        960
Glu Ser Phe Arg Phe Ser Leu Arg Ser Ser Ser Leu Thr Ser Arg Ser
305                 310                 315                 320 tct ctt gaa act gga aat ggg ttt gag aaa ctg aag att aac gtg tct       1008
Ser Leu Glu Thr Gly Asn Gly Phe Glu Lys Leu Lys Ile Asn Val Ser
                325                 330                 335 gcc agt tta tgc ggg gaa tct caa agc aag gat ctt gaa ata ttc gag       1056
Ala Ser Leu Cys Gly Glu Ser Gln Ser Lys Asp Leu Glu Ile Phe Glu
            340                 345                 350 ctt ttg tct ccg ggg cag tct tac act cac agc agg agt gaa tca gtt       1104
Leu Leu Ser Pro Gly Gln Ser Tyr Thr His Ser Arg Ser Glu Ser Val
        355                 360                 365 tgc agt gtt gtc tcg tct gtt gat tat gta cct tcg gtg aca cat gag       1152
Cys Ser Val Val Ser Ser Val Asp Tyr Val Pro Ser Val Thr His Glu
370                 375                 380 aca gaa agt ata cta ggg aat cac caa agc tcc agt gag atg tct ccc       1200
Thr Glu Ser Ile Leu Gly Asn His Gln Ser Ser Ser Glu Met Ser Pro
385                 390                 395                 400 aag aaa aac tta gaa agt tca aac aat gta aat cat gag cat agc gca       1248
Lys Lys Asn Leu Glu Ser Ser Asn Asn Val Asn His Glu His Ser Ala
                405                 410                 415 gca aag act tat gag tgt tct gta cat gat tta gat gat tca gga aca       1296
Ala Lys Thr Tyr Glu Cys Ser Val His Asp Leu Asp Asp Ser Gly Thr
            420                 425                 430 atg acg act tca cat acc ata aaa ttg gta gaa gat ctt aaa agc ggg       1344
Met Thr Thr Ser His Thr Ile Lys Leu Val Glu Asp Leu Lys Ser Gly
        435                 440                 445 tct aac aaa gtg aag act gct gct gca gct gaa ata cgt cat ctc acc       1392
Ser Asn Lys Val Lys Thr Ala Ala Ala Ala Glu Ile Arg His Leu Thr
450                 455                 460 att aac agc att gaa aat cgt gtt cac atc ggg cgt tgt ggt gct att       1440
Ile Asn Ser Ile Glu Asn Arg Val His Ile Gly Arg Cys Gly Ala Ile
465                 470                 475                 480 act cca ctg ctg tca ctt tta tac tca gaa gaa aag cta act caa gaa       1488
Thr Pro Leu Leu Ser Leu Leu Tyr Ser Glu Glu Lys Leu Thr Gln Glu
                485                 490                 495 cac gca gtc acg gct ctt ttg aat ctt tcc atc agt gaa cta aac aaa       1536
His Ala Val Thr Ala Leu Leu Asn Leu Ser Ile Ser Glu Leu Asn Lys
            500                 505                 510 gcc atg att gtg gaa gtc ggg gcg ata gaa ccg ctt gtt cat gtt ttg       1584
Ala Met Ile Val Glu Val Gly Ala Ile Glu Pro Leu Val His Val Leu
        515                 520                 525 aac aca gga aat gac aga gcc aaa gag aat tca gca gca tca ttg ttc       1632
Asn Thr Gly Asn Asp Arg Ala Lys Glu Asn Ser Ala Ala Ser Leu Phe
530                 535                 540 agt ctg tct gtt ctg cag gtc aac aga gaa cga ata ggc cag tct aac       1680
Ser Leu Ser Val Leu Gln Val Asn Arg Glu Arg Ile Gly Gln Ser Asn
545                 550                 555                 560 gca gcg ata caa gct ctg gtg aat ctt ctt ggt aaa gga aca ttt aga       1728
Ala Ala Ile Gln Ala Leu Val Asn Leu Leu Gly Lys Gly Thr Phe Arg
                565                 570                 575 gga aag aaa gac gcc gcc tct gct ttg ttc aat cta tcg att act cat       1776
```

```
Gly Lys Lys Asp Ala Ala Ser Ala Leu Phe Asn Leu Ser Ile Thr His
            580                 585                 590 gat aac aag gcc cgt atc gtg caa gct aag gcg gtt aag tac ctt gtg    1824
Asp Asn Lys Ala Arg Ile Val Gln Ala Lys Ala Val Lys Tyr Leu Val
        595                 600                 605 gag ctg tta gac cca gat tta gag atg gtt gat aaa gca gtt gct ctt    1872
Glu Leu Leu Asp Pro Asp Leu Glu Met Val Asp Lys Ala Val Ala Leu
    610                 615                 620 ctt gca aat ctt tct gca gtt gga gaa ggg cgt caa gcc atc gtg agg    1920
Leu Ala Asn Leu Ser Ala Val Gly Glu Gly Arg Gln Ala Ile Val Arg
625                 630                 635                 640 gaa ggt ggg att cca tta ctt gtt gaa act gtt gac tta gga tct cag    1968
Glu Gly Gly Ile Pro Leu Leu Val Glu Thr Val Asp Leu Gly Ser Gln
                645                 650                 655 aga ggg aaa gag aat gca gct tct gtg ctg ctt cag ttg tgt ctg aac    2016
Arg Gly Lys Glu Asn Ala Ala Ser Val Leu Leu Gln Leu Cys Leu Asn
            660                 665                 670 agt ccc aag ttt tgc act ctg gtc ttg caa gaa ggc gcc ata cct ccg    2064
Ser Pro Lys Phe Cys Thr Leu Val Leu Gln Glu Gly Ala Ile Pro Pro
        675                 680                 685 ctt gtt gcc ttg tct cag tct ggt aca cag aga gca aaa gag aag gta    2112
Leu Val Ala Leu Ser Gln Ser Gly Thr Gln Arg Ala Lys Glu Lys Val
    690                 695                 700 tat act ata ttc ttc ttc tgc ggt tac acg aaa aca cac caa gtt cag    2160
Tyr Thr Ile Phe Phe Phe Cys Gly Tyr Thr Lys Thr His Gln Val Gln
705                 710                 715                 720 ttt ctt att gat cga gat atc tga                                     2184
Phe Leu Ile Asp Arg Asp Ile
                725

<210> SEQ ID NO 26
<211> LENGTH: 727
<212> TYPE: PRT
<213> ORGANISM: Arabidopsis thaliana

<400> SEQUENCE: 26

Met Val Leu Leu Leu Lys Leu Leu Lys Pro Leu Leu Asp Glu Val Val
1               5                   10                  15

Asp Cys Lys Ile Pro Ser Asp Cys Leu Tyr Lys Gly Cys Glu Asp
            20                  25                  30

Leu Asp Ser Val Val Asn Gln Ala Arg Glu Phe Leu Glu Asp Trp Ser
        35                  40                  45

Pro Lys Leu Ser Lys Leu Phe Gly Val Phe Gln Cys Glu Val Leu Leu
    50                  55                  60

Gly Lys Val Gln Thr Cys Ser Leu Glu Ile Ser Arg Ile Leu Leu Gln
65                  70                  75                  80

Leu Ser Gln Ser Ser Pro Val Thr Ser Ser Val Gln Ser Val Glu Arg
                85                  90                  95

Cys Val Gln Glu Thr Glu Ser Phe Lys Gln Gly Thr Leu Met Glu
            100                 105                 110

Leu Met Glu Asn Ala Leu Arg Asn Gln Lys Asp Asp Ile Thr Ser Leu
        115                 120                 125

Asp Asn Asn His Leu Glu Ser Ile Ile Gln Met Leu Gly Leu Ile Ser
    130                 135                 140

Asn Gln Asp Leu Leu Lys Glu Ser Ile Thr Val Glu Lys Glu Arg Ile
145                 150                 155                 160

Arg Ser Gln Ala Ser Lys Ser Glu Glu Asp Met Glu Gln Thr Glu Gln
                165                 170                 175
```

```
Leu Ile Glu Leu Val Leu Cys Ile Arg Glu His Met Leu Lys Thr Glu
            180                 185                 190
Phe Leu Glu Val Ala Lys Gly Ile Ser Ile Pro Pro Tyr Phe Arg Cys
        195                 200                 205
Pro Leu Ser Thr Glu Leu Met Leu Asp Pro Val Ile Val Ala Ser Gly
    210                 215                 220
Gln Thr Phe Asp Arg Thr Ser Ile Lys Lys Trp Leu Asp Asn Gly Leu
225                 230                 235                 240
Ala Val Cys Pro Arg Thr Arg Gln Val Leu Thr His Gln Glu Leu Ile
                245                 250                 255
Pro Asn Tyr Thr Val Lys Ala Met Ile Ala Ser Trp Leu Glu Ala Asn
            260                 265                 270
Arg Ile Asn Leu Ala Thr Asn Ser Cys His Gln Tyr Asp Gly Gly Asp
        275                 280                 285
Ala Ser Ser Met Ala Asn Asn Met Gly Ser Gln Asp Phe Asn Arg Thr
    290                 295                 300
Glu Ser Phe Arg Phe Ser Leu Arg Ser Ser Leu Thr Ser Arg Ser
305                 310                 315                 320
Ser Leu Glu Thr Gly Asn Gly Phe Glu Lys Leu Lys Ile Asn Val Ser
                325                 330                 335
Ala Ser Leu Cys Gly Glu Ser Gln Ser Lys Asp Leu Glu Ile Phe Glu
            340                 345                 350
Leu Leu Ser Pro Gly Gln Ser Tyr Thr His Ser Arg Ser Glu Ser Val
        355                 360                 365
Cys Ser Val Val Ser Ser Val Asp Tyr Val Pro Ser Val Thr His Glu
    370                 375                 380
Thr Glu Ser Ile Leu Gly Asn His Gln Ser Ser Glu Met Ser Pro
385                 390                 395                 400
Lys Lys Asn Leu Glu Ser Ser Asn Asn Val Asn His Glu His Ser Ala
                405                 410                 415
Ala Lys Thr Tyr Glu Cys Ser Val His Asp Leu Asp Asp Ser Gly Thr
            420                 425                 430
Met Thr Thr Ser His Thr Ile Lys Leu Val Glu Asp Leu Lys Ser Gly
        435                 440                 445
Ser Asn Lys Val Lys Thr Ala Ala Ala Glu Ile Arg His Leu Thr
    450                 455                 460
Ile Asn Ser Ile Glu Asn Arg Val His Ile Gly Arg Cys Gly Ala Ile
465                 470                 475                 480
Thr Pro Leu Leu Ser Leu Leu Tyr Ser Glu Glu Lys Leu Thr Gln Glu
                485                 490                 495
His Ala Val Thr Ala Leu Leu Asn Leu Ser Ile Ser Glu Leu Asn Lys
            500                 505                 510
Ala Met Ile Val Glu Val Gly Ala Ile Glu Pro Leu Val His Val Leu
        515                 520                 525
Asn Thr Gly Asn Asp Arg Ala Lys Glu Asn Ser Ala Ala Ser Leu Phe
    530                 535                 540
Ser Leu Ser Val Leu Gln Val Asn Arg Glu Arg Ile Gly Gln Ser Asn
545                 550                 555                 560
Ala Ala Ile Gln Ala Leu Val Asn Leu Gly Lys Gly Thr Phe Arg
                565                 570                 575
Gly Lys Lys Asp Ala Ala Ser Ala Leu Phe Asn Leu Ser Ile Thr His
            580                 585                 590
Asp Asn Lys Ala Arg Ile Val Gln Ala Lys Ala Val Lys Tyr Leu Val
        595                 600                 605
```

```
Glu Leu Leu Asp Pro Asp Leu Glu Met Val Asp Lys Ala Val Ala Leu
    610                 615                 620
Leu Ala Asn Leu Ser Ala Val Gly Glu Gly Arg Gln Ala Ile Val Arg
625                 630                 635                 640
Glu Gly Gly Ile Pro Leu Leu Val Glu Thr Val Asp Leu Gly Ser Gln
            645                 650                 655
Arg Gly Lys Glu Asn Ala Ala Ser Val Leu Leu Gln Leu Cys Leu Asn
        660                 665                 670
Ser Pro Lys Phe Cys Thr Leu Val Leu Gln Glu Gly Ala Ile Pro Pro
    675                 680                 685
Leu Val Ala Leu Ser Gln Ser Gly Thr Gln Arg Ala Lys Glu Lys Val
690                 695                 700
Tyr Thr Ile Phe Phe Cys Gly Tyr Thr Lys Thr His Gln Val Gln
705                 710                 715                 720
Phe Leu Ile Asp Arg Asp Ile
            725

<210> SEQ ID NO 27
<211> LENGTH: 1983
<212> TYPE: DNA
<213> ORGANISM: Arabidopsis thaliana
<220> FEATURE:
<221> NAME/KEY: CDS
<222> LOCATION: (1)..(1983)

<400> SEQUENCE: 27 atg gag gaa gag aaa gct tct gct gca cag agc tta atc gat gta gtt      48
Met Glu Glu Glu Lys Ala Ser Ala Ala Gln Ser Leu Ile Asp Val Val
1               5                   10                  15 aac gag att gct gcg att tct gat tat cgt ata aca gtg aag aag ctt      96
Asn Glu Ile Ala Ala Ile Ser Asp Tyr Arg Ile Thr Val Lys Lys Leu
            20                  25                  30 tgt tat aat cta gcg agg aga tta aag ctg ctt gtt cct atg ttt gag     144
Cys Tyr Asn Leu Ala Arg Arg Leu Lys Leu Leu Val Pro Met Phe Glu
        35                  40                  45 gaa att aga gaa agt aac gaa ccg atc agc gaa gat acg ttg aag act     192
Glu Ile Arg Glu Ser Asn Glu Pro Ile Ser Glu Asp Thr Leu Lys Thr
    50                  55                  60 ttg atg aat ttg aag gaa gct atg tgt tca gcg aag gat tat ctc aaa     240
Leu Met Asn Leu Lys Glu Ala Met Cys Ser Ala Lys Asp Tyr Leu Lys
65                  70                  75                  80 ttt tgt agc caa ggg agc aag att tat ctg gtg atg gag agg gaa caa     288
Phe Cys Ser Gln Gly Ser Lys Ile Tyr Leu Val Met Glu Arg Glu Gln
                85                  90                  95 gtg aca agt aaa ttg atg gag gtg tct gtt aag tta gaa caa tct tta     336
Val Thr Ser Lys Leu Met Glu Val Ser Val Lys Leu Glu Gln Ser Leu
            100                 105                 110 agc cag att cca tat gaa gaa ctc gat ata tcg gat gaa gtt aga gaa     384
Ser Gln Ile Pro Tyr Glu Glu Leu Asp Ile Ser Asp Glu Val Arg Glu
        115                 120                 125 cag gtt gag ctg gtt ctt agt cag ttt cgg cga gct aaa gga aga gta     432
Gln Val Glu Leu Val Leu Ser Gln Phe Arg Arg Ala Lys Gly Arg Val
    130                 135                 140 gat gta tca gat gat gag cta tat gaa gat ctt cag tcg ctt tgc aac     480
Asp Val Ser Asp Asp Glu Leu Tyr Glu Asp Leu Gln Ser Leu Cys Asn
145                 150                 155                 160 aaa agt agt gat gta gat gct tat cag cct gtg cta gag cgg gtt gcg     528
Lys Ser Ser Asp Val Asp Ala Tyr Gln Pro Val Leu Glu Arg Val Ala
                165                 170                 175
```

```
aag aag tta cat ttg atg gag att cct gac cta gct caa gaa tca gtg         576
Lys Lys Leu His Leu Met Glu Ile Pro Asp Leu Ala Gln Glu Ser Val
            180                 185                 190 gct ctg cat gaa atg gtt gct tca agc ggt gga gat gtt ggt gaa aat         624
Ala Leu His Glu Met Val Ala Ser Ser Gly Gly Asp Val Gly Glu Asn
                195                 200                 205 att gag gag atg gca atg gta tta aag atg att aag gat ttt gtg cag         672
Ile Glu Glu Met Ala Met Val Leu Lys Met Ile Lys Asp Phe Val Gln
    210                 215                 220 acg gag gat gat aat ggc gag gag cag aaa gta gga gtt aac tct aga         720
Thr Glu Asp Asp Asn Gly Glu Glu Gln Lys Val Gly Val Asn Ser Arg
225                 230                 235                 240 agc aat gga cag act tct acg gca gcg agt cag aag ata cct gtg att         768
Ser Asn Gly Gln Thr Ser Thr Ala Ala Ser Gln Lys Ile Pro Val Ile
                245                 250                 255 cct gat gat ttt cgc tgt ccg att tcg ctg gaa atg atg aga gat cca         816
Pro Asp Asp Phe Arg Cys Pro Ile Ser Leu Glu Met Met Arg Asp Pro
                260                 265                 270 gtt att gtt tca tca ggg cag aca tac gaa cgc aca tgt att gag aaa         864
Val Ile Val Ser Ser Gly Gln Thr Tyr Glu Arg Thr Cys Ile Glu Lys
                275                 280                 285 tgg ata gaa ggt gga cac tcg aca tgt cca aaa aca cag cag gcg cta         912
Trp Ile Glu Gly Gly His Ser Thr Cys Pro Lys Thr Gln Gln Ala Leu
    290                 295                 300 aca agc aca acc ctc aca cca aac tat gtt ctc cgt agt ctc ata gct         960
Thr Ser Thr Thr Leu Thr Pro Asn Tyr Val Leu Arg Ser Leu Ile Ala
305                 310                 315                 320 cag tgg tgc gag gcc aac gat att gag cct cca aag cct ccg agc agt        1008
Gln Trp Cys Glu Ala Asn Asp Ile Glu Pro Pro Lys Pro Pro Ser Ser
                325                 330                 335 tta aga ccc aga aaa gta tcg tcc ttc tca tct ccc gca gaa gcg aac        1056
Leu Arg Pro Arg Lys Val Ser Ser Phe Ser Ser Pro Ala Glu Ala Asn
                340                 345                 350 aag att gaa gat ctt atg tgg aga ctt gcg tac gga aac ccc gag gac        1104
Lys Ile Glu Asp Leu Met Trp Arg Leu Ala Tyr Gly Asn Pro Glu Asp
                355                 360                 365 caa cga tct gca gct ggg gaa atc cgc ctt ctt gca aaa cga aat gca        1152
Gln Arg Ser Ala Ala Gly Glu Ile Arg Leu Leu Ala Lys Arg Asn Ala
370                 375                 380 gac aac cgc gtg gcc ata gcc gaa gct gga gcc ata cct ctt ctc gta        1200
Asp Asn Arg Val Ala Ile Ala Glu Ala Gly Ala Ile Pro Leu Leu Val
385                 390                 395                 400 ggt ctc ctc tca act cct gat tct cgt att caa gaa cat tcg gta aca        1248
Gly Leu Leu Ser Thr Pro Asp Ser Arg Ile Gln Glu His Ser Val Thr
                405                 410                 415 gct ctt cta aac ctc tcc ata tgt gag aac aac aaa gga gcc att gtt        1296
Ala Leu Leu Asn Leu Ser Ile Cys Glu Asn Asn Lys Gly Ala Ile Val
                420                 425                 430 tca gct gga gct att cct ggt ata gtt caa gtg ctt aag aaa gga agc        1344
Ser Ala Gly Ala Ile Pro Gly Ile Val Gln Val Leu Lys Lys Gly Ser
                435                 440                 445 atg gag gcc aga gag aat gcg gcg gct aca ctt ttc agt cta tca gtg        1392
Met Glu Ala Arg Glu Asn Ala Ala Ala Thr Leu Phe Ser Leu Ser Val
450                 455                 460 atc gat gaa aat aaa gtg act atc ggt gcc tta gga gca att ccg cca        1440
Ile Asp Glu Asn Lys Val Thr Ile Gly Ala Leu Gly Ala Ile Pro Pro
465                 470                 475                 480 ctc gtt gta tta ctt aat gaa ggt aca caa aga ggc aag aaa gat gct        1488
Leu Val Val Leu Leu Asn Glu Gly Thr Gln Arg Gly Lys Lys Asp Ala
                485                 490                 495
```

```
gct act gca ctc ttt aac ctc tgt ata tac caa gga aac aaa gga aaa      1536
Ala Thr Ala Leu Phe Asn Leu Cys Ile Tyr Gln Gly Asn Lys Gly Lys
        500                 505                 510 gct ata cgt gca gga gtg att ccc acg ttg act aga ctc ttg aca gag      1584
Ala Ile Arg Ala Gly Val Ile Pro Thr Leu Thr Arg Leu Leu Thr Glu
        515                 520                 525 ccc gga agc gga atg gtc gat gag gca ctc gcg att ttg gcg att ctc      1632
Pro Gly Ser Gly Met Val Asp Glu Ala Leu Ala Ile Leu Ala Ile Leu
530                 535                 540 tct agc cac ccc gaa gga aaa gca atc ata gga tcc tct gat gca gtc      1680
Ser Ser His Pro Glu Gly Lys Ala Ile Ile Gly Ser Ser Asp Ala Val
545                 550                 555                 560 cca agt ttg gtt gag ttt atc aga act ggc tcg cct aga aac aga gaa      1728
Pro Ser Leu Val Glu Phe Ile Arg Thr Gly Ser Pro Arg Asn Arg Glu
                565                 570                 575 aac gca gct gct gtt cta gtc cac ctc tgt tct gga gac cca caa cat      1776
Asn Ala Ala Ala Val Leu Val His Leu Cys Ser Gly Asp Pro Gln His
            580                 585                 590 ctt gtc gaa gcg cag aaa ctc ggc ctt atg ggt cca ttg ata gat tta      1824
Leu Val Glu Ala Gln Lys Leu Gly Leu Met Gly Pro Leu Ile Asp Leu
        595                 600                 605 gct gga aat ggg acg gat aga ggg aaa cga aaa gca gcg cag ttg ctt      1872
Ala Gly Asn Gly Thr Asp Arg Gly Lys Arg Lys Ala Ala Gln Leu Leu
610                 615                 620 gaa cgc atc agc cgt ctc gct gaa cag cag aag gaa acg gct gtg tca      1920
Glu Arg Ile Ser Arg Leu Ala Glu Gln Gln Lys Glu Thr Ala Val Ser
625                 630                 635                 640 caa ccg gaa gaa gaa gct gaa cca aca cat cca gaa tcc acc aca gaa      1968
Gln Pro Glu Glu Glu Ala Glu Pro Thr His Pro Glu Ser Thr Thr Glu
                645                 650                 655 gct gca gat act taa                                                  1983
Ala Ala Asp Thr
            660

<210> SEQ ID NO 28
<211> LENGTH: 660
<212> TYPE: PRT
<213> ORGANISM: Arabidopsis thaliana

<400> SEQUENCE: 28

Met Glu Glu Lys Ala Ser Ala Ala Gln Ser Leu Ile Asp Val Val
1               5                   10                  15

Asn Glu Ile Ala Ala Ile Ser Asp Tyr Arg Ile Thr Val Lys Lys Leu
            20                  25                  30

Cys Tyr Asn Leu Ala Arg Arg Leu Lys Leu Leu Val Pro Met Phe Glu
        35                  40                  45

Glu Ile Arg Glu Ser Asn Glu Pro Ile Ser Glu Asp Thr Leu Lys Thr
    50                  55                  60

Leu Met Asn Leu Lys Glu Ala Met Cys Ser Ala Lys Asp Tyr Leu Lys
65                  70                  75                  80

Phe Cys Ser Gln Gly Ser Lys Ile Tyr Leu Val Met Glu Arg Glu Gln
                85                  90                  95

Val Thr Ser Lys Leu Met Glu Val Ser Val Lys Leu Glu Gln Ser Leu
            100                 105                 110

Ser Gln Ile Pro Tyr Glu Glu Leu Asp Ile Ser Asp Glu Val Arg Glu
        115                 120                 125

Gln Val Glu Leu Val Leu Ser Gln Phe Arg Arg Ala Lys Gly Arg Val
    130                 135                 140

Asp Val Ser Asp Asp Glu Leu Tyr Glu Asp Leu Gln Ser Leu Cys Asn
```

```
            145                 150                 155                 160
        Lys Ser Ser Asp Val Asp Ala Tyr Gln Pro Val Leu Glu Arg Val Ala
                        165                 170                 175
        Lys Lys Leu His Leu Met Glu Ile Pro Asp Leu Ala Gln Glu Ser Val
                        180                 185                 190
        Ala Leu His Glu Met Val Ala Ser Gly Gly Asp Val Gly Glu Asn
                        195                 200                 205
        Ile Glu Glu Met Ala Met Val Leu Lys Met Ile Lys Asp Phe Val Gln
                        210                 215                 220
        Thr Glu Asp Asp Asn Gly Glu Glu Gln Lys Val Gly Val Asn Ser Arg
        225                 230                 235                 240
        Ser Asn Gly Gln Thr Ser Thr Ala Ala Ser Gln Lys Ile Pro Val Ile
                        245                 250                 255
        Pro Asp Asp Phe Arg Cys Pro Ile Ser Leu Glu Met Met Arg Asp Pro
                        260                 265                 270
        Val Ile Val Ser Ser Gly Gln Thr Tyr Glu Arg Thr Cys Ile Glu Lys
                        275                 280                 285
        Trp Ile Glu Gly Gly His Ser Thr Cys Pro Lys Thr Gln Gln Ala Leu
                        290                 295                 300
        Thr Ser Thr Thr Leu Thr Pro Asn Tyr Val Leu Arg Ser Leu Ile Ala
        305                 310                 315                 320
        Gln Trp Cys Glu Ala Asn Asp Ile Glu Pro Pro Lys Pro Pro Ser Ser
                        325                 330                 335
        Leu Arg Pro Arg Lys Val Ser Ser Phe Ser Ser Pro Ala Glu Ala Asn
                        340                 345                 350
        Lys Ile Glu Asp Leu Met Trp Arg Leu Ala Tyr Gly Asn Pro Glu Asp
                        355                 360                 365
        Gln Arg Ser Ala Ala Gly Glu Ile Arg Leu Leu Ala Lys Arg Asn Ala
                        370                 375                 380
        Asp Asn Arg Val Ala Ile Ala Glu Ala Gly Ala Ile Pro Leu Leu Val
        385                 390                 395                 400
        Gly Leu Leu Ser Thr Pro Asp Ser Arg Ile Gln Glu His Ser Val Thr
                        405                 410                 415
        Ala Leu Leu Asn Leu Ser Ile Cys Glu Asn Asn Lys Gly Ala Ile Val
                        420                 425                 430
        Ser Ala Gly Ala Ile Pro Gly Ile Val Gln Val Leu Lys Lys Gly Ser
                        435                 440                 445
        Met Glu Ala Arg Glu Asn Ala Ala Ala Thr Leu Phe Ser Leu Ser Val
                        450                 455                 460
        Ile Asp Glu Asn Lys Val Thr Ile Gly Ala Leu Gly Ala Ile Pro Pro
        465                 470                 475                 480
        Leu Val Val Leu Leu Asn Glu Gly Thr Gln Arg Gly Lys Lys Asp Ala
                        485                 490                 495
        Ala Thr Ala Leu Phe Asn Leu Cys Ile Tyr Gln Gly Asn Lys Gly Lys
                        500                 505                 510
        Ala Ile Arg Ala Gly Val Ile Pro Thr Leu Thr Arg Leu Leu Thr Glu
                        515                 520                 525
        Pro Gly Ser Gly Met Val Asp Glu Ala Leu Ala Ile Leu Ala Ile Leu
                        530                 535                 540
        Ser Ser His Pro Glu Gly Lys Ala Ile Ile Gly Ser Ser Asp Ala Val
        545                 550                 555                 560
        Pro Ser Leu Val Glu Phe Ile Arg Thr Gly Ser Pro Arg Asn Arg Glu
                        565                 570                 575
```

```
Asn Ala Ala Ala Val Leu Val His Leu Cys Ser Gly Asp Pro Gln His
            580                 585                 590

Leu Val Glu Ala Gln Lys Leu Gly Leu Met Gly Pro Leu Ile Asp Leu
        595                 600                 605

Ala Gly Asn Gly Thr Asp Arg Gly Lys Arg Lys Ala Ala Gln Leu Leu
    610                 615                 620

Glu Arg Ile Ser Arg Leu Ala Glu Gln Gln Lys Glu Thr Ala Val Ser
625                 630                 635                 640

Gln Pro Glu Glu Glu Ala Glu Pro Thr His Pro Glu Ser Thr Thr Glu
            645                 650                 655

Ala Ala Asp Thr
            660

<210> SEQ ID NO 29
<211> LENGTH: 1068
<212> TYPE: DNA
<213> ORGANISM: Arabidopsis thaliana
<220> FEATURE:
<221> NAME/KEY: CDS
<222> LOCATION: (1)..(1068)

<400> SEQUENCE: 29 atg gag atg gag aat cac cgc ccc ggc agt ttc acc tac atg ggc cgc      48
Met Glu Met Glu Asn His Arg Pro Gly Ser Phe Thr Tyr Met Gly Arg
1               5                   10                  15 aaa ttc agc gat tta agt ctc aac gat gac tcc tct gct ttc agc gat      96
Lys Phe Ser Asp Leu Ser Leu Asn Asp Asp Ser Ser Ala Phe Ser Asp
                20                  25                  30 tgt aac agc gac aga tcc ggc gaa ttc ccc act gct tcc tcc gag agc     144
Cys Asn Ser Asp Arg Ser Gly Glu Phe Pro Thr Ala Ser Ser Glu Ser
            35                  40                  45 cgt cgt ctc ctc ctc tct tgc gcc tct gag aat tcc gat gat ctc atc     192
Arg Arg Leu Leu Leu Ser Cys Ala Ser Glu Asn Ser Asp Asp Leu Ile
        50                  55                  60 aat cat ctc gtg tcg cat ctt gat tcc tcc tat tcg atc gat gag cag     240
Asn His Leu Val Ser His Leu Asp Ser Ser Tyr Ser Ile Asp Glu Gln
65                  70                  75                  80 aag caa gct gct atg gag atc agg ctc tta tcc aag aac aaa cct gag     288
Lys Gln Ala Ala Met Glu Ile Arg Leu Leu Ser Lys Asn Lys Pro Glu
                85                  90                  95 aat cgg atc aaa atc gcc aag gcc ggt gcg att aag ccg ttg att tct     336
Asn Arg Ile Lys Ile Ala Lys Ala Gly Ala Ile Lys Pro Leu Ile Ser
            100                 105                 110 ctg atc tct tct tcg gat ctt cag ctt cag gag tat ggt gtc act gca     384
Leu Ile Ser Ser Ser Asp Leu Gln Leu Gln Glu Tyr Gly Val Thr Ala
        115                 120                 125 atc ttg aat cta tct ctc tgc gac gag aac aaa gag tcg att gct tct     432
Ile Leu Asn Leu Ser Leu Cys Asp Glu Asn Lys Glu Ser Ile Ala Ser
    130                 135                 140 tcc ggt gcg att aag ccg ctt gtc agg gct ttg aaa atg gga aca ccg     480
Ser Gly Ala Ile Lys Pro Leu Val Arg Ala Leu Lys Met Gly Thr Pro
145                 150                 155                 160 act gct aaa gag aac gct gct tgt gct ctg ctc cgt cta tcg cag atc     528
Thr Ala Lys Glu Asn Ala Ala Cys Ala Leu Leu Arg Leu Ser Gln Ile
                165                 170                 175 gag gag aac aaa gtc gcc atc ggg aga tcc gga gcg att cct ctg ttg     576
Glu Glu Asn Lys Val Ala Ile Gly Arg Ser Gly Ala Ile Pro Leu Leu
            180                 185                 190 gtg aac ctt cta gaa aca ggc gga ttc aga gcg aag aag gac gcg tcg     624
Val Asn Leu Leu Glu Thr Gly Gly Phe Arg Ala Lys Lys Asp Ala Ser
        195                 200                 205
```

```
acg gct ctg tac tcg ttg tgc tca gct aaa gag aac aaa atc aga gcc    672
Thr Ala Leu Tyr Ser Leu Cys Ser Ala Lys Glu Asn Lys Ile Arg Ala
    210                 215                 220 gtg caa tcg gga att atg aag ccg ctt gtt gaa ttg atg gcg gat ttc    720
Val Gln Ser Gly Ile Met Lys Pro Leu Val Glu Leu Met Ala Asp Phe
225                 230                 235                 240 gga tca aac atg gtg gat aaa tcg gcg ttt gtg atg agt ctg tta atg    768
Gly Ser Asn Met Val Asp Lys Ser Ala Phe Val Met Ser Leu Leu Met
                245                 250                 255 tcg gtg ccg gaa tcg aaa ccg gcg att gtg gag gaa gga gga gtt ccg    816
Ser Val Pro Glu Ser Lys Pro Ala Ile Val Glu Glu Gly Gly Val Pro
            260                 265                 270 gtg ctg gtg gag ata gta gag gtg gga aca cag aga cag aaa gag atg    864
Val Leu Val Glu Ile Val Glu Val Gly Thr Gln Arg Gln Lys Glu Met
        275                 280                 285 gct gtg tcg ata ttg cta cag ctt tgt gag gag agt gtt gtg tat aga    912
Ala Val Ser Ile Leu Leu Gln Leu Cys Glu Glu Ser Val Val Tyr Arg
    290                 295                 300 aca atg gtg gct aga gaa gga gcg ata cct ccg cta gtg gct ctg tcg    960
Thr Met Val Ala Arg Glu Gly Ala Ile Pro Pro Leu Val Ala Leu Ser
305                 310                 315                 320 cag gca gga aca agt cga gct aag caa aag gct gag gcg ttg att gag   1008
Gln Ala Gly Thr Ser Arg Ala Lys Gln Lys Ala Glu Ala Leu Ile Glu
                325                 330                 335 ctt cta agg caa cca aga tcc att agt aat ggt ggt gct aga tca tcg   1056
Leu Leu Arg Gln Pro Arg Ser Ile Ser Asn Gly Gly Ala Arg Ser Ser
            340                 345                 350 tcc caa ctc tga                                                   1068
Ser Gln Leu
        355

<210> SEQ ID NO 30
<211> LENGTH: 355
<212> TYPE: PRT
<213> ORGANISM: Arabidopsis thaliana

<400> SEQUENCE: 30

Met Glu Met Glu Asn His Arg Pro Gly Ser Phe Thr Tyr Met Gly Arg
1               5                   10                  15

Lys Phe Ser Asp Leu Ser Leu Asn Asp Asp Ser Ser Ala Phe Ser Asp
            20                  25                  30

Cys Asn Ser Asp Arg Ser Gly Glu Phe Pro Thr Ala Ser Ser Glu Ser
        35                  40                  45

Arg Arg Leu Leu Leu Ser Cys Ala Ser Glu Asn Ser Asp Asp Leu Ile
    50                  55                  60

Asn His Leu Val Ser His Leu Asp Ser Ser Tyr Ser Ile Asp Glu Gln
65                  70                  75                  80

Lys Gln Ala Ala Met Glu Ile Arg Leu Leu Ser Lys Asn Lys Pro Glu
                85                  90                  95

Asn Arg Ile Lys Ile Ala Lys Ala Gly Ala Ile Lys Pro Leu Ile Ser
            100                 105                 110

Leu Ile Ser Ser Ser Asp Leu Gln Leu Gln Glu Tyr Gly Val Thr Ala
        115                 120                 125

Ile Leu Asn Leu Ser Leu Cys Asp Glu Asn Lys Glu Ser Ile Ala Ser
    130                 135                 140

Ser Gly Ala Ile Lys Pro Leu Val Arg Ala Leu Lys Met Gly Thr Pro
145                 150                 155                 160

Thr Ala Lys Glu Asn Ala Ala Cys Ala Leu Leu Arg Leu Ser Gln Ile
```

```
                  165                 170                 175
Glu Glu Asn Lys Val Ala Ile Gly Arg Ser Gly Ala Ile Pro Leu Leu
            180                 185                 190

Val Asn Leu Leu Glu Thr Gly Gly Phe Arg Ala Lys Lys Asp Ala Ser
            195                 200                 205

Thr Ala Leu Tyr Ser Leu Cys Ser Ala Lys Glu Asn Lys Ile Arg Ala
            210                 215                 220

Val Gln Ser Gly Ile Met Lys Pro Leu Val Glu Leu Met Ala Asp Phe
225                 230                 235                 240

Gly Ser Asn Met Val Asp Lys Ser Ala Phe Val Met Ser Leu Leu Met
            245                 250                 255

Ser Val Pro Glu Ser Lys Pro Ala Ile Val Glu Glu Gly Gly Val Pro
            260                 265                 270

Val Leu Val Glu Ile Val Glu Val Gly Thr Gln Arg Gln Lys Glu Met
            275                 280                 285

Ala Val Ser Ile Leu Leu Gln Leu Cys Glu Glu Ser Val Val Tyr Arg
            290                 295                 300

Thr Met Val Ala Arg Glu Gly Ala Ile Pro Pro Leu Val Ala Leu Ser
305                 310                 315                 320

Gln Ala Gly Thr Ser Arg Ala Lys Gln Lys Ala Glu Ala Leu Ile Glu
            325                 330                 335

Leu Leu Arg Gln Pro Arg Ser Ile Ser Asn Gly Ala Arg Ser Ser
            340                 345                 350

Ser Gln Leu
    355

<210> SEQ ID NO 31
<211> LENGTH: 1068
<212> TYPE: DNA
<213> ORGANISM: Arabidopsis thaliana
<220> FEATURE:
<221> NAME/KEY: CDS
<222> LOCATION: (1)..(1068)

<400> SEQUENCE: 31 atg gag atg gag aat cac cgc ccc ggc agt ttc acc tac atg ggc cgc       48
Met Glu Met Glu Asn His Arg Pro Gly Ser Phe Thr Tyr Met Gly Arg
1               5                  10                  15 aaa ttc agc gat tta agt ctc aac gat gac tcc tct gct ttc agc gat       96
Lys Phe Ser Asp Leu Ser Leu Asn Asp Asp Ser Ser Ala Phe Ser Asp
            20                  25                  30 tgt aac agc gac aga tcc ggc gaa ttc ccc act gct tcc tcc gag agc      144
Cys Asn Ser Asp Arg Ser Gly Glu Phe Pro Thr Ala Ser Ser Glu Ser
        35                  40                  45 cgt cgt ctc ctc ctc tct tgc gcc tct gag aat tcc gat gat ctc atc      192
Arg Arg Leu Leu Leu Ser Cys Ala Ser Glu Asn Ser Asp Asp Leu Ile
    50                  55                  60 aat cat ctc gtg tcg cat ctt gat tcc tcc tat tcg atc gat gag cag      240
Asn His Leu Val Ser His Leu Asp Ser Ser Tyr Ser Ile Asp Glu Gln
65                  70                  75                  80 aag caa gct gct atg gag atc agg ctc tta tcc aag aac aaa cct gag      288
Lys Gln Ala Ala Met Glu Ile Arg Leu Leu Ser Lys Asn Lys Pro Glu
                85                  90                  95 aat cgg atc aaa atc gcc aag gcc ggt gcg att aag ccg ttg att tct      336
Asn Arg Ile Lys Ile Ala Lys Ala Gly Ala Ile Lys Pro Leu Ile Ser
            100                 105                 110 ctg atc tct tct tcg gat ctt cag ctt cag gag tat ggt gtc act gca      384
Leu Ile Ser Ser Ser Asp Leu Gln Leu Gln Glu Tyr Gly Val Thr Ala
        115                 120                 125
```

| | | | |
|---|---|---|---|
| atc ttg aat cta tct ctc tgc gac gag aac aaa gag tcg att gct tct<br>Ile Leu Asn Leu Ser Leu Cys Asp Glu Asn Lys Glu Ser Ile Ala Ser<br>130                   135                   140 | | | 432 |
| tcc ggt gcg att aag ccg ctt gtc agg gct ttg aaa atg gga aca ccg<br>Ser Gly Ala Ile Lys Pro Leu Val Arg Ala Leu Lys Met Gly Thr Pro<br>145                   150                   155                   160 | | | 480 |
| act gct aaa gag aac gct gct tgt gct ctg ctc cgt cta tcg cag atc<br>Thr Ala Lys Glu Asn Ala Ala Cys Ala Leu Leu Arg Leu Ser Gln Ile<br>                 165                   170                   175 | | | 528 |
| gag gag aac aaa gtc gcc atc ggg aga tcc gga gcg att cct ctg ttg<br>Glu Glu Asn Lys Val Ala Ile Gly Arg Ser Gly Ala Ile Pro Leu Leu<br>            180                   185                   190 | | | 576 |
| gtg aac ctt cta gaa aca ggc gga ttc aga gcg aag aag gac gcg tcg<br>Val Asn Leu Leu Glu Thr Gly Gly Phe Arg Ala Lys Lys Asp Ala Ser<br>                 195                   200                   205 | | | 624 |
| acg gct ctg tac tcg ttg tgc tca gct aaa gag aac aaa atc aga gcc<br>Thr Ala Leu Tyr Ser Leu Cys Ser Ala Lys Glu Asn Lys Ile Arg Ala<br>210                   215                   220 | | | 672 |
| gtg caa tcg gga att atg aag ccg ctt gtt gaa ttg atg gcg gat ttc<br>Val Gln Ser Gly Ile Met Lys Pro Leu Val Glu Leu Met Ala Asp Phe<br>225                   230                   235                   240 | | | 720 |
| gga tca aac atg gtg gat aaa tcg gcg ttt gtg atg agt ctg tta atg<br>Gly Ser Asn Met Val Asp Lys Ser Ala Phe Val Met Ser Leu Leu Met<br>                 245                   250                   255 | | | 768 |
| tcg gtg ccg gaa tcg aaa ccg gcg att gtg gag gaa gga gga gtt ccg<br>Ser Val Pro Glu Ser Lys Pro Ala Ile Val Glu Glu Gly Gly Val Pro<br>            260                   265                   270 | | | 816 |
| gtg ctg gtg gag ata gta gag gtg gga aca cag aga cag aaa gag atg<br>Val Leu Val Glu Ile Val Glu Val Gly Thr Gln Arg Gln Lys Glu Met<br>                 275                   280                   285 | | | 864 |
| gct gtg tcg ata ttg cta cag ctt tgt gag gag agt gtt gtg tat aga<br>Ala Val Ser Ile Leu Leu Gln Leu Cys Glu Glu Ser Val Val Tyr Arg<br>290                   295                   300 | | | 912 |
| aca atg gtg gct aga gaa gga gcg ata cct ccg cta gtg gct ctg tcg<br>Thr Met Val Ala Arg Glu Gly Ala Ile Pro Pro Leu Val Ala Leu Ser<br>305                   310                   315                   320 | | | 960 |
| cag gca gga aca agt cga gct aag caa aag gct gag gcg ttg att gag<br>Gln Ala Gly Thr Ser Arg Ala Lys Gln Lys Ala Glu Ala Leu Ile Glu<br>                 325                   330                   335 | | | 1008 |
| ctt cta agg caa cta aga tcc att agt aat ggt ggt gct aga tca tcg<br>Leu Leu Arg Gln Leu Arg Ser Ile Ser Asn Gly Gly Ala Arg Ser Ser<br>            340                   345                   350 | | | 1056 |
| tcc caa ctc tga<br>Ser Gln Leu<br>            355 | | | 1068 |

```
<210> SEQ ID NO 32
<211> LENGTH: 355
<212> TYPE: PRT
<213> ORGANISM: Arabidopsis thaliana

<400> SEQUENCE: 32
```

Met Glu Met Glu Asn His Arg Pro Gly Ser Phe Thr Tyr Met Gly Arg
1                 5                       10                      15

Lys Phe Ser Asp Leu Ser Leu Asn Asp Asp Ser Ser Ala Phe Ser Asp
                20                       25                       30

Cys Asn Ser Asp Arg Ser Gly Glu Phe Pro Thr Ala Ser Ser Glu Ser
                   35                       40                       45

Arg Arg Leu Leu Leu Ser Cys Ala Ser Glu Asn Ser Asp Asp Leu Ile
        50                       55                       60

Asn His Leu Val Ser His Leu Asp Ser Ser Tyr Ser Ile Asp Glu Gln
65                  70                  75                  80

Lys Gln Ala Ala Met Glu Ile Arg Leu Leu Ser Lys Asn Lys Pro Glu
                85                  90                  95

Asn Arg Ile Lys Ile Ala Lys Ala Gly Ala Ile Lys Pro Leu Ile Ser
            100                 105                 110

Leu Ile Ser Ser Asp Leu Gln Leu Gln Glu Tyr Gly Val Thr Ala
        115                 120                 125

Ile Leu Asn Leu Ser Leu Cys Asp Glu Asn Lys Glu Ser Ile Ala Ser
        130                 135                 140

Ser Gly Ala Ile Lys Pro Leu Val Arg Ala Leu Lys Met Gly Thr Pro
145                 150                 155                 160

Thr Ala Lys Glu Asn Ala Ala Cys Ala Leu Leu Arg Leu Ser Gln Ile
                165                 170                 175

Glu Glu Asn Lys Val Ala Ile Gly Arg Ser Gly Ala Ile Pro Leu Leu
            180                 185                 190

Val Asn Leu Leu Glu Thr Gly Gly Phe Arg Ala Lys Lys Asp Ala Ser
        195                 200                 205

Thr Ala Leu Tyr Ser Leu Cys Ser Ala Lys Glu Asn Lys Ile Arg Ala
        210                 215                 220

Val Gln Ser Gly Ile Met Lys Pro Leu Val Glu Leu Met Ala Asp Phe
225                 230                 235                 240

Gly Ser Asn Met Val Asp Lys Ser Ala Phe Val Met Ser Leu Leu Met
                245                 250                 255

Ser Val Pro Glu Ser Lys Pro Ala Ile Val Glu Glu Gly Gly Val Pro
            260                 265                 270

Val Leu Val Glu Ile Val Glu Val Gly Thr Gln Arg Gln Lys Glu Met
        275                 280                 285

Ala Val Ser Ile Leu Leu Gln Leu Cys Glu Glu Ser Val Val Tyr Arg
        290                 295                 300

Thr Met Val Ala Arg Glu Gly Ala Ile Pro Pro Leu Val Ala Leu Ser
305                 310                 315                 320

Gln Ala Gly Thr Ser Arg Ala Lys Gln Lys Ala Glu Ala Leu Ile Glu
                325                 330                 335

Leu Leu Arg Gln Leu Arg Ser Ile Ser Asn Gly Gly Ala Arg Ser Ser
            340                 345                 350

Ser Gln Leu
        355

<210> SEQ ID NO 33
<211> LENGTH: 1068
<212> TYPE: DNA
<213> ORGANISM: Arabidopsis thaliana
<220> FEATURE:
<221> NAME/KEY: CDS
<222> LOCATION: (1)..(1068)

<400> SEQUENCE: 33 atg gag atg gag aat cac cgc ccc ggc agt ttc acc tac atg ggc cgc        48
Met Glu Met Glu Asn His Arg Pro Gly Ser Phe Thr Tyr Met Gly Arg
1               5                   10                  15 aaa ttc agc gat tta agt ctc aac gat gac tcc tct gct ttc agc gat        96
Lys Phe Ser Asp Leu Ser Leu Asn Asp Asp Ser Ser Ala Phe Ser Asp
            20                  25                  30 tgt aac agc gac aga tcc ggc gaa ttc ccc act gct tcc tcc gag agc       144
Cys Asn Ser Asp Arg Ser Gly Glu Phe Pro Thr Ala Ser Ser Glu Ser
        35                  40                  45

```
cgt cgt ctc ctc ctc tct tgc gcc tct gag aat tcc gat gat ctc atc      192
Arg Arg Leu Leu Leu Ser Cys Ala Ser Glu Asn Ser Asp Asp Leu Ile
    50              55                  60 aat cat ctc gtg tcg cat ctt gat tcc tcc tat tcg atc gat gag cag      240
Asn His Leu Val Ser His Leu Asp Ser Ser Tyr Ser Ile Asp Glu Gln
65              70                  75                  80 aag caa gct gct atg gag atc agg ctc tta tcc aag aac aaa cct gag      288
Lys Gln Ala Ala Met Glu Ile Arg Leu Leu Ser Lys Asn Lys Pro Glu
                85                  90                  95 aat cgg atc aaa atc gcc aag gcc ggt gcg att aag ccg ttg att tct      336
Asn Arg Ile Lys Ile Ala Lys Ala Gly Ala Ile Lys Pro Leu Ile Ser
            100                 105                 110 ctg atc tct tct tcg gat ctt cag ctt cag gag tat ggt gtc act gcw      384
Leu Ile Ser Ser Ser Asp Leu Gln Leu Gln Glu Tyr Gly Val Thr Ala
        115                 120                 125 atc ttg aat cta tct ctc tgc gac gag aac aaa gag tcg att gct tct      432
Ile Leu Asn Leu Ser Leu Cys Asp Glu Asn Lys Glu Ser Ile Ala Ser
    130                 135                 140 tcc ggt gcg att aag ccg ctt gtc agg gct ttg aaa atg gga aca ccg      480
Ser Gly Ala Ile Lys Pro Leu Val Arg Ala Leu Lys Met Gly Thr Pro
145                 150                 155                 160 act gct aaa gat aac gct gct tgt gct ctg ctc cgt cta tcg cag atc      528
Thr Ala Lys Asp Asn Ala Ala Cys Ala Leu Leu Arg Leu Ser Gln Ile
                165                 170                 175 gag gag aac aaa gtc gcc atc ggg aga tcc gga gcg att cct ctg ttg      576
Glu Glu Asn Lys Val Ala Ile Gly Arg Ser Gly Ala Ile Pro Leu Leu
            180                 185                 190 gtg aac ctt cta gaa aca ggc gga ttc aga gcg aag aag gac gcg tcg      624
Val Asn Leu Leu Glu Thr Gly Gly Phe Arg Ala Lys Lys Asp Ala Ser
        195                 200                 205 acg gct ctg tac tcg ttg tgc tca gct aaa gag aac aaa atc aga gcc      672
Thr Ala Leu Tyr Ser Leu Cys Ser Ala Lys Glu Asn Lys Ile Arg Ala
    210                 215                 220 gtg caa tcg gga att atg aag ccg ctt gtt gaa ttg atg gcg gat ttc      720
Val Gln Ser Gly Ile Met Lys Pro Leu Val Glu Leu Met Ala Asp Phe
225                 230                 235                 240 gga tca aac atg gtg gat aaa tcg gcg ttt gtg atg agt ctg tta atg      768
Gly Ser Asn Met Val Asp Lys Ser Ala Phe Val Met Ser Leu Leu Met
                245                 250                 255 tcg gtg ccg gaa tcg aaa ccg gcg att gtg gag gaa gga gga gtt ccg      816
Ser Val Pro Glu Ser Lys Pro Ala Ile Val Glu Glu Gly Gly Val Pro
            260                 265                 270 gtg ctg gtg gag ata gta gag gtg gga aca cag aga cag aaa gag atg      864
Val Leu Val Glu Ile Val Glu Val Gly Thr Gln Arg Gln Lys Glu Met
        275                 280                 285 gct gtg tcg ata ttg cta cag ctt tgt gag gag agt gtt gtg tat aga      912
Ala Val Ser Ile Leu Leu Gln Leu Cys Glu Glu Ser Val Val Tyr Arg
    290                 295                 300 aca atg gtg gct aga gaa gga gcg ata cct ccg cta gtg gct ctg tcg      960
Thr Met Val Ala Arg Glu Gly Ala Ile Pro Pro Leu Val Ala Leu Ser
305                 310                 315                 320 cag gca gga aca agt cga gct aag caa aag gct gag gcg ttg att gag     1008
Gln Ala Gly Thr Ser Arg Ala Lys Gln Lys Ala Glu Ala Leu Ile Glu
                325                 330                 335 ctt cta agg caa cca aga tcc att agt aat ggt ggt gct aga tca tcg     1056
Leu Leu Arg Gln Pro Arg Ser Ile Ser Asn Gly Gly Ala Arg Ser Ser
            340                 345                 350 tcc caa ctc tga                                                     1068
Ser Gln Leu
        355
```

```
<210> SEQ ID NO 34
<211> LENGTH: 355
<212> TYPE: PRT
<213> ORGANISM: Arabidopsis thaliana

<400> SEQUENCE: 34

Met Glu Met Glu Asn His Arg Pro Gly Ser Phe Thr Tyr Met Gly Arg
1               5                   10                  15

Lys Phe Ser Asp Leu Ser Leu Asn Asp Asp Ser Ser Ala Phe Ser Asp
            20                  25                  30

Cys Asn Ser Asp Arg Ser Gly Glu Phe Pro Thr Ala Ser Ser Glu Ser
        35                  40                  45

Arg Arg Leu Leu Leu Ser Cys Ala Ser Glu Asn Ser Asp Asp Leu Ile
    50                  55                  60

Asn His Leu Val Ser His Leu Asp Ser Ser Tyr Ser Ile Asp Glu Gln
65                  70                  75                  80

Lys Gln Ala Ala Met Glu Ile Arg Leu Leu Ser Lys Asn Lys Pro Glu
                85                  90                  95

Asn Arg Ile Lys Ile Ala Lys Ala Gly Ala Ile Lys Pro Leu Ile Ser
            100                 105                 110

Leu Ile Ser Ser Ser Asp Leu Gln Leu Gln Glu Tyr Gly Val Thr Ala
        115                 120                 125

Ile Leu Asn Leu Ser Leu Cys Asp Glu Asn Lys Glu Ser Ile Ala Ser
    130                 135                 140

Ser Gly Ala Ile Lys Pro Leu Val Arg Ala Leu Lys Met Gly Thr Pro
145                 150                 155                 160

Thr Ala Lys Asp Asn Ala Ala Cys Ala Leu Leu Arg Leu Ser Gln Ile
                165                 170                 175

Glu Glu Asn Lys Val Ala Ile Gly Arg Ser Gly Ala Ile Pro Leu Leu
            180                 185                 190

Val Asn Leu Leu Glu Thr Gly Gly Phe Arg Ala Lys Lys Asp Ala Ser
        195                 200                 205

Thr Ala Leu Tyr Ser Leu Cys Ser Ala Lys Glu Asn Lys Ile Arg Ala
    210                 215                 220

Val Gln Ser Gly Ile Met Lys Pro Leu Val Glu Leu Met Ala Asp Phe
225                 230                 235                 240

Gly Ser Asn Met Val Asp Lys Ser Ala Phe Val Met Ser Leu Leu Met
                245                 250                 255

Ser Val Pro Glu Ser Lys Pro Ala Ile Val Glu Gly Gly Val Pro
            260                 265                 270

Val Leu Val Glu Ile Val Glu Val Gly Thr Gln Arg Gln Lys Glu Met
        275                 280                 285

Ala Val Ser Ile Leu Leu Gln Leu Cys Glu Glu Ser Val Val Tyr Arg
    290                 295                 300

Thr Met Val Ala Arg Glu Gly Ala Ile Pro Pro Leu Val Ala Leu Ser
305                 310                 315                 320

Gln Ala Gly Thr Ser Arg Ala Lys Gln Lys Ala Glu Ala Leu Ile Glu
                325                 330                 335

Leu Leu Arg Gln Pro Arg Ser Ile Ser Asn Gly Gly Ala Arg Ser Ser
            340                 345                 350

Ser Gln Leu
        355

<210> SEQ ID NO 35
```

```
<211> LENGTH: 1971
<212> TYPE: DNA
<213> ORGANISM: Arabidopsis thaliana
<220> FEATURE:
<221> NAME/KEY: CDS
<222> LOCATION: (1)..(1971)

<400> SEQUENCE: 35 atg aca gat gaa gaa gcc aca gga gat gca gag aac cgt gat gaa        48
Met Asp Thr Asp Glu Glu Ala Thr Gly Asp Ala Glu Asn Arg Asp Glu
1               5                   10                  15 gaa gtt acc gca gaa gaa ccg att cac gat gag gtt gtg gat gcg gtg    96
Glu Val Thr Ala Glu Glu Pro Ile His Asp Glu Val Val Asp Ala Val
            20                  25                  30 gag att cat gag gaa gaa gtg aaa gaa gat gat gat gat tgt gaa gga    144
Glu Ile His Glu Glu Glu Val Lys Glu Asp Asp Asp Asp Cys Glu Gly
        35                  40                  45 ttg gtg agc gat atc gta tcg att gtc gag ttt ttg gat cag att aac    192
Leu Val Ser Asp Ile Val Ser Ile Val Glu Phe Leu Asp Gln Ile Asn
    50                  55                  60 ggt tat cga aga aca caa caa aaa gaa tgt ttt aat ctc gtt aga cga    240
Gly Tyr Arg Arg Thr Gln Gln Lys Glu Cys Phe Asn Leu Val Arg Arg
65                  70                  75                  80 ttg aag att ctt att cca ttt ttg gat gag att cga ggt ttt gaa tca    288
Leu Lys Ile Leu Ile Pro Phe Leu Asp Glu Ile Arg Gly Phe Glu Ser
                85                  90                  95 cca agt tgc aag cat ttt tta aat cgt ttg agg aaa gtg ttt ctt gct    336
Pro Ser Cys Lys His Phe Leu Asn Arg Leu Arg Lys Val Phe Leu Ala
            100                 105                 110 gcc aag aaa tta tta gaa act tgc agc aat ggc agt aaa atc tat atg    384
Ala Lys Lys Leu Leu Glu Thr Cys Ser Asn Gly Ser Lys Ile Tyr Met
        115                 120                 125 gca ttg gat ggc gaa aca atg atg acg aga ttt cat tcg att tac gaa    432
Ala Leu Asp Gly Glu Thr Met Met Thr Arg Phe His Ser Ile Tyr Glu
    130                 135                 140 aag ttg aat cgt gtt ctt gtt aaa gct cct ttt gat gaa tta atg att    480
Lys Leu Asn Arg Val Leu Val Lys Ala Pro Phe Asp Glu Leu Met Ile
145                 150                 155                 160 tct ggt gat gcg aaa gac gag att gat tca ttg tgt aaa caa ctg aaa    528
Ser Gly Asp Ala Lys Asp Glu Ile Asp Ser Leu Cys Lys Gln Leu Lys
                165                 170                 175 aaa gca aaa aga aga aca gat aca caa gac ata gag cta gca gta gac    576
Lys Ala Lys Arg Arg Thr Asp Thr Gln Asp Ile Glu Leu Ala Val Asp
            180                 185                 190 atg atg gtg gta ttc tca aaa acc gat cct cga aac gca gat agc gcg    624
Met Met Val Val Phe Ser Lys Thr Asp Pro Arg Asn Ala Asp Ser Ala
        195                 200                 205 ata ata gag agg cta gcg aaa aag ctt gag cta caa aca att gat gat    672
Ile Ile Glu Arg Leu Ala Lys Lys Leu Glu Leu Gln Thr Ile Asp Asp
    210                 215                 220 tta aag aca gaa act ata gcc ata caa agc tta atc caa gac aaa gga    720
Leu Lys Thr Glu Thr Ile Ala Ile Gln Ser Leu Ile Gln Asp Lys Gly
225                 230                 235                 240 ggt ttg aac ata gag act aaa caa cat atc att gag ctt ctt aac aag    768
Gly Leu Asn Ile Glu Thr Lys Gln His Ile Ile Glu Leu Leu Asn Lys
                245                 250                 255 ttc aag aag ctt caa ggt ctt gaa gct acc gac att ctc tac caa ccc    816
Phe Lys Lys Leu Gln Gly Leu Glu Ala Thr Asp Ile Leu Tyr Gln Pro
            260                 265                 270 gtc atc aat aaa gca atc acc aag tca acg tct cta ata tta cct cat    864
Val Ile Asn Lys Ala Ile Thr Lys Ser Thr Ser Leu Ile Leu Pro His
        275                 280                 285
```

| | | |
|---|---|---|
| gag ttt ttg tgt cct ata aca ctc gaa ata atg ctt gac ccg gtt atc<br>Glu Phe Leu Cys Pro Ile Thr Leu Glu Ile Met Leu Asp Pro Val Ile<br>290                       295                       300 | | 912 |
| atc gcc act gga cag aca tat gag aag gag agt ata cag aaa tgg ttt<br>Ile Ala Thr Gly Gln Thr Tyr Glu Lys Glu Ser Ile Gln Lys Trp Phe<br>305                     310                     315               320 | | 960 |
| gac gca gga cat aag act tgt cct aaa aca aga cag gag tta gat cat<br>Asp Ala Gly His Lys Thr Cys Pro Lys Thr Arg Gln Glu Leu Asp His<br>                   325                     330                     335 | | 1008 |
| ctc tct ctt gca cct aac ttc gct tta aag aac ttg att atg cag tgg<br>Leu Ser Leu Ala Pro Asn Phe Ala Leu Lys Asn Leu Ile Met Gln Trp<br>             340                     345                     350 | | 1056 |
| tgt gag aag aac aat ttc aag att cca gag aaa gaa gta agt cct gac<br>Cys Glu Lys Asn Asn Phe Lys Ile Pro Glu Lys Glu Val Ser Pro Asp<br>     355                     360                     365 | | 1104 |
| tca caa aat gag cag aaa gat gag gtc tct ttg ctg gtg gaa gcg tta<br>Ser Gln Asn Glu Gln Lys Asp Glu Val Ser Leu Leu Val Glu Ala Leu<br>370                       375                       380 | | 1152 |
| tcg tca agc caa ctg gaa gaa caa cga aga tca gtg aag cag atg cgt<br>Ser Ser Ser Gln Leu Glu Glu Gln Arg Arg Ser Val Lys Gln Met Arg<br>385                     390                     395               400 | | 1200 |
| ttg cta gcc aga gaa aat ccc gag aac cgc gtt tta ata gcg aat gca<br>Leu Leu Ala Arg Glu Asn Pro Glu Asn Arg Val Leu Ile Ala Asn Ala<br>                   405                     410                     415 | | 1248 |
| gga gcg att cct ttg tta gtt caa ctc ctt tct tac cct gat tca gga<br>Gly Ala Ile Pro Leu Leu Val Gln Leu Leu Ser Tyr Pro Asp Ser Gly<br>             420                     425                     430 | | 1296 |
| atc caa gaa aac gcg gta acg aca ttg ttg aat cta tct atc gac gag<br>Ile Gln Glu Asn Ala Val Thr Thr Leu Leu Asn Leu Ser Ile Asp Glu<br>                   435                     440                     445 | | 1344 |
| gtc aac aag aaa ctc att tca aat gaa gga gct att cca aac att att<br>Val Asn Lys Lys Leu Ile Ser Asn Glu Gly Ala Ile Pro Asn Ile Ile<br>     450                     455                     460 | | 1392 |
| gaa atc ctt gaa aat gga aac aga gag gca aga gag aac tct gct gca<br>Glu Ile Leu Glu Asn Gly Asn Arg Glu Ala Arg Glu Asn Ser Ala Ala<br>465                     470                     475               480 | | 1440 |
| gct ttg ttt agt tta tcg atg ctc gat gag aac aaa gta act atc gga<br>Ala Leu Phe Ser Leu Ser Met Leu Asp Glu Asn Lys Val Thr Ile Gly<br>                   485                     490                     495 | | 1488 |
| tta tcg aat ggg ata ccg cct tta gtc gat tta cta caa cat ggg aca<br>Leu Ser Asn Gly Ile Pro Pro Leu Val Asp Leu Leu Gln His Gly Thr<br>             500                     505                     510 | | 1536 |
| tta aga ggg aag aaa gat gct ctc act gca ctc ttt aac ttg tct ctt<br>Leu Arg Gly Lys Lys Asp Ala Leu Thr Ala Leu Phe Asn Leu Ser Leu<br>         515                     520                     525 | | 1584 |
| aac tca gct aat aaa gga aga gct atc gat gct ggt att gtt caa cct<br>Asn Ser Ala Asn Lys Gly Arg Ala Ile Asp Ala Gly Ile Val Gln Pro<br>530                     535                     540 | | 1632 |
| ttg ctt aac ctt ctt aaa gat aaa aac tta ggg atg atc gat gaa gcg<br>Leu Leu Asn Leu Leu Lys Asp Lys Asn Leu Gly Met Ile Asp Glu Ala<br>545                     550                     555               560 | | 1680 |
| ctt tcg att ctg ttg ctg ctt gca tca cac cct gaa gga cgt caa gcc<br>Leu Ser Ile Leu Leu Leu Leu Ala Ser His Pro Glu Gly Arg Gln Ala<br>                   565                     570                     575 | | 1728 |
| att gga caa ctc tcc ttc att gaa aca ctt gtg gaa ttc atc aga caa<br>Ile Gly Gln Leu Ser Phe Ile Glu Thr Leu Val Glu Phe Ile Arg Gln<br>             580                     585                     590 | | 1776 |
| ggc acc ccg aaa aac aaa gag tgt gcg acc tcg gtg ctg ctt gaa cta<br>Gly Thr Pro Lys Asn Lys Glu Cys Ala Thr Ser Val Leu Leu Glu Leu<br>     595                     600                     605 | | 1824 |

```
ggc tct aac aac tcg tct ttt atc ctc gca gcg ctt caa ttc gga gtt   1872
Gly Ser Asn Asn Ser Ser Phe Ile Leu Ala Ala Leu Gln Phe Gly Val
        610             615                 620 tat gaa tat ctg gta gaa ata acc acc tct gga aca aac aga gct cag   1920
Tyr Glu Tyr Leu Val Glu Ile Thr Thr Ser Gly Thr Asn Arg Ala Gln
625             630                 635                 640 aga aaa gca aat gct ctt ata caa ctc ata agc aaa tct gaa caa att   1968
Arg Lys Ala Asn Ala Leu Ile Gln Leu Ile Ser Lys Ser Glu Gln Ile
                645                 650                 655 tag                                                                1971

<210> SEQ ID NO 36
<211> LENGTH: 656
<212> TYPE: PRT
<213> ORGANISM: Arabidopsis thaliana

<400> SEQUENCE: 36
```

Met Asp Thr Asp Glu Glu Ala Thr Gly Asp Ala Glu Asn Arg Asp Glu
1               5                   10                  15

Glu Val Thr Ala Glu Glu Pro Ile His Asp Glu Val Val Asp Ala Val
            20                  25                  30

Glu Ile His Glu Glu Glu Val Lys Glu Asp Asp Asp Cys Glu Gly
        35                  40                  45

Leu Val Ser Asp Ile Val Ser Ile Val Glu Phe Leu Asp Gln Ile Asn
    50                  55                  60

Gly Tyr Arg Arg Thr Gln Gln Lys Glu Cys Phe Asn Leu Val Arg Arg
65              70                  75                  80

Leu Lys Ile Leu Ile Pro Phe Leu Asp Glu Ile Arg Gly Phe Glu Ser
                85                  90                  95

Pro Ser Cys Lys His Phe Leu Asn Arg Leu Arg Lys Val Phe Leu Ala
            100                 105                 110

Ala Lys Lys Leu Leu Glu Thr Cys Ser Asn Gly Ser Lys Ile Tyr Met
        115                 120                 125

Ala Leu Asp Gly Glu Thr Met Met Thr Arg Phe His Ser Ile Tyr Glu
130                 135                 140

Lys Leu Asn Arg Val Leu Val Lys Ala Pro Phe Asp Glu Leu Met Ile
145                 150                 155                 160

Ser Gly Asp Ala Lys Asp Glu Ile Asp Ser Leu Cys Lys Gln Leu Lys
                165                 170                 175

Lys Ala Lys Arg Arg Thr Asp Thr Gln Asp Ile Glu Leu Ala Val Asp
            180                 185                 190

Met Met Val Val Phe Ser Lys Thr Asp Pro Arg Asn Ala Asp Ser Ala
        195                 200                 205

Ile Ile Glu Arg Leu Ala Lys Lys Leu Glu Leu Gln Thr Ile Asp Asp
    210                 215                 220

Leu Lys Thr Glu Thr Ile Ala Ile Gln Ser Leu Ile Gln Asp Lys Gly
225                 230                 235                 240

Gly Leu Asn Ile Glu Thr Lys Gln His Ile Ile Glu Leu Leu Asn Lys
                245                 250                 255

Phe Lys Lys Leu Gln Gly Leu Glu Ala Thr Asp Ile Leu Tyr Gln Pro
            260                 265                 270

Val Ile Asn Lys Ala Ile Thr Lys Ser Thr Ser Leu Ile Leu Pro His
        275                 280                 285

Glu Phe Leu Cys Pro Ile Thr Leu Glu Ile Met Leu Asp Pro Val Ile
    290                 295                 300

```
Ile Ala Thr Gly Gln Thr Tyr Glu Lys Glu Ser Ile Gln Lys Trp Phe
305                 310                 315                 320

Asp Ala Gly His Lys Thr Cys Pro Lys Thr Arg Gln Glu Leu Asp His
            325                 330                 335

Leu Ser Leu Ala Pro Asn Phe Ala Leu Lys Asn Leu Ile Met Gln Trp
            340                 345                 350

Cys Glu Lys Asn Asn Phe Lys Ile Pro Glu Lys Glu Val Ser Pro Asp
            355                 360                 365

Ser Gln Asn Glu Gln Lys Asp Glu Val Ser Leu Leu Val Glu Ala Leu
        370                 375                 380

Ser Ser Ser Gln Leu Glu Glu Gln Arg Arg Ser Val Lys Gln Met Arg
385                 390                 395                 400

Leu Leu Ala Arg Glu Asn Pro Glu Asn Arg Val Leu Ile Ala Asn Ala
                405                 410                 415

Gly Ala Ile Pro Leu Leu Val Gln Leu Leu Ser Tyr Pro Asp Ser Gly
                420                 425                 430

Ile Gln Glu Asn Ala Val Thr Thr Leu Leu Asn Leu Ser Ile Asp Glu
        435                 440                 445

Val Asn Lys Lys Leu Ile Ser Asn Glu Gly Ala Ile Pro Asn Ile Ile
450                 455                 460

Glu Ile Leu Glu Asn Gly Asn Arg Glu Ala Arg Glu Asn Ser Ala Ala
465                 470                 475                 480

Ala Leu Phe Ser Leu Ser Met Leu Asp Glu Asn Lys Val Thr Ile Gly
                485                 490                 495

Leu Ser Asn Gly Ile Pro Pro Leu Val Asp Leu Leu Gln His Gly Thr
            500                 505                 510

Leu Arg Gly Lys Lys Asp Ala Leu Thr Ala Leu Phe Asn Leu Ser Leu
            515                 520                 525

Asn Ser Ala Asn Lys Gly Arg Ala Ile Asp Ala Gly Ile Val Gln Pro
            530                 535                 540

Leu Leu Asn Leu Leu Lys Asp Lys Asn Leu Gly Met Ile Asp Glu Ala
545                 550                 555                 560

Leu Ser Ile Leu Leu Leu Leu Ala Ser His Pro Glu Gly Arg Gln Ala
                565                 570                 575

Ile Gly Gln Leu Ser Phe Ile Glu Thr Leu Val Glu Phe Ile Arg Gln
            580                 585                 590

Gly Thr Pro Lys Asn Lys Glu Cys Ala Thr Ser Val Leu Leu Glu Leu
            595                 600                 605

Gly Ser Asn Asn Ser Ser Phe Ile Leu Ala Ala Leu Gln Phe Gly Val
            610                 615                 620

Tyr Glu Tyr Leu Val Glu Ile Thr Thr Ser Gly Thr Asn Arg Ala Gln
625                 630                 635                 640

Arg Lys Ala Asn Ala Leu Ile Gln Leu Ile Ser Lys Ser Glu Gln Ile
                645                 650                 655

<210> SEQ ID NO 37
<211> LENGTH: 1983
<212> TYPE: DNA
<213> ORGANISM: Arabidopsis thaliana
<220> FEATURE:
<221> NAME/KEY: CDS
<222> LOCATION: (1)..(1983)

<400> SEQUENCE: 37 atg gtc gat gtg atg gat aca gat gaa gaa gcc aca gga gat gca gag    48
Met Val Asp Val Met Asp Thr Asp Glu Glu Ala Thr Gly Asp Ala Glu
1               5                   10                  15
```

-continued

```
agc cgt gat gaa gaa gtt acc gca gaa gaa ccg att cac gat gag gtt        96
Ser Arg Asp Glu Glu Val Thr Ala Glu Glu Pro Ile His Asp Glu Val
         20                  25                  30 gtg gat gcg gtg gag att cat gag gaa gaa gtg aaa gaa gat gat gat       144
Val Asp Ala Val Glu Ile His Glu Glu Glu Val Lys Glu Asp Asp Asp
                 35                  40                  45 gat tgt gaa gga ttg gtg agc gat atc gta tcg att gtc gag ttt ttg       192
Asp Cys Glu Gly Leu Val Ser Asp Ile Val Ser Ile Val Glu Phe Leu
 50                  55                  60 gat cag att aac ggt tat cga aga aca caa caa aaa gaa tgt ttt aat       240
Asp Gln Ile Asn Gly Tyr Arg Arg Thr Gln Gln Lys Glu Cys Phe Asn
 65                  70                  75                  80 ctc gtt aga cga ttg aag att ctt att cca ttt ttg gat gag att cga       288
Leu Val Arg Arg Leu Lys Ile Leu Ile Pro Phe Leu Asp Glu Ile Arg
                 85                  90                  95 ggt ttt gaa tca cca agt tgc aag cat ttt tta aat cgt ttg agg aaa       336
Gly Phe Glu Ser Pro Ser Cys Lys His Phe Leu Asn Arg Leu Arg Lys
            100                 105                 110 gtg ttt ctt gct gcc aag aaa tta tta gaa act tgc agc aat ggc agt       384
Val Phe Leu Ala Ala Lys Lys Leu Leu Glu Thr Cys Ser Asn Gly Ser
        115                 120                 125 aaa atc tat atg gca ttg gat ggc gaa aca atg atg acg aga ttt cat       432
Lys Ile Tyr Met Ala Leu Asp Gly Glu Thr Met Met Thr Arg Phe His
130                 135                 140 tcg att tac gaa aag ttg aat cgt gtt ctt gtt aaa gct cct ttt gat       480
Ser Ile Tyr Glu Lys Leu Asn Arg Val Leu Val Lys Ala Pro Phe Asp
145                 150                 155                 160 gaa tta atg att tct ggt gat gcg aaa gac gag att gat tca ttg tgt       528
Glu Leu Met Ile Ser Gly Asp Ala Lys Asp Glu Ile Asp Ser Leu Cys
                165                 170                 175 aaa caa ctg aaa aaa gca aaa aga aga aca gat aca caa gac ata gag       576
Lys Gln Leu Lys Lys Ala Lys Arg Arg Thr Asp Thr Gln Asp Ile Glu
            180                 185                 190 cta gca gta gac atg atg gtg gta ttc tca aaa acc gat cct cga aac       624
Leu Ala Val Asp Met Met Val Val Phe Ser Lys Thr Asp Pro Arg Asn
        195                 200                 205 gca gat agc gcg ata ata gag agg cta gcg aaa aag ctt gag cta caa       672
Ala Asp Ser Ala Ile Ile Glu Arg Leu Ala Lys Lys Leu Glu Leu Gln
210                 215                 220 aca att gat gat tta aag aca gaa act ata gcc ata caa agc tta atc       720
Thr Ile Asp Asp Leu Lys Thr Glu Thr Ile Ala Ile Gln Ser Leu Ile
225                 230                 235                 240 caa gac aaa gga ggt ttg aac ata gag act aaa caa cat atc att gag       768
Gln Asp Lys Gly Gly Leu Asn Ile Glu Thr Lys Gln His Ile Ile Glu
                245                 250                 255 ctt ctt aac aag ttc aag aag ctt caa ggt ctt gaa gct acc gac att       816
Leu Leu Asn Lys Phe Lys Lys Leu Gln Gly Leu Glu Ala Thr Asp Ile
            260                 265                 270 ctc tac caa ccc gtc atc aat aaa gca atc acc aag tca acg tct cta       864
Leu Tyr Gln Pro Val Ile Asn Lys Ala Ile Thr Lys Ser Thr Ser Leu
        275                 280                 285 ata tta cct cat gag ttt ttg tgt cct ata aca ctc gga ata atg ctt       912
Ile Leu Pro His Glu Phe Leu Cys Pro Ile Thr Leu Gly Ile Met Leu
290                 295                 300 gac ccg gtt atc atc gcc act gga cag aca tat gag aag gag agt ata       960
Asp Pro Val Ile Ile Ala Thr Gly Gln Thr Tyr Glu Lys Glu Ser Ile
305                 310                 315                 320 cag aaa tgg ttt gac gca gga cat aag act tgt cct aaa aca aga cag      1008
Gln Lys Trp Phe Asp Ala Gly His Lys Thr Cys Pro Lys Thr Arg Gln
                325                 330                 335
```

| | |
|---|---|
| gag tta gat cat ctc tct ctt gca cct aac ttc gct tta aag aac ttg<br>Glu Leu Asp His Leu Ser Leu Ala Pro Asn Phe Ala Leu Lys Asn Leu<br>340 345 350 | 1056 |
| att atg cag tgg tgt gag aag aac aat ttc aag att cca gag aaa gaa<br>Ile Met Gln Trp Cys Glu Lys Asn Asn Phe Lys Ile Pro Glu Lys Glu<br>355 360 365 | 1104 |
| gta agt cct gac tca caa aat gag cag aaa gat gag gtc tct ttg ctg<br>Val Ser Pro Asp Ser Gln Asn Glu Gln Lys Asp Glu Val Ser Leu Leu<br>370 375 380 | 1152 |
| gtg gaa gcg tta tcg tca agc caa ctg gaa gaa caa cga aga tca gtg<br>Val Glu Ala Leu Ser Ser Ser Gln Leu Glu Glu Gln Arg Arg Ser Val<br>385 390 395 400 | 1200 |
| aag cag atg cgt ttg cta gcc aga gaa aat ccc gag aac cgc gtt tta<br>Lys Gln Met Arg Leu Leu Ala Arg Glu Asn Pro Glu Asn Arg Val Leu<br>405 410 415 | 1248 |
| ata gcg aat gca gga gcg att cct ttg tta gtt caa ctc ctt tct tac<br>Ile Ala Asn Ala Gly Ala Ile Pro Leu Leu Val Gln Leu Leu Ser Tyr<br>420 425 430 | 1296 |
| cct gat tca gga atc caa gaa aac gcg gta acg aca ttg ttg aat cta<br>Pro Asp Ser Gly Ile Gln Glu Asn Ala Val Thr Thr Leu Leu Asn Leu<br>435 440 445 | 1344 |
| tct atc gac gag gtc aac aag aaa ctc att tca aat gaa gga gct att<br>Ser Ile Asp Glu Val Asn Lys Lys Leu Ile Ser Asn Glu Gly Ala Ile<br>450 455 460 | 1392 |
| cca aac att att gaa atc ctt gaa aat gga aac aga gag gca aga gag<br>Pro Asn Ile Ile Glu Ile Leu Glu Asn Gly Asn Arg Glu Ala Arg Glu<br>465 470 475 480 | 1440 |
| aac tct gct gca gct ttg ttt agt tta tcg atg ctc gat gag aac aaa<br>Asn Ser Ala Ala Ala Leu Phe Ser Leu Ser Met Leu Asp Glu Asn Lys<br>485 490 495 | 1488 |
| gta act atc gga tta tcg aat ggg ata ccg cct tta gtc gat tta cta<br>Val Thr Ile Gly Leu Ser Asn Gly Ile Pro Pro Leu Val Asp Leu Leu<br>500 505 510 | 1536 |
| caa cat ggg aca tta aga ggg aag aaa gat gct ctc act gca ctc ttt<br>Gln His Gly Thr Leu Arg Gly Lys Lys Asp Ala Leu Thr Ala Leu Phe<br>515 520 525 | 1584 |
| aac ttg tct ctt aac tca gct aat aaa gga aga gct atc gat gct ggt<br>Asn Leu Ser Leu Asn Ser Ala Asn Lys Gly Arg Ala Ile Asp Ala Gly<br>530 535 540 | 1632 |
| att gtt caa cct ttg ctt aac ctt ctt aaa gat aaa aac tta ggg atg<br>Ile Val Gln Pro Leu Leu Asn Leu Leu Lys Asp Lys Asn Leu Gly Met<br>545 550 555 560 | 1680 |
| atc gat gaa gcg ctt tcg att ctg ttg ctg ctt gca tca cac cct gaa<br>Ile Asp Glu Ala Leu Ser Ile Leu Leu Leu Leu Ala Ser His Pro Glu<br>565 570 575 | 1728 |
| gga cgt caa gcc att gga caa ctc tcc ttc att gaa aca ctt gtg gaa<br>Gly Arg Gln Ala Ile Gly Gln Leu Ser Phe Ile Glu Thr Leu Val Glu<br>580 585 590 | 1776 |
| ttc atc aga caa ggc acc ccg aaa aac aaa gag tgt gcg acc tcg gtg<br>Phe Ile Arg Gln Gly Thr Pro Lys Asn Lys Glu Cys Ala Thr Ser Val<br>595 600 605 | 1824 |
| ctg ctt gaa cta ggc tct aac aac tcg tct ttt atc ctc gca gcg ctt<br>Leu Leu Glu Leu Gly Ser Asn Asn Ser Ser Phe Ile Leu Ala Ala Leu<br>610 615 620 | 1872 |
| caa ttc gga gtt tat gaa tat ctg gta gaa ata acc acc tct gga aca<br>Gln Phe Gly Val Tyr Glu Tyr Leu Val Glu Ile Thr Thr Ser Gly Thr<br>625 630 635 640 | 1920 |
| aac aga gct cag aga aaa gca aat gct ctt ata caa ctc ata agc aaa<br>Asn Arg Ala Gln Arg Lys Ala Asn Ala Leu Ile Gln Leu Ile Ser Lys<br>645 650 655 | 1968 |

```
tct gaa caa att tag                                      1983
Ser Glu Gln Ile
        660

<210> SEQ ID NO 38
<211> LENGTH: 660
<212> TYPE: PRT
<213> ORGANISM: Arabidopsis thaliana

<400> SEQUENCE: 38

Met Val Asp Val Met Asp Thr Asp Glu Glu Ala Thr Gly Asp Ala Glu
1               5                   10                  15

Ser Arg Asp Glu Glu Val Thr Ala Glu Glu Pro Ile His Asp Glu Val
            20                  25                  30

Val Asp Ala Val Glu Ile His Glu Glu Val Lys Glu Asp Asp
        35                  40                  45

Asp Cys Glu Gly Leu Val Ser Asp Ile Val Ser Ile Val Glu Phe Leu
    50                  55                  60

Asp Gln Ile Asn Gly Tyr Arg Arg Thr Gln Gln Lys Glu Cys Phe Asn
65              70                  75                  80

Leu Val Arg Arg Leu Lys Ile Leu Ile Pro Phe Leu Asp Glu Ile Arg
                85                  90                  95

Gly Phe Glu Ser Pro Ser Cys Lys His Phe Leu Asn Arg Leu Arg Lys
            100                 105                 110

Val Phe Leu Ala Ala Lys Lys Leu Leu Glu Thr Cys Ser Asn Gly Ser
        115                 120                 125

Lys Ile Tyr Met Ala Leu Asp Gly Glu Thr Met Met Thr Arg Phe His
    130                 135                 140

Ser Ile Tyr Glu Lys Leu Asn Arg Val Leu Val Lys Ala Pro Phe Asp
145                 150                 155                 160

Glu Leu Met Ile Ser Gly Asp Ala Lys Asp Glu Ile Asp Ser Leu Cys
                165                 170                 175

Lys Gln Leu Lys Lys Ala Lys Arg Arg Thr Asp Thr Gln Asp Ile Glu
            180                 185                 190

Leu Ala Val Asp Met Met Val Val Phe Ser Lys Thr Asp Pro Arg Asn
        195                 200                 205

Ala Asp Ser Ala Ile Ile Glu Arg Leu Ala Lys Lys Leu Glu Leu Gln
    210                 215                 220

Thr Ile Asp Asp Leu Lys Thr Glu Thr Ile Ala Ile Gln Ser Leu Ile
225                 230                 235                 240

Gln Asp Lys Gly Gly Leu Asn Ile Glu Thr Lys Gln His Ile Ile Glu
                245                 250                 255

Leu Leu Asn Lys Phe Lys Lys Leu Gln Gly Leu Glu Ala Thr Asp Ile
            260                 265                 270

Leu Tyr Gln Pro Val Ile Asn Lys Ala Ile Thr Lys Ser Thr Ser Leu
        275                 280                 285

Ile Leu Pro His Glu Phe Leu Cys Pro Ile Thr Leu Gly Ile Met Leu
    290                 295                 300

Asp Pro Val Ile Ile Ala Thr Gly Gln Thr Tyr Glu Lys Glu Ser Ile
305                 310                 315                 320

Gln Lys Trp Phe Asp Ala Gly His Lys Thr Cys Pro Lys Thr Arg Gln
                325                 330                 335

Glu Leu Asp His Leu Ser Leu Ala Pro Asn Phe Ala Leu Lys Asn Leu
            340                 345                 350

Ile Met Gln Trp Cys Glu Lys Asn Asn Phe Lys Ile Pro Glu Lys Glu
```

```
                    355                 360                 365
Val Ser Pro Asp Ser Gln Asn Glu Gln Lys Asp Glu Val Ser Leu Leu
    370                 375                 380

Val Glu Ala Leu Ser Ser Gln Leu Glu Glu Gln Arg Arg Ser Val
385                 390                 395                 400

Lys Gln Met Arg Leu Leu Ala Arg Glu Asn Pro Glu Asn Arg Val Leu
                405                 410                 415

Ile Ala Asn Ala Gly Ala Ile Pro Leu Leu Val Gln Leu Leu Ser Tyr
                420                 425                 430

Pro Asp Ser Gly Ile Gln Glu Asn Ala Val Thr Thr Leu Leu Asn Leu
                435                 440                 445

Ser Ile Asp Glu Val Asn Lys Lys Leu Ile Ser Asn Glu Gly Ala Ile
    450                 455                 460

Pro Asn Ile Ile Glu Ile Leu Glu Asn Gly Asn Arg Glu Ala Arg Glu
465                 470                 475                 480

Asn Ser Ala Ala Ala Leu Phe Ser Leu Ser Met Leu Asp Glu Asn Lys
                485                 490                 495

Val Thr Ile Gly Leu Ser Asn Gly Ile Pro Pro Leu Val Asp Leu Leu
                500                 505                 510

Gln His Gly Thr Leu Arg Gly Lys Lys Asp Ala Leu Thr Ala Leu Phe
                515                 520                 525

Asn Leu Ser Leu Asn Ser Ala Asn Lys Gly Arg Ala Ile Asp Ala Gly
    530                 535                 540

Ile Val Gln Pro Leu Leu Asn Leu Leu Lys Asp Lys Asn Leu Gly Met
545                 550                 555                 560

Ile Asp Glu Ala Leu Ser Ile Leu Leu Leu Ala Ser His Pro Glu
                565                 570                 575

Gly Arg Gln Ala Ile Gly Gln Leu Ser Phe Ile Glu Thr Leu Val Glu
                580                 585                 590

Phe Ile Arg Gln Gly Thr Pro Lys Asn Lys Glu Cys Ala Thr Ser Val
                595                 600                 605

Leu Leu Glu Leu Gly Ser Asn Asn Ser Ser Phe Ile Leu Ala Ala Leu
610                 615                 620

Gln Phe Gly Val Tyr Glu Tyr Leu Val Glu Ile Thr Thr Ser Gly Thr
625                 630                 635                 640

Asn Arg Ala Gln Arg Lys Ala Asn Ala Leu Ile Gln Leu Ile Ser Lys
                645                 650                 655

Ser Glu Gln Ile
            660

<210> SEQ ID NO 39
<211> LENGTH: 1920
<212> TYPE: DNA
<213> ORGANISM: Arabidopsis thaliana
<220> FEATURE:
<221> NAME/KEY: CDS
<222> LOCATION: (1)..(1920)

<400> SEQUENCE: 39 atg gga tta acg aat tgt tgt tcc cac gag gag cta atg agt cga ctc    48
Met Gly Leu Thr Asn Cys Cys Ser His Glu Glu Leu Met Ser Arg Leu
1               5                   10                  15 gtt gac tcc gtt aaa gaa ata tca ggg ttt tca tct tca agg ggt ttt    96
Val Asp Ser Val Lys Glu Ile Ser Gly Phe Ser Ser Ser Arg Gly Phe
                20                  25                  30 att ggg aag atc caa ggc gat ctt gtt cgt agg atc acg ctt ctc agc   144
Ile Gly Lys Ile Gln Gly Asp Leu Val Arg Arg Ile Thr Leu Leu Ser
```

-continued

```
                35                  40                  45
cct ttc ttc gag gaa ttg att gac gtc aat gtt gaa ttg aaa aag gat    192
Pro Phe Phe Glu Glu Leu Ile Asp Val Asn Val Glu Leu Lys Lys Asp
 50                  55                  60 cag att aca ggg ttt gag gct atg aga atc gct ctt gat tca agt ctt    240
Gln Ile Thr Gly Phe Glu Ala Met Arg Ile Ala Leu Asp Ser Ser Leu
 65                  70                  75                  80 gag ctt ttt cga tcg gtt aat gga gga agc aag ctt ttt cag ctt ttc    288
Glu Leu Phe Arg Ser Val Asn Gly Gly Ser Lys Leu Phe Gln Leu Phe
                 85                  90                  95 gat aga gat tct ctt gtg gag aag ttc cgt gac atg aca gtg gag ata    336
Asp Arg Asp Ser Leu Val Glu Lys Phe Arg Asp Met Thr Val Glu Ile
            100                 105                 110 gaa gca gcg tta agt cag att cct tat gag aag att gag gta tca gag    384
Glu Ala Ala Leu Ser Gln Ile Pro Tyr Glu Lys Ile Glu Val Ser Glu
        115                 120                 125 gaa gtc aga gaa cag gtt cag ctt ctg cat ttt cag ttc aag aga gca    432
Glu Val Arg Glu Gln Val Gln Leu Leu His Phe Gln Phe Lys Arg Ala
    130                 135                 140 aaa gaa aga tgg gag gag tct gat cta cag ctt agc cat gat cta gct    480
Lys Glu Arg Trp Glu Glu Ser Asp Leu Gln Leu Ser His Asp Leu Ala
145                 150                 155                 160 atg gca gag aat gtg atg gat cct gac cct ata atc ctc aaa aga ctt    528
Met Ala Glu Asn Val Met Asp Pro Asp Pro Ile Ile Leu Lys Arg Leu
                165                 170                 175 tca caa gag ctc caa ctt act acc att gat gag ctg aag aaa gaa tcg    576
Ser Gln Glu Leu Gln Leu Thr Thr Ile Asp Glu Leu Lys Lys Glu Ser
            180                 185                 190 cat gcg ata cat gag tat ttt ctt tca tat gat gga gat cct gat gac    624
His Ala Ile His Glu Tyr Phe Leu Ser Tyr Asp Gly Asp Pro Asp Asp
        195                 200                 205 tgt ttc gag agg atg tct tca ctt ctt aaa aac ctg gta gac ttt gta    672
Cys Phe Glu Arg Met Ser Ser Leu Leu Lys Asn Leu Val Asp Phe Val
    210                 215                 220 aca atg gaa agt tca gac cct gat cca tcc act ggc agc aga atc gtt    720
Thr Met Glu Ser Ser Asp Pro Asp Pro Ser Thr Gly Ser Arg Ile Val
225                 230                 235                 240 tcg aga cat cgt tct cct gtt ata cca gag tat ttt cgg tgt ccg ata    768
Ser Arg His Arg Ser Pro Val Ile Pro Glu Tyr Phe Arg Cys Pro Ile
                245                 250                 255 tca ctt gaa ctg atg aag gat cct gtt atc gtc tcc act gga cag ctg    816
Ser Leu Glu Leu Met Lys Asp Pro Val Ile Val Ser Thr Gly Gln Leu
            260                 265                 270 aat ttt tcg acc ttg cag aca tat gaa aga tca tca att cag aag tgg    864
Asn Phe Ser Thr Leu Gln Thr Tyr Glu Arg Ser Ser Ile Gln Lys Trp
        275                 280                 285 ctt gat gct ggt cat aaa aca tgt ccg aaa tct cag gag aca ctt tta    912
Leu Asp Ala Gly His Lys Thr Cys Pro Lys Ser Gln Glu Thr Leu Leu
    290                 295                 300 cat gct gga tta acc cct aat tat gtg tta aag agt ctc att gct ttg    960
His Ala Gly Leu Thr Pro Asn Tyr Val Leu Lys Ser Leu Ile Ala Leu
305                 310                 315                 320 tgg tgt gaa agc aac ggc att gag cta ccg caa aat caa ggg agc tgt   1008
Trp Cys Glu Ser Asn Gly Ile Glu Leu Pro Gln Asn Gln Gly Ser Cys
                325                 330                 335 aga acc aca aaa ata gga gga agc agc tct tca gat tgt gat cga aca   1056
Arg Thr Thr Lys Ile Gly Gly Ser Ser Ser Ser Asp Cys Asp Arg Thr
            340                 345                 350 ttt gtc ctt tcc ttg tta gag aaa ttg gcc aac ggt act aca gaa cag   1104
Phe Val Leu Ser Leu Leu Glu Lys Leu Ala Asn Gly Thr Thr Glu Gln
```

```
                      355                 360                 365
caa aga gct gca gct gga gaa tta agg tta cta gcc aag agg aac gtg    1152
Gln Arg Ala Ala Ala Gly Glu Leu Arg Leu Leu Ala Lys Arg Asn Val
    370                 375                 380 gat aac aga gtt tgt atc gct gag gct gga gcc ata cca ctc ctt gta    1200
Asp Asn Arg Val Cys Ile Ala Glu Ala Gly Ala Ile Pro Leu Leu Val
385                 390                 395                 400 gag ctt cta tcc tca cca gat cct cgg act cag gaa cat tct gtg aca    1248
Glu Leu Leu Ser Ser Pro Asp Pro Arg Thr Gln Glu His Ser Val Thr
            405                 410                 415 gct ctt ctg aat ctt tcc ata aat gaa ggg aac aaa gga gcc att gtt    1296
Ala Leu Leu Asn Leu Ser Ile Asn Glu Gly Asn Lys Gly Ala Ile Val
        420                 425                 430 gat gca gga gcc ata acg gat ata gta gaa gtc cta aag aac gga agc    1344
Asp Ala Gly Ala Ile Thr Asp Ile Val Glu Val Leu Lys Asn Gly Ser
    435                 440                 445 atg gaa gct aga gag aac gct gct gca acc ctt ttc agt tta tct gtt    1392
Met Glu Ala Arg Glu Asn Ala Ala Ala Thr Leu Phe Ser Leu Ser Val
450                 455                 460 ata gat gaa aac aaa gtg gca ata ggt gct gct gga gct atc caa gca    1440
Ile Asp Glu Asn Lys Val Ala Ile Gly Ala Ala Gly Ala Ile Gln Ala
465                 470                 475                 480 ctt ata agc ttg ctt gag gaa gga acc cga aga ggc aaa aaa gat gct    1488
Leu Ile Ser Leu Leu Glu Glu Gly Thr Arg Arg Gly Lys Lys Asp Ala
            485                 490                 495 gct aca gcg att ttc aac tta tgc ata tac cag ggg aac aaa tca agg    1536
Ala Thr Ala Ile Phe Asn Leu Cys Ile Tyr Gln Gly Asn Lys Ser Arg
        500                 505                 510 gcg gtt aaa ggc ggt att gtt gac cct ctg acc aga tta ctg aaa gat    1584
Ala Val Lys Gly Gly Ile Val Asp Pro Leu Thr Arg Leu Leu Lys Asp
    515                 520                 525 gca ggt ggc gga atg gtg gat gag gct ctg gcc att tta gca att ctt    1632
Ala Gly Gly Gly Met Val Asp Glu Ala Leu Ala Ile Leu Ala Ile Leu
530                 535                 540 tca act aac caa gaa ggg aaa aca gcg ata gct gaa gca gaa tct atc    1680
Ser Thr Asn Gln Glu Gly Lys Thr Ala Ile Ala Glu Ala Glu Ser Ile
545                 550                 555                 560 ccg gtt ttg gtt gag att ata agg aca ggg tca cca agg aac cgg gaa    1728
Pro Val Leu Val Glu Ile Ile Arg Thr Gly Ser Pro Arg Asn Arg Glu
            565                 570                 575 aat gct gca gca ata ctt tgg tat cta tgt att ggg aat ata gaa agg    1776
Asn Ala Ala Ala Ile Leu Trp Tyr Leu Cys Ile Gly Asn Ile Glu Arg
        580                 585                 590 cta aat gta gca aga gag gtt ggt gca gat gtg gcc ttg aag gaa ctt    1824
Leu Asn Val Ala Arg Glu Val Gly Ala Asp Val Ala Leu Lys Glu Leu
    595                 600                 605 act gag aat ggc act gat aga gca aag agg aaa gct gcg agc ttg ttg    1872
Thr Glu Asn Gly Thr Asp Arg Ala Lys Arg Lys Ala Ala Ser Leu Leu
610                 615                 620 gag ctt att cag caa acc gaa ggt gtt gca gta act act gtt cca tga    1920
Glu Leu Ile Gln Gln Thr Glu Gly Val Ala Val Thr Thr Val Pro
625                 630                 635

<210> SEQ ID NO 40
<211> LENGTH: 639
<212> TYPE: PRT
<213> ORGANISM: Arabidopsis thaliana

<400> SEQUENCE: 40

Met Gly Leu Thr Asn Cys Cys Ser His Glu Glu Leu Met Ser Arg Leu
1               5                   10                  15
```

```
Val Asp Ser Val Lys Glu Ile Ser Gly Phe Ser Ser Arg Gly Phe
         20                  25                  30
Ile Gly Lys Ile Gln Gly Asp Leu Val Arg Arg Ile Thr Leu Leu Ser
         35                  40                  45
Pro Phe Phe Glu Glu Leu Ile Asp Val Asn Val Glu Leu Lys Lys Asp
50                   55                  60
Gln Ile Thr Gly Phe Glu Ala Met Arg Ile Ala Leu Asp Ser Ser Leu
65                   70                  75                  80
Glu Leu Phe Arg Ser Val Asn Gly Gly Ser Lys Leu Phe Gln Leu Phe
                 85                  90                  95
Asp Arg Asp Ser Leu Val Glu Lys Phe Arg Asp Met Thr Val Glu Ile
                 100                 105                 110
Glu Ala Ala Leu Ser Gln Ile Pro Tyr Glu Lys Ile Glu Val Ser Glu
                 115                 120                 125
Glu Val Arg Glu Gln Val Gln Leu Leu His Phe Gln Phe Lys Arg Ala
                 130                 135                 140
Lys Glu Arg Trp Glu Glu Ser Asp Leu Gln Leu Ser His Asp Leu Ala
145                  150                 155                 160
Met Ala Glu Asn Val Met Asp Pro Asp Ile Ile Leu Lys Arg Leu
                 165                 170                 175
Ser Gln Glu Leu Gln Leu Thr Thr Ile Asp Glu Leu Lys Lys Glu Ser
                 180                 185                 190
His Ala Ile His Glu Tyr Phe Leu Ser Tyr Asp Gly Asp Pro Asp Asp
                 195                 200                 205
Cys Phe Glu Arg Met Ser Ser Leu Leu Lys Asn Leu Val Asp Phe Val
                 210                 215                 220
Thr Met Glu Ser Ser Asp Pro Asp Pro Ser Thr Gly Ser Arg Ile Val
225                  230                 235                 240
Ser Arg His Arg Ser Pro Val Ile Pro Glu Tyr Phe Arg Cys Pro Ile
                 245                 250                 255
Ser Leu Glu Leu Met Lys Asp Pro Val Ile Val Ser Thr Gly Gln Leu
                 260                 265                 270
Asn Phe Ser Thr Leu Gln Thr Tyr Glu Arg Ser Ser Ile Gln Lys Trp
                 275                 280                 285
Leu Asp Ala Gly His Lys Thr Cys Pro Lys Ser Gln Glu Thr Leu Leu
                 290                 295                 300
His Ala Gly Leu Thr Pro Asn Tyr Val Leu Lys Ser Leu Ile Ala Leu
305                  310                 315                 320
Trp Cys Glu Ser Asn Gly Ile Glu Leu Pro Gln Asn Gln Gly Ser Cys
                 325                 330                 335
Arg Thr Thr Lys Ile Gly Gly Ser Ser Ser Asp Cys Asp Arg Thr
                 340                 345                 350
Phe Val Leu Ser Leu Leu Glu Lys Leu Ala Asn Gly Thr Thr Glu Gln
                 355                 360                 365
Gln Arg Ala Ala Ala Gly Glu Leu Arg Leu Leu Ala Lys Arg Asn Val
                 370                 375                 380
Asp Asn Arg Val Cys Ile Ala Glu Ala Gly Ala Ile Pro Leu Leu Val
385                  390                 395                 400
Glu Leu Leu Ser Ser Pro Asp Pro Arg Thr Gln Glu His Ser Val Thr
                 405                 410                 415
Ala Leu Leu Asn Leu Ser Ile Asn Glu Gly Asn Lys Gly Ala Ile Val
                 420                 425                 430
Asp Ala Gly Ala Ile Thr Asp Ile Val Glu Val Leu Lys Asn Gly Ser
```

```
                435              440                 445
Met Glu Ala Arg Glu Asn Ala Ala Thr Leu Phe Ser Leu Ser Val
    450                 455                 460

Ile Asp Glu Asn Lys Val Ala Ile Gly Ala Ala Gly Ala Ile Gln Ala
465             470                 475                 480

Leu Ile Ser Leu Leu Glu Gly Thr Arg Arg Gly Lys Lys Asp Ala
            485                 490                 495

Ala Thr Ala Ile Phe Asn Leu Cys Ile Tyr Gln Gly Asn Lys Ser Arg
                500                 505                 510

Ala Val Lys Gly Gly Ile Val Asp Pro Leu Thr Arg Leu Leu Lys Asp
            515                 520                 525

Ala Gly Gly Met Val Asp Glu Ala Leu Ala Ile Leu Ala Ile Leu
        530                 535                 540

Ser Thr Asn Gln Glu Gly Lys Thr Ala Ile Ala Glu Ala Glu Ser Ile
545                 550                 555                 560

Pro Val Leu Val Glu Ile Ile Arg Thr Gly Ser Pro Arg Asn Arg Glu
                565                 570                 575

Asn Ala Ala Ala Ile Leu Trp Tyr Leu Cys Ile Gly Asn Ile Glu Arg
            580                 585                 590

Leu Asn Val Ala Arg Glu Val Gly Ala Asp Val Ala Leu Lys Glu Leu
        595                 600                 605

Thr Glu Asn Gly Thr Asp Arg Ala Lys Arg Lys Ala Ala Ser Leu Leu
610                 615                 620

Glu Leu Ile Gln Gln Thr Glu Gly Val Ala Val Thr Thr Val Pro
                625                 630                 635

<210> SEQ ID NO 41
<211> LENGTH: 1899
<212> TYPE: DNA
<213> ORGANISM: Arabidopsis thaliana
<220> FEATURE:
<221> NAME/KEY: CDS
<222> LOCATION: (1)..(1899)

<400> SEQUENCE: 41 atg gga tta acg aat tgt tgt tcc cac gag gag cta atg agt cga ctc      48
Met Gly Leu Thr Asn Cys Cys Ser His Glu Glu Leu Met Ser Arg Leu
1               5                   10                  15 gtt gac tcc gtt aaa gaa ata tca ggg ttt tca tct tca agg ggt ttt      96
Val Asp Ser Val Lys Glu Ile Ser Gly Phe Ser Ser Ser Arg Gly Phe
                20                  25                  30 att ggg aag atc caa ggc gat ctt gtt cgt agg atc acg ctt ctc agc     144
Ile Gly Lys Ile Gln Gly Asp Leu Val Arg Arg Ile Thr Leu Leu Ser
            35                  40                  45 cct ttc ttc gag gaa ttg att gac gtc aat gtt gaa ttg aaa aag gat     192
Pro Phe Phe Glu Glu Leu Ile Asp Val Asn Val Glu Leu Lys Lys Asp
        50                  55                  60 cag att aca ggg ttt gag gct atg aga atc gct ctt gat tca agt ctt     240
Gln Ile Thr Gly Phe Glu Ala Met Arg Ile Ala Leu Asp Ser Ser Leu
65                  70                  75                  80 gag ctt ttt cga tcg gtt aat gga gga agc aag ctt ttt cag ctt ttc     288
Glu Leu Phe Arg Ser Val Asn Gly Gly Ser Lys Leu Phe Gln Leu Phe
                85                  90                  95 gat aga gat tct ctt gtg gag aag ttc cgt gac atg aca gtg gag ata     336
Asp Arg Asp Ser Leu Val Glu Lys Phe Arg Asp Met Thr Val Glu Ile
                100                 105                 110 gaa gca gcg tta agt cag att cct tat gag aag att gag gta tca gag     384
Glu Ala Ala Leu Ser Gln Ile Pro Tyr Glu Lys Ile Glu Val Ser Glu
            115                 120                 125
```

-continued

```
gaa gtc aga gaa cag gtt cag ctt ctg cat ttt cag ttc aag aga gca      432
Glu Val Arg Glu Gln Val Gln Leu Leu His Phe Gln Phe Lys Arg Ala
130                 135                 140 aaa gaa aga tgg gag gag tct gat cta cag ctt agc cat gat cta gct      480
Lys Glu Arg Trp Glu Glu Ser Asp Leu Gln Leu Ser His Asp Leu Ala
145                 150                 155                 160 atg gca gag aat gtg atg gat cct gac cct ata atc ctc aaa aga ctt      528
Met Ala Glu Asn Val Met Asp Pro Asp Pro Ile Ile Leu Lys Arg Leu
                165                 170                 175 tca caa gag ctc caa ctt act acc att gat gag ctg aag aaa gaa tcg      576
Ser Gln Glu Leu Gln Leu Thr Thr Ile Asp Glu Leu Lys Lys Glu Ser
            180                 185                 190 cat gcg ata cat gag tat ttt ctt tca tat gat gga gat cct gat gac      624
His Ala Ile His Glu Tyr Phe Leu Ser Tyr Asp Gly Asp Pro Asp Asp
        195                 200                 205 tgt ttc gag agg atg tct tca ctt ctt aaa aac ctg gta gac ttt gta      672
Cys Phe Glu Arg Met Ser Ser Leu Leu Lys Asn Leu Val Asp Phe Val
    210                 215                 220 aca atg gaa agt tca gac cct gat cca tcc act ggc agc aga atc gtt      720
Thr Met Glu Ser Ser Asp Pro Asp Pro Ser Thr Gly Ser Arg Ile Val
225                 230                 235                 240 tcg aga cat cgt tct cct gtt ata cca gag tat ttt cgg tgt ccg ata      768
Ser Arg His Arg Ser Pro Val Ile Pro Glu Tyr Phe Arg Cys Pro Ile
                245                 250                 255 tca ctt gaa ctg atg aag gat cct gtt atc gtc tcc act gga cag aca      816
Ser Leu Glu Leu Met Lys Asp Pro Val Ile Val Ser Thr Gly Gln Thr
            260                 265                 270 tat gaa aga tca tca att cag aag tgg ctt gat gct ggt cat aaa aca      864
Tyr Glu Arg Ser Ser Ile Gln Lys Trp Leu Asp Ala Gly His Lys Thr
        275                 280                 285 tgt ccg aaa tct cag gag aca ctt tta cat gct gga tta acc cct aat      912
Cys Pro Lys Ser Gln Glu Thr Leu Leu His Ala Gly Leu Thr Pro Asn
    290                 295                 300 tat gtg tta aag agt ctc att gct ttg tgg tgt gaa agc aac ggc att      960
Tyr Val Leu Lys Ser Leu Ile Ala Leu Trp Cys Glu Ser Asn Gly Ile
305                 310                 315                 320 gag cta ccg caa aat caa ggg agc tgt aga acc aca aaa ata gga gga     1008
Glu Leu Pro Gln Asn Gln Gly Ser Cys Arg Thr Thr Lys Ile Gly Gly
                325                 330                 335 agc agc tct tca gat tgt gat cga aca ttt gtc ctt tcc ttg tta gag     1056
Ser Ser Ser Ser Asp Cys Asp Arg Thr Phe Val Leu Ser Leu Leu Glu
            340                 345                 350 aaa ttg gcc aac ggt act aca gaa cag caa aga gct gca gct gga gaa     1104
Lys Leu Ala Asn Gly Thr Thr Glu Gln Gln Arg Ala Ala Ala Gly Glu
        355                 360                 365 tta agg tta cta gcc aag agg aac gtg gat aac aga gtt tgt atc gct     1152
Leu Arg Leu Leu Ala Lys Arg Asn Val Asp Asn Arg Val Cys Ile Ala
    370                 375                 380 gag gct gga gcc ata cca ctc ctt gta gag ctt cta tcc tca cca gat     1200
Glu Ala Gly Ala Ile Pro Leu Leu Val Glu Leu Leu Ser Ser Pro Asp
385                 390                 395                 400 cct cgg act cag gaa cat tct gtg aca gct ctt ctg aat ctt tcc ata     1248
Pro Arg Thr Gln Glu His Ser Val Thr Ala Leu Leu Asn Leu Ser Ile
                405                 410                 415 aat gaa ggg aac aaa gga gcc att gtt gat gca gga gcc ata acg gat     1296
Asn Glu Gly Asn Lys Gly Ala Ile Val Asp Ala Gly Ala Ile Thr Asp
            420                 425                 430 ata gta gaa gtc cta aag aac gga agc atg gaa gct aga gag aac gct     1344
Ile Val Glu Val Leu Lys Asn Gly Ser Met Glu Ala Arg Glu Asn Ala
        435                 440                 445
```

```
gct gca acc ctt ttc agt tta tct gtt ata gat gaa aac aaa gtg gca    1392
Ala Ala Thr Leu Phe Ser Leu Ser Val Ile Asp Glu Asn Lys Val Ala
    450             455                 460 ata ggt gct gct gga gct atc caa gca ctt ata agc ttg ctt gag gaa    1440
Ile Gly Ala Ala Gly Ala Ile Gln Ala Leu Ile Ser Leu Leu Glu Glu
465             470                 475                 480 gga acc cga aga ggc aaa aaa gat gct gct aca gcg att ttc aac tta    1488
Gly Thr Arg Arg Gly Lys Lys Asp Ala Ala Thr Ala Ile Phe Asn Leu
            485                 490                 495 tgc ata tac cag ggg aac aaa tca agg gcg gtt aaa ggc ggt att gtt    1536
Cys Ile Tyr Gln Gly Asn Lys Ser Arg Ala Val Lys Gly Gly Ile Val
        500                 505                 510 gac cct ctg acc aga tta ctg aaa gat gca ggt ggc gga atg gtg gat    1584
Asp Pro Leu Thr Arg Leu Leu Lys Asp Ala Gly Gly Gly Met Val Asp
    515                 520                 525 gag gct ctg gcc att tta gca att ctt tca act aac caa gaa ggg aaa    1632
Glu Ala Leu Ala Ile Leu Ala Ile Leu Ser Thr Asn Gln Glu Gly Lys
530                 535                 540 aca gcg ata gct gaa gca gaa tct atc ccg gtt ttg gtt gag att ata    1680
Thr Ala Ile Ala Glu Ala Glu Ser Ile Pro Val Leu Val Glu Ile Ile
545                 550                 555                 560 agg aca ggg tca cca agg aac cgg gaa aat gct gca gca ata ctt tgg    1728
Arg Thr Gly Ser Pro Arg Asn Arg Glu Asn Ala Ala Ala Ile Leu Trp
            565                 570                 575 tat cta tgt att ggg aat ata gaa agg cta aat gta gca aga gag gtt    1776
Tyr Leu Cys Ile Gly Asn Ile Glu Arg Leu Asn Val Ala Arg Glu Val
        580                 585                 590 ggt gca gat gtg gcc ttg aag gaa ctt act gag aat ggc act gat aga    1824
Gly Ala Asp Val Ala Leu Lys Glu Leu Thr Glu Asn Gly Thr Asp Arg
    595                 600                 605 gca aag agg aaa gct gcg agc ttg ttg gag ctt att cag caa acc gaa    1872
Ala Lys Arg Lys Ala Ala Ser Leu Leu Glu Leu Ile Gln Gln Thr Glu
610                 615                 620 ggt gtt gca gta act act gtt cca tga                                1899
Gly Val Ala Val Thr Thr Val Pro
625             630

<210> SEQ ID NO 42
<211> LENGTH: 632
<212> TYPE: PRT
<213> ORGANISM: Arabidopsis thaliana

<400> SEQUENCE: 42

Met Gly Leu Thr Asn Cys Cys Ser His Glu Glu Leu Met Ser Arg Leu
1               5                   10                  15

Val Asp Ser Val Lys Glu Ile Ser Gly Phe Ser Ser Arg Gly Phe
            20                  25                  30

Ile Gly Lys Ile Gln Gly Asp Leu Val Arg Arg Ile Thr Leu Leu Ser
        35                  40                  45

Pro Phe Phe Glu Glu Leu Ile Asp Val Asn Val Glu Leu Lys Lys Asp
    50                  55                  60

Gln Ile Thr Gly Phe Glu Ala Met Arg Ile Ala Leu Asp Ser Ser Leu
65                  70                  75                  80

Glu Leu Phe Arg Ser Val Asn Gly Gly Ser Lys Leu Phe Gln Leu Phe
                85                  90                  95

Asp Arg Asp Ser Leu Val Glu Lys Phe Arg Asp Met Thr Val Glu Ile
            100                 105                 110

Glu Ala Ala Leu Ser Gln Ile Pro Tyr Glu Lys Ile Glu Val Ser Glu
        115                 120                 125
```

```
Glu Val Arg Glu Gln Val Gln Leu Leu His Phe Gln Phe Lys Arg Ala
    130                 135                 140
Lys Glu Arg Trp Glu Glu Ser Asp Leu Gln Leu Ser His Asp Leu Ala
145                 150                 155                 160
Met Ala Glu Asn Val Met Asp Pro Asp Pro Ile Ile Leu Lys Arg Leu
                165                 170                 175
Ser Gln Glu Leu Gln Leu Thr Thr Ile Asp Glu Leu Lys Lys Glu Ser
                180                 185                 190
His Ala Ile His Glu Tyr Phe Leu Ser Tyr Asp Gly Asp Pro Asp Asp
                195                 200                 205
Cys Phe Glu Arg Met Ser Ser Leu Leu Lys Asn Leu Val Asp Phe Val
    210                 215                 220
Thr Met Glu Ser Ser Asp Pro Asp Pro Ser Thr Gly Ser Arg Ile Val
225                 230                 235                 240
Ser Arg His Arg Ser Pro Val Ile Pro Glu Tyr Phe Arg Cys Pro Ile
                245                 250                 255
Ser Leu Glu Leu Met Lys Asp Pro Val Ile Val Ser Thr Gly Gln Thr
                260                 265                 270
Tyr Glu Arg Ser Ser Ile Gln Lys Trp Leu Asp Ala Gly His Lys Thr
                275                 280                 285
Cys Pro Lys Ser Gln Glu Thr Leu Leu His Ala Gly Leu Thr Pro Asn
    290                 295                 300
Tyr Val Leu Lys Ser Leu Ile Ala Leu Trp Cys Glu Ser Asn Gly Ile
305                 310                 315                 320
Glu Leu Pro Gln Asn Gln Gly Ser Cys Arg Thr Thr Lys Ile Gly Gly
                325                 330                 335
Ser Ser Ser Ser Asp Cys Asp Arg Thr Phe Val Leu Ser Leu Leu Glu
                340                 345                 350
Lys Leu Ala Asn Gly Thr Thr Glu Gln Gln Arg Ala Ala Ala Gly Glu
                355                 360                 365
Leu Arg Leu Leu Ala Lys Arg Asn Val Asp Asn Arg Val Cys Ile Ala
    370                 375                 380
Glu Ala Gly Ala Ile Pro Leu Leu Val Glu Leu Leu Ser Ser Pro Asp
385                 390                 395                 400
Pro Arg Thr Gln Glu His Ser Val Thr Ala Leu Leu Asn Leu Ser Ile
                405                 410                 415
Asn Glu Gly Asn Lys Gly Ala Ile Val Asp Ala Gly Ala Ile Thr Asp
                420                 425                 430
Ile Val Glu Val Leu Lys Asn Gly Ser Met Glu Ala Arg Glu Asn Ala
                435                 440                 445
Ala Ala Thr Leu Phe Ser Leu Ser Val Ile Asp Glu Asn Lys Val Ala
    450                 455                 460
Ile Gly Ala Ala Gly Ala Ile Gln Ala Leu Ile Ser Leu Leu Glu Glu
465                 470                 475                 480
Gly Thr Arg Arg Gly Lys Lys Asp Ala Ala Thr Ala Ile Phe Asn Leu
                485                 490                 495
Cys Ile Tyr Gln Gly Asn Lys Ser Arg Ala Val Lys Gly Gly Ile Val
                500                 505                 510
Asp Pro Leu Thr Arg Leu Leu Lys Asp Ala Gly Gly Met Val Asp
                515                 520                 525
Glu Ala Leu Ala Ile Leu Ala Ile Leu Ser Thr Asn Gln Glu Gly Lys
    530                 535                 540
Thr Ala Ile Ala Glu Ala Glu Ser Ile Pro Val Leu Val Glu Ile Ile
```

```
                   545                 550                 555                 560
Arg Thr Gly Ser Pro Arg Asn Arg Glu Asn Ala Ala Ala Ile Leu Trp
                565                 570                 575

Tyr Leu Cys Ile Gly Asn Ile Glu Arg Leu Asn Val Ala Arg Glu Val
            580                 585                 590

Gly Ala Asp Val Ala Leu Lys Glu Leu Thr Glu Asn Gly Thr Asp Arg
        595                 600                 605

Ala Lys Arg Lys Ala Ala Ser Leu Leu Glu Leu Ile Gln Gln Thr Glu
    610                 615                 620

Gly Val Ala Val Thr Thr Val Pro
625                 630

<210> SEQ ID NO 43
<211> LENGTH: 1419
<212> TYPE: DNA
<213> ORGANISM: Arabidopsis thaliana
<220> FEATURE:
<221> NAME/KEY: CDS
<222> LOCATION: (1)..(1419)

<400> SEQUENCE: 43 atg gta tcg gtg gag gaa cct tta tct cat tcc aat tcc act cgc ttt      48
Met Val Ser Val Glu Glu Pro Leu Ser His Ser Asn Ser Thr Arg Phe
1               5                  10                  15 ccg tta aca acc gat ttc tac ggt tca tca tcg ccg tcg gcg gcg agg      96
Pro Leu Thr Thr Asp Phe Tyr Gly Ser Ser Ser Pro Ser Ala Ala Arg
            20                  25                  30 tta cac cgt caa gct ggc cgg tcg atg aga aca gtg aga tct aac ttc     144
Leu His Arg Gln Ala Gly Arg Ser Met Arg Thr Val Arg Ser Asn Phe
        35                  40                  45 tat caa agc gga gat caa tct tgc tca ttc gtc ggc tca atc ggc gat     192
Tyr Gln Ser Gly Asp Gln Ser Cys Ser Phe Val Gly Ser Ile Gly Asp
    50                  55                  60 aaa tca gag tat gcg tcg gag ttt ctc tcg gat tcc gtc atc gac atg     240
Lys Ser Glu Tyr Ala Ser Glu Phe Leu Ser Asp Ser Val Ile Asp Met
65                  70                  75                  80 aga ctc ggc gag ctt gct ttg aaa aac agt aat tct ctc aat tca aac     288
Arg Leu Gly Glu Leu Ala Leu Lys Asn Ser Asn Ser Leu Asn Ser Asn
                85                  90                  95 gct tcc tca atg aaa gag gaa gcg ttt ctc gac att tct cag gcg ttt     336
Ala Ser Ser Met Lys Glu Glu Ala Phe Leu Asp Ile Ser Gln Ala Phe
            100                 105                 110 agt gat ttt tcc gct tgt agt agt gat atc tcc ggc gag tta cag cgt     384
Ser Asp Phe Ser Ala Cys Ser Ser Asp Ile Ser Gly Glu Leu Gln Arg
        115                 120                 125 ctt gct tgc ttg ccg tcg ccg gag gct gat aga aat gag agc ggc gga     432
Leu Ala Cys Leu Pro Ser Pro Glu Ala Asp Arg Asn Glu Ser Gly Gly
    130                 135                 140 gat aac gaa gcg gag cat gat cca gag tta gag aga gag cct tgt cta     480
Asp Asn Glu Ala Glu His Asp Pro Glu Leu Glu Arg Glu Pro Cys Leu
145                 150                 155                 160 ggg ttt cta cag aga gaa aac ttc tct aca gag att atc gag tgt att     528
Gly Phe Leu Gln Arg Glu Asn Phe Ser Thr Glu Ile Ile Glu Cys Ile
                165                 170                 175 tcg ccg gaa gat ctg cag cca act gtg aaa cta tgc atc gac gga ctt     576
Ser Pro Glu Asp Leu Gln Pro Thr Val Lys Leu Cys Ile Asp Gly Leu
            180                 185                 190 cgt tcc tct tcg gtg gcg ata aag cga tct gct gcg gcg aag cta cgg     624
Arg Ser Ser Ser Val Ala Ile Lys Arg Ser Ala Ala Ala Lys Leu Arg
        195                 200                 205
```

```
cta ttg gcg aag aat cga gcg gat aat cgt gtg ttg att ggg gaa tct      672
Leu Leu Ala Lys Asn Arg Ala Asp Asn Arg Val Leu Ile Gly Glu Ser
    210                 215                 220 gga gct att caa gct ttg att cca ctt ctt cgt tgt aac gat cca tgg      720
Gly Ala Ile Gln Ala Leu Ile Pro Leu Leu Arg Cys Asn Asp Pro Trp
225                 230                 235                 240 acg caa gag cgc gca gtt aca gct ctg tta aac ctc tcg tta cac gac      768
Thr Gln Glu Arg Ala Val Thr Ala Leu Leu Asn Leu Ser Leu His Asp
                245                 250                 255 cag aac aaa gct gta atc gcc gca gga gga gcg att aaa tca cta gtg      816
Gln Asn Lys Ala Val Ile Ala Ala Gly Gly Ala Ile Lys Ser Leu Val
            260                 265                 270 tgg gta ctc aaa acg ggg acg gag act tca aag cag aac gct gca tgt      864
Trp Val Leu Lys Thr Gly Thr Glu Thr Ser Lys Gln Asn Ala Ala Cys
        275                 280                 285 gct ttg ctt agt ttg gcg cta ttg gag gag aac aaa ggc tca atc gga      912
Ala Leu Leu Ser Leu Ala Leu Leu Glu Glu Asn Lys Gly Ser Ile Gly
    290                 295                 300 gct tgc ggt gct att ccg ccg ctg gtt tct ctt ctg ttg aac gga tct      960
Ala Cys Gly Ala Ile Pro Pro Leu Val Ser Leu Leu Leu Asn Gly Ser
305                 310                 315                 320 tgc agg gga aag aag gat gcg ttg acg gcg ctc tac aag ctg tgt acg     1008
Cys Arg Gly Lys Lys Asp Ala Leu Thr Ala Leu Tyr Lys Leu Cys Thr
                325                 330                 335 ctt cag caa aac aag gag aga gcg gtc act gct gga gcg gtg aag ccg     1056
Leu Gln Gln Asn Lys Glu Arg Ala Val Thr Ala Gly Ala Val Lys Pro
            340                 345                 350 ttg gtg gac ctt gtg gct gag gaa ggg act ggt atg gcg gag aaa gct     1104
Leu Val Asp Leu Val Ala Glu Glu Gly Thr Gly Met Ala Glu Lys Ala
        355                 360                 365 atg gtg gtt ctg agt agc ctt gca gcg ata gat gat ggc aaa gag gct     1152
Met Val Val Leu Ser Ser Leu Ala Ala Ile Asp Asp Gly Lys Glu Ala
    370                 375                 380 att gtc gag gaa gga ggg atc gca gcg ctt gtt gag gcc atc gag gat     1200
Ile Val Glu Glu Gly Gly Ile Ala Ala Leu Val Glu Ala Ile Glu Asp
385                 390                 395                 400 gga tct gtg aaa ggg aaa gaa ttt gcg atc ttg acg ctg ttg cag ctt     1248
Gly Ser Val Lys Gly Lys Glu Phe Ala Ile Leu Thr Leu Leu Gln Leu
                405                 410                 415 tgt tct gat agc gtt aga aac cgt ggg ttg ctt gtg agg gaa ggc gcg     1296
Cys Ser Asp Ser Val Arg Asn Arg Gly Leu Leu Val Arg Glu Gly Ala
            420                 425                 430 att cct ccg ctt gtg ggc ctc tct cag agc ggc tcc gtc agt gtt aga     1344
Ile Pro Pro Leu Val Gly Leu Ser Gln Ser Gly Ser Val Ser Val Arg
        435                 440                 445 gct aag cgc aag gca gaa aga ctt ctg ggg tat ctt cgg gag cca agg     1392
Ala Lys Arg Lys Ala Glu Arg Leu Leu Gly Tyr Leu Arg Glu Pro Arg
    450                 455                 460 aag gag gca agt tca tca agc cca tga                                  1419
Lys Glu Ala Ser Ser Ser Ser Pro
465                 470

<210> SEQ ID NO 44
<211> LENGTH: 472
<212> TYPE: PRT
<213> ORGANISM: Arabidopsis thaliana

<400> SEQUENCE: 44

Met Val Ser Val Glu Glu Pro Leu Ser His Ser Asn Ser Thr Arg Phe
1               5                   10                  15

Pro Leu Thr Thr Asp Phe Tyr Gly Ser Ser Ser Pro Ser Ala Ala Arg
```

```
                     20                  25                  30
Leu His Arg Gln Ala Gly Arg Ser Met Arg Thr Val Arg Ser Asn Phe
             35                  40                  45

Tyr Gln Ser Gly Asp Gln Ser Cys Ser Phe Val Gly Ser Ile Gly Asp
 50                  55                  60

Lys Ser Glu Tyr Ala Ser Glu Phe Leu Ser Asp Ser Val Ile Asp Met
 65                  70                  75                  80

Arg Leu Gly Glu Leu Ala Leu Lys Asn Ser Asn Ser Leu Asn Ser Asn
                 85                  90                  95

Ala Ser Ser Met Lys Glu Glu Ala Phe Leu Asp Ile Ser Gln Ala Phe
                100                 105                 110

Ser Asp Phe Ser Ala Cys Ser Ser Asp Ile Ser Gly Glu Leu Gln Arg
            115                 120                 125

Leu Ala Cys Leu Pro Ser Pro Glu Ala Asp Arg Asn Glu Ser Gly Gly
            130                 135                 140

Asp Asn Glu Ala Glu His Asp Pro Glu Leu Glu Arg Glu Pro Cys Leu
145                 150                 155                 160

Gly Phe Leu Gln Arg Glu Asn Phe Ser Thr Glu Ile Ile Glu Cys Ile
                165                 170                 175

Ser Pro Glu Asp Leu Gln Pro Thr Val Lys Leu Cys Ile Asp Gly Leu
            180                 185                 190

Arg Ser Ser Val Ala Ile Lys Arg Ser Ala Ala Lys Leu Arg
            195                 200                 205

Leu Leu Ala Lys Asn Arg Ala Asp Asn Arg Val Leu Ile Gly Glu Ser
            210                 215                 220

Gly Ala Ile Gln Ala Leu Ile Pro Leu Leu Arg Cys Asn Asp Pro Trp
225                 230                 235                 240

Thr Gln Glu Arg Ala Val Thr Ala Leu Leu Asn Leu Ser Leu His Asp
                245                 250                 255

Gln Asn Lys Ala Val Ile Ala Ala Gly Gly Ala Ile Lys Ser Leu Val
            260                 265                 270

Trp Val Leu Lys Thr Gly Thr Glu Thr Ser Lys Gln Asn Ala Ala Cys
            275                 280                 285

Ala Leu Leu Ser Leu Ala Leu Leu Glu Glu Asn Lys Gly Ser Ile Gly
290                 295                 300

Ala Cys Gly Ala Ile Pro Pro Leu Val Ser Leu Leu Asn Gly Ser
305                 310                 315                 320

Cys Arg Gly Lys Lys Asp Ala Leu Thr Ala Leu Tyr Lys Leu Cys Thr
                325                 330                 335

Leu Gln Gln Asn Lys Glu Arg Ala Val Thr Ala Gly Ala Val Lys Pro
            340                 345                 350

Leu Val Asp Leu Val Ala Glu Glu Gly Thr Gly Met Ala Glu Lys Ala
            355                 360                 365

Met Val Val Leu Ser Ser Leu Ala Ala Ile Asp Asp Gly Lys Glu Ala
            370                 375                 380

Ile Val Glu Glu Gly Gly Ile Ala Ala Leu Val Glu Ala Ile Glu Asp
385                 390                 395                 400

Gly Ser Val Lys Gly Lys Glu Phe Ala Ile Leu Thr Leu Leu Gln Leu
                405                 410                 415

Cys Ser Asp Ser Val Arg Asn Arg Gly Leu Leu Val Arg Glu Gly Ala
            420                 425                 430

Ile Pro Pro Leu Val Gly Leu Ser Gln Ser Gly Ser Val Ser Val Arg
            435                 440                 445
```

```
Ala Lys Arg Lys Ala Glu Arg Leu Leu Gly Tyr Leu Arg Glu Pro Arg
    450                 455                 460

Lys Glu Ala Ser Ser Ser Ser Pro
465                 470

<210> SEQ ID NO 45
<211> LENGTH: 54
<212> TYPE: DNA
<213> ORGANISM: Artificial Sequence
<220> FEATURE:
<223> OTHER INFORMATION: GeneRacer Oligo dT Primer

<400> SEQUENCE: 45
gctgtcaacg atacgctacg taacggcatg acagtgtttt tttttttttt tttt           54

<210> SEQ ID NO 46
<211> LENGTH: 25
<212> TYPE: DNA
<213> ORGANISM: Artificial Sequence
<220> FEATURE:
<223> OTHER INFORMATION: Primer MWG 1

<400> SEQUENCE: 46
gcagacatga cccaatcttg gcagg                                           25

<210> SEQ ID NO 47
<211> LENGTH: 23
<212> TYPE: DNA
<213> ORGANISM: Artificial Sequence
<220> FEATURE:
<223> OTHER INFORMATION: GeneRacer 5' Primer (Invitrogen)

<400> SEQUENCE: 47
cgactggagc acgaggacac tga                                             23

<210> SEQ ID NO 48
<211> LENGTH: 25
<212> TYPE: DNA
<213> ORGANISM: Artificial Sequence
<220> FEATURE:
<223> OTHER INFORMATION: Primer, MWG 2

<400> SEQUENCE: 48
ccacggtcag caacctctcc agacg                                           25

<210> SEQ ID NO 49
<211> LENGTH: 26
<212> TYPE: DNA
<213> ORGANISM: Artificial Sequence
<220> FEATURE:
<223> OTHER INFORMATION: GeneRacer 5' nested Primer

<400> SEQUENCE: 49
ggacactgac atggactgaa ggagta                                          26

<210> SEQ ID NO 50
<211> LENGTH: 27
<212> TYPE: DNA
<213> ORGANISM: Artificial Sequence
<220> FEATURE:
<223> OTHER INFORMATION: Primer, MWG 3

<400> SEQUENCE: 50
cagatgatag ttattgttgt tgactgg                                         27

<210> SEQ ID NO 51
```

```
<211> LENGTH: 25
<212> TYPE: DNA
<213> ORGANISM: Artificial Sequence
<220> FEATURE:
<223> OTHER INFORMATION: GeneRacer 3' Primer

<400> SEQUENCE: 51
gctgtcaacg atacgctacg taacg                                         25

<210> SEQ ID NO 52
<211> LENGTH: 24
<212> TYPE: DNA
<213> ORGANISM: Artificial Sequence
<220> FEATURE:
<223> OTHER INFORMATION: Primer MWG 4

<400> SEQUENCE: 52
ctcatcttct caagctactg gtgg                                          24

<210> SEQ ID NO 53
<211> LENGTH: 23
<212> TYPE: DNA
<213> ORGANISM: Artificial Sequence
<220> FEATURE:
<223> OTHER INFORMATION: GeneRacer 3' nested Primer

<400> SEQUENCE: 53
cgctacgtaa cggcatgaca gtg                                           23

<210> SEQ ID NO 54
<211> LENGTH: 21
<212> TYPE: DNA
<213> ORGANISM: Artificial Sequence
<220> FEATURE:
<223> OTHER INFORMATION: Primer MWG 29

<400> SEQUENCE: 54
atatgcaaat ggctctgcta g                                             21

<210> SEQ ID NO 55
<211> LENGTH: 21
<212> TYPE: DNA
<213> ORGANISM: Artificial Sequence
<220> FEATURE:
<223> OTHER INFORMATION: Primer MWG 30

<400> SEQUENCE: 55
tatcatctcc ttcccgagtt c                                             21

<210> SEQ ID NO 56
<211> LENGTH: 27
<212> TYPE: DNA
<213> ORGANISM: Artificial Sequence
<220> FEATURE:
<223> OTHER INFORMATION: Primer MWG 31

<400> SEQUENCE: 56
cccgggatga ttttgcggtt ttggcgg                                       27
```

```
<210> SEQ ID NO 57
<211> LENGTH: 31
<212> TYPE: DNA
<213> ORGANISM: Artificial Sequence
<220> FEATURE:
<223> OTHER INFORMATION: Primer MWG 32

<400> SEQUENCE: 57
cccgggtcac aagacaaaac ataaaaatag g                              31

<210> SEQ ID NO 58
<211> LENGTH: 21
<212> TYPE: DNA
<213> ORGANISM: Artificial Sequence
<220> FEATURE:
<223> OTHER INFORMATION: Primer MWG 32b

<400> SEQUENCE: 58
gactcacact actctaatac c                                         21

<210> SEQ ID NO 59
<211> LENGTH: 20
<212> TYPE: DNA
<213> ORGANISM: Artificial Sequence
<220> FEATURE:
<223> OTHER INFORMATION: Primer MWG 33

<400> SEQUENCE: 59
gacatcgttt gtctcacacc                                           20

<210> SEQ ID NO 60
<211> LENGTH: 249
<212> TYPE: PRT
<213> ORGANISM: Artificial sequence
<220> FEATURE:
<223> OTHER INFORMATION: Consensus sequence 1
<220> FEATURE:
<221> NAME/KEY: MISC_FEATURE
<222> LOCATION: (1)..(106)
<223> OTHER INFORMATION: Xaa at positions 2, 4-10, 12-13, 15-18, 21-22,
      24-25, 27-34, 36-38, 41-42, 47-50, 52-54, 56-59, 62-67, 69-70,
      72-78, 80, 82-83, 85-86, 88-96, 99-106 can be any amino acid. Xaa
      can be no or one amino acid. Preferably, Xaa is one amino acid.
<220> FEATURE:
<221> NAME/KEY: MISC_FEATURE
<222> LOCATION: (108)..(230)
<223> OTHER INFORMATION: Xaa at positions 108-109, 112-113, 115-118,
      123-128, 130-135, 137-147, 149-150, 152-169, 171-188, 192-195,
      197-201, 203, 205-207, 209-210, 212-230 can be any amino acid.
      Xaa can be no or one amino acid.  Preferably, Xaa is one amino
      acid.
<220> FEATURE:
<221> NAME/KEY: MISC_FEATURE
<222> LOCATION: (232)..(249)
<223> OTHER INFORMATION: Xaa at positions 232-237, 239-242, 244-246,
      248-249 can be any amino acid. Xaa can be no or one amino acid.
      Preferably, Xaa is one amino acid.

<400> SEQUENCE: 60

Arg Xaa Leu Xaa Xaa Xaa Xaa Xaa Xaa Xaa Arg Xaa Xaa Ile Xaa Xaa
1               5                   10                  15

Xaa Xaa Ala Ile Xaa Xaa Leu Xaa Xaa Leu Xaa Xaa Xaa Xaa Xaa Xaa
            20                  25                  30

Xaa Xaa Gln Xaa Xaa Xaa Val Thr Xaa Xaa Leu Asn Leu Ser Xaa Xaa
        35                  40                  45

Xaa Xaa Asn Xaa Xaa Xaa Ile Xaa Xaa Xaa Xaa Ala Ile Xaa Xaa Xaa
    50                  55                  60

Xaa Xaa Xaa Leu Xaa Xaa Gly Xaa Xaa Xaa Xaa Xaa Xaa Xaa Asn Xaa
65                  70                  75                  80
```

```
Ala Xaa Xaa Leu Xaa Xaa Leu Xaa Xaa Xaa Xaa Xaa Xaa Xaa
            85                  90                  95

Ile Gly Xaa Xaa Xaa Xaa Xaa Xaa Leu Xaa Xaa Leu Leu Xaa
            100                 105                 110

Xaa Gly Xaa Xaa Xaa Xaa Lys Lys Asp Ala Xaa Xaa Xaa Xaa Xaa
            115                 120                 125

Leu Xaa Xaa Xaa Xaa Xaa Lys Xaa Xaa Xaa Xaa Xaa Xaa Xaa
            130                 135                 140

Xaa Xaa Xaa Leu Xaa Xaa Leu Xaa Xaa Xaa Xaa Xaa Xaa Xaa Xaa
145                 150                 155                 160

Xaa Xaa Xaa Xaa Xaa Xaa Xaa Xaa Leu Xaa Xaa Xaa Xaa Xaa Xaa
            165                 170                 175

Xaa Xaa Xaa Xaa Xaa Xaa Xaa Xaa Xaa Xaa Xaa Xaa Leu Val Glu Xaa
            180                 185                 190

Xaa Xaa Xaa Gly Xaa Xaa Xaa Xaa Xaa Glu Xaa Ala Xaa Xaa Xaa Leu
            195                 200                 205

Xaa Xaa Leu Xaa Xaa Xaa Xaa Xaa Xaa Xaa Xaa Xaa Xaa Xaa
            210                 215                 220

Xaa Xaa Xaa Xaa Xaa Xaa Leu Xaa Xaa Xaa Xaa Xaa Gly Xaa Xaa
225                 230                 235                 240

Xaa Xaa Arg Xaa Xaa Xaa Lys Xaa Xaa
            245

<210> SEQ ID NO 61
<211> LENGTH: 249
<212> TYPE: PRT
<213> ORGANISM: Artificial sequence
<220> FEATURE:
<223> OTHER INFORMATION: Consensus sequence of sequences derived from
      plants as listed
<220> FEATURE:
<221> NAME/KEY: MISC_FEATURE
<222> LOCATION: (1)..(147)
<223> OTHER INFORMATION: Xaa at positions 6-8, 13, 16-17, 21-22, 25, 28,
      30, 32-33, 37 48, 50, 53, 57, 62, 65-66, 69-70, 72-74, 95-96, 99,
      101, 105, 113, 116, 132-133, 137, 139, 146-147 can be any amino
      acid. Xaa can be no or one amino acid. Preferably, Xaa is one
      amino acid.
<220> FEATURE:
<221> NAME/KEY: MISC_FEATURE
<222> LOCATION: (153)..(249)
<223> OTHER INFORMATION: Xaa at positions 153, 156-157, 173, 178,
      181-182, 188, 192, 198, 200, 207, 213, 216-217, 220-221, 228,
      239-240, 242, 249 can be any amino acid. Xaa can be no or one
      amino acid. Preferably, Xaa is one amino acid.

<400> SEQUENCE: 61

Arg Leu Leu Ala Lys Xaa Xaa Xaa Glu Asn Arg Ile Xaa Ile Ala Xaa
1               5                   10                  15

Xaa Gly Ala Ile Xaa Xaa Leu Val Xaa Leu Leu Xaa Ser Xaa Asp Xaa
            20                  25                  30

Xaa Thr Gln Glu Xaa Ala Val Thr Ala Leu Leu Asn Leu Ser Ile Xaa
            35                  40                  45

Asp Xaa Asn Lys Xaa Ala Ile Ala Xaa Ala Gly Ala Ile Xaa Pro Leu
50                  55                  60

Xaa Xaa Val Leu Xaa Xaa Gly Xaa Xaa Xaa Glu Ala Lys Glu Asn Ser
65                  70                  75                  80

Ala Ala Thr Leu Phe Ser Leu Ser Val Ile Glu Glu Asn Lys Xaa Xaa
            85                  90                  95

Ile Gly Xaa Ser Xaa Gly Ala Ile Xaa Pro Leu Val Asp Leu Leu Gly
            100                 105                 110
```

```
Xaa Gly Thr Xaa Arg Gly Lys Lys Asp Ala Ala Thr Ala Leu Phe Asn
        115                 120                 125

Leu Ser Ile Xaa Xaa Glu Asn Lys Xaa Arg Xaa Val Gln Ala Gly Ala
    130                 135                 140

Val Xaa Xaa Leu Val Glu Leu Met Xaa Asp Pro Xaa Xaa Gly Met Val
145                 150                 155                 160

Asp Lys Ala Val Ala Val Leu Ala Asn Leu Ala Thr Xaa Pro Glu Gly
                165                 170                 175

Arg Xaa Ala Ile Xaa Xaa Glu Gly Gly Ile Pro Xaa Leu Val Glu Xaa
        180                 185                 190

Val Glu Leu Gly Ser Xaa Arg Xaa Lys Glu Asn Ala Ala Ala Xaa Leu
        195                 200                 205

Leu Gln Leu Cys Xaa Asn Ser Xaa Xaa Phe Cys Xaa Xaa Val Leu Gln
        210                 215                 220

Glu Gly Ala Xaa Pro Pro Leu Val Ala Leu Ser Gln Ser Gly Xaa Xaa
225                 230                 235                 240

Thr Xaa Arg Ala Lys Glu Lys Ala Xaa
            245
```

<210> SEQ ID NO 62
<211> LENGTH: 249
<212> TYPE: PRT
<213> ORGANISM: Artificial sequence
<220> FEATURE:
<223> OTHER INFORMATION: Consensus sequence 3 of sequences derived from
      plants as listed
<220> FEATURE:
<221> NAME/KEY: MISC_FEATURE
<222> LOCATION: (1)..(216)
<223> OTHER INFORMATION: Xaa at positions 6-7, 13, 16, 21-22, 25, 30,
      32-33, 37, 48, 50 53, 57, 62, 69-70, 72, 74, 96, 99, 101, 105,
      116, 132-133, 137, 153, 178, 182, 198, 216 can be any amino acid.
      Xaa can be no or one amino acid. Preferably, Xaa is one amino
      acid.
<220> FEATURE:
<221> NAME/KEY: MISC_FEATURE
<222> LOCATION: (220)..(242)
<223> OTHER INFORMATION: Xaa at positions 220, 239-240, 242 can be any
      amino acid. Xaa can be no or one amino acid. Preferably, Xaa is
      one amino acid.

<400> SEQUENCE: 62

```
Arg Leu Leu Ala Lys Xaa Xaa Met Glu Asn Arg Ile Xaa Ile Ala Xaa
1               5                   10                  15

Ala Gly Ala Ile Xaa Xaa Leu Val Xaa Leu Leu Tyr Ser Xaa Asp Xaa
            20                  25                  30

Xaa Thr Gln Glu Xaa Ala Val Thr Ala Leu Leu Asn Leu Ser Ile Xaa
        35                  40                  45

Asp Xaa Asn Lys Xaa Ala Ile Ala Xaa Ala Gly Ala Ile Xaa Pro Leu
    50                  55                  60

Ile His Val Leu Xaa Xaa Gly Xaa Ser Xaa Glu Ala Lys Glu Asn Ser
65                  70                  75                  80

Ala Ala Thr Leu Phe Ser Leu Ser Val Ile Glu Glu Asn Lys Val Xaa
                85                  90                  95

Ile Gly Xaa Ser Xaa Gly Ala Ile Xaa Pro Leu Val Asp Leu Leu Gly
            100                 105                 110

Xaa Gly Thr Xaa Arg Gly Lys Lys Asp Ala Ala Thr Ala Leu Phe Asn
        115                 120                 125

Leu Ser Ile Xaa Xaa Glu Asn Lys Xaa Arg Ile Val Gln Ala Gly Ala
    130                 135                 140
```

-continued

```
Val Lys Tyr Leu Val Glu Leu Met Xaa Asp Pro Ala Ala Gly Met Val
145                 150                 155                 160

Asp Lys Ala Val Ala Val Leu Ala Asn Leu Ala Thr Val Pro Glu Gly
                165                 170                 175

Arg Xaa Ala Ile Gly Xaa Glu Gly Gly Ile Pro Val Leu Val Glu Val
            180                 185                 190

Val Glu Leu Gly Ser Xaa Arg Gly Lys Glu Asn Ala Ala Ala Val Leu
        195                 200                 205

Leu Gln Leu Cys Thr Asn Ser Xaa Arg Phe Cys Xaa Leu Val Leu Gln
        210                 215                 220

Glu Gly Ala Ile Pro Pro Leu Val Ala Leu Ser Gln Ser Gly Xaa Xaa
225                 230                 235                 240

Thr Xaa Arg Ala Lys Glu Lys Ala Gln
                245
```

USE OF ARMADILLO REPEAT (ARM1) POLYNUCLEOTIDES FOR OBTAINING PATHOGEN RESISTANCE IN PLANTS

RELATED APPLICATIONS

This application is a national stage application (under 35 U.S.C. 371) of PCT/EP2006/067865 filed Oct. 27, 2006, which claims benefit of European application 05110468.5 filed Nov. 8, 2005.

SEQUENCE LISTING SUBMISSION

The Sequence Listing associated with this application is filed in electronic format via EFS-Web and hereby incorporated by reference into the specification in its entirety. The name of the text file containing the Sequence Listing is Revised_Sequence_List_13987_00093_US. The size of the text file is 333 KB, and the text file was created on Nov. 13, 2008.

The invention relates to a method of generating or increasing a pathogen resistance in plants by reducing the expression of at least one Armadillo repeat polypeptide or a functional equivalent thereof. The invention relates to novel nucleic acid sequences coding for a *Hordeum vulgare* Armadillo repeat (HvARM) polynucleotide and describes homologous sequences (ARM1) thereof, and to their use in methods for obtaining a pathogen resistance in plants, and to nucleic acid constructs, expression cassettes and vectors which comprise these sequences and which are suitable for mediating a fungal resistance in plants. The invention furthermore relates to transgenic organisms, in particular plants, which are transformed with these expression cassettes or vectors, and to cultures, parts or transgenic propagation material derived therefrom.

There are only few approaches which confer a resistance to pathogens, mainly fungal pathogens, to plants. This shortcoming can partly be attributed to the complexity of the biological systems in question. Another fact which stands in the way of obtaining resistances to pathogens is that little is known about the interactions between pathogen and plant. The large number of different pathogens, the infection mechanisms developed by these organisms and the defense mechanisms developed by the plant phyla, families and species interact with one another in many different ways.

Fungal pathogens have developed essentially two infection strategies. Some fungi enter into the host tissue via the stomata (for example rusts, *Septoria* species, *Fusarium* species) and penetrate the mesophyll tissue, while others penetrate via the cuticles into the epidermal cells underneath (for example *Blumeria* species).

The infections caused by the fungal pathogens lead to the activation of the plants defense mechanisms in the infected plants. Thus, it has been possible to demonstrate that defense reactions against epidermis-penetrating fungi frequently start with the formation of a penetration resistance (formation of papillae, strengthening of the cell wall with callose as the main constituent) underneath the fungal penetration hypha (Elliott et al. Mol Plant Microbe Interact. 15: 1069-77; 2002).

In some cases, however, the plant's defense mechanisms only confer an insufficient protection mechanism against the attack by pathogens.

The formation of a penetration resistance to pathogens whose infection mechanism comprises a penetration of the epidermal cells or of the mesophyll cells is of great importance both for monocotyledonous and for dicotyledonous plants. In contrast to described mlo-mediated resistance, it can probably make possible the development of a broad-spectrum resistance against obligatory biotrophic, hemibiotrophic and necrotrophic fungi.

The present invention was therefore based on the object of providing a method for generating a resistance of plants to penetrating pathogens.

The object is achieved by the embodiments characterized in the claims.

The invention therefore relates to a method of increasing the resistance to one or more penetrating pathogen(s) in a monocotyledonous or dicotyledonous plant, or a part of a plant, for example in an organ, tissue, a cell or a part of a plant cell, for example in an organelle, which comprises lessening or reducing the activity or amount of an Armadillo repeat ARM1 protein in the plant, or a part of the plant, for example in an organ, tissue, a cell or a part of a cell, for example in a cell compartment, for example in an organelle, in comparison with a control plant or a part of a control plant, for example its organ, tissue, cell or part of a cell, for example in a cell compartment, for example in an organelle.

Preferably, a race-unspecific resistance is obtained in the method according to the invention. Thus, for example, a broad-spectrum resistance against obligatorily biotrophic and/or hemibiotrophic and/or necrotrophic fungi of plants, in particular against mesophyll, epidermis or mesophyll-penetrating pathogens, can be obtained by the method according to the invention.

Surprisingly, it has been observed that the gene silencing by means of dsRNAi of a gene which codes for an Armadillo repeat protein HvARM of barley results in an increase in the resistance of monocotyledonous and dicotyledonous plants to fungal pathogens. Thus, this negative control function in the event of attack by fungal pathogens has been demonstrated for the Armadillo repeat ARM1 protein from barley (*Hordeum vulgare*) (HvARM1), wheat (*Triticum aestivum*) and thale cress (*Arabidopsis thaliana*).

It has been determined within the scope of a TIGS (=Transient Induced Gene Silencing) analysis in barley by the method of Schweizer et al. (Plant J. 2000 December; 24(6): 895-903) that a dsRNAi-mediated silencing of the gene HvARM greatly increases the resistance to *Blumeria graminis* f. sp. *hordei* (synonym: *Erysiphe graminis* DC. f. sp. *hordei*). This effect has also been obtained in dicotyledonous species such as, for example, *Arabidopsis thaliana* by inducing the post-transcriptional gene silencing (PTGS). This emphasizes the universal importance of the loss-of-function of HvARM1-homologous genes for the development of a broad-spectrum pathogen resistance of the plant.

The Armadillo repeat motif was originally found in the *Drosophila melanogaster* segment polarity gene armadillo. It codes for a beta-catenin which plays an important part in cell-cell adhesion and in cell differentiation. Armadillo (Arm) repeat proteins comprise copies arranged in tandem of a degenerated sequence of approx. 42 amino acids, which encodes a three dimensional structure for mediating protein-protein interactions (Azevedo et al. (2001) Trends Plant Sci. 6, 354-358). Most of these proteins are involved in intracellular signal transduction or in regulating gene expression within the framework of cellular developmental processes. Contrary to the situation in animals, only two plant Armadillo repeat proteins have been functionally characterized: the first gene is potato PHOR1 (photoperiod-responsive 1) which was shown to play a part in gibberellic acid signal transduction (Amador V, Cell 10; 106(3):343-54.). The second Armadillo repeat protein is oilseed rape ARC1 (Armadillo repeat-containing protein 1) which interacts with the SRK1 receptor kinase (Gu et al. (1998) Proc. Natl. Acad. Sci. USA 95, 382-387). It therefore plays an important part in the regulation of oilseed rape self-incompatibility. Transgenic plants whose ARC1 expression has been reduced by silencing exhibit reduced self-incompatibility. Interestingly, ARC1 belongs to the U-Box comprising subclass of Armadillo repeat proteins, which class includes 18 genes in *Arabidopsis* (Azevedo et al. (2001) Trends Plant Sci. 6, 354-358). The U-box is a motif comprising approx. 70 amino acid residues. Besides the HECT and the RING Finger proteins they presumably form a third class of ubiquitin E3 ligases whose primary function is that of establishing substrate specificity of the ubiquitination apparatus (Hatakeyama et al. (2001) J. Biol. Chem. 76, 33111-33120).

The genes or the nucleic acids used or the expressed proteins whose expression is reduced preferably have an identity of 40% or more, preferably 50%, 60%, 70%, 80%, 85%, 90%, 95%, 97%, 98%, 99%, or more, compared to the particular sequence of HvARM (SEQ ID NO: 1 and SEQ ID NO: 2). The genes with the highest homologies to HvArm, from rice (Acc. No.: XM_479734.1, XM_463544, AP003561, or XM_506432), tobacco (AY219234) and *Arabidopsis* (Acc. No. NM_127878, AC004401, BT020206, AB007645, NM_115336, AK118613, AL138650, AL133314, AC010870, AY125543, AY087360, AB016888, AK175585, AL049655, AY096530 and AK118730), thus presumably carry out similar functions as HvARM in the plant. These are therefore included in the generic term "Armadillo repeat ARM1" or "ARM1" protein hereinbelow. In contrast, HvARM and HvARM1 refer to such a protein from barley.

Recently, another plant Armadillo repeat protein, SpI11 in corn, has been described, for which a regulation of the plant cell death response within the framework of abiotic stress response has been detected. The loss of function of the corresponding gene results in a "lesion mimic" phenotype which impairs the agronomic performance of the plant (Zeng L R, (2004) Plant Cell. 16(10):2795-808). Interestingly, the sequence homology of SpI11 to HvARM is only 23.4% at the amino acid level. Without being bound or limited by theory, the low sequence homology, in addition to the different functions, also indicates that HvARM and SpI11 belong to different subclasses of Armadillo repeat proteins.

Consequently, it came as a surprise that reducing HvARM1 gene expression by RNAi-mediated silencing results in an increase in the resistance of barley to barley mildew and that this negative control function with an attack by fungal pathogens was likewise shown in wheat (*Triticum aestivum*) and thale cress (*Arabidopsis thaliana*).

In a further embodiment, the invention therefore relates to a method of generating a plant with an increased resistance to one or more plant pathogen(s), preferably with a broad-spectrum resistance, in particular to fungal pathogens, for example from the classes Ascomycetes, Basidiomycetes, Chytridiomycetes or Oomycetes, preferably of mildews of the family Erysiphaceae, and particularly preferably of the genus *Blumeria*, that is by reducing expression of a protein which is characterized in that it comprises at least one Armadillo repeat. The protein preferably comprises two, particularly preferably more than two, Armadillo repeats.

In a further embodiment of the method of the invention, the activity of an Armadillo repeat polypeptide is reduced, for example blocked or eliminated, which polypeptide essentially does not comprise a U-box, i.e. which does not comprise any U-box or any functional U-box.

In a further embodiment, in the method according to the invention the activity of a polypeptide is reduced or eliminated, which is encoded by a polynucleotide comprising at least one nucleic acid molecule selected from the group consisting of:

(a) nucleic acid molecule which codes for at least one polypeptide comprising the sequence as shown in SEQ ID No: 2, 4, 6, 8, 10, 12, 14, 16, 18, 20, 22, 24, 26, 28, 30, 32, 34, 36, 38, 40, 42, 44, 60, 61 or 62;
(b) nucleic acid molecule which comprises at least one polynucleotide of the sequence as shown in SEQ ID No: 1, 3, 5, 7, 9, 11, 13, 15, 17, 19, 21, 23, 25, 27, 29, 31, 33, 35, 37, 39, 41, or 43;
(c) nucleic acid molecule which codes for a polypeptide whose sequence has at least 50% identity to the sequences SEQ ID No: 2;
(d) nucleic acid molecule according to (a) to (c) which codes for a fragment or an epitope of the sequences as shown in SEQ. ID No.: 2, 4, 6, 8, 10, 12, 14, 16, 18, 20, 22, 24, 26, 28, 30, 32, 34, 36, 38, 40, 42, 44, 60, 61 or 62;
(e) nucleic acid molecule which codes for a polypeptide which is recognized by a monoclonal antibody directed against a polypeptide which is encoded by the nucleic acid molecules as shown in (a) to (c);
(f) nucleic acid molecule which hybridizes under stringent conditions with a nucleic acid molecule as shown in (a) to (c); and
(g) nucleic acid molecule which can be isolated from a DNA library using a nucleic acid molecule as shown in (a) to (c) or their part-fragments of at least 15 nt, preferably 20 nt, 30 nt, 50 nt, 100 nt, 200 nt or 500 nt, as probe under stringent hybridization conditions;

or comprises a complementary sequence thereof is reduced, for example eliminated.

In the method according to the invention, it is in particular the resistance to mesophyll- and/or epidermis-cell-penetrating pathogens which is preferably increased.

In one embodiment, the resistance is obtained by lessening, reducing or blocking the expression of a polypeptide, preferably of a polypeptide which is encoded by the above-described nucleic acid molecule, for example that of an ARM1 from rice (Acc. No.: XM_479734.1, XM_463544, AP003561, or XM_506432), tobacco (AY219234) and *Arabidopsis* (Acc. No. NM_127878, AC004401, BT020206, AB007645, NM_115336, AK118613, AL138650, AL133314, AC010870, AY125543, AY087360, AB016888, AK175585, AL049655, AY096530 and AK118730).

On the other hand, it is also possible to reduce, lessen or block the endogenous activity of one of these polypeptides by methods known to the skilled worker, for example by mutating a genomic coding region for the active center, for binding sites, for localization signals, for domains, clusters and the like, such as, for example, of coding regions for coiled coil, HEAT, FBOX, LRR, IBIB, C2, WD40, beach, U-box or UND domains. The activity can be reduced in accordance with the invention by mutations which affect the secondary, tertiary or quaternary structure of the protein.

Mutations can be inserted for example by an EMS mutagenesis. Domains can be identified by suitable computer programs such as, for example, SMART or InterPRO, for example as described in Andersen P., The Journal of Biol. Chemistry, 279, 38, pp. 40053-40061, 2004 or Y. Mudgil, Plant Physiology, 134, 59-66, 2004, and literature cited therein. The suitable mutants can then be identified for example by tilling (Henikoff et al. Plant Physiol. 2004 June; 135(2):630-6).

In another embodiment, the lessening of the polypeptide quantity, activity or function of an Armadillo repeat ARM1 protein in a plant is combined with increasing the polypeptide quantity, activity or function of other resistance factors, preferably of a Bax inhibitor 1 protein (BI-1), preferably of the Bax inhibitor 1 protein from *Hordeum vulgare* (GenBank Acc. No.: AJ290421), from *Nicotiana tabacum* (GenBank Acc. No.: AF390556), rice (GenBank Ace. No.: AB025926), *Arabidopsis* (GenBank Acc. No.: AB025927) or tobacco and oilseed rape (GenBank Acc. No.: AF390555, Bolduc N et al. (2003) Planta 216:377-386) or of ROR2 (for example from barley (GenBank Acc. No.: AY246906), SnAP34 (for example from barley (GenBank Acc. No.: AY247208) and/or of the lumenal binding protein BiP for example from rice (GenBank Acc. No. AF006825). An increase can be achieved for example by mutagenesis or overexpression of a transgene, inter alia.

In one embodiment, a lowering of the protein quantity or activity or function of the proteins RacB (for example from barley (GenBank Ace. No.: AJ344223)), CSL1 (for example from *Arabidopsis* (GenBank Acc. No.: NM116593), HvNaOX (for example from barley (GenBank Acc. No.: AJ251717), MLO (for example from barley (GenBank Acc. No. Z83834) is achieved.

The activity or function of MLO, BI-1 and/or NaOX can be reduced or inhibited analogously to what has been described for MLO in WO 98/04586; WO 00/01722; WO 99/47552 and the further publications mentioned hereinbelow, whose content is herewith expressly and expressis verbis incorporated by reference, in particular in order to describe the activity and inhibition of MLO. The description of the abovementioned publications describes processes, methods and especially preferred embodiments for lessening or inhibiting the activity or function of MLO; the examples indicate specifically how this can be realized.

The reduction of the activity or function and, if appropriate of the expression of BI-1 is described in detail in WO 2003020939, which is herewith expressly and expressis verbis incorporated into the present description. The description of the abovementioned publication describes processes and methods for lessening or inhibiting the activity or function of BI-1; the examples indicate specifically how this can be realized. The reduction or inhibition of the activity or function of BI-1 is especially preferably carried out in accordance with the embodiments especially preferred in WO 2003020939 and the examples and in the organisms shown therein as being especially preferred, in particular in a plant, for example constitutively, or in a part thereof, for example in a tissue, but especially at least in the epidermis or in a considerable part of the epidermal cells. The reduction of the activity or function and, if appropriate of the expression, of BI-1 is described extensively in WO 2003020939. The skilled worker finds in WO 2003020939 the sequences which code for BI-1 proteins and can also identify BI-1 with the method provided in WO 2003020939.

The reduction of the activity or function and, if appropriate of the expression, of NaOX is described extensively in PCT/EP/03/07589, which is herewith expressly and expresses verbis incorporated into the present description. The description of the abovementioned publication describes processes and methods for lessening or inhibiting the activity or function of NaOX, and the examples indicate specifically how this can be realized. The reduction or inhibition of the activity or function of NaOX is especially preferably carried out in accordance with the embodiments especially preferred in PCT/EP/03/07589 and the examples and in the organisms shown therein as being especially preferred, in particular in a plant, for example constitutively, or a part thereof for example in a tissue, but especially advantageously at least in the epidermis or in a considerable part of the epidermal cells. The skilled worker finds in PCT/EP/03/07589 the sequences which code for NaOX proteins and can also identify NaOX with the method provided in PCT/EP/03/07589.

The terms "to lessen", "to reduce" or "to repress" or their substantives are used synonymously in the present text.

"Lessening", "reduction" or "repression" or their verbs are understood as meaning, in accordance with the invention, that the activity in the plant is lower than in a control plant or is lower in a part of a plant than in a corresponding part of a control plant, for example in an organ, an organelle, a tissue or a cell. In preferred embodiments, the activity of the abovementioned polypeptide is 10%, 20%, 30%, 40%, 50%, 60%, 70%, 80%, 90%, 95%, 97%, 99% or even lower than in the control. In one embodiment, essentially no expression or particularly preferably no expression at all of the abovementioned polypeptide takes place. As a consequence, these terms also comprise the complete inhibition or blocking of an activity, for example by the knock-out of a gene.

"Reduction", "to reduce", "lessening" or "to lessen", "repression" or "to repress" comprise the partial or essentially complete inhibition or blocking of the functionality of a protein, based on a variety of cell-biological mechanisms.

Lessening within the purpose of the invention also comprises a quantitative reducing of a protein down to an essentially complete (i.e. lack of detectability of activity or function or lack of immunological detectability of the protein) or complete absence of the protein. Here, the expression of a certain protein or the activity or function in a cell or an organism is reduced by preferably more than 50%, especially preferably by more than 80%, and in particular by more than 90%.

In a further embodiment, the expression of a nucleic acid molecule for an ARM1 protein, for example in combination with a tissue-specific increase in the activity of a Bax inhibitor-1 protein may take place in the mesophyll tissue. The reduction of the Armadillo repeat ARM1 protein quantity in a transgenic plant which for example overexpresses BI-1 in the mesophyll tissue offers the possibility of generating a complete and comprehensive fungal resistance in the plant.

In a further embodiment, the increase in the polypeptide quantity, activity or function of a Bax Inhibitor 1 protein from *Hordeum vulgare* (GenBank Acc. No.: AJ290421), from *Nicotiana tabacum* (GenBank Acc. No. AF390556), rice (GenBank Acc. No.: AB025926), *Arabidopsis* (GenBank Acc. No.: AB025927) or tobacco and oilseed rape (GenBank Acc. No.: AF390555, Bolduc N et al. (2003) Planta 216:377-386) or of ROR2 (for example from barley (GenBank Acc. No.: AY246906), SnAP34 (for example from barley (GenBank Acc. No.: AY247208) and/or of the lumenal binding protein BiP for example from rice (GenBank Acc. No. AF006825) is effected in combination with the reduction in the protein quantity or activity or function of the proteins RacB (for example from barley (GenBank Acc. No.: AJ344223), CSL1 (for example from *Arabidopsis* (GenBank Acc. No.: NM116593), HvNaOX (for example from barley (GenBank Acc. No.: AJ251717), and/or MLO (for example from barley (GenBank Acc. No. Z83834). As a consequence, in one embodiment, at least one of the abovementioned genes which are suitable for overexpression or increased activity is activated or overexpressed and/or at least one of the abovementioned genes which is suitable for reduction is reduced.

An increase in the expression can be obtained as described herein. An increase in the expression or function is understood as meaning herein both the activation or enhancement of the expression or function of the endogenous protein, including a de novo expression, and an increase or enhancement by expression of a transgenic protein or factor.

For the purposes of the invention, "organism" means "non-human organisms" as long as the term relates to a viable multi-celled organism.

For the purposes of the invention, "plants" means all dicotyledonous or monocotyledonous plants. Preferred are plants which can be subsumed under the class of the Liliatae (Monocotyledoneae or monocotyledonous plants). The term includes the mature plants, seeds, shoots and seedlings, and parts, propagation material, plant organs, tissue, protoplasts, callus and other cultures, for example cell cultures derived from the above, and all other types of associations of plant cells which give functional or structural units. Mature plants means plants at any developmental stage beyond the seedling stage. Seedling means a young, immature plant in an early developmental stage.

"Plant" also comprises annual and perennial dicotyledonous or monocotyledonous plants and includes by way of example, but not by limitation, those of the genera *Bromus, Asparagus, Pennisetum, Lolium, Oryza, Zea, Avena, Hordeum, Secale, Triticum, Sorghum* and *Saccharum*.

In a preferred embodiment, the method is applied to monocotyledonous plants, for example from the family Poaceae, especially preferably to the genera *Oryza, Zea, Avena, Hordeum, Secale, Triticum, Sorghum* and *Saccharum*, very especially preferably to agriculturally important plants such as, for example, *Hordeum vulgare* (barley), *Triticum aestivum* (wheat), *Triticum aestivum* subsp. *spelta* (spelt), *Triticale, Avena sativa* (oats), *Secale cereale* (rye), *Sorghum bicolor* (sorghum), *Zea mays* (maize), *Saccharum officinarum* (sugar cane) or *Oryza sativa* (rice).

"Epidermal tissue" or epidermis means the external tissue layers of the plants. It can be single layered or multiple layered; and there is epidermis-"enriched" gene expression, such as, for example, Cer3, which can act as marker, exists; Hannoufa, A. (1996) Plant J. 10 (3), 459-467.

By "epidermis", the skilled worker preferably means the predominant dermal tissue of primary aerial plant parts, such as of the shoots, the leaves, flowers, fruits and seeds. The epidermal cells excrete a water-repellent layer, the cuticle, towards the outside. The roots are surrounded by the rhizodermis, which resembles the epidermis in many ways, but also differs substantially therefrom. The epidermis develops from the outermost layer of the apical meristem. The origin of the rhizodermis, in contrast, is less clear. Phylogenetically speaking, it can be assigned either to the calyptra or to the primary bark, depending on the species. A large number of functions can be ascribed to the epidermis: it protects the plant from dehydration and regulates the transpiration rate. It protects the plant from a wide range of chemical and physical external factors and against feeding animals and attack by parasites. It is involved in the gas exchange, in the secretion of certain metabolites and in the absorption of water. It contains receptors for light and mechanical stimuli. It therefore acts as signal transformer between the environment and the plant. In accordance with the various functions, the epidermis comprises a number of differently differentiated cells. Other aspects are species having specific variants and different organization of the epidermides in the individual parts of a plant. Essentially, it consists of three categories of cells: the "actual" epidermal cells, the cells of the stomata and of the trichomes (Greek: trichoma, hair), which are epidermal appendages with different shapes, structures and functions.

The "actual", i.e. the least specialized epidermal cells, account for most of the bulk of the cells of the epidermal tissue. In topview, they appear either polygonal (slab or plate shaped) or elongated. The walls between them are often wavy or sinuate. It is not known what induces this shape during development; existing hypotheses only offer unsatisfactory explanations herefor. Elongated epidermal cells can be found in organs or parts of organs that are elongated themselves, thus, for example, in stems, petioles, leaf veins and on the leaves of most monocots. The upper surface and undersurface of laminae can be covered in epidermides with different structures, it being possible for the shape of the cells, the wall thickness and the distribution and number of specialized cells (stomata and/or trichomes) per unit area to vary. A high degree of variation is also found within individual families, for example in the Crassulaceae. In most cases, the epidermis consists of a single layer, though multi-layered water-storing epidermides have been found among species from a plurality of families (Moraceae: most *Ficus* species; Piperaceae: Peperonia, Begoniaceae, Malvaceae and the like). Epidermal cells secrete a cuticle to the outside which covers all epidermal surfaces as an uninterrupted film. It may either be smooth or structured by bulges, rods, folds and furrows. However, the folding of the cuticle, which can be observed when viewing the surface, is not always caused by the formation of cuticular rods. Indeed, there are cases where cuticular folding is merely the expression of the underlying bulges of the cell wall. Epidermal appendages of various form, structure and function are referred to as trichomes and, in the present context, likewise come under the term "epidermis". They occur in the form of protective hairs, supportive hairs and gland hairs in the form of scales, different papillae and, in the case of roots, as absorbent hairs. They are formed exclusively by epidermal cells. Frequently, a trichome is formed by only one such cell, however, occasionally, more than one cell is involved in its formation.

The term "epidermis" likewise comprises papillae. Papillae are bulges of the epidermal surface. The textbook example thereof is the papillae on flower surfaces of the pansy (*Viola tricolor*) and the leaf surfaces of many species from tropical rain forests. They impart a velvet-like consistency to the surface. Some epidermal cells can form water stores. A typical example is the water vesicles at the surfaces of many *Mesembryanthemum* species and other succulents. In some plants, for example in the case of campanula (*Campanula persicifolia*), the outer walls of the epidermis are thickened like a lens.

The main biomass of all tissues is the parenchyma. The parenchymatic tissues include the mesophyll which, in leaves, can be differentiated into palisade parenchyma and spongy parenchyma. Accordingly the skilled worker understands, by mesophyll, a parenchymatic tissue. Parenchymatic cells are always alive, in most cases isodiametric, rarely elongated. The pith of the shoots, the storage tissues of the fruits, seeds, the root and other underground organs are also to be considered as parenchymas, as is the mesophyll. "Mesophyll tissue" means the foliar tissue between the epidermal layers, and consists of palisade tissue, spongy tissue and the vascular bundles of the leaf.

In the leaves of most ferns and phanerogams, especially in the case of the dicots and many monocots, the mesophyll is subdivided into palisade parenchymas and spongy parenchymas. A "typical" leaf is of dorsiventral organization. In most cases, the palisade parenchyma is at the upper surface of the leaf immediately underneath the epidermis. The spongy parenchyma fills the underlying space. It is interspersed by a voluminous intercellular system whose gas space is in direct contact with the external space via the stomata.

The palisade parenchyma consists of elongated cylindrical cells. In some species, the cells are irregular, occasionally bifurcate (Y-shaped: arm palisade parenchyma). Such variants are found in ferns, conifers and a few angiosperms (for example in some Ranunculaceae and Caprifoliaceae species [example: elder]). Besides the widest-spread organization form which has just been described, the following variants have been found:

palisade parenchyma at the leaf undersurface. Particularly conspicuously in scaly leaves. (For example arbor vitae (*thuja*), and in the leaves of wild garlic (*Allium ursinum*).

Palisade parenchyma at both leaf surfaces (upper surface and undersurface). Frequently found in plants of dry habitats (xerophytes). Example: prickly lettuce (*Lactuca serriola*);

Ring-shaped closed palisade parenchyma: in cylindrically organized leaves and in needles from conifers.

The variability of the cells of the spongy parenchyma, and the organization of the spongy parenchyma itself, are even more varied than that of the palisade parenchyma. It is most frequently referred to as aerenchyma since it comprises a multiplicity of interconnected intercellular spaces.

The mesophyll may comprise what is known as the assimilation tissue, but the terms mesophyll and assimilation tissue are not to be used synonymously. There are chloroplast-free leaves whose organization differs only to a minor extent from comparable green leaves. As a consequence, they comprise mesophyll, but assimilation does not take place; conversely, assimilation also takes place in, for example, sections of the shoot. Further aids for characterizing epidermis and mesophyll can be found by the skilled worker for example in v. GUTTENBERG, H.: Lehrbuch der Allgemeinen Botanik [Textbook of general botany]. Berlin: Akademie-Verlag 1955 (5th Ed.), HABERLANDT, G: Physiologische Pflanzenanatomie [Physiological plant anatomy]. Leipzig: W. Engelmann 1924 (6th Ed.); TROLL, W.: Morphologie der Pflanzen [Plant morphology]. Volume 1: Vegetationsorgane [Vegetation organs]. Berlin: Gebr. Borntraeger, 1937; TROLL, W.: Praktische Einführung in die Pflanzenmorphologie [Practical introduction to plant morphology]. Jena: VEB G. Thieme Verlag 1954/1957; TROLL, W., HÖHN, K.: Allgemeine Botanik [General botany]. Stuttgart: F. Enke Verlag, 1973 (4th Ed.)

As a consequence, epidermis or epidermal cells can be characterized in histological or biochemical, including molecular-biochemical, terms. In one embodiment, the epidermis is characterized in biochemical terms. In one embodiment, the epidermis can be characterized by the activity of one or more of the following promoters:

WIR5 (=GstA1), acc. X56012, Dudler & Schweizer, unpublished.

GLP4, acc. AJ310534; Wei, Y.; (1998) Plant Molecular Biology 36, 101-112.

GLP2a, acc. AJ237942, Schweizer, P., (1999). Plant J 20, 541-552.

Prx7, acc. AJ003141, Kristensen B K, 2001. Molecular Plant Pathology, 2(6), 311-317

GerA, acc. AF250933; Wu S, 2000. Plant Phys Biochem 38, 685-698

OsROC1, acc. AP004656

RTBV, acc. AAV62708, MV62707; Klöti, A, 1999, PMB 40, 249-266

Cer3; Hannoufa, A. (1996), Plant J. 10 (3), 459-467.

In another embodiment, the epidermis is characterized in that only some of the promoters are active, for example 2, 3, 5 or 7 or more, but at least one of the abovementioned promoters is active. In one embodiment, the epidermis is characterized in that all the abovementioned promoters are active in the tissue or the cell.

As a consequence, mesophyll or mesophyll cells can be characterized in biochemical, including molecular-biological, or histological terms. In one embodiment, the mesophyll is characterized in biochemical terms. In one embodiment, the mesophyll can be characterized by the activity of one or more of the following promoters:

PPCZm1 (=PEPC); Kausch, A. P., (2001) Plant Mot. Biol. 45, 1-15

OsrbcS, Kyozuka et al PlaNT Phys: 1993 102: Kyozuka J, 1993. Plant Phys 102, 991-1000

OsPPDK, acc. AC099041.

TaGF-2.8, acc. M63223; Schweizer, P., (1999). Plant J 20, 541-552.

TaFBPase, acc. X53957.

TaWIS1, acc. AF467542; US 200220115849

HvBIS1, acc. AF467539; US 200220115849

ZmMIS1, acc. AF467514; US 200220115849

HvPR1a, acc. X74939; Bryngeisson et al. Molecular Plant-Microbe Interactions (1994)

HvPR1b, acc. X74940; Bryngelsson et al. Molecular Plant-Microbe Interactions (1994)

HvB1,3gluc; acc. AF479647

HvPrx8, acc. AJ276227; Kristensen et al MPP 2001 (see above)

HvPAL, acc. X97313; Wei, Y.; (1998) Plant Molecular Biology 36, 101-112.

In another embodiment, the mesophyll is characterized in that only some of the promoters are active, for example 2, 3, 5 or 7 or more, but at least one of the abovementioned promoters is active. In one embodiment, the mesophyll is characterized in that all the abovementioned promoters are active in the tissue or the cell.

In one embodiment, all of the abovementioned promoters are active in the epidermis of a plant which is used or generated in accordance with the invention or of a plant according to the invention in the epidermis and in the mesophyll. In one embodiment, only some of the abovementioned promoters are active, for example 2, 5, 7 or more, but at least one of the promoters enumerated above is in each case active.

"Nucleic acids" means biopolymers of nucleotides which are linked with one another via phosphodiester bonds (polynucleotides, polynucleic acids). Depending on the type of sugar in the nucleotides (ribose or deoxyribose), one distinguishes the two classes of the ribonucleic acids (RNA) and the deoxyribonucleic acids (DNA).

The term "crop" means all plant parts obtained by growing plants agriculturally and collected within the harvesting process.

"Resistance" means the preventing, the repressing, the reducing or the weakening of disease symptoms of a plant as the result of infection by a pathogen. The symptoms can be manifold, but preferably comprise those which directly or indirectly lead to an adversely affect on the quality of the plant, on the quantity of the yield, on the suitability for use as feed or foodstuff, or else which make sowing, growing, harvesting or processing of the crop more difficult.

In a preferred embodiment, the following disease symptoms are weakened, reduced or prevented: formation of pustules and hymenia on the surfaces of the affected tissues, maceration of the tissues, spreading necroses of the tissue, accumulation of mycotoxins, for example from *Fusarium graminearum* or *F. culmorum*, penetration of the epidermis and/or of the mesophyll, etc.

"Conferring", "existing", "generating" or increasing a pathogen resistance or the like means that the defense mechanisms of a certain plant or in a part of a plant, for example in an organ, a tissue, a cell or an organelle, have an increased resistance to one or more pathogens as the result of using the method according to the invention in comparison with a suitable control, for example the wildtype of the plant ("control plant", "starting plant"), to which the method according to the invention has not been applied, under otherwise identical conditions (such as, for example, climatic conditions, growing conditions, type of pathogen and the like). Preferably, at least the epidermis and/or mesophyll tissue in a plant, or the organs which have an epidermis and/or mesophyll tissue, have an increased resistance to the pathogen(s). For example, the resistance in the leaves is increased. In one embodiment, the resistance in lemma, palea and/or glume (anther primordium) is increased.

In one embodiment, the activity of the protein according to the invention, Armadillo repeat ARM1, is therefore reduced in the abovementioned organs and tissues.

In this context, the increased resistance preferably manifests itself in a reduced manifestation of the disease symptoms, where disease symptoms—in addition to the abovementioned adverse effects—also comprises for example the penetration efficiency of a pathogen into the plant or the plant cell, or the proliferation efficiency in or on the same. Changes in the cell wall structure may, for example, constitute a basic mechanism of pathogen resistance, as shown, for example, in Jacobs A K et al. (2003) Plant Cell, 15(11):2503-13.

In the present case, the disease symptoms are preferably reduced by at least 10% or at least 20%, especially preferably by at least 40% or 60%, very especially preferably by at least 70% or 80%, most preferably by at least 90% or 95% or more.

For the purposes of the invention, "pathogen" means organisms whose interactions with a plant lead to the above-described disease symptoms; in particular, pathogens means organisms from the Kingdom Fungi. Preferably, pathogen is understood as meaning a pathogen which penetrates epidermis or mesophyll cells, especially preferably pathogens which penetrate plants via stomata and subsequently penetrate mesophyll cells. Organisms which are preferably mentioned in this context are those from the phyla Ascomycota and Basidiomycota. Especially preferred in this context are the families Blumeriaceae, Pucciniaceae, Mycosphaerellaceae and Hypocreaceae.

Especially preferred are organisms of these families which belong to the genera *Blumeria, Puccinia, Fusarium* or *Mycosphaerella*.

Very especially preferred are the species *Blumeria graminis, Puccinia triticina, Puccinia striiformis, Mycosphaerella graminicola, Stagonospora nodorum, Fusarium graminearum, Fusarium culmorum, Fusarium avenaceum, Fusarium poae* and *Microdochium nivale*.

However, it is to be assumed that the reduction in the expression of HvARM, its activity or function also brings about a resistance to further pathogens.

Especially preferred are Ascomycota such as, for example, *Fusarium oxysporum* (*fusarium* wilt on tomato), *Septoria nodorurm* and *Septoria tritici* (glume blotch on wheat), Basidiomycetes such as, for example, *Puccinia graminis* (stem rust on wheat, barley, rye, oats), *Puccinia recondita* (leaf rust on wheat), *Puccinia dispersa* (leaf rust on rye), *Puccinia hordei* (leaf rust on barley), *Puccinia coronata* (crown rust on oats).

In preferred embodiments, the method according to the invention leads to a resistance in
barley to the pathogen:
 *Puccinia graminis* f.sp. *hordei* (barley stem rust), *Blumeria graminis* f.sp. *hordei* (barley mildew, Bgh);
in wheat to the pathogens:
 *Fusarium graminearum, Fusarium avenaceum, Fusarium culmorum, Puccinia graminis* f.sp. *tritici, Puccinia recondita* f.sp. *tritici, Puccinia striiformis, Septoria nodorum, Septoria tritici, Septoria avenae, Blumeria graminis* f.sp. *tritici* (barley mildew, Bgt) or *Puccinia graminis* f.sp. *tritici* (wheat stem rust), in maize to the pathogens:
 *Fusarium moniliforme* var. *subglutinans, Puccinia sorghi* or *Puccinia polysora,*
in *sorghum* to the pathogens;
 *Puccinia purpurea, Fusarium moniliforme, Fusarium graminearum* or *Fusarium oxysporum,*
in soybean to the pathogens
 *Phakopsora pachyrhizi* and *Phakopsora meibromae.*

"Armadillo repeat Arm1 polypeptide" or "Armadillo repeat ARM1 protein" or "Arm" or "Arm1" and modifications thereof mean in the context of the invention a protein having one or more Armadillo repeats.

In a particularly preferred embodiment, the invention relates to an Armadillo repeat ARM1 polypeptide which has the activity shown in the examples. In one embodiment, an Armadillo repeat ARM1 protein is understood as meaning a protein with a homology to one of the amino acid sequences shown in SEQ ID No: 2, 4, 6, 8, 10, 12, 14, 16, 18, 20, 22, 24, 26, 28, 30, 32, 34, 36, 38, 42, 44, 60, 61 or 62 or in the figures, for example an Armadillo repeat ARM1 polypeptide from barley (HvARM) as in SEQ ID NO: 2 and/or from rice (*Oryza sativa*) as shown in SEQ ID NO: 4, 6, 8, and/or 10, and/or from tobacco (*Nicotiana tabacum*) as shown in SEQ ID NO.: 12 and/or from *A. thaliana* as shown in SEQ ID NO: 14, 16, 18, 20, 22, 24, 26, 28, 30, 32, 34, 36, 38, 42, and/or 44, or according to one of the consensus sequences as shown in SEQ ID NO.: 60, 61 or 62, or a functional fragment thereof. In one embodiment, the invention relates to functional equivalents of the abovementioned polypeptide sequences.

"Polypeptide quantity" means for example the number of molecules, or moles, of Armadillo repeat ARM1 polypeptide molecules in an organism, a tissue, a cell or a cell compartment "Reducing" the polypeptide quantity means the molar reduction in the number of Armadillo repeat ARM1 polypeptides, in particular of those shown in SEQ ID No: 2, 4, 6, 8, 10, 12, 14, 16, 18, 20, 22, 24, 26, 28, 30, 32, 34, 36, 38, 42, 44, 60, 61 or 62, in an organism, a tissue, a cell or a cell compartment—for example by one of the methods described hereinbelow—in comparison with a suitable control, for example the wildtype (control plant) of the same genus and species to which this method has not been applied, under otherwise identical conditions (such as, for example, culture conditions, age of the plants and the like). The reduction in this context amounts to at least 5%, preferably at least 10% or at least 20%, especially preferably at least 40% or 60%, very especially preferably at least 70% or 80%, most preferably at least 90%, 95% or 99% and in particular 100%.

The present invention furthermore relates to the generation of a pathogen resistance by reducing the function or activity of an Armadillo repeat ARM1 polypeptide comprising the sequences shown in SEQ ID No: 2, 4, 6, 8, 10, 12, 14, 16, 18, 20, 22, 24, 26, 28, 30, 32, 34, 36, 38, 42, 44, 60, 61 or 62 or of a homolog thereof and/or a polypeptide which has a homology of at least 40% with the above, and/or of a functional equivalent of the abovementioned polypeptides.

Homology between two nucleic acid sequences is understood as meaning the identity of the nucleic acid sequence over in each case the entire sequence length, which is calculated by comparison with the aid of the program algorithm GAP (Wisconsin Package Version 10.0, University of Wisconsin, Genetics Computer Group (GCG), Madison, USA; Altschul et al. (1997) Nucleic Acids Res. 25:3389ff), setting the following parameters:

| | |
|---|---|
| Gap weight: 50 | Length weight: 3 |
| Average match: 10 | Average mismatch: 0 |

For example, a sequence which has at least 80% homology with the sequence SEQ ID NO: 1 at the nucleic acid level is understood as meaning a sequence which, upon comparison with the sequence SEQ ID NO: 1 by the above program algorithm with the above parameter set, has at least 80% homology.

Homology between two polypeptides is understood as meaning the identity of the amino acid sequence over the indicated entire sequence length which is calculated by comparison with the aid of the program algorithm GAP (Wisconsin Package Version 10.0, University of Wisconsin, Genetics Computer Group (GCG), Madison, USA), setting the following parameters:

| | |
|---|---|
| Gap weight: 8 | Length weight: 2 |
| Average match: 2.912 | Average mismatch: −2.003 |

For example, a sequence which has at least 80% homology at the polypeptide level with the sequence SEQ ID NO: 2 is understood as meaning a sequence which, upon comparison with the sequence SEQ ID NO: 2 by the above program algorithm with the above parameter set has at least 80% homology.

In a preferred embodiment of the present invention, the Armadillo repeat ARM1 protein activity, function or polypeptide quantity is reduced in the plant or in a part of the plant, for example in a plant organ, plant tissue, a plant cell or a part of a plant cell, for example a plant-specific organelle.

In one embodiment of the method of the invention, the activity of a polypeptide comprising at least one, preferably two or more, Armadillo repeats is reduced.

In one embodiment, the polypeptide which is reduced in a plant or in a part of the plant does not have a U box in the 5'-UTR.

"Armadillo repeat" means a sequence which comprises the copies arranged in tandem of a degenerated sequence of approx. 42 amino acids, which sequence encodes a three-dimensional structure for mediating protein-protein interactions (Azevedo et al. (2001) Trends Plant Sci. 6, 354-358). For example, the polypeptide employed in the method of the invention or the polypeptide of the invention has an activity which is involved in intracellular signal transduction or in regulating gene expression within the framework of cellular development of processes.

For example, the Armadillo repeat ARM1 protein is encoded by a nucleic acid molecule comprising a nucleic acid molecule selected from the group consisting of:
a) nucleic acid molecule which codes for a polypeptide which comprises the sequence shown in SEQ ID No: 2, 4, 6, 8, 10, 12, 14, 16, 18, 20, 22, 24, 26, 28, 30, 32, 34, 36, 38, 42, 44, 60, 61 or 62;
b) nucleic acid molecule which comprises at least one polynucleotide of the sequence according to SEQ ID No: 1, 3, 5, 7, 9, 11, 13, 15, 17, 19, 21, 23, 25, 27, 29, 31, 33, 35, 37, 39, 41, or 43;
c) nucleic acid molecule which codes for a polypeptide whose sequence has 40%, 50%, 60%, 70%, 80%, 90%, 95%, 97%, 98%, 99% or more identity to the sequences SEQ ID No: 2, 4, 6, 8, 10, 12, 14, 16, 18, 20, 22, 24, 26, 28, 30, 32, 34, 36, 38, 42, 44, 60, 61 or 62;
d) nucleic acid molecule according to (a) to (c) which codes for a functional fragment or an epitope of the sequences as shown in SEQ ID No: 2, 4, 6, 8, 10, 12, 14, 16, 18, 20, 22, 24, 26, 28, 30, 32, 34, 36, 38, 42, 44, 60, 61 or 62;
e) nucleic acid molecule which codes for a polypeptide which is recognized by a monoclonal antibody directed against a polypeptide which is encoded by the nucleic acid molecules as shown in (a) to (c); and
f) nucleic acid molecule which hybridizes under stringent conditions with a nucleic acid molecule as shown in (a) to (c); or their part-fragments of at least 15 nucleotides (nt), preferably 20 nt, 30 nt, 50 nt, 100 nt, 200 nt or 500 nt;
g) nucleic acid molecule which can be isolated from a DNA library using a nucleic acid molecule as shown in (a) to (c) or their part-fragments of at least 15 nt, preferably 20 nt, 30 nt, 50 nt, 100 nt, 200 nt or 500 nt, as probe under stringent hybridization conditions;
or comprises a complementary sequence thereof or constitutes a functional equivalent thereof.

According to the invention, the activity of the abovementioned polypeptides is reduced in a plant or a part of a plant, preferably in the epidermal and/or mesophyll cells of a plant as detailed above.

In one embodiment, the activity of ARM1 is reduced in lemma, palea and/or glume.

"Epitope" is understood as meaning the regions of an antigen which determine the specificity of the antibodies (the antigenic determinant).

Accordingly, an epitope is the portion of an antigen which actually comes into contact with the antibody.

Such antigenic determinants are those regions of an antigen to which the T-cell receptors react and, as a consequence, produce antibodies which specifically bind the antigenic determinant/the epitope of an antigen. Accordingly, antigens, or their epitopes, are capable of inducing the immune response of an organism with the consequence of the formation of specific antibodies which are directed against the epitope. Epitopes consist for example of linear sequences of amino acids in the primary structure of proteins, or of complex secondary or tertiary protein structures. A hapten is understood as meaning a epitope which is dissociated from the context of the antigen environment. Although haptens have by definition an antibody directed against them, haptens are, under certain circumstances, not capable of inducing an immune response in an organism, for example after an injection. To this end, haptens are coupled with carrier molecules. An example which may be mentioned is dinitrophenol (DNP), which, after coupling to BSA (bovine serum albumin), has been used for generating antibodies which are directed against DNP. (Bohn, A., König, W. 1982). Haptens are therefore in particular (frequently low molecular weight or small) substances which, while they themselves do not trigger immune response, will indeed trigger such a response when coupled to a large molecular carrier.

The antibodies generated thus also include those which can bind to the hapten as such.

In one embodiment, the present invention relates to an antibody against a polypeptide characterized herein, in particular to a monoclonal antibody which binds a polypeptide which comprises an AA sequence or consists thereof, as shown in the sequences shown in SEQ ID No: 2, 4, 6, 8, 10, 12, 14, 16, 18, 20, 22, 24, 26, 28, 30, 32, 34, 36, 38, 40, 42, 44, 60, 61 or 62.

Antibodies within the scope of the present invention can be used for identifying and isolating polypeptides disclosed in accordance with the invention from organisms, preferably plants, especially preferably monocotyledonous plants. The antibodies can either be monoclonal, polyclonal or else synthetic in nature or else consist of antibody fragments such as Fab, Fv or scFv fragments, which are formed by proteolytic degradation. "Single chain" Fv (scFv) fragments are single-chain fragments which, linked via a flexible linker sequence only comprise the variable regions of the heavy and light antibody chains. Such scFv fragments can also be produced as recombinant antibody derivatives. A presentation of such antibody fragments on the surface of filamentous phages makes possible the direct selection, from combinatory phage libraries, of scFv molecules which bind with high affinity.

Monoclonal antibodies can be obtained in accordance with the method described by Köhler and Milstein (Nature 256 (1975), 495).

"Functional equivalents" of an Armadillo repeat ARM1 protein preferably means those polypeptides which have at least 40% homology with the polypeptides described by the sequences SEQ ID No: 2, 4, 6, 8, 10, 12, 14, 16, 18, 20, 22, 24, 26, 28, 30, 32, 34, 36, 38, 42, 44, 60, 61 or 62 and which have essentially the same properties or function. Preferably, the homology amounts to 50%, 60%, 70%, 80%, 90%, particularly preferably 95%, 97%, 98%, 99% or more.

The functional equivalence can be determined for example by comparing the phenotypes of test organisms after expression of the polypeptides in question, under the most identical conditions possible, or after reduction of the expression or activity of the polypeptides to be compared, in the source organisms in question.

"Essentially identical properties" of a functional equivalent means above all imparting a pathogen-resistant phenotype or imparting or increasing the pathogen resistance to at least one pathogen when reducing the polypeptide quantity, activity or function of said functional Armadillo repeat ARM1 protein equivalent in a plant, organ, tissue, part or cells, in particular in epidermal or mesophyll cells of same, preferably measured by the penetration efficiency of a pathogen, as shown in the examples.

"Analogous conditions" means that all basic conditions such as, for example, culture or growth conditions, assay conditions (such as buffers, temperature, substrates, pathogen concentration and the like) between the experiments to be compared are essentially kept identical and that the set-ups only differ by the sequence of the Armadillo repeat ARM1 polypeptides to be compared, by their source organism and, if appropriate, by the pathogen.

"Functional equivalents" also means natural or artificial mutation variants of the Armadillo repeat ARM1 polypeptides as shown in SEQ ID No: 2, 4, 6, 8, 10, 12, 14, 16, 18, 20, 22, 24, 26, 28, 30, 32, 34, 36, 38, 42, 44, 60, 61 or 62 and homologous polypeptides from other monocotyledonous and dicotyledonous plants which furthermore have essentially identical properties. Preferred are homologous polypeptides from preferred plants described herein. The sequences from other plants, which sequences are homologous to the Armadillo repeat ARM1 protein sequences disclosed within the scope of the present invention, can be found readily for example by database search or by screening gene libraries using the Armadillo repeat ARM1 protein sequences as search sequence or probe.

Functional equivalents can also be derived for example from one of the polypeptides according to the invention as shown in SEQ ID No: 2, 4, 6, 8, 10, 12, 14, 16, 18, 20, 22, 24, 26, 28, 30, 32, 34, 36, 38, 42, 44, 60, 61 or 62 by substitution, insertion or deletion and can have at least 40%, 50%, 60%, preferably at least 80%, by preference at least 90%, especially preferably at least 95%, very especially preferably at least 98% homology with these polypeptides and are distinguished by essentially identical functional properties to the polypeptides as shown in SEQ ID No: 2, 4, 6, 8, 10, 12, 14, 16, 18, 20, 22, 24, 26, 28, 30, 32, 34, 36, 38, 42, 44, 60, 61 or 62.

Functional equivalents are also any nucleic acid molecules which are derived from the nucleic acid sequences according to the invention as shown in SEQ ID No: 1, 3, 5, 7, 9, 11, 13, 15, 17, 19, 21, 23, 25, 27, 29, 31, 33, 35, 37, 39, 41, or 43 by substitution, insertion or deletion and have at least 40%, 50%, 60%, preferably 80%, by preference at least 90%, especially preferably at least 95%, very especially preferably at least 98% homology with one of the polynucleotides according to the invention as shown in SEQ ID No: 1, 3, 5, 7, 9, 11, 13, 15, 17, 19, 21, 23, 25, 27, 29, 31, 33, 35, 37, 39, 41, or 43 and code for polypeptides with essentially identical functional properties to polypeptides as shown in SEQ ID No: 2, 4, 6, 8, 10, 12, 14, 16, 18, 20, 22, 24, 26, 28, 30, 32, 34, 36, 38, 42, 44, 60, 61 or 62.

Examples of the functional equivalents of the Armadillo repeat ARM1 proteins as shown in SEQ ID No: 2, 4, 6, 8, 10, 12, 14, 16, 18, 20, 22, 24, 26, 28, 30, 32, 34, 36, 38, 42, 44, 60, 61 or 62 which are to be reduced in the method according to the invention can be found by homology comparisons from databases, from organisms whose genomic sequence is known.

Screening cDNA libraries or genomic libraries of other organisms, preferably of the plant species mentioned further below, which are suitable as transformation hosts, using the nucleic acid sequence described in SEQ ID No: 1, 3, 5, 7, 9, 11, 13, 15, 17, 19, 21, 23, 25, 27, 29, 31, 33, 35, 37, 39, 41, or 43 or parts of the same as probe is also a method known to the skilled worker for identifying homologs in other species. In this context, the probes derived from the nucleic acid sequence as shown in SEQ ID No: 1, 3, 5, 7, 9, 11, 13, 15, 17, 19, 21, 23, 25, 27, 29, 31, 33, 35, 37, 39, 41, or 43 have a length of at least 20 bp, preferably at least 50 bp, especially preferably at least 100 bp, very especially preferably at least 200 bp, most preferably at least 400 bp. The probe can also be one or more kilobases in length, for example 1 kb, 1.5 kb or 3 kb. A DNA strand which is complementary to the sequences described in SEQ ID No: 1, 3, 5, 7, 9, 11, 13, 15, 17, 19, 21, 23, 25, 27, 29, 31, 33, 35, 37, 39, 41, or 43, or a fragment of same strand with a length of between 20 bp and several kilobases may also be employed for screening the libraries.

In the method according to the invention, those DNA molecules which hybridize under standard conditions with the nucleic acid molecules described by SEQ ID No: 1, 3, 5, 7, 9, 11, 13, 15, 17, 19, 21, 23, 25, 27, 29, 31, 33, 35, 37, 39, 41, or 43 and which code for Armadillo repeat ARM1 proteins, with the nucleic acid molecules which are complementary to the above or with parts of the above and which, as complete sequences, code for polypeptides which have essentially identical properties, preferably functional properties, to the polypeptides described in SEQ ID No: 2, 4, 6, 8, 10, 12, 14, 16, 18, 20, 22, 24, 26, 28, 30, 32, 34, 36, 38, 42, 44, 60, 61 or 62, may also be used.

"Standard hybridization conditions" is to be understood in the broad sense and means, depending on the application, stringent or else less stringent hybridization conditions. Such hybridization conditions are described, inter alia, in Sambrook J, Fritsch E F, Maniatis T et al., in Molecular Cloning (A Laboratory Manual), 2nd edition, Cold Spring Harbor Laboratory Press, 1989, pages 9.31-9.57) or in Current Protocols in Molecular Biology, John Wiley & Sons, N.Y. (1989), 6.3.1-6.3.6.

The skilled worker would choose hybridization conditions from his specialist knowledge which allow him to differentiate between specific and unspecific hybridizations.

For example, the conditions during the wash step can be selected from among low-stringency conditions (with approximately 2×SSC at 50° C.) and high-stringency conditions (with approximately 0.2×SSC at 50° C., preferably at 65° C.) (20×SSC: 0.3M sodium citrate, 3M NaCl, pH 7.0). Moreover, the temperature during the wash step can be raised from low-stringency conditions at room temperature, approximately 22° C., to higher-stringency conditions at approximately 65° C. The two parameters, salt concentration and temperature can be varied simultaneously or else singly, keeping in each case the other parameter constant. During the hybridization, it is also possible to employ denaturant agents such as, for example, formamide or SOS. In the presence of 50% formamide, the hybridization is preferably carried out at 42° C. Some preferred conditions for hybridization and wash step are detailed hereinbelow:

(1) Hybridization conditions can be selected for example among the following conditions:
  a) 4×SSC at 65° C.,
  b) 6×SSC at 45° C.,
  c) 6×SSC, 100 µg/ml denatured fragmented fish sperm DNA at 68° C.,
  d) 6×SSC, 0.5% SDS, 100 µg/ml denatured salmon sperm DNA at 68° C.,
  e) 6×SSC, 0.5% SDS, 100 µg/ml denatured fragmented salmon sperm DNA, 50% formamide at 42° C.,
  f) 50% formamide, 4×SSC at 42° C., or
  g) 50% (vol/vol) formamide, 0.1% bovine serum albumin, 0.1% Ficoll, 0.1% polyvinylpyrrolidone, 50 mM sodium phosphate buffer pH 6.5, 750 mM NaCl, 75 mM sodium citrate at 42° C., or
  h) 2× or 4×SSC at 50° C. (low-stringency condition),
  i) 30 to 40% formamide, 2× or 4×SSC at 42° C. (low-stringency condition),
  j) 500 mN sodium phosphate buffer pH 7.2, 7% SDS (g/V), 1 mM EDTA, 10 µg/ml single stranded DNA, 0.5% BSA (g/V) (Church and Gilbert, Genomic sequencing. Proc. Natl. Acad. Sci. U.S.A. 81:1991. 1984)

(2) Wash steps can be selected for example among the following conditions:
  a) 0.015 M NaCl/0.0015 M sodium citrate/0.1% SDS at 50° C.
  b) 0.1×SSC at 65° C.
  c) 0.1×SSC, 0.5% SDS at 68° C.
  d) 0.1×SSC, 0.5% SDS, 50% formamide at 42° C.
  e) 0.2×SSC, 0.1% SDS at 42° C.
  f) 2×SSC at 65° C. (low-stringency condition).

In one embodiment, the hybridization conditions are selected as follows:

A hybridization buffer comprising formamide, NaCl and PEG 6000 is chosen. The presence of formamide in the hybridization buffer destabilizes double-strand nucleic acid molecules, whereby the hybridization temperature can be lowered to 42° C. without thereby reducing the stringency. The use of salt in the hybridization buffer increases the renaturation rate of a duplex DNA, in other words the hybridization efficiency. Although PEG increases the viscosity of the solution, which has a negative effect on the renaturation rates, the presence of the polymer in the solution increases the concentration of the probe in the remaining medium, which increases the hybridization rate. The composition of the buffer is:

| Hybridization buffer |
| --- |
| 250 mM sodium phosphate buffer pH 7.2 |
| 1 mM EDTA |
| 7% SDS (g/v) |
| 250 mM NaCl |
| 10 µg/ml ssDNA |
| 5% polyethylene glycol (PEG) 6000 |
| 40% formamide |

The hybridizations are carried out overnight at 42° C. On the following morning, the filters are washed 3× with 2×SSC+ 0.1% SOS for in each case approximately 10 minutes.

In a further preferred embodiment of the present invention, an increase in the resistance in the method according to the invention is achieved by
(a) reducing the expression of at least one Armadillo repeat ARM1 protein;
(b) reducing the stability of at least one Armadillo repeat ARM1 protein or of the mRNA molecules which correspond to this Armadillo repeat ARM1 protein;
(c) reducing the activity of at least one Armadillo repeat ARM1 protein;
(d) reducing the transcription of at least one gene which codes for Armadillo repeat ARM1 protein by expressing an endogenous or artificial transcription factor; or
(e) adding, to the food or to the medium, an exonogous factor which reduces the Armadillo repeat ARM1 protein activity.

"Gene expression" and "expression" are to be understood as being synonymous and mean the realization of the information which is stored in a nucleic acid molecule. Reducing the expression of a gene therefore comprises the reduction of the polypeptide quantity of the encoded protein, for example of the Armadillo repeat ARM1 polypeptide or of the Armadillo repeat ARM1 protein function. The reduction of the gene expression of an Armadillo repeat ARM1 protein gene can be realized in many different ways, for example by one of the methods listed hereinbelow.

"Reduction", "reducing" or "to reduce" in the context of an Armadillo repeat ARM1 protein or Armadillo repeat ARM1 protein function is to be interpreted in the broad sense and comprises the partial or essentially complete inhibition or blockage of the functionality of an Armadillo repeat ARM1 polypeptide in a plant or a part, tissue, organ, cells or seeds derived therefrom, based on different cell-biological mechanisms.

Reducing within the meaning of the invention also comprises a quantitive reduction of an Armadillo repeat ARM1 polypeptide down to an essentially complete absence of the Armadillo repeat ARM1 polypeptide (i.e. lack of detectability of Armadillo repeat ARM1 protein function or lack of immunological detectability of the Armadillo repeat ARM1 protein). Here, the expression of a certain Armadillo repeat ARM1 polypeptide or the Armadillo repeat ARM1 protein function in a cell or an organism is preferably reduced by more than 50%, especially preferably by more than 80%, very especially preferably by more than 90%, in comparison with a suitable control, i.e. to the wildtype of the same type, for example of the same genus, species, variety, cultivar and the like ("control plants"), to which this method has not been applied, under otherwise essentially identical conditions (such as, for example, culture conditions, age of the plants and the like).

In accordance with the invention, there are described various strategies for reducing the expression of an Armadillo repeat ARM1 protein or an Armadillo repeat ARM1 protein function. The skilled worker recognizes that a series of further methods is available for influencing the expression of an Armadillo repeat ARM1 polypeptide or of the Armadillo repeat ARM1 protein function in the desired manner.

In one embodiment, a reduction in the Armadillo repeat ARM1 protein function is achieved in the method according to the invention by applying at least one method selected from the group consisting of:

a) introducing a nucleic acid molecule coding for ribonucleic acid molecules suitable for forming double-strand ribonucleic acid molecules (dsRNA), where the sense strand of the dsRNA molecule has at least 30% homology with the nucleic acid molecule according to the invention, for example with one of the nucleic acid molecules as shown in SEQ ID No: 1, 3, 5, 7, 9, 11, 13, 15, 17, 19, 21, 23, 25, 27, 29, 31, 33, 35, 37, 39, 41 or 43, or coding for a consensus sequence as shown in SEQ ID NO.: 60, 61, or 62, or comprises a fragment of at least 17 base pairs, which has at least 50% homology with a nucleic acid molecule according to the invention, for example as shown in SEQ ID No: 1, 3, 5, 7, 9, 11, 13, 15, 17, 19, 21, 23, 25, 27, 29, 31, 33, 35, 37, 39, 41 or 43 or coding for a consensus sequence as shown in SEQ ID NO.: 60, 61 or 62, or with a functional equivalent of same, or introducing (an) expression cassette(s) which ensure(s) their expression.

b) introducing a nucleic acid molecule coding for an antisense ribonucleic acid molecule which has at least 30% homology with the noncoding strand of one of the nucleic acid molecules according to the invention, for example a nucleic acid molecule as shown in SEQ ID No: 1, 3, 5, 7, 9, 11, 13, 15, 17, 19, 21, 23, 25, 27, 29, 31, 33, 35, 37, 39, 41 or 43 or coding for a consensus sequence as shown in SEQ ID NO.: 60, 61 or 62, or comprising a fragment of at least 15 base pairs with at least 50% homology with a noncoding strand of a nucleic acid molecule according to the invention, for example as shown in SEQ ID No: 1, 3, 5, 7, 9, 11, 13, 15, 17, 19, 21, 23, 25, 27, 29, 31, 33, 35, 37, 39, 41 or 43 or coding for a consensus sequence as shown in SEQ ID NO.: 60, 61 or 62, or with a functional equivalent thereof. Comprised are those methods in which the antisense nucleic acid sequence against an Armadillo repeat ARM1 protein gene (i.e. genomic DNA sequences) or an Armadillo repeat ARM1 protein gene transcript (i.e. RNA sequences). Also comprised are α-anomeric nucleic acid sequences.

c) introducing a ribozyme which specifically cleaves, for example catalytically, the ribonucleic acid molecules encoded by a nucleic acid molecule according to the invention, for example as shown in SEQ ID No: 1, 3, 5, 7, 9, 11, 13, 15, 17, 19, 21, 23, 25, 27, 29, 31, 33, 35, 37, 39, 41 or 43 or coding for a consensus sequence as shown in SEQ ID NO.: 60, 61 or 62 or by their functional equivalents, by introducing an expression cassette which ensures the expression of such a ribozyme.

d) introducing an antisense nucleic acid molecule as specified in b), in combination with a ribozyme or with an expression cassette which ensures the expression of the ribozyme.

e) introducing nucleic acid molecules coding for sense ribonucleic acid molecules of a polypeptide according to the invention, for example as shown in the sequences SEQ ID No: 2, 4, 6, 8, 10, 12, 14, 16, 18, 20, 22, 24, 26, 28, 30, 32, 34, 36, 38, 42, 44, 60, 61 or 62, for polypeptides with at least 40% homology with the amino acid sequence of a protein according to the invention, or is a functional equivalent thereof.

f) introducing a nucleic acid sequence coding for a dominant-negative polypeptide suitable for suppressing the Armadillo repeat ARM1 protein function, or introducing an expression cassette which ensures the expression of this nucleic acid sequence.

g) introducing a factor which can specifically bind Armadillo repeat ARM1 polypeptides or the DNA or RNA molecules coding for these polypeptides, or introducing an expression cassette which ensures the expression of this factor.

h) introducing a viral nucleic acid molecule which brings about a degradation of mRNA molecules which code for Armadillo repeat ARM1 protein, or introducing an expression cassette which ensures the expression of this nucleic acid molecule.

i) introducing a nucleic acid construct suitable for inducing a homologous recombination on genes coding for Armadillo repeat ARM1 protein.

j) introducing one or more mutations into one or more coding gene(s) coding for Armadillo repeat ARM1 proteins for generating a loss of function (for example generation of stop codons, reading-frame shifts and the like).

Each one of these methods can bring about a reduction in the Armadillo repeat ARM1 protein expression or Armadillo repeat ARM1 protein function for the purposes of the invention. A combined use is also feasible. Further methods are known to the skilled worker and can comprise the hindering or prevention of the processing of the Armadillo repeat ARM1 polypeptide, of the transport of the Armadillo repeat ARM1 polypeptide or its mRNA, inhibition of the ribosome attachment, inhibition of the RNA splicing, induction of an Armadillo repeat ARM1-protein-RNA-degrading enzyme and/or inhibition of the translational elongation or termination.

A reduction in the Armadillo repeat ARM1 protein function or Armadillo repeat ARM1 polypeptide quantity is preferably achieved by a reduced expression of an endogenous Armadillo repeat ARM1 protein gene.

The individual preferred processes are described briefly hereinbelow:

a) Introducing a Double-stranded Armadillo Repeat ARM1 Protein RNA Nucleic Acid Sequence (Armadillo Repeat ARM1 Protein dsRNA)

The method of regulating genes by means of double-stranded RNA ("double-stranded RNA interference"; dsRNAi) has been described many times for animal and plant organisms (e.g. Matzke M A et al. (2000) Plant Mol Biol 43:401-415; Fire A. et al (1998) Nature 391:806-811; WO 99/32619; WO 99/53050; WO 00/68374; WO 00/44914; WO 00/44895; WO 00/49035; WO 00/63364). Efficient gene suppression can also be demonstrated in the case of transient expression, or following the transient transformation, for example as the result of a biolistic transformation (Schweizer P et al. (2000) Plant J 2000 24: 895-903). dsRNAi processes are based on the phenomenon that simultaneously introducing the complementary strand and counterstrand of a gene transcript suppresses the expression of the corresponding gene in a highly efficient manner. The phenotype caused is very similar to that of a corresponding knock-out mutant (Waterhouse P M et al. (1998) Proc Natl Acad Sci USA 95:13959-64).

The dsRNAi method has proved to be particularly efficient and advantageous when reducing the protein expression (WO 99/32619).

With regard to the double-stranded RNA molecules, Armadillo repeat ARM1 protein nucleic acid sequence preferably means one of the sequences as shown in SEQ ID No: 1, 3, 5, 7, 9, 11; 13, 15, 17, 19, 21, 23, 25, 27, 29, 31, 33, 35, 37, 39, 41 or 43, or coding for a consensus sequence as shown in SEQ ID NO.: 60, 61 or 62, or sequences which are essentially identical to those, preferably which have at least 50%, 60%, 70%, 80% or 90% or more identity to these, for example approximately 95%, 96%, 97%, 98%, 99% or more identity to these, or fragments of these with a length of at least 17 base pairs. "Essentially identical" means here that the dsRNA sequence may also have insertions, deletions and individual point mutations in comparison with the Armadillo repeat ARM1 protein target sequence while still bringing about an efficient reduction in the expression. In one embodiment, the homology as defined above is at least 50%, for example approximately 80%, or approximately 90%, or approximately 100%, between the "sense" strand of an inhibitory dsRNA and a subsection of an Armadillo repeat ARM1 protein nucleic acid sequence (or between the "antisense" strand and the complementary strand of an Armadillo repeat ARM1 protein nucleic acid sequence). The length of the subsection is approximately 17 bases or more, for example approximately 25 bases, or approximately 50 bases, approximately 100 bases, approximately 200 bases or approximately 300 bases. Alternatively, an "essentially identical" dsRNA can also be defined as a nucleic acid sequence which is capable of hybridizing under stringent conditions with a part of an Armadillo repeat ARM1 protein gene transcript.

The "antisense" RNA strand, too, can have insertions, deletions and individual point mutations in comparison with the complement of the "sense" RNA strand. The homology is preferably at least 80%, for example approximately 90%, or approximately 95%, or approximately 100%, between the "antisense" RNA strand and the complement of the "sense" RNA strand.

"Subsection of the "sense" RNA transcript" of a nucleic acid molecule coding for an Armadillo repeat ARM1 polypeptide or a functional equivalent thereof means fragments of an RNA or mRNA transcribed by a nucleic acid molecule coding for an Armadillo repeat ARM1 polypeptide or a functional equivalent thereof, preferably by an Armadillo repeat ARM1 protein gene. In this context, the fragments preferably have a sequence length of approximately 20 bases or more, for example approximately 50 bases, or approximately 100 bases, or approximately 200 bases, or approximately 500 bases. Also comprised is the complete transcribed RNA or mRNA.

The dsRNA can consist of one or more strands of polymerized ribonucleotides. Modifications both of the sugar-phosphate backbone and of the nucleosides may also be present. For example, the phosphodiester bonds of the natural RNA can be modified in such a way that they comprise at least one nitrogen or sulfur heteroatom.

Bases can be modified in such a way that the activity of, for example, adenosin deaminase is restricted. Such and further modifications are described hereinbelow in the methods of stabilizing antisense RNA.

To achieve the same purpose, it is, of course, also possible to introduce, into the cell or the organism, a plurality of individual dsRNA molecules, each of which comprises one of the above-defined ribonucleotide sequence segments.

The dsRNA can be prepared enzymatically or fully or partially by chemical synthesis.

If the two strands of the dsRNA are to be combined in one cell or plant, this can be accomplished in various ways,
a) transformation of the cell or plant with a vector which comprises both expression cassettes,
b) cotransformation of the cell or plant with two vectors, where one comprises the expression cassettes with the "sense" strand while the other one comprises the expression cassettes with the "antisense" strand, and/or
c) hybridization of two plants which have been transformed with in each case one vector, where one comprises the expression cassettes with the "sense" strand, while the other one comprises the expression cassettes with the "antisense" strand.

The formation of the RNA duplex can be initiated either externally or internally of the cell. As described in WO 99/53050, the dsRNA can also comprise a hairpin structure, by linking "sense" and "antisense" strand by means of a "linker" (for example an intron). The autocomplementary dsRNA structures are preferred since they only require the expression of a construct and always comprise the complementary strands in an equimolar ratio.

The expression cassettes coding for the "antisense" or "sense" strand of a dsRNA or for the autocomplementary strand of the dsRNA are preferably inserted into a vector and stably (for example using selection markers) inserted into the genome of a plant using the methods described hereinbelow in order to ensure permanent expression of the dsRNA.

The dsRNA can be introduced using a quantity which makes possible at least one copy per cell. Higher quantities (for example at least 5, 10, 100, 500 or 1000 copies per cell) can make, if appropriate, a more efficient reduction.

In order to bring about an efficient reduction in the Armadillo repeat ARM1 protein expression, 100% sequence identity between dsRNA and an Armadillo repeat ARM1 protein gene transcript or the gene transcript of a functionally equivalent gene is a possible embodiment, but not necessarily required. Accordingly, there is the advantage that the method tolerates sequence deviations as they can exist as the result of genetic mutations, polymorphisms or evolutionary divergences. The large number of highly conserved amino acid residues between different Armadillo repeat ARM1 protein sequences of different plants, as shown in the figures with reference to the consensus sequences, allows the conclusion that this polypeptide is highly conserved within plants, so that the expression of a dsRNA derived from one of the disclosed Armadillo repeat ARM1 protein sequences as shown in SEQ ID No: 1, 3, 5, 7, 9, 11, 13, 15, 17, 19, 21, 23, 25, 27, 29, 31, 33, 35, 37, 39, 41 or 43 will also have an advantageous effect in other plant species.

As the result of the high number of conserved residues and of the homology between the individual Armadillo repeat ARM1 polypeptides and their functional equivalents, it may also be possible to suppress the expression of further homologous Armadillo repeat ARM1 polypeptides and/or their functional equivalents of the same organism, or else the expression of Armadillo repeat ARM1 polypeptides in other, related species, using a single dsRNA sequence which has been generated starting from a specific Armadillo repeat ARM1 protein sequence of an organism. For this purpose, the dsRNA preferably comprises sequence regions of Armadillo repeat ARM1 protein gene transcripts which correspond to conserved regions. Said conserved regions can be derived readily from sequence alignments, for example as shown in the figures. It is preferred to derive dsRNA sequences from the conserved regions of the consensus sequence which are shown in the figures. Regions which are regarded as being particularly conserved are: AA702 to AA739, AA742 to AA752, AA760 to AA762, AA771 to 779, AA789 to AA790, AA799 to AA821, AA829 to AA843, M879 to AA905, AA924 to AA939, of the consensus sequence depicted in the figures.

A dsRNA can be synthesized chemically or enzymatically. To this end, it is possible to use cellular RNA polymerases or bacteriophage RNA polymerases (such as, for example, T3, T7 or SP6 RNA polymerase). Suitable methods for the in vitro expression of RNA are described (WO 97/32016; U.S. Pat. Nos. 5,593,874; 5,698,425, 5,712,135, 5,789,214, 5,804, 693). A dsRNA which has been synthesized chemically or enzymatically in vitro can be purified from the reaction mixture fully or in part, for example by extraction, precipitation, electrophoresis, chromatography or combinations of these methods, before it is introduced into a cell, tissue or organism. The dsRNA can be introduced into the cell directly or else applied extracellularly (for example into the interstitial space).

However, it is preferred to transform the plant stably with an expression construct which realizes the expression of the dsRNA. Suitable methods are described hereinbelow.

b) Introduction of an Armadillo Repeat ARM1 Protein Antisense Nucleic Acid Sequence Methods of suppressing a certain polypeptide by preventing the accumulation of its mRNA by means of the "antisense" technology have been described many times, including in plants (Sheehy et al. (1988) Proc Natl Acad Sci USA 85; 8805-8809; U.S. Pat. No. 4,801,340; Mol J N et al. (1990) FEBS Lett 268(2):427-430). The antisense nucleic acid molecule hybridizes with, or binds to, the cellular mRNA and/or genomic DNA coding for the callose synthase target polypeptide to be suppressed. The transcription and/or translation of the target polypeptide is thereby suppressed. The hybridization can be accomplished in a traditional manner via the formation of a stable duplex or, in the case of genomic DNA, by binding the antisense nucleic acid molecule to the duplex of the genomic DNA as the result of specific interaction in the large groove of the DNA helix.

An antisense nucleic acid molecule suitable for reducing an Armadillo repeat ARM1 polypeptide can be derived using the nucleic acid sequence which codes for this polypeptide, for example the nucleic acid molecule according to the invention as shown in SEQ ID No: 1, 3, 5, 7, 9, 11, 13, 15, 17, 19, 21, 23, 25, 27, 29, 31, 33, 35, 37, 39, 41 or 43 or a nucleic acid molecule coding for a functional equivalent thereof following Watson's and Crick's base-pairing rules. The antisense nucleic acid molecule can be complementary to all of the transcribed mRNA of the said polypeptide, be limited to the coding region or else only consist of an oligonucleotide which is complementary to part of the coding or noncoding sequence of the mRNA. Thus, for example, the oligonucleotide can be complementary to the region which comprises the translation start for said polypeptide. Antisense nucleic acid molecules can have a length of, for example, 20, 25, 30, 35, 40, 45 or 50 nucleotides, but they may also be longer and comprise 100, 200, 500, 1000, 2000 or 5000 nucleotides. Antisense nucleic acid molecules can be expressed recombinantly or synthesized chemically or enzymatically, using methods known to the skilled worker. In the case of chemical synthesis, natural or modified nucleotides can be used. Modified nucleotides can impart an increased biochemical stability to the antisense nucleic acid molecule and lead to an increased physical stability of the duplex formed of antisense nucleic acid sequence and sense target sequence. Examples which can be used are phosphorus thioate derivatives and acridine-substituted nucleotides such as 5-fluorouracil, 5-bromouracil, 5-chlorouracil, 5-iodouracil, hypoxanthine, xanthine, 4-acetylcytosine, 5-(carboxyhydroxylmethyl)-uracil, 5-carboxymethylaminomethyl-2-thiouridine, 5-carboxymethylaminomethyluracil, dihydrouracil, β-D-galactosylqueosine, inosine, N6-isopentenyladenine, 1-methyl-guanine, 1-methylinosine, 2,2-dimethylguanine, 2-methyladenine, 2-methylguanine, 3-methylcytosine, 5-methylcytosine, N6-adenine, 7-methylguanine, 5-methylamino-methyluracil, 5-methoxyaminomethyl-2-thiouracil, β-D-mannosylqueosine, 5'-methoxy-carboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid, 5-methyl-2-thiouracil, 3-(3-amino-3-N2-carboxypropyl)uracil and 2,6-diaminopurine.

In a further preferred embodiment, the expression of an Armadillo repeat ARM1 polypeptide can be inhibited by nucleic acid molecules which are complementary to a conserved region (for example a region which has been conserved as described above) or to a regulatory region of an Armadillo repeat ARM1 protein gene (for example an Armadillo repeat ARM1 protein promoter and/or enhancer) and which form triple-helical structures with the DNA double helix therein, so that the transcription of the Armadillo repeat ARM1 protein gene is reduced. Suitable methods have been described (Helene C (1991) Anticancer Drug Res 6(6):569-84; Helene C et al. (1992) Ann NY Acad Sci 660:27-36; Maher L J (1992) Bioassays 14(12):807-815).

In a further embodiment, the antisense nucleic acid molecule can be an α-anomeric nucleic acid. Such α-anomeric nucleic acid molecules form specific double-stranded hybrids with complementary RNA in which—as opposed to the conventional β-nucleic acids—the two strands run in parallel with one another (Gautier C et al. (1987) Nucleic Acids Res 15:6625-6641). The antisense nucleic acid molecule can furthermore also comprise 2'-O-methylribonucleotides (Inoue et al. (1987) Nucleic Acids Res 15:6131-6148) or chimeric RNA-DNA analogs (Inoue et al. (1987) FEBS Lett 215:327-330).

c) Introduction of a Ribozyme which Specifically, for Example Catalytically, Cleaves the Ribonucleic Acid Molecules Coding for Armadillo Repeat Protein.

Catalytic RNA molecules or ribozymes can be adapted to any target RNA and cleave the phosphodiester backbone at specific positions, whereby the target RNA is functionally deactivated (Tanner N K (1999) FEMS Microbiol Rev 23(3): 257-275). As the result, the ribozyme is not modified itself, but is capable of cleaving further target RNA molecules in an analogous manner, whereby it obtains the characteristics of an enzyme.

In this manner, it is possible to use ribozymes (for example hammerhead ribozymes; Haselhoff and Gerlach (1988) Nature 334:585-591) in order to cleave the mRNA of an enzyme to be suppressed, for example callose syntheses, and to prevent translation. Methods of expressing ribozymes for reducing certain polypeptides are described in (EP 0 291 533, EP 0 321 201, EP 0 360 257). A ribozyme expression has also been described in plant cells (Steinecke P et al. (1992) EMBO J 11(4):1525-1530; de Feyter R et al. (1996) Mol Gen Genet. 250(3):329-338). Ribozymes can be identified from a library of various ribozymes via a selection process (Bartel D and Szostak J W (1993) Science 261:1411-1418). Preferably, the binding regions of the ribozyme hybridize with the conserved regions of the ARM protein as described above.

d) Introduction of an Armadillo Repeat ARM1 Protein Antisense Nucleic Acid Sequence in Combination with a Ribozyme.

The above-described antisense strategy can advantageously be coupled with a ribozyme method. The incorporation of ribozyme sequences into "antisense" RNAs imparts this enzyme-like, RNA-cleaving characteristic to precisely these antisense RNAs and thus increases their efficiency in the inactivation of the target RNA. The preparation and use of suitable ribozyme "antisense" RNA molecules is described, for example, in Haselhoff et al. (1988) Nature 334: 585-591.

The ribozyme technology can increase the efficiency of an antisense strategy. Suitable target sequences and ribozymes can be determined for example as described in "Steinecke P, Ribozymes, Methods in Cell Biology 50, Galbraith et al. eds., Academic Press, Inc. (1995), p. 449-460", by calculating the secondary structure of ribozyme RNA and target RNA and by their interaction (Bayley C C et al. (1992) Plant Mol Biol. 18(2):353-361; Lloyd A M and Davis R W et al. (1994) Mol Gen Genet. 242(6):653-657). For example, it is possible to construct derivatives of the Tetrahymena L-19 IVS RNA which derivatives have complementary regions to the mRNA of the Armadillo repeat ARM1 protein to be suppressed (see also U.S. Pat. Nos. 4,987,071 and 5,116,742).

e) Introduction of an Armadillo Repeat ARM1 Protein Sense Nucleic Acid Sequence for Inducing a Cosuppression The expression of an Armadillo repeat ARM1 protein nucleic acid sequence in sense orientation can lead to a cosuppression of the corresponding homologous, endogenous gene. The expression of sense RNA with homology to an endogenous gene can reduce or cancel the expression of the former, similar to what has been described for antisense approaches (Jorgensen et al. (1996) Plant Mol Biol 31(5): 957-973; Goring et al. (1991) Proc Natl Acad Sci USA 88:1770-1774; Smith et al. (1990) Mol Gen Genet 224:447-481; Napoli et al. (1990) Plant Cell 2:279-289; Van der Krol et al. (1990) Plant Cell 2:291-99). Here, the construct introduced can represent the homologous gene to be reduced either fully or only in part. The possibility of translation is not required. The application of this technology to plants is described for example in Napoli et al. (1990) The Plant Cell 2: 279-289 and in U.S. Pat. No. 5,034,323.

The cosuppression is preferably realized using a sequence which is essentially identical to at least part of the nucleic acid sequence coding for an Armadillo repeat ARM1 protein or a functional equivalent thereof, for example of the nucleic acid molecule according to the invention, for example of the nucleic acid sequence as shown in SEQ ID No: 1, 3, 5, 7, 9, 11, 13, 15, 17, 19, 21, 23, 25, 27, 29, 31, 33, 35, 37, 39, 41 or 43, or of the nucleic acid sequence coding for a functional equivalent thereof.

f) Introduction of Nucleic Acid Sequences Coding for a Dominant-negative Armadillo Repeat ARM1 Protein.

The activity of an Armadillo repeat ARM1 protein can probably also be reduced by expression of a dominant-negative variant of this Armadillo repeat ARM1 protein. Methods of reducing the function or activity of a polypeptide by means of coexpression of its dominant-negative form are known to the skilled worker (Lagna G and Hemmati-Brivanlou A (1998) Current Topics in Developmental Biology 36:75-98; Perlmutter R M and Alberola-lla J (1996) Current Opinion in Immunology 8(2):285-90; Sheppard D (1994) American Journal of Respiratory Cell & Molecular Biology, 11(1):1-6; Herskowitz I (1987) Nature 329(6136):219-22).

A dominant-negative Armadillo repeat ARM1 protein variant can be accomplished for example by altering amino acid residues which are part of the Armadillo repeat ARM1 and, as the result of their mutation, the polypeptide loses its function. Amino acid residues which are preferably to be mutated are those which are conserved in the Armadillo repeat ARM1 proteins of different organisms. Such conserved regions can be determined for example by means of computer-aided comparison ("alignment"). These mutations for obtaining a dominant-negative Armadillo repeat ARM1 protein variant are preferably carried out at the level of the nucleic acid sequence coding for Armadillo repeat ARM1 proteins. A suitable mutation can be realized for example by PCR-mediated in vitro mutagenesis using suitable oligonucleotide primers, by means of which the desired mutation is introduced. Methods which are known to the skilled worker are used for this purpose. For example, the "LA PCR in vitro Mutagenesis Kit" (Takara Shuzo, Kyoto) can be used for this purpose.

g) Introduction of Armadillo Repeat ARM1 Protein Genes, RNAs or Polypeptide-binding Factors.

A reduction of an Armadillo repeat ARM1 protein/gene expression is also possible using specific DNA-binding factors, for example using factors of the zinc finger transcription factor type. These factors attach to the genomic sequence of the endogenous target gene, preferably in the regulatory regions, and bring about a repression of the endogenous gene. The use of such a method makes possible the reduction of the expression of an endogenous Armadillo repeat ARM1 protein gene without it being necessary to recombinantly manipulate the sequence of the latter. Suitable methods for the preparation of suitable factors are described (Dreier B et al. (2001) J Biol Chem 276(31):29466-78; Dreier B et al. (2000) J Mol Biol 303(4):489-502; Beerli R R et al. (2000) Proc Natl Acad Sci USA 97 (4):1495-1500; Beerli R R et al. (2000) J Biol Chem 275(42):32617-32627; Segal D J and Barbas C F 3rd. (2000) Curr Opin Chem Biol 4(1):34-39; Kang J S and Kim J S (2000) J Biol Chem 275(12):8742-8748; Beerli R R et al. (1998) Proc Natl Acad Sci USA 95(25):14628-14633; Kim J S et al. (1997) Proc Natl Acad Sci USA 94(8):3616-3620; Klug A (1999) J Mol Biol 293(2):215-218; Tsai S Y et al. (1998) Adv Drug Deliv Rev 30(1-3):23-31; Mapp A K et al. (2000) Proc Natl Acad Sci USA 97(8):3930-3935; Sharrocks A D et al. (1997) Int J Biochem Cell Biol 29(12):1371-1387; Zhang L et al. (2000) J Biol Chem 275(43):33850-33860).

The selection of these factors can be accomplished using a suitable portion of an Armadillo repeat ARM1 protein gene. This segment is preferably located in the region of the promoter region. However, for the purpose of suppressing a gene, it may also be located in the region of the coding exons or introns. The corresponding segments are obtainable for the skilled worker by means of database search from the gene library or, starting from an Armadillo repeat ARM1 protein cDNA whose gene is not present in the gene library, by screening a genomic library for corresponding genomic clones. The methods required for this purpose are known to the skilled worker.

Furthermore, it is possible to introduce, into a cell, factors which themselves inhibit the Armadillo repeat ARM1 protein target polypeptide. The polypeptide-binding factors can be, for example, aptamers (Famulok M and Mayer G (1999) Curr Top Microbiol Immunol 243:123-36) or antibodies or antibody fragments. The preparation of these factors is described and known to the skilled worker. For example, a cytoplasmic scFv antibody has been employed for modulating the activity of the phytochrome A protein in recombinantly modified tobacco plants (Owen M et al. (1992) Biotechnology (NY) 10(7):790-794; Franken E et al. (1997) Curr Opin Biotechnol 8(4):411-416; Whitelam (1996) Trend Plant Sci 1:286-272).

Gene expression can also be suppressed by customized, low-molecular-weight synthetic compounds, for example of the polyamide type (Dervan P B and Bürli R W (1999) Current Opinion in Chemical Biology 3:688-693; Gottesfeld J M et al. (2000) Gene Expr 9(1-2):77-91). These oligomers consist of the units 3-(dimethylamino)-propylamine, N-methyl-3-hydroxypyrrole, N-methylimidazole and N-methylpyrrole and can be adapted to each segment of double-stranded DNA in such a way that they bind into the major group in a sequence-specific fashion and block the expression of the gene sequences therein. Suitable methods are described (see, inter alia, Bremer R E et al. (2001) Bioorg Med Chem. 9(8): 2093-103; Ansari A Z et al. (2001) Chem Biol. 8(6):583-92;

Gottesfeld J M et al. (2001) J Mol Biol. 309(3):615-29; Wurtz N R et al. (2001) Org Lett 3(8):1201-3; Wang C C et al. (2001) Bioorg Med Chem 9(3):653-7; Urbach A R and Dervan P B (2001) Proc Natl Acad Sci USA 98(8):4343-8; Chiang S Y et al. (2000) J Biol Chem. 275(32):24246-54).

h) Introduction of the Viral Nucleic Acid Molecules and Expression Constructs which Bring about the Degradation of Armadillo Repeat ARM1 Protein RNA.

The Armadillo repeat ARM1 protein expression can also be realized efficiently by induction of the specific Armadillo repeat ARM1 protein RNA degradation by the plant with the aid of a viral expression system (Amplikon) (Angell, S M et al. (1999) Plant J. 20(3):357-362). These systems—also referred to as "VIGS" (viral-induced gene silencing)—introduce, by means of viral vectors, nucleic acid sequences with homology to the transcripts to be suppressed into the plant. Transcription is then cancelled, probably mediated by plant defense mechanisms against viruses. Suitable techniques and methods are described (Ratcliff F et al. (2001) Plant J 25(2): 237-45; Fagard M and Vaucheret H (2000) Plant Mol Biol 43(2-3):285-93; Anandalakshmi R et al. (1998) Proc Natl Acad Sci USA 95(22):13079-84; Ruiz M T (1998) Plant Cell 10(6): 937-46).

The methods of the dsRNAi, of cosuppression by means of sense RNA and of "VIGS" ("virus-induced gene silencing") are also referred to as "post-transcriptional gene silencing" (PTGS). PTGS methods are particularly advantageous because the demands for the homology between the endogenous gene to be suppressed and the recombinantly expressed sense or dsRNA nucleic acid sequence are less stringent than, for example, in a traditional antisense approach. Suitable homology criteria are mentioned in the description of the dsRNAI method and can generally be applied to PTGS methods or dominant-negative approaches. As the result of the high degree of homology between the Armadillo repeat ARM1 proteins from maize, wheat, rice and barley, it can be concluded that this polypeptide is highly conserved in plants. Thus, it is probably also possible, using the Armadillo repeat ARM1 protein nucleic acid molecules as they are shown herein, in particular by means of the nucleic acid molecules which are derived from the consensus sequences, or else for example from the nucleic acid molecules from *Arabidopsis*, barley, maize or rice, also efficiently to suppress the expression of homologous Armadillo repeat ARM1 polypeptides in other species without the isolation and structure elucidation of the Armadillo repeat ARM1 protein homologs found in these species being compulsory. This substantially simplifies the labor required.

i) Introduction of a Nucleic Acid Construct Suitable for Inducing a Homologous Recombination on Genes Coding for Armadillo Repeat ARM1 Proteins, for Example for the Generation of Knockout Mutants.

To generate a homologously-recombinant organism with reduced Armadillo repeat ARM1 protein function, one uses for example a nucleic acid construct which comprises at least part of an endogenous Armadillo repeat ARM1 protein gene which is modified by a deletion, addition or substitution of at least one nucleotide, for example in the conserved regions, in such a way that the functionality is reduced or entirely nullified.

For example, the primary, secondary, tertiary or quaternary structure can be disrupted, for example in such a manner that the binding ability of one or more Armadillo repeats no longer exists. Such a disruption can be accomplished for example by the mutation of one or more residues which are indicated in the consensus sequence as being conserved or highly conserved.

The modification can also relate to the regulatory elements (for example the promoter) of the gene, so that the coding sequence remains unaltered, but that expression (transcription and/or translation) does not take place and is reduced.

In the case of conventional homologous recombination, the modified region is flanked at its 5' and 3' terminus by further nucleic acid sequences which must be of sufficient length for making possible the recombination. As a rule, the length is in the range of from several hundred or more bases up to several kilobases (Thomas K R and Capecchi M R (1987) Cell 51:503; Strepp et al. (1998) Proc Natl Acad Sci USA 95(8): 4368-4373). To carry out the homologous recombination, the host organism—for example a plant—is transformed with the recombination construct using the methods described hereinbelow, and clones which have undergone successful recombination are selected using for example a resistance to antibiotics or herbicides.

j) Introduction of Mutations into Endogenous Armadillo Repeat ARM1 Protein Genes for Generating a Loss of Function (for Example Generation of Stop Codons, Reading-frame Shifts and the Like)

Further suitable methods for reducing the Armadillo repeat ARM1 protein function are the introduction of nonsense mutations into endogenous Armadillo repeat ARM1 protein genes, for example by means of generation of knockout mutants with the aid of, for example, T-DNA mutagenesis (Koncz et al. (1992) Plant Mol Biol 20(5):963-976), ENU (N-ethyl-N-nitrosourea)-mutagenesis or homologous recombination (Hohn B and Puchta (1999) H Proc Natl Acad Sci USA 96:8321-8323.) or EMS mutagenesis (Birchler J A, Schwartz D. Biochem Genet. 1979 December; 17(11-12): 1173-80; Hoffmann G R. Mutat Res. 1980 January; 75(1):63-129). Point mutations can also be generated by means of DNA-RNA hybrid oligonucleotides, which are also known as "chimeraplasty" (Zhu et al. (2000) Nat Biotechnol 18(5):555-558, Cole-Strauss et al. (1999) Nucl Acids Res 27(5):1323-1330; Kmiec (1999) Gene therapy American Scientist 87(3): 240-247).

The cell- or tissue-specific reduction in the activity of an sARM1 can be effected for example by expressing a suitable construct, which, for example, an abovementioned nucleic acid molecule, for example the antisense RNA, dsRNA, RNAi, ribozyme, with a suitable tissue-specific promoter, for example a promoter as described herein as being specific for epidermis or mesophyll.

For the purposes of the present invention, "mutations" means the modification of the nucleic acid sequence of a gene variant in a plasmid or in the genome of an organism. Mutations can arise for example as the result of errors in the replication, or they can be caused by mutagens. While the spontaneous mutation rate in the cell genome of organisms is very low, the skilled worker is familiar with a multiplicity of biological, chemical or physical mutagens.

Mutations comprise substitutions, additions, deletions of one or more nucleic acid residues. Substitutions are understood as meaning the exchange of individual nucleic acid bases; one distinguishes between transitions (substitution of a purine base for a purine base, or of a pyrimidine base for a pyrimidine base) and transversions (substitution of a pyrimidine base for a purine base (or vice versa)).

Additions or insertions are understood as meaning the incorporation of additional nucleic acid residues into the DNA, it being possible to result in reading-frame shifts. In the case of such reading-frame shifts, one distinguishes between "in-frame" insertions/additions and "out-of-frame" insertions. In the case of the "in-frame" insertions/additions, the reading frame is retained, and a polypeptide which is enlarged by the number of the amino acids encoded by the inserted nucleic acids results. In the case of "out-of-frame" insertions/additions, the original reading frame is lost, and the formation of a complete and functional polypeptide is no longer possible in many cases, naturally dependent on the location of the mutation.

Deletions describe the loss of one or more base pairs, which likewise lead to "in-frame" or "out-of-frame" reading-frame shifts and the consequences which this entails regarding the formation of an intact protein.

The mutagenic agents (mutagens) which can be used for generating random or site-specific mutations, and the methods and techniques which can be applied, are known to the skilled worker. Such methods and mutagens are described for example in A. M. van Harten [(1998), "Mutation breeding: theory and practical applications", Cambridge University Press, Cambridge, UK], E Friedberg, G Walker, W Siede [(1995), "DNA Repair and Mutagenesis", Blackwell Publishing], or K. Sankaranarayanan, J. M. Gentile, L. R. Ferguson [(2000) "Protocols in Mutagenesis", Elsevier Health Sciences].

Usual molecular-biological methods and processes, such as the in vitro mutagenesis kit, LA PCR in vitro Mutagenesis Kit (Takara Shuzo, Kyoto), or PCR mutageneses using suitable primers may be employed for introducing site-specific mutations.

As has already been mentioned above, a multiplicity of chemical, physical and biological mutagens exists.

Those mentioned hereinbelow are given by way of example, but not by limitation.

Chemical mutagens can be distinguished by their mechanism of action. Thus, there are base analogs (for example 5-bromouracil, 2-aminopurine), mono- and bifunctional alkylating agents (for example monofunctional agents such as ethylmethylsulfonate, dimethyl sulfate, or bifunctional agents such as dichloroethyl sulfite, mitomycin, nitrosoguanidine-dialkylnitrosamine, N-nitrosoguanidine derivatives) or intercalating substances (for example acridine, ethidium bromide).

Physical mutagens are, for example, ionizing radiation. Ionizing radiation is electromagnetic waves or particle radiation capable of ionizing molecules, i.e. of removing electrons from the latter. The remaining ions are highly reactive in most cases, so that, if they are generated in live tissue, are capable of causing great damage, for example to the DNA, and (at low intensity) thereby inducing mutations. Ionizing radiation is, for example, gamma-radiation (photo energy of approximately one megaelectron volt MeV), X-rays (photo energy of a plurality of or many kiloelectron volts keV) or else ultraviolet light (UV light, photon energy of above 3.1 eV). UV light causes the formation of dimers between bases; with thymidine dimers, which give rise to mutations, being the most frequent here.

The traditional generation of mutants by treating the seeds with mutagenic agents such as, for example, ethylmethylsulfonate (EMS) (Birchler J A, Schwartz D. Biochem Genet. 1979 December; 17(11-12):1173-80; Hoffmann G R. Mutat Res. 1980 January; 75(1):63-129) or ionizing radiation has been joined by the use of biological mutagens, for example transposons (for example Tn5, Tn903, Tn916, Tn1000, Balcells et al., 1991, May B P et al. (2003) Proc Natl Acad Sci USA. September 30; 100(20):11541-6.) or molecular-biological methods such as the mutagenesis by means of T-DNA insertion (Feldman, K. A. Plant J. 1:71-82.1991, Koncz et al. (1992) Plant Mol Biol 20(5):963-976).

The use of chemical or biological mutagens is preferred for the generation of mutated gene variants. In the case of chemical agents, the generation of mutants by use of EMS (ethylmethylsulfonate) mutagenesis is mentioned by particular preference. In the case of the generation of mutants using biological mutagenesis, the T-DNA mutagenesis or transposon mutagenesis may be mentioned by preference.

Thus, it is also possible to employ those polypeptides for the method according to the invention which are obtained as the result of a mutation of a polypeptide according to the invention, for example as shown in SEQ ID No: 2, 4, 6, 8, 10, 12, 14, 16, 18, 20, 22, 24, 26, 28, 30, 32, 34, 36, 38, 42, 44, 60, 61 or 62.

All substances and compounds which directly or indirectly bring about a reduction in the polypeptide quantity, RNA quantity, gene activity or polypeptide activity of an Armadillo repeat ARM1 protein will be summarized in this application under the term "anti-Armadillo repeat ARM1 protein compounds". The term "anti-Armadillo repeat ARM1 protein compound" explicitly includes the nucleic acid sequences, peptides, proteins or other factors which are employed in the above-described methods.

In a further preferred embodiment of the present invention, an increase in the resistance to pathogens from the families Blumeriaceae, Pucciniaceae, Mycosphaerellaceae and Hypocreaceae in a monocotyledonous or dicotyledonous plant or an organ, tissue or a cell thereof is obtained by:
a) introduction, into a plant cell, of a recombinant expression cassette comprising an "anti-Armadillo repeat ARM1 protein compound" in operable linkage with a promoter which is active in plants;
b) regeneration of the plant from the plant cell; and
c) expression of said "anti-Armadillo repeat ARM1 protein compound" in a sufficient quantity and over a sufficiently long period to generate, or to increase, a pathogen resistance in said plant.

For example, regarding a nucleic acid sequence, an expression cassette or a vector comprising said nucleic acid sequence or an organism transformed with said nucleic acid sequence, expression cassette or vector, "transgenic" means all those constructs or organisms which are the result of recombinant methods and in which either
a) the Armadillo repeat ARM1 protein nucleic acid sequence, or
b) a genetic control sequence which is operably linked with the Armadillo repeat ARM1 protein nucleic acid sequence, for example a promoter, or
c) (a) and (b)
are not in their natural genetic environment or have been modified by recombinant methods, it being possible for the modification to be for example a substitution, addition, deletion or insertion of one or more nucleotide residue(s). Natural genetic environment means the natural chromosomal locus in the original organism, or else the presence in a genomic library. In the case of a genomic library, the natural genetic environment of the nucleic acid sequence is preferably retained, at least in part, the environment flanks the nucleic acid sequence at least on one side and has a sequence length of at least 50 bp, preferably at least 500 bp, especially preferably at least 1000 bp, very especially preferably at least 5000 bp. A naturally occurring expression cassette—for example the naturally occurring combination of the Armadillo repeat ARM1 protein promoter with the corresponding Armadillo repeat ARM1 protein gene—becomes a transgenic expression cassette when the latter is modified by non-natural, synthetic ("artificial") methods, such as, for example, treatment with a mutagen. Suitable methods are described (U.S. Pat. No. 5,565,350; WO 00/15815).

For the purposes of the invention, "introduction" comprises all those methods which are suitable for introducing an "anti-Armadillo repeat ARM1 protein compound" directly or indirectly into a plant or into a cell, compartment, tissue, organ or seeds thereof, or for generating such a compound therein. It comprises direct and indirect methods. The introduction can lead to a transient presence of one "anti-Armadillo repeat ARM1 protein compound" (for example of a dsRNA) or else to a stable presence.

As the result of the differing nature of the above-described approaches, the "anti-Armadillo repeat ARM1 protein compound" can exert its function directly (for example by insertion into an endogenous Armadillo repeat ARM1 protein gene). However, the function can also be exerted indirectly after transcription into an RNA (for example in the case of antisense approaches) or after transcription and translation into a protein (for example in the case of binding factors). Both direct and indirectly acting "anti callose synthase compounds" are comprised in accordance with the invention.

"Introduction" comprises, in the context of this description, in general for example methods such as transfection, transduction or transformation.

Thus, "anti-Armadillo repeat ARM1 compound" also comprises for example recombinant expression constructs which bring about an expression (i.e. transcription and, if appropriate, translation) of, for example, an Armadillo repeat ARM1 protein dsRNA or an Armadillo repeat ARM1 protein "antisense" RNA, preferably in a plant or in a part, tissue, organ or seed thereof.

In said expression constructs/expression cassettes, a nucleic acid molecule whose expression (transcription and, if appropriate, translation) generates an "anti-Armadillo repeat ARM1 protein compound" is preferably in operable linkage with at least one genetic control element (for example a promoter) which ensures an expression in plants. If the expression construct is to be introduced directly into the plant and the "anti-Armadillo repeat ARM1 protein compound" (for example the Armadillo repeat ARM1 protein dsRNA) is to be generated therein in p/ante, plant-specific genetic control elements (for example promoters) are preferred. However, the "anti-Armadillo repeat ARM1 protein compound" can also be generated in other organisms or in vitro and then be introduced into the plant. Here, all prokaryotic or eukaryotic genetic control elements (for example promoters) which permit the expression in the respective plant which has been chosen for the generation are preferred.

An "operable" linkage is understood as meaning for example the sequential arrangement of a promoter with the nucleic acid sequence to be expressed (for example an "anti-Armadillo repeat ARM1 protein compound") and, if appropriate, further regulatory elements such as, for example, a terminator in such a way that each of the regulatory elements is capable of fulfilling its function in the transgenic expression of the nucleic acid sequence, depending on the arrangement of the nucleic acid sequences to sense or antisense RNA. A direct linkage in the chemical sense is not necessarily required for this purpose. Genetic control sequences such as, for example, enhancer sequences, can also exert their function on the target sequence from positions which are further removed or else from other DNA molecules. Preferred arrangements are those in which the nucleic acid sequence to be expressed recombinantly is positioned behind the sequence which acts as promoter, so that the two sequences are bonded covalently with one another. In this context, the distance between the promoter sequence and nucleic acid sequence to be expressed recombinantly is preferably less than 200 base pairs, especially preferably less than 100 base pairs, very especially preferably less than 50 base pairs.

The preparation of a functional linkage and the preparation of an expression cassette can be accomplished by means of customary recombination and cloning techniques as are described for example in Maniatis. T, Fritsch E F and Sambrook J (1989) Molecular Cloning: A Laboratory Manual, Cold Spring Harbor Laboratory, Cold Spring Harbor (NY), in Silhavy T J, Berman M L and Enquist L W (1984) Experiments with Gene Fusions, Cold Spring Harbor Laboratory, Cold Spring Harbor (NY), in Ausubel F M et al. (1987) Current Protocols in Molecular Biology, Greene Publishing Assoc. and Wiley Interscience and in Gelvin et al. (1990) in: Plant Molecular Biology Manual. However, it is also possible to position further sequences which, for example, act as a linker with specific restriction enzyme cleavage sites or as a signal peptide between the two sequences. Moreover, the insertion of sequences can lead to the expression of fusion proteins. Preferably, the expression cassette consisting of a linkage of promoter and nucleic acid sequence to be expressed can be present in vector-integrated form and can be inserted into a plant genome by, for example, transformation.

However an expression cassette is also understood as meaning those constructs in which a promoter is placed behind an element of choice, for example by a homologous recombination, for example an endogenous Armadillo repeat ARM1 protein gene, and, in said example, expression of an antisense Armadillo repeat ARM1 protein RNA effects reduction according to the invention of an Armadillo repeat ARM1 protein. Similarly, it is also possible to place an element, for example an "anti-Armadillo repeat ARM1 protein compound" (for example a nucleic acid sequence coding for an Armadillo repeat ARM1 protein dsRNA or an Armadillo repeat ARM1 protein antisense RNA) behind an endogenous promoter in such a way that the same effect occurs. Both approaches result in expression cassettes for the purposes of the invention.

Plant-specific promoters means in principle any promoter which is capable of controlling the expression of genes, in particular foreign genes, in plants or plant parts, plant cells, plant tissues, plant cultures. Here, the expression can be for example constitutional, inducible or development-dependent.

The following promoters are preferred:
a) Constitutive Promoters

Preferred vectors are those which make possible a constitutive expression in plants (Benfey et al. (1989) EMBO J 8:2195-2202). "Constitutive" promoter means those promoters which ensure expression in numerous, preferably all, tissues over a relatively large period of plant development, preferably at all times during plant development. In particular, a plant promoter or a promoter derived from a plant virus is preferably used. The promoter of the 35S transcript of the CaMV cauliflower mosaic virus (Franck et al. (1980) Cell 21:285-294; Odell et al. (1985) Nature 313:810-812; Shewmaker et al. (1985) Virology 140:281-288; Gardner et al. (1986) Plant Mol Biol 6:221-228) or the 19S CaMV Promoter (U.S. Pat. No. 5,352,605; WO 84/02913; Benfey et al. (1989) EMBO J 8:2195-2202) is particularly preferred. A further suitable constitutive promoter is the rubisco small subunit (SSU) promoter (U.S. Pat. No. 4,962,028), the promoter of *agrobacterium* nopaline synthase, the TR double promoter, the *agrobacterium* OCS (octopine synthase) promoter, the ubiquitin promoter (Holtorf S et al. (1995) Plant Mol Biol 29:637-649), the ubiquitin 1 promoter (Christensen et al. (1992) Plant Mol Biol 18:675-689; Bruce et al. (1989) Proc Natl Acad Sci USA 86:9692-9696), the Smas promoter, the cinnamyl-alcohol dehydrogenase promoter (U.S. Pat. No. 5,683,439), the promoters of vacuolar ATPase subunits or the promoter of a proline-rich protein from wheat (WO 91/13991), and further promoters of genes whose constitutive expression in plants is known to the skilled worker. Especially preferred as constitutive promoter is the promoter of nitrilase-1 (nit1) gene from *A. thaliana* (GenBank Acc. No.: Y07648.2, Nukleotide 2456-4340, Hillebrand et al. (1996) Gene 170:197-200).

b) Tissue-specific Promoters

Some embodiments employ promoters with specificities for the anthers, ovaries, flowers, leaves, stems, roots and seeds.

Seed-specific promoters such as, for example, the promoter of phaseolin (U.S. Pat. No. 5,504,200; Bustos M M et al. (1989) Plant Cell 1(9):839-53), of the 2S albumin gene (Joseffson L G et al. (1987) J Biol Chem 262:12196-12201), of legumin (Shirsat A et al. (1989) Mol Gen Genet 215(2): 326-331), of the USP (unknown seed protein; Bäumlein H et al. (1991) Mol Gen Genet 225(3):459-67), of the napin gene (U.S. Pat. No. 5,608,152; Stalberg K et al. (1996) L Planta 199:515-519), of sucrose binding protein (WO 00/26388) or the legumin B4 promoter (LeB4; Bäumlein H et al., (1991) Mol Gen Genet 225: 121-128; Baeumlein et al. (1992) Plant Journal 2(2):233-9; Fiedler U et al. (1995) Biotechnology (NY) 13(10):1090f), the oleosin promoter from *arabidopsis* (WO 98/45461), the Bce4 promoter from *Brassica* (WO 91/13980). Further suitable seed-specific promoters are those of the genes coding for the high molecular weight glutenin (HMWG), gliadin, branching enzyme, ADP glucose pyrophosphatase (AGPase) or starch synthase. Further preferred promoters are those allowing seed-specific expression in monocotyledons such as maize, barley, wheat, rye, rice etc. It is possible and advantageous to employ the promoter of the Ipt2 or Ipt1 gene (WO 95/15389, WO 95/23230) or the promoters described in WO 99/16890 (promoters of the hordein gene, of the glutelin gene, of the oryzin gene, of the prolamin gene, of the gliadin gene, of the zein gene, of the kasirin gene or of the secalin gene).

Tuber-, storage root- or root-specific promoters, for example the patatin class I promoter (B33) or the promoter of the potato cathepsin D inhibitor.

Leaf-specific promoters, for example for example the promoter of the cytosolic FBPase from potato (WO 97/05900), the SSU promoter (small subunit) of the rubisco (ribulose-1, 5-bisphosphate carboxylase) or the ST-LSI promoter from potato (Stockhaus et al. (1989) EMBO J 8:2445-2451). Epidermis-specific promoters, for example the promoter of the OXLP gene ("oxalate oxidase like protein"; Wei et al. (1998) Plant Mol. Biol. 36:101-112).

Examples of other tissue-specific promoters are:
Flower-specific Promoters
for example the phytoen synthase promoter (WO 92/16635) or the promoter of the P-rr gene (WO 98/22593).
Anther-specific Promoters
for example the 5126 promoter (U.S. Pat. Nos. 5,689,049, 5,689,051), the glob-I promoter and the γ-zein promoter.

c) Chemically Inducible Promoters

The expression cassettes may also comprise a chemically inducible promoter (review article: Gatz et al. (1997) Annu. Rev. Plant Physiol Plant Mol Biol 48:89-108) through which expression of the exogenous gene in the plant can be controlled at a particular point in time. Promoters of this type, such as, for example, the PRP1 promoter (Ward et al. (1993) Plant Mol Biol 22:361-366), a salicylic acid-inducible promoter (WO 95/19443), a benzenesulfonamide-inducible promoter (EP 0 388 186), a tetracycline-inducible promoter (Gatz et al. (1992) Plant J 2:397-404), an abscisic acid-inducible promoter (EP 0 335 528) and an ethanol- or cyclohexanone-inducible promoter (WO 93/21334) can likewise be used. Thus, for example, the expression of a molecule which reduces or inhibits the Armadillo repeat ARM1 protein function, such as, for example, the dsRNA, ribozymes, antisense nucleic acid molecules and the like which have been listed above can be induced at suitable points in time.

d) Stress- or Pathogen-inducible Promoters

Very especially advantageous is the use of inducible promoters for expressing the RNAi constructs employed for reducing the callose synthase polypeptide quantity, activity or function, which, for example, when pathogen-inducible promoters are used, makes possible an expression only when required, i.e. in the case of attack by pathogens).

In one embodiment, the method according to the invention therefore uses promoters which are active in plants which are pathogen-inducible promoters.

Pathogen-inducible promoters comprise the promoters of genes which are induced as a result of pathogen attack, such as, for example, genes of PR proteins, SAR proteins, β-1,3-glucanase, chitinase, etc. (for example Redolfi et al. (1983) Neth J Plant Pathol 89:245-254; Uknes, et al. (1992) Plant Cell 4:645-656; Van Loon (1985) Plant Mol Viral 4:111-116; Marineau et al. (1987) Plant Mol Biol 9:335-342; Matton et al. (1987) Molecular Plant-Microbe Interactions 2:325-342; Somssich et al. (1986) Proc Natl Acad Sci USA 83:2427-2430; Somssich et al. (1988) Mol Gen Genetics 2:93-98; Chen et al. (1996) Plant J 10:955-966; Zhang and Sing (1994) Proc Natl Acad Sci USA 91:2507-2511; Warner, et al. (1993) Plant J 3:191-201; Siebertz et al. (1989) Plant Cell 1:961-968) (1989).

Also comprised are wound-inducible promoters such as that of the pinII gene (Ryan (1990) Ann Rev Phytopath 28:425-449; Duan et al. (1996) Nat Biotech 14:494-498), of the wun1 and wun2 gene (U.S. Pat. No. 5,428,148), of the win1 and win2 gene (Stanford et al. (1989) Mol Gen Genet 215:200-208), of the systemin gene (McGurl et al. (1992) Science 225:1570-1573), of the WIP1 gene (Rohmeier et al. (1993) Plant Mol Biol 22:783-792; Eckelkamp et al. (1993) FEBS Letters 323:73-76), of the MPI gene (Corderok et al. (1994) Plant J 6(2):141-150) and the like.

A source of further pathogen-inducible promoters is the PR gene family. A series of elements in these promoters have proved advantageous. Thus, the region −364 to −288 in the promoter of PR-2d mediates salicylate specificity (Buchel et al. (1996) Plant Mol Biol 30, 493-504). The sequence 5'-TCATCTTCTT-3' occurs repeatedly in the promoter of the barley β-1,3-glucanase and in more than 30 other stress-induced genes. In tobacco, this region binds a nuclear protein whose abundance is increased by salicylate. The PR-1 promoters from tobacco and *Arabidopsis* (EP-A 0 332 104, WO 98/03536) are also suitable as pathogen-inducible promoters Preferred, since particularly specifically induced by pathogens, are the "acidic PR-5"-(aPR5) promoters from barley (Schweizer et al. (1997) Plant Physiol 114:79-88) and wheat (Rebmann et al. (1991) Plant Mol Biol 16:329-331). aPR5 proteins accumulate within approximately 4 to 6 hours after attack by pathogens and only show very little background expression (WO 99/66057). One approach for obtaining an increased pathogen-induced specificity is the generation of synthetic promoters from combinations of known pathogen-responsive elements (Rushton et al. (2002) Plant Cell 14, 749-762; WO 00/01830; WO 99/66057). Other pathogen-inducible promoters from different species are known to the skilled worker (EP-A 1 165 794; EP-A 1 062 356; EP-A 1 041 148; EP-A 1 032 684).

Further pathogen-inducible promoters comprise the Flachs Fis1 promoter (WO 96/34949), the Vst1 promoter (Schubert et al. (1997) Plant Mol Biol 34:417-426) and the tobacco EAS4 sesquiterpene cyclase promoter (U.S. Pat. No. 6,100,451).

Other preferred promoters are those which are induced by biotic or abiotic stress, such as, for example, the pathogen-inducible promoter of the PRP1 gene (or gst1 promoter), for example from potato (WO 96/28561; Ward et al. (1993) Plant Mol Biol 22:361-366), the heat-inducible hsp70 or hsp80 promoter from tomato (U.S. Pat. No. 5,187,267), the chill-inducible alpha-amylase promoter from potato (WO 96/12814), the light-inducible PPDK promoter or the wounding-inducible pinII promoter (EP-A 0 375 091).

e) Mesophyll-tissue-specific Promoters

In one embodiment, the method according to the invention employs mesophyll-tissue-specific promoters such as, for example, the promoter of the wheat germin 9f-3.8 gene (GenBank Acc.-No.: M63224) or the barley GerA promoter (WO 02/057412). Said promoters are particularly advantageous since they are both mesophyll-tissue-specific and pathogen-inducible. Also suitable is the mesophyll-tissue-specific *Arabidopsis* CAB-2 promoter (GenBank Acc. No.: X15222), and the *Zea mays* PPCZm1 promoter (GenBank Acc. No.: X63869) or homologs thereof. Mesophyll-tissue-specific means that the transcription of a gene is limited to as few as possible plant tissues which comprise the mesophyll tissue as the result of the specific interaction of cis elements present in the promoter sequence and transcription factors binding to these elements; preferably, it means a transcription which is limited to the mesophyll tissue.

As regards further promoters which are expressed essentially in the mesophyll or in the epidermis, see the enumeration inserted further above.

f) Development-dependent Promoters

Examples of further suitable promoters are fruit ripening-specific promoters such as, for example, the fruit ripening-specific promoter from tomato (WO 94/21794, EP 409 625). Development-dependent promoters include some of the tissue-specific promoters because the development of individual tissues naturally takes place in a development-dependent manner.

Constitutive, and leaf- and/or stem-specific, pathogen-inducible, root-specific, mesophyll-tissue-specific promoters are particularly preferred, with constitutive, pathogen-inducible, mesophyll-tissue-specific and root-specific promoters being most preferred.

A further possibility is for further promoters which make expression possible in further plant tissues or in other organisms such as, for example, *E. coli* bacteria to be operably linked to the nucleic acid sequence to be expressed. All the promoters described above are in principle suitable as plant promoters.

Other promoters which are suitable for expression in plants are described (Rogers et al. (1987) Meth in Enzymol 153: 253-277; Schardl et al. (1987) Gene 61:1-11; Berger et al. (1989) Proc Natl Acad Sci USA 86:8402-8406).

The nucleic acid sequences present in the expression cassettes or vectors of the invention may be operably linked to further genetic control sequences besides a promoter. The term genetic control sequences has a wide meaning and means all sequences which have an influence on the coming into existence or the function of the expression cassette of the invention. For example, genetic control sequences modify transcription and translation in prokaryotic or eukaryotic organisms. The expression cassettes of the invention preferably comprise a promoter with an abovementioned specificity 5'-upstream from the particular nucleic acid sequence which is to be expressed transgenically, and a terminator sequence as additional genetic control sequence 3'-downstream, and if appropriate further conventional regulatory elements, in each case operably linked to the nucleic acid sequence to be expressed transgenically.

Genetic control sequences also comprise further promoters, promoter elements or minimal promoters capable of modifying the expression-controlling properties. It is thus possible for example through genetic control sequences for tissue-specific expression to take place additionally dependent on particular stress factors. Corresponding elements are described for example for water stress, abscisic acid (Lam E and Chua N H, J Biol Chem 1991; 266(26): 17131-17135) and heat stress (Schoffl F et al., Molecular & General Genetics 217(2-3):246-53, 1989).

It is possible in principle for all natural promoters with their regulatory sequences like those mentioned above to be used for the method of the invention. It is additionally possible also for synthetic promoters to be used advantageously.

Genetic control sequences further comprise also the 5'-untranslated regions, introns or noncoding 3' region of genes such as, for example, the actin-1 intron, or the Adh1-S introns 1, 2 and 6 (generally: The Maize Handbook, Chapter 116, Freeling and Walbot, Eds., Springer, New York (1994)). It has been shown that these may play a significant function in the regulation of gene expression. It has thus been shown that 5'-untranslated sequences are capable of enhancing transient expression of heterologous genes. An example of a translation enhancer which may be mentioned is the 5' leader sequence from the tobacco mosaic virus (Gailie et al. (1987) Nucl Acids Res 15:8693-8711) and the like. They may in addition promote tissue specificity (Rouster J et al. (1998) Plant J 15:435-440).

The expression cassette may advantageously comprise one or more so-called enhancer sequences in operable linkage with the promoter, which make increased transgenic expression of the nucleic acid sequence possible. Additional advantageous sequences such as further regulatory elements or terminators can also be inserted at the 3' end of the nucleic acid sequences to be expressed recombinantly. The nucleic acid sequences to be expressed recombinantly may be present in one or more copies in the gene construct.

Polyadenylation signals suitable as control sequences are plant polyadenylation signals, preferably those which correspond essentially to T-DNA polyadenylation signals from *Agrobacterium tumefaciens*, in particular to gene 3 of the T-DNA (octopine synthase) of the Ti plasmid pTiACHS (Gielen et al. (1984) EMBO J 3:835 ff) or functional equivalents thereof. Examples of particularly suitable terminator sequences are the OCS (octopine synthase) terminator and the NOS (nopaline synthase) terminator.

Control sequences additionally mean those which make homologous recombination or insertion into the genome of a host organism possible or allow deletion from the genome. In homologous recombination, for example, the natural promoter of a particular gene can be specifically replaced by a promoter with specificity for the embryonal epidermis and/or the flower.

An expression cassette and/or the vectors derived from it may comprise further functional elements. The term functional element has a wide meaning and means all elements which have an influence on the production, replication or function of the expression cassettes, the vectors or the transgenic organisms of the invention. Non-restrictive examples which may be mentioned are:

a) Selection markers which confer a resistance to a metabolism inhibitor such as 2 deoxyglucose 6-phosphate (WO 98/45456), antibiotics or biocides, preferably herbicides, for example kanamycin, G 418, bleomycin, hygromycin or phosphinotricin and the like. Especially preferred selection markers are those which confer a resistance to herbicides. DNA sequences which code for phosphinothricin acetyltransferases (PAT), which inactivate glutamine synthase inhibitors (bar and pat gene), 5-enolpyruvylshikimate-3-phosphate synthase (EPSP synthase genes) which confer resistance to Glyphosat® (N-(phosphono-methyl)glycine), the gox gene, which codes for the Glyphosat®-degrading enzyme (glyphosate oxidoreductase), the deh gene (coding for a dehalogenase which inactivates dalapon), sulfonylurea- and imidazolinone-inactivating acetolactate synthases and bxn genes which code for bromoxynil-degrading nitrilase enzymes, the aasa gene, which confers a resistance to the antibiotic apectinomycin, the streptomycin phosphotransferase (SPT) gene, which makes possible a resistance to streptomycin, the neomycin phosphotransferase (NPTII) gene, which confers a resistance to kanamycin or geneticidin, the hygromycin phosphotransferase (HPT) gene, which mediates a resistance to hygromycin, the acetolactate synthase gene (ALS), which mediates a resistance to sulfonylurea herbicides (for example mutated ALS variants with, for example, the S4 and/or Hra mutation).

b) Reporter genes which code for easily quantifiable proteins and ensure via an intrinsic color or enzymic activity an assessment of the transformation efficiency or of the location or timing of expression. Very particular preference is given in this connection to reporter proteins (Schenborn E, Groskreutz D. Mol Biotechnol. 1999; 13(1):29-44) such as the green fluorescence protein (GFP) (Sheen et al. (1995) Plant Journal 8(5):777-784; Haselhoff et al. (1997) Proc Natl Acad Sci. USA 94(6):2122-2127; Reichel et al. (1996) Proc Natl Acad Sci USA 93(12):5888-5893; Tian et al. (1997) Plant Cell Rep 16:267-271; WO 97/41228; Chui W L et al. (1996) Curr Biol 6:325-330; Leffel S M et al. (1997) Biotechniques. 23(5):912-8), the chloramphenicoltransferase, a luciferase (Ow et al. (1986) Science 234:856-859; Millar et al. (1992) Plant Mol Biol Rep 10:324-414), the aequorin gene (Prasher et al. (1985) Biochem Biophys Res Commun 126(3):1259-1268), the β-galactosidase, R-locus gene (code for a protein which regulates the production of anthocyanin pigments (red coloration) in plant tissue and thus makes possible the direct analysis of the promoter activity without the addition of additional adjuvants or chromogenic substrates; Dellaporta et al., In: Chromosome Structure and Function: Impact of New Concepts, 18th Stadler Genetics Symposium, 11:263-282, (1988), with β-glucuronidase being very especially preferred (Jefferson et al., EMBO J. 1987, 6, 3901-3907).

c) Origins of replication which ensure replication of the expression cassettes or vectors of the invention in, for example, E. coli. Examples which may be mentioned are ORI (origin of DNA replication), the pBR322 ori or the P15A ori (Sambrook et al.: Molecular Cloning. A Laboratory Manual, $2^{nd}$ ed. Cold Spring Harbor Laboratory Press, Cold Spring Harbor, N.Y., 1989).

d) Elements which are necessary for *agrobacterium*-mediated plant transformation such as, for example, the right or left border of the T-DNA or the vir region.

To select successfully transformed cells, it is generally required additionally to introduce a selectable marker which confers to the successfully transformed cells a resistance to a biocide (for example a herbicide), a metabolism inhibitor such as 2 deoxyglucose 6-phosphate (WO 98/45456) or an antibiotic. The selection marker permits the selection of the transformed cells from untransformed cells (McCormick et al. (1986) Plant Cell Reports 5:81-84).

The introduction of an expression cassette according to the invention into an organism or into cells, tissues, organs, parts or seeds thereof (preferably into plants or plant cells, tissues, organs, parts or seeds) can advantageously be accomplished using vectors in which the expression cassettes are present. The expression cassette can be introduced into the vector (for example a plasmid) via a suitable restriction cleavage site. The resulting plasmid is first introduced into E. coli. Correctly transformed E. coli are selected, cultured, and the recombinant plasmid is obtained using methods known to the skilled worker. Restriction analysis and sequencing can be used for verifying the cloning step.

Examples of vectors can be plasmids, cosmids, phages, viruses or else *agrobacteria*. In an advantageous embodiment, the introduction of the expression cassette is accomplished by means of plasmid vectors. Preferred vectors are those which make possible a stable integration of the expression cassette into the host genome.

The generation of a transformed organism (or a transformed cell) requires the introduction of suitable DNA molecules, and thus of the RNA molecules or proteins formed as the result of their gene expression, into the host cell in question.

A multiplicity of methods (Keown et al. (1990) Methods in Enzymology 185:527-537) is available for this procedure, which is referred to as transformation (or transduction or transfection). Thus, DNA or RNA can be introduced for example directly by means of microinjection or by bombardment with DNA-coated microparticles. Also, it is possible to permeabilize the cell chemically, for example with polyethylene glycol, so that the DNA can enter the cell by diffusion. Alternatively, the DNA can be introduced by protoplast fusion with other DNA-comprising units such as minicells, cells, lysosomes or liposomes. Another suitable method for introducing DNA is electroporation, where the cells are reversibly permeabilized by means of an electrical pulse. Suitable methods are described (for example in Bilang et al. (1991) Gene 100:247-250; Scheid et al. (1991) Mol Gen Genet 228:104-112; Guerche et al. (1987) Plant Science 52:111-116; Neuhause et al. (1987) Theor Appl Genet 75:30-36; Klein et al. (1987) Nature 327:70-73; Howell et al. (1980) Science 208:1265; Horsch et al. (1985) Science 227:1229-1231; DeBlock et al. (1989) Plant Physiology 91:694-701; Methods for Plant Molecular Biology (Weissbach and Weissbach, eds.) Academic Press Inc. (1988); and Methods in Plant Molecular Biology (Schuler and Zielinski, eds.) Academic Press Inc. (1989)).

In plants, the described methods for the transformation and regeneration of plants from plant tissues or plant cells for the transient or stable transformation are used. Suitable methods are mainly the transformation of protoplasts by means of polyethylene-glycol-induced DNA uptake, the biolistic method with the gene gun, i.e. the so-called particle bombardment method, electroporation, the incubation of dry embryos in DNA-comprising solution, and Microinjection.

In addition to these "direct" transformation techniques, a transformation can also be carried out by bacterial infection, for example by means of *Agrobacterium tumefaciens* or *Agrobacterium rhizogenes*. The methods are described for example in Horsch R B et al. (1985) Science 225: 1229f.

If *agrobacteria* are used, the expression cassette is to be integrated into specific plasmids, either into a shuttle or intermediate vector or into a binary vector. If a Ti or Ri plasmid is used for the transformation, preferably at least the right border, but in most cases preferably the right and the left border, of the Ti or Ri plasmid T-DNA is linked as flanking region with the expression cassette to be introduced.

It is preferred to use binary vectors. Binary vectors are capable of replicating both in *E. coli* and in *Agrobacterium*. As a rule, they comprise a selection marker gene and a linker or polylinker flanked by the right and left T-DNA border sequence. They can be transformed directly into *Agrobacterium* (Holsters et al. (1978) Mol Gen Genet 163:181-187). The selection marker gene permits a selection of transformed *agrobacteria* and is, for example, the nptII gene, which confers a resistance to kanamycin. The *agrobacterium* which acts as host organism in this case should already comprise a plasmid with the vir region. This is required for transferring the T-DNA to the plant cell. An *agrobacterium* thus transformed can be used for the transformation of plant cells. The use of T-DNA for the transformation of plant cells has been studied and described extensively (EP 120 516; Hoekema, in: The Binary Plant Vector System, Offsetdrukkerij Kanters B.V., Alblasserdam, Chapter V, An et al. (1985) EMBO J 4:277-287). Various binary vectors are known and in some cases commercially available, such as, for example, pBI101.2 or pBIN19 (Clontech Laboratories, Inc. USA).

In the case of the injection or electroporation of DNA or RNA into plant cells, the plasmid used need not meet any particular requirements. Simple plasmids such as those from the pUC series can be used. If intact plants are to be regenerated from the transformed cells, it is necessary for an additional selectable marker gene to be located on the plasmid.

Stably transformed cells, i.e. those which comprise the introduced DNA integrated into the DNA of the host cell, can be selected from untransformed cells when a selectable marker is a component of the introduced DNA. For example, any gene which is capable of conferring a resistance to antibiotics or herbicides (such as kanamycin, G 418, bleomycin, hygromycin or phosphinothricin and the like) can act as marker (see hereinabove). Transformed cells which express such a marker gene are capable of surviving in the presence of concentrations of a suitable antibiotic or herbicide which kill an untransformed wild type. Examples are mentioned above and preferably comprise the bar gene, which confers resistance to the herbicide phosphinothricin (Rathore K S et al. (1993) Plant Mol Biol 21(5):871-884), the nptII gene, which confers resistance to kanamycin, the hpt gene, which confers resistance to hygromycin, or the EPSP gene, which confers resistance to the herbicide glyphosate. The selection marker permits the selection of transformed cells from untransformed cells (McCormick et al. (1986) Plant Cell Reports 5:81-84). The plants obtained can be bred and hybridized in the customary manner. Two or more generations should preferably be grown in order to ensure that the genomic integration is stable and hereditary.

The abovementioned methods are described for example in Jenes B et al. (1993) Techniques for Gene Transfer, in: Transgenic Plants, Vol. 1, Engineering and Utilization, edited by SD Kung and R Wu, Academic Press, p. 128-143 and in Potrykus (1991) Annu Rev Plant Physiol Plant Molec Biol 42:205-225). The construct to be expressed is preferably cloned into a vector which is suitable for transforming *Agrobacterium tumefaciens*, for example pBin19 (Bevan et al. (1984) Nucl Acids Res 12:8711f).

As soon as a transformed plant cell has been generated, an intact plant can be obtained using methods known to the skilled worker. Here, the starting material is, for example, callus cultures. The development of shoot and root can be induced in the known manner from these as yet undifferentiated cell lumps. The plantlets obtained can be potted on and bred.

The skilled worker is also familiar with methods of regenerating plant parts and intact plants from plant cells. For example, methods described by Fennell et al. (1992) Plant Cell Rep. 11: 567-570: Stoeger et al (1995) Plant Cell Rep. 14:273-278; Jahne et al. (1994) Theor Appl Genet 89:525-533 are used for this purpose.

The method according to the invention can advantageously be combined with other methods which bring about a pathogen resistance (for example to insects, fungi, bacteria, nematodes and the like), stress resistance or another improvement of the plant's characteristics. Examples are mentioned inter alia in Dunwell J M, Transgenic approaches to crop improvement, J Exp Bot. 2000; 51 Spec No; pages 487-96.

In a preferred embodiment, the reduction of the function of an Armadillo repeat ARM1 protein in a plant is accomplished in combination with an increase in the activity of a Bax inhibitor 1 protein. This can be effected for example by expressing a nucleic acid sequence which codes for a Bax inhibitor 1 protein, for example in the mesophyll tissue and/or root tissue.

In the method according to the invention, the Bax inhibitor 1 proteins from *Horoeum vulgare* or *Nicotiana tabacum* are especially preferred.

Another subject matter of the invention relates to nucleic acid molecules which comprise nucleic acid molecules coding for Armadillo repeat ARM1 proteins from barley as shown by the polynucleotides SEQ, ID No: 1, and to the nucleic acid sequences which are complementary thereto, and to the sequences derived as the result of the degeneracy (degeneration) of the genetic code and to the nucleic acid molecules which code for functional equivalents of the polypeptides as shown in SEQ. ID No. 1, the nucleic acid molecules not consisting of the SEQ ID NO: 3, 5, 7, 9, 11, 13, 15, 17, 19, 21, 23, 25, 27, 29, 31, 33, 35, 37, 39, 41 or 43.

Another subject matter of the invention relates to the Armadillo repeat ARM1 protein from barley as shown in SEQ. ID No.: 2 or to one which comprises these sequences, and to functional equivalents thereof, which do not correspond to one of the SEQ ID NO: 4, 6, 8, 10, 12, 14, 16, 18, 20, 22, 24, 26, 28, 30, 32, 34, 36, 38, 42 or 44.

Another subject matter of the invention relates to doublestranded RNA nucleic acid molecules (dsRNA molecule) which, when introduced into a plant (or into a cell, tissue, organ or seed thereof), bring about the reduction of an Armadillo repeat ARM1 protein, where the sense strand of said dsRNA molecule has at least 30%, preferably at least 40%, 50%, 60%, 70% or 80%, especially preferably at least 90%, very especially preferably 100%, homology with a nucleic acid molecule as shown in SEQ ID No: 1, 3, 5, 7, 9, 11, 13, 15, 17, 19, 21, 23, 25, 27, 29, 31, 33, 35, 37, 39, 41 or 43, or to a fragment of at least 17 base pairs, preferably at least 18, 19, 20, 21, 22, 23, 24, 25, 26, 27, 28, 29 or 30 base pairs, especially preferably at least 40, 50, 60, 70, 80 or 90 base pairs, very especially preferably at least 100, 200, 300 or 400 base pairs, most preferably at least 500, 600, 700, 800, 900, at least 1000, base pairs and which has at least 50%, 60%, 70% or 80%, especially preferably at least 90%, very especially preferably 100%, homology with a nucleic acid molecule as shown in SEQ ID No: 1, 3, 5, 7, 9, 11, 13, 15, 17, 19, 21, 23, 25, 27, 29, 31, 33, 35, 37, 39, 41 or 43 but do not correspond to SEQ ID NO: 3, 5, 7, 9, 11, 13, 15117, 19, 21, 23, 25, 27, 29, 31, 33, 35, 37, 39, 41 or 43.

The double-stranded structure can be formed starting from a single, autocomplementary strand or starting from two complementary strands. In an especially preferred embodiment, sense and antisense sequence are linked by a linking sequence (linker) and can form for example a hairpin structure. The linking sequence can very especially preferably be an intron, which is spliced out after the dsRNA has been synthesized.

The nucleic acid sequence coding for a dsRNA can comprise further elements, such as, for example, transcription termination signals or polyadenylation signals.

A further subject matter of the invention relates to transgenic expression cassettes which comprise one of the nucleic acid sequences according to the invention. In the transgenic expression cassettes according to the invention, the nucleic acid sequence coding for the Armadillo repeat ARM1 proteins from barley, wheat and maize is linked with at least one genetic control element as defined above in such a manner that the expression (transcription and, if appropriate, translation) can be accomplished in a desired organism, preferably monocotyledonous plants. Genetic control elements which are suitable for this purpose are described above. The transgenic expression cassettes can also comprise further functional elements as defined above.

Such expression cassettes comprise for example a nucleic acid sequence according to the invention, for example one which is essentially identical to a nucleic acid molecule. SEQ ID No: 1, 3, 5, 7, 9, 11, 13, 15, 17, 19, 21, 23, 25, 27, 29, 31, 33, 35, 37, 39, 41 or 43, or a fragment thereof according to the invention, where said nucleic acid sequence is preferably arranged in sense orientation or in antisense orientation relative to a promoter and can therefore lead to the expression of sense or antisense RNA, where said promoter is a promoter which is active in plants, preferably a promoter which is inducible by pathogen attack. Also comprised according to the invention are transgenic vectors which comprise said transgenic expression cassettes.

Another subject matter of the invention relates to plants which, as the result of natural processes or of artificial induction, comprise one or more mutations in a nucleic acid molecule which comprises the nucleic acid sequence as shown in SEQ ID No: 1, 3, 5, 7, 9, 11, 13, 15, 17, 19, 21, 23, 25, 27, 29, 31, 33, 35, 37, 39, 41 or 43, where said mutation brings about a reduction in the activity, function or polypeptide quantity of a polypeptide encoded by the nucleic acid molecules as shown in SEQ ID No: 1, 3, 5, 7, 9, 11, 13, 15, 17, 19, 21, 23, 25, 27, 29, 31, 33, 35, 37, 39, 41 or 43. For example a mutation prepared and identified by tilling.

Preferred in this context are plants which belong to the family Poaceae, especially preferred are plants selected among the plant genera Hordeum, Avena, Secale, Triticum, Sorghum, Zea, Saccharum and Oryza, very especially preferably plants selected from the species Hordeum vulgare (barley), Triticum aestivum (wheat), Triticum aestivum subsp. spelta (spelt), Triticale, Avena sativa (oats), Secale cereale (rye), Sorghum bicolor (sorghum), Zea mays (maize), Saccharum officinarum (sugar cane) and Oryza sativa (rice).

One embodiment of the invention therefore relates to a monocotyledonous organism comprising a nucleic acid sequence according to the invention which comprises a mutation which brings about, in the organisms or parts thereof, a reduction in the activity of one of the proteins encoded by the nucleic acid molecules according to the invention. For example, the mutation relates to one or more amino acid residues which are identified as being conserved or highly conserved in the consensus sequence shown in the figures.

Accordingly, another subject matter of the invention relates to transgenic plants, transformed with at least
a) one nucleic acid sequence, which comprises the nucleic acid molecules as shown in SEQ ID No: 1, 3, 5, 7, 9, 11, 13, 15, 17, 19, 21, 23, 25, 27, 29, 31, 33, 35, 37, 39, 41 or 43, the nucleic acid sequences complementary thereto, and the nucleic acid molecules which code for functional equivalents of the polypeptides as shown in SEQ ID No: 2, 4, 6, 8, 10, 12, 14, 16, 18, 20, 22, 24, 26, 28, 30, 32, 34, 36, 38, 40, 42, 44, 60, 61 or 62,
b) one double-stranded RNA nucleic acid molecule (dsRNA molecule) which brings about the reduction of an Armadillo repeat ARM1 protein, where the sense strand of said dsRNA molecule has at least 30%, preferably at least 40%, 50%, 60%, 70% or 80%, especially preferably at least 90%, very especially preferably 100%, homology with a nucleic acid molecule as shown in S SEQ ID No: 1, 3, 5, 7, 9, 11, 13, 15, 17, 19, 21, 23, 25, 27, 29, 31, 33, 35, 37, 39, 41 or 43, or a fragment of at least 17 base pairs, preferably at least 18, 19, 20, 21, 22, 23, 24, 25, 26, 27, 28, 29 or 30 base pairs, especially preferably at least 40, 50, 60, 70, 80 or 90 base pairs, very especially preferably at least 100, 200, 300 or 400 base pairs, most preferably at least 500, 600, 700, 800, 900 or more base pairs, which has at least 50%, 60%, 70% or 80%, especially preferably at least 90%, very especially preferably 100%, homology with a nucleic acid molecule as shown in SEQ ID No: 1, 3, 5, 7, 9, 11, 13, 15, 17, 19, 21, 23, 25, 27, 29, 31, 33, 35, 37, 39, 41 or 43,
c) one transgenic expression cassette which comprises one of the nucleic acid sequences according to the invention, or a vector according to the invention, and cells, cell cultures, tissues, parts—such as, for example in the case of plant organisms, leaves, roots and the like—or propagation material derived from such organisms,
where in one embodiment the nucleic acid molecules do not consist of the nucleic acid molecules shown in SEQ ID No: 1, 3, 5, 7, 9, 11, 13, 15, 17, 19, 21, 23, 25, 27, 29, 31, 33, 35, 37, 39, 41 or 43 and in one embodiment do not consist of the polypeptide molecules shown in SEQ ID No: 2, 4, 6, 8, 10, 12, 14, 16, 18, 20, 22, 24, 26, 28, 30, 32, 34, 36, 38, 40, 42, 44, 60, 61 or 62 and In one embodiment, the plant according to the invention or the plant used in accordance with the invention is not *Arabidopsis thaliana*.

Host or starting organisms which are preferred as "transgenic organisms" are mainly plants in accordance with the above definition. In one embodiment, the transgenic organism is a mature plant, seed, shoot and seedling, and parts, propagation material and cultures derived therefrom, for example cell cultures. "Mature plants" means plants at any desired developmental stage beyond the seedling. "Seedling" means a young immature plant in an early developmental stage. Plants which are especially preferred as host organisms are plants to which the method according to the invention of obtaining a pathogen resistance in accordance with abovementioned criteria can be applied. In one embodiment, the plant is a monocotyledonous plant such as, for example, wheat, oats, sorghum and millet, barley, rye, maize, rice, buckwheat, sorghum, triticale, spelt or sugar cane, in particular selected from the species *Hordeum vulgare* (barley), *Triticum aestivum* (wheat), *Triticum aestivum* subsp. *spelta* (spelt), Triticale, *Avena sativa* (oats), *Secale cereale* (rye), *Sorghum bicolor* (sorghum), *Zea mays* (maize), *Saccharum officinarum* (sugar cane) and *Oryza sativa* (rice).

The generation of the transgenic organisms can be accomplished with the above-described methods for the transformation or transfection of organisms.

Another subject matter of the invention relates to the transgenic plants described in accordance with the invention which additionally have an increased Bax inhibitor 1 activity, with plants which have an increased Bax inhibitor 1 activity in mesophyll cells or root cells being preferred, with transgenic plants which belong to the family Poaceae and which have an increased Bax inhibitor 1 activity in mesophyll cells or root cells being especially preferred, with transgenic plants selected among the plant genera *Hordeum, Avena, Secale, Triticum, Sorghum, Zea, Saccharum* and *Oryza* being even more preferred, and with the plant species *Hordeum vulgare* (barley), *Triticum aestivum* (wheat), *Triticum aestivum* subsp. *spelta* (spelt), Triticale, *Avena sativa* (oats), *Secale cereale* (rye), *Sorghum bicolor* (sorghum), *Zea mays* (maize), *Saccharum officinarum* (sugar cane) and *Oryza sativa* (rice) being preferred most of all.

Another subject matter of the invention relates to the use of the transgenic organisms according to the invention and of the cells, cell cultures, parts—such as, for example in the case of transgenic plant organisms, roots, leaves and the like—and transgenic propagation material such as seeds or fruits derived therefrom for the preparation of foodstuffs or feedstuffs, pharmaceuticals or fine chemicals.

In one embodiment, the invention furthermore relates to a method for the recombinant production of pharmaceuticals or fine chemicals in host organisms, where a host organism or a part thereof is transformed with one of the above-described nucleic acid molecule expression cassettes and this expression cassette comprises one or more structural genes which code for the desired fine chemical or catalyze the biosynthesis of the desired fine chemical, where the transformed host organism is grown and where the desired fine chemical is isolated from the growth medium. This method can be applied widely to fine chemicals such as enzymes, vitamins, amino acids, sugars, fatty acids, natural and synthetic flavorings, aroma substances and colorants. Especially preferred is the production of tocopherols and tocotrienols and carotenoids. The growing of the transformed host organisms and the isolation from the host organisms or the growth medium are accomplished by methods known to the skilled worker. The production of pharmaceuticals such as, for example, antibodies or vaccines, is described in Hood E E, Jilka J M (1999). Curr Opin Biotechnol. 10(4):382-6; Ma J K, Vine N D (1999). Curr Top Microbiol Immunol. 236:275-92.

In accordance with the invention, the expression of a structural gene can, of course, also take place, or be influenced, independently of carrying out the method according to the invention or using the subject matters according to the invention.

Sequences
1. SEQ ID NO: 1 and 2: HvArm
2. SEQ ID NO: 3 and 4: OS_1_XM_479734.1
3. SEQ ID NO: 5 and 6 Os2_XM_463544
4. SEQ ID NO: 7 and 8 Os_3_AP003561
5. SEQ ID NO: 9 and 10 Os_4_XM_506432
6. SEQ ID NO: 11 and 12 NT_1_AY219234
7. SEQ ID NO: 13 and 14 At_1_NM_127878
8. SEQ ID NO: 15 and 16 At_2_AC004401
9. SEQ ID NO: 17 and 18 At_3_BT020206
10. SEQ ID NO: 19 and 20 At_4_AB007645
11. SEQ ID NO: 21 and 22 At_5_NM135336 (At3g54790)
12. SEQ ID NO: 23 and 24 At_6_AK118613
13. SEQ ID NO: 25 and 26 At_7_AL138650
14. SEQ ID NO: 27 and 28 At_8_AL133314
15. SEQ ID NO: 29 and 30 At_9_AC010870
16. SEQ ID NO: 31 and 32 At_10_AY125543 (At3g01400)
17. SEQ ID NO:33 and 34 At_11_AY087360
18. SEQ ID NO: 35 and 36 At_12_AB1016888
19. SEQ ID NO: 37 and 38 At_13_AK175585
20. SEQ ID NO: 39 and 40 At_14_AL049655
21. SEQ ID NO:41 and 42 At_15_AY096530 (At3g54850)
22. SEQ ID NO: 43 and 44 At_16_AK118730 (At4g16490)
23. SEQ ID NO: 45 to 59: primers
24. SEQ ID NO: 60, 61, 63: consensus sequences of polynucleotide SEQ ID NO. from 1. to 22.

In the figures:
FIG. 1 (12 pages): depicts ARM1 nucleic acid sequences from barley, rice, and *Arabidopsis thaliana*.

FIG. 2 (6 pages): depicts ARM1 polypeptide sequences from barley, rice, and *Arabidopsis thaliana*.

Figure 3R:
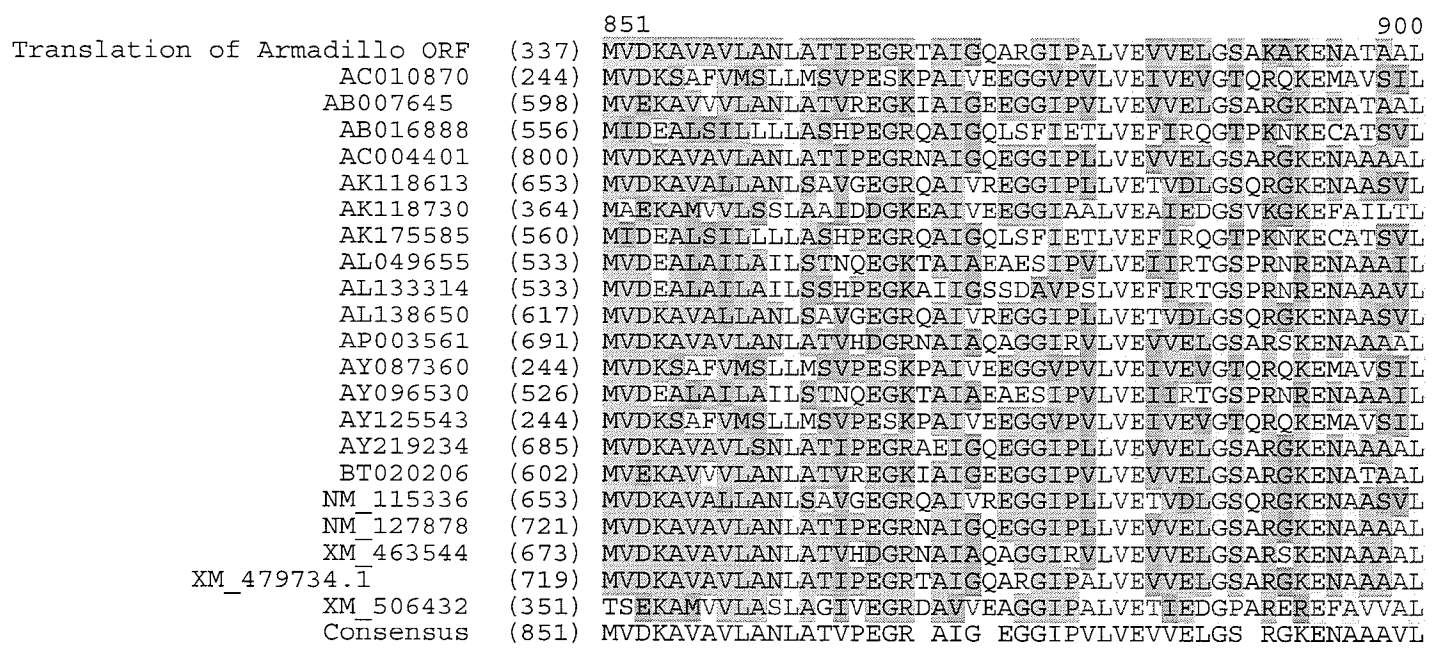

FIG. 3 (20 pages): depicts a sequence alignment of ARM1 protein sequences polypeptides from barley, rice, and *Arahidopsis thaliana*. The sequences shown are: Translation of Armidillo ORF (SEQ ID NO: 2), AC010870 (SEQ ID NO: 30), AB007645 (SEQ ID NO: 20), AB016888 (SEQ ID NO: 36), AC004401 (SEQ ID NO: 16), AK118613 (SEQ ID NO: 24), AK118730 (SEQ ID NO: 44), AK175585 (SEQ ID NO: 38), AL049655 (SEQ ID NO: 40), AL133314 (SEQ ID NO: 28), AL138650 (SEQ ID NO: 26), AP003561 (SEQ ID NO: 8), AY087360 (SEQ ID NO: 34), AY096530 (SEQ ID NO: 42), AY125543 (SEQ ID NO: 32), AY219234 (SEQ ID NO: 12), BT020206 (SEQ ID NO: 18), NM_115336 (SEQ ID NO: 22), NM_127878 (SEQ ID NO; 14), XM_463544 (SEQ ID NO: 6), XM_479734.1 (SEQ ID NO: 4), XM_506432 (SEQ ID NO: 10).

FIG. 4 (1 page): depicts increase in mildew resistance of barley due to RNAi of ARM repeat proteins FIG. 5 (2 pages): depicts consensus sequences of the sequence alignment of ARM1 protein sequences polypeptides from barley, rice, and *Arabidopsis thaliana*.

EXAMPLES

General Methods

The chemical synthesis of oligonucleotides can take place for example in a known manner by the phosphoamidite method (Voet, Voet, 2nd edition, Wiley Press New York, page 896-897). The cloning steps carried out for the purposes of the present invention, such as, for example, restriction cleavages, agarose gel electrophoresis, purification of DNA fragments, transfer of nucleic acids to nitrocellulose and nylon membranes, linkage of DNA fragments, transformation of *E. coli* cells, culturing of bacteria, replication of phages and sequence analysis of recombinant DNA are carried out as described in Sambrook et al. (1989) Cold Spring Harbor Laboratory Press; ISBN 0-87969-309-6. The sequencing of recombinant DNA molecules takes place using a laser fluorescence DNA sequencer from the company MWG-Licor by the method of Sanger (Sanger et al. (1977) Proc Natl Acad Sci USA 74:5463-5467).

Example 1

Plants, Pathogens and Inoculation

The barley variety Golden Promise is from Patrick Schweizer, Institut für Pflanzengenetik und Kulturpflanzenforschung Gatersleben. The variety Pallas and the backcrossed line BCIngrid-mlo5 was provided by Lisa Munk, Department of Plant Pathology, Royal Veterinary and Agricultural University, Copenhagen, Denmark. Its preparation is described (Kølster P et al. (1986) Crop Sci 26: 903-907).

Unless otherwise described, the seed which has been pregerminated for 12 to 36 hours in the dark on moist filter paper is placed in batches of 5 grains along the edge of a square pot (8×8 cm) in Fruhstorfer soil type P, covered with soil and watered regularly with tap water. All plants are grown in controlled-environment cabinets or chambers at from 16 to 18° C. for 5 to 8 days, at a relative atmospheric humidity of from 50 to 60% and in a 16/8-hour photo period with 3000 and 5000 lux, respectively (50 and 60 $\mu mols^{-1} m^{-2}$ photon flux density, respectively) and employed in the experiments in the seedling stage. In the case of experiments where primary leaves are treated, the latter are fully developed.

Before the plants are subjected to the transient transfection experiments, they are grown in controlled-environment cabinets or chambers at a daytime temperature of 24° C., nighttime temperature of 20° C., relative atmospheric humidity of 50 to 60% and a 16/8-hour photo period with 30 000 lux.

Powdery mildew of barley *Blumeria graminis* (DC) Speer f.sp. *hordei* Em. Marchal der Rasse A6 (Wiberg A (1974) Hereditas 77: 89-148) (BghA6) is used to inoculate barley plants. The mildew was provided by the Institut für Biometrie, JLU Gießen. The inoculum is maintained in controlled-environment cabinets under conditions which are identical to those which have been described above for the plants by transferring the conidia from infected plant material to 7-day old barley plants cv. Golden Promise which have been raised at regular intervals, at a density of 100 conidia/mm$^2$.

The inoculation with BghA6 is carried out using 7-day-old seedlings by shaking the conidia of infected plants in an inoculation tower at a density of approximately 100 conidia/mm$^2$ (unless otherwise stated).

Example 2

RNA Extraction

Total RNA is extracted from 8 to 10 primary leaf segments (5 cm in length) by means of "RNA extraction buffer" (AGS, Heidelberg, Germany).

To this end, central primary leaf segments 5 cm in length are harvested and homogenized in liquid nitrogen using a pestle and mortar. The homogenate is stored at –70° C. until the RNA is extracted.

Total RNA is extracted from the frozen leaf material with the aid of an RNA extraction kit (AGS, Heidelberg). To this end, 200 mg of the frozen leaf material is covered with 1.7 ml of RNA extraction buffer (AGS) in a microcentrifuge tube (2 ml) and immediately subjected to thorough mixing. After the addition of 200 µl of chloroform, the mixture is again mixed thoroughly and shaken for 45 minutes at room temperature on an orbital shaker at 200 rpm. Thereafter, the mixture is centrifuged for 15 minutes at 20 000 g and 4° C. in order to separate the phases, the aqueous top phase is transferred into a fresh microcentrifuge tube, and the bottom phase is discarded. The aqueous phase is again purified with 900 µl of chloroform by homogenizing 3 times for 10 seconds and recentrifuging (see above) and removing the top phase. To precipitate the RNA, 850 µl of 2-propanol are then added, the mixture is homogenized and placed on ice for 30 to 60 minutes. Thereafter, the mixture is centrifuged for 20 minutes (see above), the supernatant is carefully decanted off, 2 ml of 70% strength ethanol (–20° C.) are added, using a pipette, and the batch is mixed and again centrifuged for 10 minutes. The supernatant is then again decanted off and the pellet is carefully freed from residual fluid, using a pipette, and then dried in a stream of pure air on a sterile workbench. Thereafter, the RNA is dissolved in 50 µl of DEPC water on ice, and the batch is mixed and centrifuged for 5 minutes (see above) 40 µl of the supernatant are transferred into a fresh microcentrifuge tube as RNA solution and stored at –70° C.

The RNA concentration is determined photometrically. To this end, the RNA solution is diluted 1:99 (v/v) with distilled water and the absorbance (Photometer DU 7400, Beckman) is measured at 260 nm ($E_{260\,nm}$=1 at 40 µg RNA/ml). In accordance with the calculated RNA contents, the concentrations of the RNA solutions are subsequently standardized with DEPC water to 1 µg/µl and verified in an agarose gel.

To verify the RNA concentrations in a horizontal agarose gel (1% agarose in 1×MOPS buffer with 0.2 µg/ml ethidium bromide), 1 µl of RNA solution is treated with 1 µl of 10×MOPS, 1 µl of color marker and 7 µl of DEPC water, separated according to size at a voltage of 120 V in the gel in 1×MOPS running buffer in the course of 1.5 hours and photographed under UV light. Any differences in concentration of the RNA extracts are standardized with DEPC water, and the standardization is again verified in the gel.

Example 3

Cloning the Barley HvARM cDNA Sequence

The cDNA fragments required for isolating, cloning and sequencing armadillo cDNA were obtained by means of RT PCR using the GeneRacer kit (Invitrogen Life Technologies). For this purpose, total RNA from barley epidermis was used as template. RNA was isolated from epidermal cells of Ingrid+Bgt barley 12 h and 24 h after infection.

The HvArm cDNA sequence was extended by means of the RACE technology using the GeneRacer kit (INVITROGEN Life Technologies). For this purpose, 4000 ng of total mRNA, 1 µl of 10×CIP buffer, 10 units of RNAse inhibitor, 10 units of CIP (calf intestinal phosphatase) and DEPC-treated water to a total volume of 10 µl were treated at 50° C. for 1 h. The RNA was precipitated by adding a further 90 µl of DEPC water and 100 µl of phenol:chloroform and mixing thoroughly for approx. 30 sec. After centrifugation at 20 000 g for 5 min, the upper phase was admixed with 2 µl of 10 mg/ml mussel glycogen, 10 µl of 3 M sodium acetate (pH 5.2) in a new micro-reaction vessel. The mixture was treated with 220 µl of 95% ethanol and incubated on ice. RNA was subsequently precipitated by centrifugation at 20 000 g and 4° C. for 20 min. The supernatant was discarded, 500 µl of 75% ethanol were added, the mixture was briefly vortexed and again centrifuged for 2 min (20 000 g). The supernatant was again discarded, the precipitate was dried in air at room temperature for 2 min and subsequently suspended in 6 µl of DEPC water. mRNA CAP structures were removed by adding 1 µl of 10×TAP buffer, 10 units of RNAsin and 1 unit of TAP (tobacco acid pyrophosphatase). The mixture was incubated at 37° C. for 1 h and then cooled on ice. The RNA was again precipitated, as described above, and transferred to a reaction vessel containing 0.25 µg of GeneRacer oligonucleotide primer. The oligonucleotide primer was resuspended in the RNA solution, the mixture was incubated at 70° C. for 5 min and then cooled on ice. To this 1 µl of 10× ligase buffer, 10 mM ATP, 1 unit of RNAsin and 5 units of T4 RNA ligase were added and the reaction mixture was incubated at 37° C. for 1 h. The RNA was again precipitated, as described above, and resuspended in 7 µl of DEPC water. The RNA was admixed with 10 pmol GeneRacer Oligo-dT primer and 2 µl of each dNTP solution (25 mM), the mixture was heated to 70° C. for 10 min and then again cooled on ice. This was followed by adding a mix of 2 µl of 10×RT buffer, 4 µl of 25 mM MgCl$_2$, 2 µl of 0.1M DTT, 5 U (1 µl) of SuperscriptIII transcriptase (200 U/μl) and 1 μl RNAse Out (40 U/μl), incubating the reaction solution at 50° C. for 50 min and then inactivating it at 85° C. for 5 min. After incubating with 1 μl RNAse H (2 U/μl) at 37° C. for 20 min, the first strand cDNA prepared in this way was stored at −20° C.

The following primers were used for the RT PCR:
GeneRacer Oligo-dT Primer (Invitrogen Life Technologies):

```
                                              (Seq ID No.: 45)
GCTGTCAACGATACGCTACGTAACGGCATGACAGTG (T)18
```

For each reaction (total volume: 20 μL) 4000 ng of total RNA, 10 mM dNTPs, 50 μM GeneRacer Oligo-dT primer (Invitrogen Life Technologies), 1 μl of RNase inhibitor and 1 μl of enzyme mix in 1×RT buffer (GeneRacer Kit Invitrogen) were used.

The reaction was incubated at 50° C. for 50 minutes.

The subsequent primers were used for amplifying the 5, cDNA ends:

```
MWG 1:
5'GCAGACATGACCCAATCTTGGCAGG 3'        (Seq ID No.: 46)

GR 5' primer (Invitrogen):
5'cgactggagcacgaggacactga 3'          (Seq ID No.: 47)

MWG 2:
5'CCACGGTCAGCAACCTCTCCAGACG 3'        (Seq ID No.: 48)

GeneRacer 5'nested primer (Invitrogen):
5'ggacactgacatggactgaaggagta 3'       (Seq ID No.: 49)

MWG 3:
5' cagatgatagttattgttgttgactgg 3'     (Seq ID No.: 50)

GR 3' primer (Invitrogen):
5' GCTGTCAACGATACGCTACGTAACG 3'       (Seq ID No.: 51)

MWG 4:
5'ctcatcttctcaagctactggtgg 3'         (Seq ID No.: 52)

GeneRacer 3'nested primer (Invitrogen):
5'CGCTACGTAACGGCATGACAGTG 3'          (Seq ID No.: 53)
```

The mixture (total volume: 50 μL) was composed as follows:
4 μl of MWG1 (10 pmol/μl)
4.5 μl of 5'Gene Racer (10 pmol/μl)
5 μl of 10× buffer Roche
1.5 μl of 10 mM dNTPs
1 μl of cDNA
1 μl of Taq (Roche)
33 μl of H2O The following temperature program was used (GeneAmp PCR System 9700; Applied Biosystems):

| | 94° C., 2 min denaturation |
|---|---|
| 5 cycles of | 94° C., 30 sec (denaturation) |
| | 72° C., 2 min (extension) |
| 5 cycles of | 94° C., 30 sec (denaturation) |
| | 70° C., 2 min (extension) |
| 30 cycles of | 94° C., 30 sec (denaturation) |
| | 65° C., 30 sec (annealing) |
| | 68° C., 2 min (extension) |
| | 68° C., 7 min final extension |
| | 4° C., cooling until further processing |

The PCR did not produce any product. Starting from this, a nested RACE with MWG2, the armadillo-specific oligonucleotide primer and the GeneRacer Nested 5' primer was carried out:

| | 94° C., 2 min denaturation |
|---|---|
| 30 cycles of | 94° C., 30 sec (denaturation) |
| | 65° C., 30 sec (annealing) |
| | 68° C., 2 min (extension) |
| | 68° C., 7 min final extension |
| | 4° C., cooling until further processing |

The PCR resulted in a product of approx. 850 bp. The PCR product obtained was isolated via a 1% agarose gel, extracted from the gel and cloned into pCR4-Topo (Invitrogen Life Technologies) by means of T-overhang ligation and sequenced. The sequence depicted under SEQ ID NO: is also identical to the barley armadillo sequence.

The full length HvArm sequence was amplified using the following primers:

```
MWG 29:
5'atatgcaaatggctctgctag 3'     (Seq ID No.: 54)

MWG 30:
5'TATCATCTCCTTCCCGAGTTC 3'     (Seq ID No.: 55)
```

The mixture (total volume: 50 μL) was composed as follows:
4 μl of MWG29 (10 pmol/μl)
4 μl of MWG30 (10 pmol/μl)
5 μl of 10×Pfu Ultra buffer (Stratagene)
1.5 μl of 10 μM dNTPs
1 μl of cDNA
1 μl of Pfu Ultra (Stratagene)
33 μl of H2O The following temperature program was used (GeneAmp PCR System 9700; Applied Biosystems):

| | 94° C., 2 min denaturation |
|---|---|
| 30 cycles of | 94° C., 30 sec (denaturation) |
| | 55° C., 30 sec (annealing) |
| | 72° C., 1.5 min (extension) |
| | 72° C., 7 min, final extension |
| | 4° C., cooling until further processing |

The PCR resulted in a product of 1326 bp. The PCR product obtained was isolated via a 1% agarose gel, extracted from the gel and cloned into pCR4-Topo (Invitrogen Life Technologies) by means of T-overhang ligation and sequenced. The sequence depicted under SEQ ID NO: is also identical to the barley armadillo sequence.

Example 4

Cloning of the Full Length cDNA Sequence of *Arabidopsis thaliana* AtARM (At2g23140)

The full length AtArm sequence was amplified using the following primers:

```
MWG 31:
                                 (Seq ID No.: 56)
5' cccgggatgattttgcggttttggcgg 3'

MWG 32:
                                 (Seq ID No.: 57)
5' CCCGGGTCACAAGACAAAACATAAAAATAGG 3'
```

```
                                    -continued
MWG 32b:
                                                     (Seq ID No.: 58)
5'gactcacactactctaatacc 3'

MWG 33:
                                                     (Seq ID No.: 59)
5'GACATCGTTTGTCTCACACC 3'
```

The mixture (total volume: 50 µL) was composed as follows (due to its size of 2775 bp, the gene was divided into two parts for the PCR):
4 µl of MWG31 (10 pmol/µl)
4 µl of MWG34 (10 pmol/µl)
5 µl of 10×Pfu Ultra buffer (Stratagene)
1.5 µl of 10 mM dNTPs
1 µl of cDNA
1 µl of Pfu Ultra (Stratagene)
33 µl of H2O
and
4 µl of MWG32 (10 pmol/µl)
4 µl of MWC33 (10 pmol/µl)
5 µl of 10×Pfu Ultra buffer (Stratagene)
1.5 µl of 10 mM dNTPs
1 µl of cDNA
1 µl of Pfu Ultra (Stratagene)
33 µl of H2O The following temperature program was used (GeneAmp PCR System 9700; Applied Biosystems):

| | |
|---|---|
| | 94° C., 2 min denaturation |
| 30 cycles of | 94° C., 30 sec (denaturation) |
| | 59° C., 30 sec (annealing) |
| | 72° C., 1.5 min (extension) |
| | 72° C., 7 min final extension |
| | 4° C., cooling until further processing |

The PCR results in a product of 1143 bp and 1705 bp, respectively. The PCR product obtained is isolated via a 1% agarose gel, extracted from the gel and cloned into pCR4-Topo (Invitrogen Life Technologies) by means of T-overhang ligation and sequenced. The sequence depicted under SEQ ID NO: is also identical to the *Arabidopsis thaliana* armadillo sequence.

In order to assemble the gene, the 1705 bp PCR product is cloned into pUC18. This is followed by cloning AtArm (1143 bp) into pUC18-AtArm (1705 bp).

An antisense construct is generated for constitutive expression. To this end, HvArm antisense is cloned into the binary vector 1bxSuperGus by excising HvArm via SmaI from pUC18 and cloning it via said cleavage sites into the 5'-terminally blunted 1 bxSuperGus (SacI/SmaI). The orientation is verified by means of a test digest.

Example 5

Carrying Out the Transient Single-cell RNAi Analysis

Biological Material

Barley near-isogenic lines (NiLs) of the cultivars cv Ingrid (Mlo) and Ingrid BC$_7$ mlo5 or barley cv Golden Promise were grown in controlled-environment chambers in pots filled with potting compost (provenance: IPK Gatersleben) (16 hours light from metal halogen lamps; 8 hours darkness, relative atmospheric humidity of 70%, constant temperature of 18° C.). *Blumeria graminis* DC Speer f.sp. *hordei* (Bgh) (isolate 4.8 comprising AvrMla9) was grown at 22° C. and 16 hours light by weekly transfer to fresh barley leaves of the cultivar cv. Golden Promise. *Blumeria graminis* DC Speer f.sp. *tritici* Em Marchal (Bgt) of the Swiss isolate FAL (Reckenholz) was propagated at 22° C. and 16 hours light by weekly transfer to fresh leaves of wheat of the cultivar cv. Kanzler.

Plasmid Vectors

The vector pIPKTA38 was used as entry vector for the Gateway™ cloning system (Invitrogen). The vector is a pENTR1a derivative where the ccdB gene had been removed and a novel multiple cloning site had been inserted. The destination vector used was pIPKTA30N, which is based on a pUC18 background and which comprises a constitutive promoter, terminator and two Gateway cassettes comprising attr sites, ccdB gene and a chloramphenicol resistance gene. The two cassettes are arranged in opposite directions and separated from one another by a spacer from the wheat RGA2 gene (accession number AF326781). This vector system permits a one-step transfer of two copies of a PCR fragment via entry vector into the dsRNAi vector by means of Gateway LR clonase reaction (Invitrogen).

PCR and Primer Design

EST sequences of the target gene were amplified via PCR. Purified DNA from the selected cDNA clones was used as template for the PCR reaction. The primers were derived with the aid of the software package "Primer3" in the batch-file mode using the 5'-EST sequences. The EST sequences were typically amplified with a universal forward primer and a reverse EST-specific primer. The amplificates were in the range of from 400-700 bp. The primers were 20-22 bp in length and had a T$_m$ of approx. 65° C. The PCR reactions were carried out in 96-well microtiter plates using a DNA polymerase which produces blunt ends (ThermalAce; Invitrogen). The PCR products were purified with the aid of the MinElute UF Kit (Qiagen, Hilden, Germany) and eluted with 25 µl of water.

Ligation into the Entry Vector

The PCR fragments were cloned into the Swa I cleavage site of this vector pIPKTA38. The ligation was carried out at 25° C. in the presence of the N U T4 DNA ligase (MBI Fermentas) and 5 U of Swa I per reaction. To optimize the reaction conditions for Swa I, the buffer was supplemented with NaCl to a final concentration of 0.05 M. After 1 h, the reaction was terminated by heating for 15 minutes at 65° C. Thereafter, an additional 5 U of Swa I were added in order to suppress a religation of the plasmid. The Swa I buffer was supplemented with additional NaCl to a final concentration of 0.1 M. The reaction mixtures were incubated for a further hour at 25° C.

The resulting recombinant pIPKTA38-EST clones were employed for the transformation of chemically competent *E. coli* DH10B cells in 96-well PCR microtiter plates (5 µl of ligation mixture per 20 µl of competent cells) and plated onto LB agar plates with kanamycin. One colony of each cloning reaction was picked and taken up in 1.2 ml of LB+kanamycin liquid culture and distributed in 96-deep-well plates. The plates were covered with an air-permeable film and incubated for 18 hours at 37° C. on a shaker. Thereupon, the deep-well plates were centrifuged for 10 minutes at 750 g, and the pellets were used for isolating the plasmid by means of the NucleoSpin Robot-96 plasmid kit (Macherey-Nagel). The presence of the pIPKTA38 plasmid was verified via restriction digest with EcoRI. The positive pIPKTA38 clones were employed as donor vector in the LR reaction.

LR Reaction and Preparation of RNAi Constructs

EST fragments in pIPKTA38 were cloned as inverted repeats into the RNAi destination vector pIPKTA30N via a single LR recombination reaction. The reaction volume was reduced to 6 μl and comprised 1 μl of the pIPKTA38 donor clone, 1 μl pIPKTA30N destination vector (150 ng/μl), 0.8 μL LR clonase enzyme mix and 3.2 μl of H$_2$O. The reaction was incubated overnight at room temperature, and 5 μl of it were transformed into 20 μl of chemically competent *E. coli* cells in 96-well PCR plates. Two 96-deep-well plates with LB+ampicillin were half-filled with half the volume of the transformation mix, sealed with an air-permeable film and incubated for 24 hours at 37° C. on a plate shaker. Thereafter, the deep-well plates were centrifuged for 10 minutes at 750 g, and the pellets of two duplicates of each clone were combined and subjected to the plasmid preparation. The NucleoSpin Robot-96 plasmid kit (Macherey-Nagel) was used for this purpose. The DNA quantity was on average 20-30 μg of DNA per clone.

Particle Bombardment and Inoculation with Fungal Spores

Segments of primary leaves of 7-day-old barley seedlings were placed on 0.5% w/v Phytoagar (Ducheva) in water comprising 20 ppm of benzimidazole and bombarded with gold particles (diameter 1 μm) in a PDS-1000/He system (Bio-Rad, Munich, Germany) using the Hepta adaptor with a helium pressure of 900 psi. Seven leaf segments were employed per bombardment. The particle coating with 0.5 M Ca(NO$_3$)$_2$ was carried out as described by Schweizer et al., 1999, except that the stock solution comprised 25 mg ml$^{-1}$ gold. After the coating, all of the supernatant was removed, and the particles were resuspended in 30 μl of pure ethanol. 2.18 mg of gold microcarrier were employed per bombardment. Four hours after the bombardment, the leaf segments were placed on 1% w/v Phytoagar (Ducheva) in water comprising 20 ppm of benzimidazole in 20×20 cm plates and weighted down at both ends.

The leaf segments were inoculated with spores of Bgt and Bgh 48 hours or 96 hours after the particle bombardment. The plasmid pUbiGUS, which comprises the β-glucuronicse (GUS) gene under the control of the maize ubiquitin promoter, was employed as reporter construct for transformed epidermal cells. 40 hours after the inoculation, the leaf segments were stained on GUS activity and destained for 5 minutes with 7.5% w/v trichloroacetic acid and 50% methanol. The GUS staining solution has been described in Schweizer et al. 1999.

To evaluate the interaction of phenotypes, GUS-stained cells were counted under an optical microscope, and the number of haustoria in these transformed cells was determined, whereby the haustorial index is derived. As an alternative, the number of GUS-stained cells which comprised at least one haustorium was determined and the susceptibility index was calculated thereby.

Results: Increase in mildew resistance of barley due to RNAi of ARM repeat proteins

| Susceptibility* | Spores/mm$^2$ |
|---|---|
| 0.08 | 200 |
| 0.07 | |
| 0 | |
| 0.04 | |
| 0.01 | |
| 0.06 | |
| 0.08 | |
| 0.07 | 200 |
| 0.13 | |
| 0.01 | |
| 0.02 | |
| 0.01 | |
| 0.07 | |
| 0.07 | |
| 0.1 | 200 |
| 0.06 | |
| 0.01 | |
| 0.05 | |
| 0.06 | |
| 0.08 | |

| Construct | Rel HAU Index (%) | | GUS Cells |
|---|---|---|---|
| | Mean | SDM | |
| TA30 (control) | 100 | 0 | 5499 |
| HO14H18 | 48.57 | 10.03 | 1572 |
| TA36 (Mlo RNAi) | 8.88888889 | 0.88377212 | 2024 |

*Susceptibility presented as the percentage of GUS-stained cells which comprised at least on haustorium

---

We claim:

1. A method of increasing the resistance to a pathogen in a plant or in a part of a plant, comprising reducing activity of an Armadillo repeat ARM1 protein in a plant cell, a plant, or in a part of the plant, and selecting for a plant, plant cell, or plant part having increased pathogen resistance as compared to a corresponding control plant, plant cell, or plant part, wherein the protein is encoded by a polynucleotide comprising at least one nucleic acid molecule selected from the group consisting of:
   a) a nucleic acid molecule which encodes a polypeptide comprising the amino acid sequence of SEQ ID NO: 2;
   b) a nucleic acid molecule which comprises the polynucleotide sequence of SEQ ID NO: 1; and
   c) a nucleic acid molecule which encodes a polypeptide comprising a sequence having at least 95% sequence identity to the amino acid sequence of SEQ ID NO: 2;
   wherein the reducing activity comprises introducing a nucleic acid molecule encoding a dsRNA, an antisense RNA, or a RNAi which targets mRNA encoding the ARM1 protein; and
   wherein the plant cell, plant, or part of the plant has increased resistance to a pathogen relative to a corresponding wild type plant or part thereof.

2. The method of claim 1, wherein the activity in mesophyll cells and/or epidermal cells is reduced.

3. The method of claim 1, wherein the activity in a lemma, palea, or glume is reduced.

4. The method of claim 1, wherein the resistance is achieved by reducing expression of a polypeptide comprising two or more Armadillo repeats.

5. The method of claim 1, further comprising obtaining a plant cell, plant, part of the plant, or progeny of the plant, wherein the plant cell, plant, part of the plant, or progeny of the plant has increased resistance to a pathogen relative to a corresponding wild type plant cell, plant, or part thereof.

6. The method of claim 1, wherein the pathogens are selected from among the families Pucciniaceae, Mycosphaerellaceae, and Hypocreaceae.

7. The method of claim 1, wherein
   a) the nucleic acid molecule encoding a dsRNA comprises a sense strand having at least 90% homology with a nucleic acid molecule selected from the group consisting of:
      i) a nucleic acid molecule which encodes a polypeptide comprising the amino acid sequence of SEQ ID NO: 2;
      ii) a nucleic acid molecule which comprises the polynucleotide sequence of SEQ ID NO: 1;
      iii) a nucleic acid molecule which encodes a polypeptide comprising a sequence having at least 95% sequence identity to the amino acid sequence of SEQ ID NO: 2; and
      iv) a nucleic acid molecule which comprises a fragment of at least 19 base pairs, which has at least 95% homology with a corresponding fragment of the nucleic acid molecule of i) or ii), or
   b) the nucleic acid molecule encoding an antisense RNA comprises a sequence having at least 90% homology with the complement of the nucleic acid molecule of i) or ii), or comprises a fragment of 19 to about 21 base pairs with at least 90% homology with a corresponding fragment of the complementary nucleic acid molecule of i) or ii).

8. The method of claim 7, wherein the nucleic acid molecule is introduced into the plant cell in a recombinant expression cassette comprising the nucleic acid molecule in operable linkage with a promoter which is active in plants, the method further comprising
   a) regenerating a plant from the plant cell, and
   b) expressing the nucleic acid molecule in a sufficient amount and over a sufficient period of time to generate, or to increase, a pathogen resistance in said plant relative to a corresponding wild-type plant.

9. The method of claim 8, wherein the promoter is a pathogen-inducible promoter.

10. The method of claim 8, wherein the promoter is an epidermis- or mesophyll-specific promoter.

11. The method of claim 8, further comprising obtaining a plant cell, plant, part of the plant, or progeny of the plant, wherein the plant cell, plant, part of the plant, or progeny of the plant has increased resistance to a pathogen relative to a corresponding wild type plant cell, plant, or part thereof.

12. The method of claim 1, wherein the activity of a polypeptide coding for Bax inhibitor 1, ROR2, SnAP34 and/or Lumenal Binding protein BiP is increased in a plant, plant organ, plant tissue or plant cell.

13. The method of claim 1, wherein the activity of a polypeptide coding for RacB, CSL1, HvNaOX and/or MLO is decreased in a plant, plant organ, plant tissue or plant cell.

14. The method of claim 12, wherein the Bax inhibitor 1 is expressed under the control of a mesophyll- or root-specific promoter.

15. The method of claim 1, wherein the pathogen is selected from among the species *Puccinia triticina, Puccinia striiformis, Mycosphaerella graminicola, Stagonospora nodorum, Fusarium graminearum, Fusarium culmorum, Fusarium avenaceum, Fusarium poae*, or *Microdochium nivale*.

16. The method of claim 1, wherein the plant is selected from the plant genera *Hordeum, Avena, Secale, Triticum, Sorghum, Zea, Saccharum*, and *Oryza*.

17. A transgenic plant cell, plant, or part of the plant produced by the method of claim 1, wherein the transgenic plant cell, plant, or part of the plant has increased resistance to a pathogen relative to a corresponding wild type plant cell, plant or part thereof.

18. A method for generating a plant which is resistant to a mesophyll-cell-penetrating pathogen comprising generating a plant from the plant cell of claim 17, wherein the plant is resistant to a mesophyll-cell-penetrating pathogen.

* * * * *